US012202897B2

(12) United States Patent
Jensen

(10) Patent No.: US 12,202,897 B2
(45) **Date of Patent: *Jan. 21, 2025**

(54) DRUG REGULATED TRANSGENE EXPRESSION

(71) Applicant: Seattle Children's Hospital, Seattle, WA (US)

(72) Inventor: Michael C. Jensen, Bainbridge Island, WA (US)

(73) Assignee: Seattle Children's Hospital, Seattle, WA (US)

( * ) Notice: Subject to any disclaimer, the term of this patent is extended or adjusted under 35 U.S.C. 154(b) by 653 days.

This patent is subject to a terminal disclaimer.

(21) Appl. No.: 17/472,284

(22) Filed: Sep. 10, 2021

(65) Prior Publication Data

US 2022/0064292 A1 Mar. 3, 2022

Related U.S. Application Data

(63) Continuation of application No. 16/287,074, filed on Feb. 27, 2019, now Pat. No. 11,155,616, which is a (Continued)

(51) Int. Cl.

| | |
|---|---|
| ***A61K 35/28*** | (2015.01) |
| ***A61K 35/12*** | (2015.01) |
| ***A61K 38/17*** | (2006.01) |
| ***A61K 39/00*** | (2006.01) |
| ***A61K 39/395*** | (2006.01) |
| ***C07K 14/705*** | (2006.01) |
| ***C07K 14/71*** | (2006.01) |
| ***C07K 14/715*** | (2006.01) |
| ***C07K 14/725*** | (2006.01) |
| ***C07K 16/28*** | (2006.01) |
| ***C07K 16/32*** | (2006.01) |
| ***C12N 5/0783*** | (2010.01) |

(Continued)

(52) U.S. Cl.

CPC .......... *C07K 16/2803* (2013.01); *A61K 35/28* (2013.01); *A61K 38/1774* (2013.01); *A61K 38/179* (2013.01); *A61K 38/1793* (2013.01); *A61K 39/3955* (2013.01); *A61K 39/4611* (2023.05); *A61K 39/4631* (2023.05); *A61K 39/464412* (2023.05); *C07K 14/7051* (2013.01); *C07K 14/70517* (2013.01); *C07K 14/70521* (2013.01); *C07K 14/70578* (2013.01); *C07K 14/71* (2013.01); *C07K 14/7151* (2013.01); *C07K 16/2818* (2013.01); *C07K 16/32* (2013.01); *C12N 5/0636* (2013.01); *C12N 5/0638* (2013.01); *C12N 9/12* (2013.01); *C12N 15/85* (2013.01); *C12Y 207/10001* (2013.01); *A61K 2035/124* (2013.01); *A61K 2039/505* (2013.01); *A61K 2039/572* (2013.01); *C07K 2317/14* (2013.01); *C07K 2317/524* (2013.01); *C07K 2317/526* (2013.01); *C07K 2317/53* (2013.01); *C07K 2317/622* (2013.01); *C07K 2317/73* (2013.01); *C07K 2319/02* (2013.01); *C07K 2319/03* (2013.01); *C07K 2319/33* (2013.01); *C12N 2510/00* (2013.01); *C12N 2800/90* (2013.01)

(58) Field of Classification Search

CPC ........ A61K 35/12; A61K 35/28; A61K 38/17; A61K 39/00; A61K 39/395; C12N 5/0783; C12N 9/12; C07K 14/705; C07K 14/711; C07K 14/715; C07K 16/32

See application file for complete search history.

(56) References Cited

U.S. PATENT DOCUMENTS

| | | | |
|---|---|---|---|
| 5,783,186 | A | 7/1998 | Arakawa et al. |
| 6,040,177 | A | 3/2000 | Riddell et al. |

(Continued)

FOREIGN PATENT DOCUMENTS

| | | |
|---|---|---|
| CN | 1809277 | 7/2006 |
| DE | 10 2011118018 | 4/2013 |

(Continued)

OTHER PUBLICATIONS

Roscilli et al, Mol. Therapy 6(5): 653-663, 2002.*
Sentman, Immunotherapy 5(8): 783-785, Aug. 1, 2013.*
Kim et al, Efficiency of the Elongation Factor-1alpha Promoter in Mammalian Embryonic Stem Cells Using Lentiviral Gene Delivery Systems, Stem Cells and Development 16:537-545, 2007.*
Aalberse et al., "IgG4 breaking the rules," Immunology (2002) 105:9-19.
Aertgeerts et al., "Structural analysis of the mechanism of inhibition and allosteric activation of the kinase domain of HER2 protein," Journal of Biological Chemistry (2011) vol. 286, No. 21, p. 18756-18765, 18759-18765.

(Continued)

*Primary Examiner* — Kevin K Hill
(74) *Attorney, Agent, or Firm* — Knobbe, Martens, Olson & Bear LLP

(57) ABSTRACT

The present invention provides nucleic acids, vectors, host cells, methods and compositions to confer and/or augment immune responses mediated by cellular immunotherapy, such as by adoptively transferring CD8+ central memory T cells or combinations of central memory T cells with CD4+ T cells that are genetically modified to express a chimeric receptor under the control of an inducible promoter. In some alternatives the genetically modified host cell comprises a nucleic acid comprising a polynucleotide coding for a chimeric antigen receptor comprising a ligand binding domain, a polynucleotide comprising a spacer region, a polynucleotide comprising a transmembrane domain, and a polynucleotide comprising an intracellular signaling domain under the control of a drug inducible promoter. Controlling the expression of the chimeric receptor provides for the ability to turn expression on and off depending on the status of the patient. Pharmaceutical formulations produced by the method, and methods of using the same, are also described.

23 Claims, 19 Drawing Sheets

Specification includes a Sequence Listing.

Related U.S. Application Data continuation of application No. 15/302,415, filed as application No. PCT/US2015/024947 on Apr. 8, 2015, now Pat. No. 10,266,592.

(60) Provisional application No. 61/977,751, filed on Apr. 10, 2014, provisional application No. 61/986,479, filed on Apr. 30, 2014, provisional application No. 62/058,973, filed on Oct. 2, 2014, provisional application No. 62/088,363, filed on Dec. 5, 2014, provisional application No. 62/089,730, filed on Dec. 9, 2014, provisional application No. 62/090,845, filed on Dec. 11, 2014.

(51) Int. Cl.
*C12N 9/12* (2006.01)
*C12N 15/85* (2006.01)

(56) References Cited

U.S. PATENT DOCUMENTS 6,133,027 A 10/2000 Yee et al.
7,070,995 B2 7/2006 Jensen
7,446,179 B2 11/2008 Jensen et al.
7,709,253 B2 5/2010 Gambhir et al.
7,910,101 B2 3/2011 Cunningham et al.
8,802,374 B2 8/2014 Jensen
8,822,647 B2 9/2014 Jensen
8,916,381 B1 12/2014 June et al.
8,975,071 B1 3/2015 June et al.
9,328,156 B2 5/2016 June et al.
9,447,194 B2 9/2016 Jensen
9,481,728 B2 11/2016 June et al.
9,499,629 B2 11/2016 June et al.
9,518,123 B2 12/2016 June et al.
9,540,445 B2 1/2017 June et al.
9,629,877 B2 4/2017 Cooper et al.
9,701,758 B2 7/2017 Cooper et al.
9,856,322 B2 1/2018 Campana et al.
10,125,193 B2 11/2018 Cooper et al.
10,172,885 B2 1/2019 Pule
10,221,245 B2 3/2019 Brogdon et al.
10,266,592 B2 * 4/2019 Jensen .................... A61P 15/00
10,287,350 B2 5/2019 Kochenderfer
10,358,474 B2 7/2019 Baeuerle et al.
10,457,730 B2 10/2019 Pule et al.
10,533,055 B2 1/2020 Chen et al.
10,604,740 B2 3/2020 Li et al.
10,611,837 B2 4/2020 Jensen et al.
10,626,187 B2 4/2020 Wiltzius et al.
10,639,329 B2 5/2020 Dropulic et al.
10,738,279 B2 8/2020 Lee
10,780,118 B2 9/2020 Jensen
10,800,833 B2 10/2020 Jantz et al.
10,828,352 B2 11/2020 Berger et al.
10,844,120 B2 11/2020 Wiltzius et al.
10,865,242 B2 12/2020 Jensen
10,869,888 B2 12/2020 Xiao et al.
10,927,184 B2 2/2021 Brogdon et al.
11,034,763 B2 6/2021 Wu et al.
11,104,732 B2 8/2021 Cao et al.
11,123,369 B2 9/2021 Jensen et al.
11,155,616 B2 * 10/2021 Jensen ............. C07K 14/70517
11,408,005 B2 * 8/2022 Jensen .................... A61P 11/00
2002/0111474 A1 8/2002 Capon et al.
2003/0143559 A1 7/2003 Bracken et al.
2003/0148982 A1 8/2003 Brenner et al.
2003/0215427 A1 11/2003 Jensen
2005/0060762 A1 3/2005 Bleck
2005/0129671 A1 6/2005 Cooper et al.
2006/0160090 A1 7/2006 Anzures et al.
2006/0246548 A1 11/2006 Jensen
2007/0020237 A1 * 1/2007 Yoon ...................... C12N 15/86
435/456
2007/0087346 A1 * 4/2007 Ciliberto ................ C12N 15/85
435/7.1
2007/0166318 A1 7/2007 Macina et al.
2008/0044413 A1 2/2008 Hammond
2008/0096813 A1 4/2008 Frankel et al.
2009/0098142 A1 4/2009 Kasaian et al.
2009/0098604 A1 4/2009 Gallo et al.
2010/0226901 A1 9/2010 Smolke
2011/0287020 A1 11/2011 Gruber et al.
2012/0046645 A1 2/2012 Cal
2012/0148552 A1 * 6/2012 Jensen ................... A61K 35/17
536/23.4
2012/0297493 A1 11/2012 Cooper et al.
2012/0301447 A1 11/2012 Jenser
2013/0011394 A1 1/2013 Knoetgen
2013/0071414 A1 3/2013 Dotti et al.
2013/0143559 A1 6/2013 Nishida et al.
2013/0280220 A1 10/2013 Ahmed et al.
2013/0287748 A1 10/2013 June et al.
2014/0056868 A1 2/2014 Zechiedrich et al.
2014/0099309 A1 4/2014 Power
2014/0112956 A1 4/2014 Karlsson-Parra et al.
2014/0120622 A1 5/2014 Gregory
2014/0271635 A1 9/2014 Brogdon et al.
2014/0314795 A1 10/2014 Riddell et al.
2015/0038684 A1 2/2015 Jensen
2015/0038694 A1 2/2015 Nicotra
2015/0120622 A1 4/2015 Kobatake
2015/0299656 A1 10/2015 Gattinoni et al.
2015/0329640 A1 11/2015 Finer
2016/0017048 A1 1/2016 Dotti et al.
2017/0015746 A1 1/2017 Jensen
2017/0029774 A1 2/2017 Jensen et al.
2017/0209543 A9 7/2017 Jensen
2017/0224733 A1 8/2017 Badie et al.
2018/0028567 A1 2/2018 Li et al.
2020/0181624 A1 6/2020 Jensen et al.
2020/0215108 A1 7/2020 Jensen et al.
2021/0002364 A1 1/2021 Jensen et al.
2021/0139583 A1 5/2021 Jensen et al.
2021/0371517 A1 12/2021 Jensen
2022/0372140 A1 11/2022 Jensen
2022/0380461 A1 12/2022 Jensen
2022/0411805 A1 12/2022 Jensen
2023/0130938 A1 4/2023 Jensen

FOREIGN PATENT DOCUMENTS

JP 2006-518753 8/2006
RU 2003 129 528 A 4/2005
WO WO 92/08796 5/1992
WO WO 94/00143 1/1994
WO WO 98/18923 5/1998
WO WO 00/23573 4/2000
WO WO 01/098506 12/2001
WO WO 02/33101 4/2002
WO WO 02/072605 9/2002
WO WO 02/097099 12/2002
WO WO 03/025228 3/2003
WO WO 03/087338 10/2003
WO WO 04/029284 4/2004
WO WO 05/017102 2/2005
WO WO 05/040212 5/2005
WO WO 05/108617 11/2005
WO WO 07/073499 6/2007
WO WO 07/137267 11/2007
WO WO 08/012237 1/2008
WO WO 09/013359 1/2009
WO WO 09/091826 7/2009
WO WO 10/036986 4/2010
WO WO 10/141543 12/2010
WO WO 11/041093 4/2011
WO WO 11/056894 5/2011
WO WO 12/031744 3/2012
WO WO 12/079000 6/2012
WO WO 12/099973 7/2012
WO WO 12/129514 9/2012
WO WO 12/140130 10/2012
WO WO 12/167192 12/2012

(56) References Cited

FOREIGN PATENT DOCUMENTS

| WO | WO 13/059593 | 4/2013 |
|---|---|---|
| WO | WO 13/074916 | 5/2013 |
| WO | WO 13/123061 | 8/2013 |
| WO | WO 13/126733 | 8/2013 |
| WO | WO 13/154760 | * 10/2013 |
| WO | WO 13/177533 | 11/2013 |
| WO | WO 13/178635 | 12/2013 |
| WO | WO 14/031687 | 2/2014 |
| WO | WO 14/039044 | 3/2014 |
| WO | WO 14/055657 | 4/2014 |
| WO | WO 14/055668 | 4/2014 |
| WO | WO 14/139672 | 9/2014 |
| WO | WO 14/153270 | 9/2014 |
| WO | WO 15/066551 | 5/2015 |
| WO | WO 15/075468 | 5/2015 |
| WO | WO 15/092024 | 6/2015 |
| WO | WO 15/105522 | 7/2015 |
| WO | WO 15/142675 | 9/2015 |
| WO | WO 15/157399 | 10/2015 |
| WO | WO 15/157432 | 10/2015 |

OTHER PUBLICATIONS

Ahmed et al., "Regression of experimental medulloblastoma following transfer of HER2-specific T cells," Cancer Res. (Jun. 15, 2007) 67(12):5957-64.

Ahmed, Nabil, "CMV-specific Cytotoxic T Lymphocytes Expressing CAR Targeting HER2 in Patients With GBM (HERT-GBM)," ClinicalTrials.gov Identifier: NCT01109095 (Apr. 22, 2010) pp. 1-8.

Ahmed, Nabil, "Her2 Chimeric Antigen Receptor Expressing T Cells in Advanced Sarcoma," ClinicalTrials.gov Identifier: NCT00902044 (May 14, 2009) pp. 1-11.

Altschul et al., "Local Alignment Statistics, [27] Multiple Alignment and Phylogenetic Trees," Methods in Enzymology (1996) 266:460-480.

Bejcek et al. "Development and Characterization of Three Recombinant Single Chain Antibody Fragments (scFvs) Directed against the CD19 Antigen," Cancer Res (1995) 55:2346-2351.

Berglund et al., "The epitope space of the human proteome," Protein Science (2008) 17:606-613.

Brentjens et al: "CD19-targeted T cells rapidly induce molecular remissions in adults with chemotherapy-refractory acute lymphoblastic leukemia", Science Translational Medicine, 5(177), Mar. 20, 2013.

Budde et al., "Combining a CD20 Chimeric Antigen Receptor and an Inducible Caspase 9 Suicide Switch to Improve the Efficacy and Safety of T Cell Adoptive Immunotherapy for Lymphoma", PLOS ONE (2013) 8(12): e82742. https://doi.org/10.1371/journal.pone.0082742.

Cartellieri et al., "A Novel Ex Vivo Isolation and Expansion Procedure for Chimeric Antigen Receptor Engrafted Human T Cells," PLOS ONE (Apr. 3, 2014) vol. 9, No. 4, e93745, pp. 1-12.

Cha et al., "IL-7 + IL-15 are superior to IL-2 for the ex vivo expansion of 4T1 mammary carcinoma- specific T cells with greater efficacy against tumors in vivo," Breast Cancer Research and Treatment, Springer, NY, US (Oct. 14, 2009) vol. 122, No. 2, pp. 359-369.

Chen et al., "Ex vivo expansion of dendritic-cell-activated antigen-specific CD4+ T cells with anti-CD3/CD28, interleukin 7, and interleukin-15: Potential for adoptive T-cell immunotherapy," Clinical Immunology (2006) vol. 119, pp. 21-31.

Chen et al., "Minicircle DNA vectors devoid of bacterial DNA result in persistent and high-level transgene expression in vivo", Mol Ther. (2003) 8(3), 495-500.

Chen et al., 2013, Fusion protein linkers: property, design and functionality, Advanced Drug Delivery Reviews, 65(10):1357-1369.

Cho et al., "Structure of the extracellular region of HER2 alone and in complex with the Herceptin Fab", Nature (Feb. 13, 2003) 421(6924):756-760.

Circosta et al., "T Cell Receptor (TCR) Gene Transfer with Lentiviral Vectors Allows Efficient Redirection of Tumor Specificity in Naïve and Memory T Cells Without Prior Stimulation of Endogenous TCR," Human Gene Therapy (Nov. 18, 2009) vol. 20, No. 12, pp. 1576-1588.

Converse et al: "Counterselection and Co-Delivery of Transposon and Transposase Functions for Sleeping Beauty-Mediated Transposition in Cultured Mammalian Cells", Bioscience Reports, Kluwer Academic Publishers-Plenum Publishers, NE (Dec. 1, 2004) vol. 24, No. 6, pp. 577-594.

Crewe et al., "Metabolism of Tamoxifen by recombinant human cytochrome P-450 enzymes: Formation of the 4-hydroxy, 4'-hydroxy and N-desmethyl metabolites and isomerization of trans-4-hydroxytamoxifen,"Drug Metab Dispos (2002) 30(8): 869-874.

Database Geneseq [Online] May 5, 2005 (May 5, 2005), "Human splice variant protein expressed in ovary cells DEX0487 002.orf.4.", XP002771301, retrieved from EBI accession No. GSP:ADY30515. Database accession No. ADY30515 ; & WO 2005/017102 A2 (Diadexus Inc [US]; Macina Roberto A [US]; Turner Leah R [US]; Sun Yong) Feb. 24, 2005 (Feb. 24, 2005).

Database UniProt [Online] Oct. 3, 2012 (Oct. 3, 2012), "SubName: Full=Receptor tyrosine-protein kinase erbB-2 {ECO: 00003131Ensembl:ENSP00000464252}; Flags: Fragment;", XP002771300, retrieved from EBI accession No. UNIPROT:J3QRJ7 Database accession No. J3QRJ7.

Dotti, Gianpietro, et al. "Design and development of therapies using chimeric antigen receptor—expressing T cells." Immunological reviews 257.1 (2014): 107-126.

Ercikan-Abali et al., "Active Site-Directed Double Mutants of Dihydrofolate Reductase," Cancer Res., (1996) vol. 56, No. 18, pp. 4142-4145.

Frankel et al., "Characterization of diphtheria fusion proteins targeted to the human interleukin-3 receptor," Protein engineering (2000) vol. 13, No. 8, p. 575-581.

Gagnon et al., "IL-6, in Synergy with IL-7 or IL-15, Stimulates TCR-Independent Proliferation and Functional Differentiation of CD8+ T Lymphocytes," The Journal of Immunology (2008) 180:7958-7968.

Gallinari et al., "A Functionally Orthogonal Estrogen Receptor-Based Transcription Switch Specifically Induced by a Nonsteroid Synthetic Ligand," Chemistry and Biology (Aug. 1, 2005) vol. 12, No. 8, pp. 883-893.

Gargett et al., "Different cytokine and stimulation conditions influence the expansion and immune phenotype of third-generation chimeric antigen receptor T cells specific for tumor antigen GD2," Cytotherapy (2015) 17.4: 487-495.

Garrett et al., "Novel engineered trastuzumab conformational epitopes demonstrate in vitro and in vivo antitumor properties against HER-2/neu," The Journal of Immunology (Jun. 1, 2007) 178:7120-7131.

Ghatar et al., "Epitope Mapping of Human HER2 Specific Mouse Monoclonal Antibodies Using Recombinant Extracellular Subdomains," Asian Pacific Journal of Cancer Prevention (2017) 18(11):3103-3110.

Giry-Laterriere et al. "Polyswitch lentivectors: 'all-in-one' lentiviral vectors for drug-inducible gene expression, live selection, and recombination cloning, *Human Gene Therapy*", Oct. 2011, 22:1255-1267.

Godiska et al., "Linear plasmid vector for cloning of repetitive or unstable sequences in *Excherichia coli*," (Dec. 29, 2009) Nuc Acids Res, vol. 38, No. 6, e88, pp. 1-9.

Gottschalk, Stephen, "Her2 and TGFBeta CTLs in Treatment of Her2 Positive Malignancy (HERCREEM)", ClinicalTrials.gov Identifier: NCT00889954 (Apr. 29, 2009) pp. 1-9.

Grada et al., "TanCAR: A Novel Bispecific Chimeric Antigen Receptor for Cancer Immunotherapy", Mol Ther Nucleic Acids, (Jul. 9, 2013) 2:e105. doi: 10.1038/mtna.2013.32.

Han Weidong, "Treatment of Chemotherapy Refractory Human Epidermal growth Factor Receptor-2(HER-2) Positive Advanced Solid Tumors (CART-HER-2)", (Sep. 5, 2013) ClinicalTrials.gov Identifier: NCT01935843, pp. 1-7.

(56) References Cited

OTHER PUBLICATIONS

Holtkamp et al., "Modification of antigen-encoding RNA increases stability, translational efficacy, and T-cell stimulatory capacity of dendritic cells," Blood (Oct. 28, 2014), 2006/108:509-4017.
Hong et al., "Diverse solid tumors expressing a restricted epitope of L1-CAM can be targeted by chimeric antigen receptor redirected T lymphocytes," J Immunotherapy (2014) vol. 37, No. 2, pp. 93-104.
Hudecek et al. Receptor affinity and extracellular domain modifications affect tumor recognition by ROR1-specific chimeric antigen receptor T-cells. Clin Cancer Res. Jun. 15, 2013: 19(12): 3153-3164.
Hudecek et al., Nov. 16, 2012, The Non-Signaling Extracellular Spacer Domain of CD19-Specific Chimeric Antigen Receptors Is Decisive for in Vivo Anti-Tumor Activity, Blood, 120(21):951, 3 pp.
Hudecek et al., Sep. 11, 2014, "The Nonsignaling Extracellular Spacer Domain of Chimeric Antigen Receptors Is Decisive for In Vivo Antitumor Activity", Cancer Immunology Research, 3(2):125-135.
Huls et al., "First Clinical Trials Employing Sleeping Beauty Gene Transfer System and Artificial Antigen Presenting Cells to Generate and Infuse T Cells Expressing CD19-Specific Chimeric Antigen Receptor," Blood (2013) 122:166-166.
Jensen et al., "Designing chimeric antigen receptors to effectively and safely target tumors," Curr Opin Immunol. (Apr. 2015) 33:9-15.
Jensen et al: "Design and implementation of adoptive therapy with chimeric antigen receptor-modified T cells", Immunological Reviews., Special Issue, Dec. 13, 2013 vol. 257, No. 1; 127-144.
Johansen et al., "Evaluation of Tet-on system to avoid transgene down-regulation in ex vivo gene transfer to the CNS," Gene Therapy (2002) 9:1291-1301.
Johnston et al. "Regulated expression of erythropoietin from an AAV vector safely improves the anemia of beta-thalassemia in a mouse model," Mol Ther. Apr. 1, 2003, 7(4):493-497.
Jonnalagadda et al., "Efficient selection of genetically modified human T cells using methotrexate-resistant human dihydrofolate reductase," Gene Therapy, vol. 20, No. 8, Jan. 10, 2013, pp. 853-860.
Kacherovsky et al., "Combination of Sleeping Beauty transposition and chemically induced dimerization selection for robust production of engineered cells," Nucleic Acids Research (2012) 49(11):e85.
Kacherovsky et al., "Multiplexed 1-16 gene transfer to a human T-cell line by combining Sleeping Beauty transposon system with methotrexate selection", Biotechnology and Bioengineering (Jul. 23, 2015) vol. 112, No. 7, pp. 1429-1436.
Kay et al, "A robust system for production of minicircle DNA vectors", Nature Biotechnology, vol. 28, No. 12, Nov. 21, 2010, pp. 1287-1289.
Klebanoff et al., "IL-15 enhances the in vivo antitumor activity of tumor-reactive CD8+ T Cells," PNAS (Feb. 17, 2004) vol. 101, No. 7, pp. 1969-1974.
Kowolik et al., "CD28 costimulation provided through a CD19-specific chimeric antigen receptor enhances in vivo persistence and antitumor efficacy of adoptively transferred T cells," Cancer Res. (2006) 66(22):10995-11004.
Kunkele et al., "Functional Tuning of CARs Reveals Signaling Threshold above which CD8+ CTL Antitumor Potency is Attenuated Due to Cell Fas-FasL-Dependent AICD," Cancer Immunol Res. (Jan. 9, 2015) vol. 3, No. 4, pp. 368-379.
Lemaigre et al., "Transcriptional control of genes that regulate glycolysis and gluconeogenesis in adult liver," Biochem. J. (1994) 303:1-14.
Leung et al., "Luminescent detection of DNA-binding proteins," Nuc Acids Res (2012) 40(3): 941-955.
Likar et al., "Using a mutated variant human deoxycytidine-kinase as a reporter gene for assessing adoptive T-cell therapy," Questions hematology, oncology and immunopathology in pediatrics (2012) vol. 11, No. 2, pp. 23-31. (Russian Language).
Littlewood et al., "A modified oestrogen receptor ligand-binding domain as an improved switch for the regulation of heterologous proteins," Nucleic Acids Res (May 25, 1995) 23(10):1686-1690.
Litvinova et al., "The influence of immunoregulatory cytokines IL-2, IL-7, and IL-15 upon activation, proliferation, and apoptosis of immune memory T-cells in vitro," Cell and Tissue Biology (Dec. 11, 2013) vol. 7, No. 6, pp. 539-544.
Liu et al., "IL-21 synergizes with IL-7 to augment expansion and anti-tumor function of cytotoxic T cells," International Immunology (2007) vol. 19, No. 10, pp. 1213-1221.
Loeken, Mary R., "Effects of mutation of the CREB binding site of the somatostatin promoter on cyclic AMP responsiveness in CV-1 cells", *Gene Expr*. (1993) 3(3):253-264.
Lupton et al., "Dominant positive and negative selection using a hygromycin phosphotransferase-thymidine kinase fusion gene," Mol Cell Biol. (Jun. 1991) 11(6):3374-3378.
Maher, "Immunotherapy of Malignant Disease Using Chimeric Antigen Receptor Engrafted T Cells", *ISRN Oncology*, vol. 2012, pp. 1-23, Nov. 14, 2012.
Mátés et al., "Molecular evolution of a novel hyperactive Sleeping Beauty transposase enables robust stable gene transfer in vertebrates," Nature Genetics (Jun. 2009) vol. 41, No. 6, pp. 753-761.
Mcgehee et al., "Differentiation-specific element: a cis-acting developmental switch required for the sustained transcriptional expression of the angiotensinogen gene during hormonal-induced differentiation of 3T3-L1 fibroblasts to adipocytes," Mol. Endocrinol. (Apr. 1993) 7(4):551-560.
Mckinlay et al., "Blood monocytes, myeloid dendritic cells and the cytokines interleukin (IL)-7 and IL-15 maintain human CD4+ T memory cells with mixed helper/regulatory function," Immunology (2006) vol. 120, pp. 392-403.
Morgan et al., "Case report of a serious adverse event following the administration of T cells transduced with a chimeric antigen receptor recognizing ERBB2," Mol Ther. (Apr. 2010) 18(4):843-51. doi: 10.1038/mt.2010.24. Epub Feb. 23, 2010.
Muftuoglu et al., "CD161 Expression Identifies a Distinct Subset of Drug-Effluxing Viral-Specific Memory CD4+ T Cells That Preferentially Survive Cytotoxic Chemotherapy," Blood (2012) 122(21):2024.
O'Reilly et al., "Identification of an activating transcription factor (ATF) binding site in the human transforming growth factor-beta 2 promoter," J. Biol. Chem. (Oct. 5, 1992) 267:19938-19943.
Pakula et al., "Genetic analysis of protein stability and function," Annual review of genetics (1989) vol. 23, No. 1, p. 289-310, c.305-306.
Papapetrou et al. "Harnessing endogenous miR-181a to segregate transgenic antigen receptor expression in developing versus post-thymic T cells in murine hematopoietic chimeras", The Journal of clinical investigation. Jan. 5, 2009;119(1):157-68.
Park et al., "Adoptive Transfer of Chimeric Antigen Receptor Re-Directed Cytolytic T Lymphocyte Clones in Patients with Neuroblastoma," Mol. Ther. (Apr. 2007) vol. 15, No. 4; pp. 825-833.
Pezutto et al., May 1, 1987, CD19 monoclonal antibody HD37 inhibits anti-immunoglobulin-induced B cell activation and proliferation, The Journal of Immunology, 138(9):2793-2799.
Pollock et al. "Delivery of a stringent dimerizer-regulated gene expression system in a single retroviral vector," Proc Natl Acad Sci. USA Nov. 21, 2000, 97(24):13221-1326.
Promega, "pSP64 Poly(A) Vector Sequence and Map," Technical Bulletin No. 052, Revised May 2000, pp. 1-8.
Riddell et al. "Adoptive therapy with chimeric antigen receptor modified T cells of defined subset composition." Cancer journal (Sudbury, Mass. ) 20.2 (2014): 141-144.
Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington," Human Gene Therapy (1992) 3(3):319-338.
Roscilli et al., "Long-term and tight control of gene expression in mouse skeletal muscle by a new hybrid human transcription factor," Molecular Therapy (Nov. 2002) 1;6(5):653-63.
Sadelain et al., "The basic principles of chimeric antigen receptor (CAR) design," Cancer discovery (2013) 3 (4): 388-98. DOI: 10.1158/2159-8290.CD-12-0548.
Schmittgen et al. "Analyzing real-time PCR data by the comparative C(T) method", *Nat Protoc*. 2008;3(6):1101-8.

(56) References Cited

OTHER PUBLICATIONS

Sengupta et al., "Interleukin-13 Receptor Alpha 2-Targeted Glioblastoma Immunotherapy," BioMed Research International, (Aug. 27, 2014) vol. 2014, Article ID: 952128, pp. 1-8.
Sharma et al., "Efficient Sleeping Beauty DNA Transposition from DNA Minicircles," Mol Ther Nuc Acids (2013) 2:e74, 1-10.
Surh et al., "Homeostasis of memory T cells," Immunological Reviews (2006) vol. 211, pp. 154-163.
Terakura et al., "Generation of CD19-chimeric antigen receptor modified CD8+ T cells derived from virus-specific central memory T cells," Gene Therapy (Oct. 26, 2011) 119(1), pp. 72-82.
Treisman, R. "The SRE: a growth factor responsive transcriptional regulator. (PMID:2133110)", *Seminars in Cancer Biology*, Feb. 1, 1990, 1(1):47-58.
Vigna et al., "Robust and Efficient Regulation of Transgene Expression in Vivo by Improved Tetracycline-Dependent Lentiviral Vectors," Mol. Therapy (2002) 5(3):252-261.
Vogt et al., "Doxycycline-regulated gene expression in the opportunistic fungal pathogen Aspergillus fumigatus," BMC Microbiol. (2005) 5(1):11 pages.
Wang et al., "Phenotypic and Functional Attributes of Lentivirus Modified CD19-specific Human CD8+ Central Memory Tcells Manufactured at Clinical Scale," J Immunotherapy (2012) vol. 35, pp. 689-701.
Wang et al., "A transgene-encoded cell surface polypeptide for selection, in vivo tracking, and ablation of engineered cells", Blood, vol. 118, No. 5, Aug. 4, 2011 (Aug. 4, 2011), pp. 1255-1263.
Weill et al., "Translational control by changes in poly(A) tail length: recycling mRNAs," Nature Structural & Molecular Biology (Jun. 2012) vol. 19, No. 6, pp. 577-585.
Xu et al., "Closely related T-memory stem cells correlate with in vivo expansion of CAR.CD19-T cells and are preserved by IL-7 and IL-15," Blood (Jun. 12, 2014) vol. 123, No. 24, pp. 3750-3759.
Yant et al. "Mutational Analysis of the N-Terminal DNA-Binding Domain of Sleeping Beauty Transposase: Critical Residues for DNA Binding and Hyperactivity in Mammalian Cells," Mol. Cell. Biol. (2004) 24(20):9239-9247.
Ye et al., "Characterization of a silencer regulatory element in the human interferon-gamma promoter," J. Biol. Chem., (Oct. 14, 1994) 269:25728-25734.
Zambon et al., "Increased Expression of the Pro-Apoptotic Protein BIM: A Mechanism for cAMP/PKA-Induced Apoptosis of Immature T Cells," J. Biol. Chem. (2011) 286(38):33260-33267.
Zeng et al., "Synergy of IL-21 and IL-15 in regulating CD8+ T cell expansion and function," JEM (Jan. 3, 2005) vol. 201, No. 1, pp. 139-148.
Zheng, Changyu et al., "All Human EF1 Promoters Are Not Equal: Markedly Affect Gene Expression in Constructs from Different Sources," International Journal of Medical Sciences (2014) 11(5):404-408.
Burns et al., 2010, A high molecular weight melanoma-associated antigen-specific chimeric antigen receptor redirects lymphocytes to target human melanomas, Cancer Research, 70(8):3027-3033.
Chen et al., Jan. 2007, Generation of a transgenic mouse model with chondrocyte-specific and tamoxifen-inducible expression of cre recombinase, Genesis, 45:44-50.
Chen et al., Sep. 15, 2005, NF-κ-B RelA phosphorylation regulates RelA acetylation, Molecular and Cellular Biology, 25(18):7966-7975.
Courtney et al., 2018, TCR signaling: mechanisms of initiation and propagation, Trends in Biochemical Sciences, 43(2):108-123.
Dolezal et al., 2000, ScFv multimers of the anti-neuraminidase antibody NC10: shortening of the linker in single-chain Fv fragment assembled in VL to VH orientation drives the formation of dimers, trimers, tetramers and higher molecular mass multimers, Protein Engineering, 13(8):565-574.
Edwards et al., 2003, The remarkable flexibility of the human antibody repertoire; isolation of over one thousand different antibodies to a single protein, BLyS, J. Mol. Biol., 334:103-118.
Guedan et al., 2018, Enhancing CAR T cell persistence through ICOS and 4-1BB costimulation, JCI Insight, 3(1):11-13.
Guha et al., 2017, Frontline science: functionally impaired geriatric CAR-T cells rescued by increased a5β1 integrin expression, Journal of Leukocyte Biology, 102(2):201-208.
Hege et al., 2017, Safety, tumor trafficking and immunogenicity of chimeric antigen receptor (CAR)-T cells specific for TAG-72 in colorectal cancer, Journal for Immunotherapy of Cancer, 5(1):1-14.
Kanamori et al., A human-tissue type whose host is a human cell expression of plasminogen activator, Tissue Culture Research, 8(2):31-39, 1990.
Kochenderfer et al., Accession No. ADM64594.1, FMC63-28Z receptor protein, Jun. 11, 2012, Genbank.
Lin et al., 2009, Optimization and validation of a robust human T-cell culture method for monitoring phenotypic and polyfunctional antigen-specific CD4 and CD8 T-cell responses, Cytotherapy, 11(7):912-922.
Lloyd et al., 2009, Modelling the human immune response: performance of a $10^{11}$ human antibody repertoire against a broad panel of therapeutically relevant antigens, Protein Engineering, Design & Selection 22(3):159-168.
Long et al., 2015, 4-1BB costimulation ameliorates T cell exhaustion induced by tonic signaling of chimeric antigen receptors, Nature Medicine, 21(6):581-590.
Maeda et al., 1997, Engineering of functional chimeric protein G—Vargula Luciferase, Analytical Biochemistry, 249(2):147-152.
Maus et al., 2013, T cells expressing chimeric antigen receptors can cause anaphylaxis in humans, Cancer Immunology Research, 1(1):26-31.
Pelloquin et al., Dec. 1986, Human B lymphocytes immortalization by Epstein-Barr virus in the presence of cyclosporin A, In Vitro Cell Dev Biol, 22(12):689-694.
Richman et al., 2018, High-affinity GD2-specific CAR T cells induce fatal encephalitis in a preclinical neuroblastoma model, Cancer Immunology Research, 6(1):36-46.
Robinsons et al., Jan. 1991, Metabolites, pharmacodynamics, and pharmacokinetics of tamoxifen in rats and mice compared to the breast cancer patient, Drug Metab Dispos, 19(1):36-43.
Sadelain et al., 2009, The promise and potential pitfalls of chimeric antigen receptors, Current Opinion in Immunology, 21:215-223.
Schamel et al., 2019, The TOR is an allosterically regulated macromolecular machinery changing its conformation while working, Immunological Reviews, 291(1):8-25.
Teplyakov et al., 2014, Antibody modeling assessment II. Structures and models, Proteins: Structure, Function, and Bioinformatics, 82(8):1563-1582.
Turtle et al., 2016, CD19 CAR-T cells of defined CD4+: CD8+ composition in adult B cell ALL patients, The Journal of Clinical Investigation, 126(6):2123-2138.
Wilke et al., Apr. 27, 2012, Dual targeting of ErbB2 and MUC1 in breast cancer using chimeric antigen receptors engineered to provide complementary signaling, Journal of Clinical Immunology, 32(5):1059-1070.
Yang et al., Feb. 16, 2010, Functional interplay between acetylation and methylation of the RelA subunit of NF-κ-B, Molecular and Cellular Biology, 30(9):2170-2180.
International Search Report and Written Opinion dated Sep. 11, 2015 in PCT/US2015/024947.
Dolgikh et al., 2013, Heterologous expression of the extracellular domain of the HER2 receptor in bacteria, Scientific notes of St. Petersburg State Medical University named after. I. P. Pavlova, 20(4):70-73.
Hu et al., 2004, Insufficient p65 phosphorylation at S536 specifically contributes to the lack of NF-KB activation and transformation in resistant JB6 cells, Carcinogenesis, 25(10):1991-2003.
Jost et al., 2013, Structural basis for eliciting a cytotoxic effect in HER2-overexpressing cancer cells via binding to the extracellular domain of HER2, Structure, 21(11):1979-1991.
Majowicz et al., 2012, Murine CD4+ CD25-cells activated in vitro with PMA/ionomycin and anti-CD3 acquire regulatory function and ameliorate experimental colitis in vivo, BMC Gastroenterology, 12:1-9.

(56) References Cited

OTHER PUBLICATIONS

Nakazawa et al., May 2009, 231. Expression of multiple transgenes in human T cells from PiggyBac transposons, Molecular Therapy, 17(Suppl 1):S91.

* cited by examiner

```
                      M V   S K L S   Q L Q     T E L     L A A L   L E S     G L S     K E A L   I Q A
                      ATGGTG TCCAAGCTGT CCCAGCTGCA GACAGAACTG CTGGCAGCAC TGCTGGAAAG CGGCCTGAGC AAAGAGGCCC TGATTCAGGC
                      TACCAC AGGTTCGACA GGGTCGACGT CTGTCTTGAC GACCGTCGTG ACGACCTTTC GCCGGACTCG TTTCTCCGGG ACTAAGTCCG

* L G E   P G P Y   L L A     G E G     P L D K   G E S     C G G     G R G E   L A E     L P N
ACTCGGCGAA CCTGGACCTT ATCTGCTCGC TGGCGAAGGC CCTCTGGATA AGGGCGAGAG CTGTGGCGGA GGAAGAGGAG AGCTGGCCGA GCTGCCTAAC
TGAGCCGCTT GGACCTGGAA TAGACGAGCG ACCGCTTCCG GGAGACCTAT TCCCGCTCTC GACACCGCCT CCTTCTCCTC TCGACCGGCT CGACGGATTG

G L G E   T R G     S E D     E T D D   D G E     D F T     P P I L   K E L     E N L     S P E E
GGCCTGGGCG AGACAAGAGG CAGCGAGGAC GAGACAGACG ACGACGGCGA GGACTTCACC CCCCCCATCC TGAAAGAGCT GGAAAACCTG AGCCCCGAGG
CCGGACCCGC TCTGTTCTCC GTCGCTCCTG CTCTGTCTGC TGCTGCCGCT CCTGAAGTGG GGGGGGTAGG ACTTTCTCGA CCTTTTGGAC TCGGGGCTCC

* A A H   Q K A     V V E T   L L Q     E D P     W R V A   K M V     K S Y     L Q Q H   N I P *
AAGCCGCCCA CCAGAAAGCC GTGGTGGAGA CACTGCTGCA GGAAGATCCC TGGCGGGTCG CCAAGATGGT CAAGAGCTAC CTGCAGCAGC ACAACATCCC
TTCGGCGGGT GGTCTTTCGG CACCACCTCT GTGACGACGT CCTTCTAGGG ACCGCCCAGC GGTTCTACCA GTTCTCGATG GACGTCGTCG TGTTGTAGGG

* Q R E   V V D T   T G L     N Q S     H L S Q   H L N     K G T     P M K T   Q K R     A A L
CCAGCGGGAG GTGGTGGACA CCACCGGCCT GAACCAGAGC CACCTGAGCC AGCACCTGAA CAAGGGCACC CCCATGAAAA CCCAGAAGAG AGCCGCCCTG
GGTCGCCCTC CACCACCTGT GGTGGCCGGA CTTGGTCTCG GTGGACTCGG TCGTGGACTT GTTCCCGTGG GGGTACTTTT GGGTCTTCTC TCGGCGGGAC

Y T W Y   V R K     Q R E     V A Q Q   F T H     A G Q     G G L I   E E P     T G D     E L P T
TACACTTGGT ACGTGCGGAA GCAGAGAGAG GTGGCCCAGC AGTTTACACA CGCCGGCCAG GGCGGCCTGA TCGAGGAACC TACCGGCGAC GAGCTGCCCA
ATGTGAACCA TGCACGCCTT CGTCTCTCTC CACCGGGTCG TCAAATGTGT GCGGCCGGTC CCGCCGGACT AGCTCCTTGG ATGGCCGCTG CTCGACGGGT

* K K G   R R N     R F K W   G P A     S Q Q     I L F Q   A Y E     R Q K     N P S K   E E R *
CCAAGAAGGG CAGACGGACC CGGTTTAAGT GGGGCCCTGC ATCTCAGCAG ATCCTGTTCC AGGCCTACGA GCGGCAGAAG AACCCCAGCA AAGAGGAACG
GGTTCTTCCC GTCTGCCTTG GCCAAATTCA CCCCGGGACG TAGAGTCGTC TAGGACAAGG TCCGGATGCT CGCCGTCTTC TTGGGGTCGT TTCTCCTTGC

* E T L   V E E C   N R A     E C I     Q R G V   S P S     Q A Q     G L G S   N L V     T E V
GGAGACACTG GTGGAAGAGT GCAACCGGGC CGAGTGCATC CAGAGAGGCG TGAGCCCTTC TCAGGCTCAG GGCCTCGGCA GCAATCTGGT CACCGAAGTG
CCTCTGTGAC CACCTTCTCA CGTTGGCCCG GCTCACGTAG GTCTCTCCGC ACTCGGGAAG AGTCCGAGTC CCGGAGCCGT CGTTAGACCA GTGGCTTCAC

R V Y N   W F A     N R R     K E E A   F R H     K L S     A G D M   R A A     N L W     P S P L
CGGGTGTACA ATTGGTTCGC CAACCGGCGG AAAGAGGAAG CCTTCCGGCA CAAGCTGTCT GCTGGCGATA TGAGAGCCGC CAACCTGTGG CCCAGCCCCC
GCCCACATGT TAACCAAGCG GTTGGCCGCC TTTCTCCTTC GGAAGGCCGT GTTCGACAGA CGACCGCTAT ACTCTCGGCG GTTGGACACC GGGTCGGGGG

* M I K   R S K     K N S L   A L S     L T A     D Q M V   S A L     L D A     E P P I   L Y S *
TGATGATCAA GCGGAGCAAG AAGAACAGCC TGGCCCTGAG CCTGACCGCC GATCAGATGG TGTCCGCTCT GCTGGACGCC GAGCCCCCTA TCCTGTACAG
ACTACTAGTT CGCCTCGTTC TTCTTGTCGG ACCGGGACTC GGACTGGCGG CTAGTCTACC ACAGGCGAGA CGACCTGCGG CTCGGGGGAT AGGACATGTC
```

FIG. 9A

```
* E Y D     P T R P     F S E       A S M       M G L L     T N L       A D R       E L V H     M I N       W A K
CGAGTACGAC  CCCACCAGAC  CCTTCAGCGA  GGCCAGCATG  ATGGGCCTGC  TGACCAACCT  GGCCGACCGG  GAGCTGGTGC  ACATGATCAA  CTGGGCCAAG
GCTCATGCTG  GGGTGGTCTG  GGAAGTCGCT  CCGGTCGTAC  TACCCGGACG  ACTGGTTGGA  CCGGCTGGCC  CTCGACCACG  TGTACTAGTT  GACCCGGTTC

R V P G     F V D       L T L       H D Q V     H L L       E C A       W L E I     L M I       G L V       W R S M
CGGGTGCCCG  GCTTCGTGGA  CCTGACCCTG  CACGACCAGG  TCCACCTGCT  GGAATGTGCC  TGGCTGGAAA  TCCTGATGAT  CGGCCTCGTG  TGGAGAAGCA
GCCCACGGGC  CGAAGCACCT  GGACTGGGAC  GTGCTGGTCC  AGGTGGACGA  CCTTACACGG  ACCGACCTTT  AGGACTACTA  GCCGGAGCAC  ACCTCTTCGT

* E H P     G K L       L F A P     N L L       L D R       N Q G K     C V E       G M V       E I F D     M L L *
TGGAACACCC  CGGCAAGCTG  CTGTTCGCCC  CCAACCTGCT  CCTGGACCGG  AACCAGGGAA  AGTGCGTGGA  GGGCATGGTG  GAGATCTTCG  ACATGCTGCT
ACCTTGTGGG  GCCGTTCGAC  GACAAGCGGG  GGTTGGACGA  GGACCTGGCC  TTGGTCCCTT  TCACGCACCT  CCCGTACCAC  CTCTAGAAGC  TGTACGACGA

* A T S     S R F R     M M N       L Q G       E E F V     C L K       S I I       L L N S     G V Y       T F L
GGCCACCTCC  AGCCGGTTCC  GGATGATGAA  CCTGCAGGGC  GAGGAATTCG  TGTGCCTGAA  GTCCATCATC  CTGCTGAACA  GCGGCGTGTA  CACCTTCCTG
CCGGTGGAGG  TCGGCCAAGG  CCTACTACTT  GGACGTCCCG  CTCCTTAAGC  ACACGGACTT  CAGGTAGTAG  GACGACTTGT  CGCCGCACAT  GTGGAAGGAC

S S T L     K S L       E E K       D H I H     R V L       D K I       T D T L     I H L       M A K       A G L T
TCATCCACCC  TGAAGTCCCT  GGAAGAGAAG  GACCACATCC  ACCGGGTGCT  GGACAAGATC  ACCGACACCC  TGATCCACCT  GATGGCCAAG  GCTGGCCTGA
AGTAGGTGGG  ACTTCAGGGA  CCTTCTCTTC  CTGGTGTAGG  TGGCCCACGA  CCTGTTCTAG  TGGCTGTGGG  ACTAGGTGGA  CTACCGGTTC  CGACCGGACT

* L Q Q     Q H Q       R L A Q     L L L       I L S       H I R H     M S N       K R M       E H L Y     S M K *
CACTCCAGCA  GCAGCACCAG  AGACTGGCCC  AGCTGCTGCT  GATCCTGAGC  CACATCCGGC  ACATGAGCAA  CAAGCGGATG  GAACACCTGT  ACAGCATGAA
GTGAGGTCGT  CGTCGTGGTC  TCTGACCGGG  TCGACGACGA  CTAGGACTCG  GTGTAGGCCG  TGTACTCGTT  GTTCGCCTAC  CTTGTGGACA  TGTCGTACTT

* C K N     V V P L     Y D L       L L E       M L D A     H R L       H A P       T S R G     G A S       V E E
GTGCAAGAAC  GTGGTGCCCC  TGTACGACCT  GCTGCTCGAG  ATGCTGGATG  CCCACAGACT  GCACGCCCCT  ACAAGCAGAG  GCGGAGCCAG  CGTGGAGGAA
CACGTTCTTG  CACCACGGGG  ACATGCTGGA  CGACGAGCTC  TACGACCTAC  GGGTGTCTGA  CGTGCGGGGA  TGTTCGTCTC  CGCCTCGGTC  GCACCTCCTT

T D Q S     H L A       T A G       S T S S     H S L       Q K Y       Y I T G     E A E       G F P       A T V E
ACCGACCAGT  CTCACCTGGC  CACCGCCGGC  AGCACAAGCA  GCCACAGCCT  GCAGAAGTAC  TACATCACCG  GCGAGGCCGA  GGGATTCCCT  GCCACCGTGG
TGGCTGGTCA  GAGTGGACCG  GTGGCGGCCG  TCGTGTTCGT  CGGTGTCGGA  CGTCTTCATG  ATGTAGTGGC  CGCTCCGGCT  CCCTAAGGGA  CGGTGGCACC

* F Q Y     L P D       T D D R     H R I       E E K       R K R T     Y E T       F K S       I M K K     S P F *
AGTTCCAGTA  CCTGCCCGAC  ACCGACGACC  GGCACCGGAT  CGAGGAAAAG  CGGAAGCGGA  CCTACGAGAC  ATTCAAGAGC  ATCATGAAGA  AGTCCCCCTT
TCAAGGTCAT  GGACGGGCTG  TGGCTGCTGG  CCGTGGCCTA  GCTCCTTTTC  GCCTTCGCCT  GGATGCTCTG  TAAGTTCTCG  TAGTACTTCT  TCAGGGGGAA

* S G P     T D P R     P P P       R R I       A V P S     R S S       A S V       P K P A     P Q P       Y P F
CAGCGGCCCC  ACCGATCCCA  GACCCCCCCC  TAGAAGAATC  GCCGTGCCCA  GCAGATCTAG  CGCCAGCGTG  CCCAAGCCTG  CCCCCCAGCC  CTACCCTTTC
GTCGCCGGGG  TGGCTAGGGT  CTGGGGGGGG  ATCTTCTTAG  CGGCACGGGT  CGTCTAGATC  GCGGTCGCAC  GGGTTCGGAC  GGGGGGTCGG  GATGGGAAAG

T S S L     S T I       N Y D       E F P T     M V F       P S G       Q I S Q     A S A       L A P       A P P Q
ACCAGCAGCC  TGAGCACCAT  CAACTACGAC  GAGTTCCCTA  CCATGGTGTT  CCCCAGCGGC  CAGATCTCTC  AGGCCTCTGC  TCTGGCACCT  GCTCCACCTC
TGGTCGTCGG  ACTCGTGGTA  GTTGATGCTG  CTCAAGGGAT  GGTACCACAA  GGGGTCGCCG  GTCTAGAGAG  TCCGGAGACG  AGACCGTGGA  CGAGGTGGAG
```

FIG. 9B

```
* V L P    Q A P      A P A P    A P A      M V S      A L A Q    A P A      P V P      V L A P    G P P *
AGGTGCTGCC TCAGGCCCCT GCTCCAGCCC CAGCCCCTGC CATGGTGTCT GCACTGGCCC AGGCTCCAGC TCCTGTGCCT GTGCTGGCCC CTGGACCTCC
TCCACGACGG AGTCCGGGGA CGAGGTCGGG GTCGGGGACG GTACCACAGA CGTGACCGGG TCCGAGGTCG AGGACACGGA CACGACCGGG GACCTGGAGG

* Q A V    A P P A    P K P      T Q A      G E G T    L S E      A L L      Q L Q F    D D E      D L G
TCAGGCTGTG GCCCCTCCTG CCCCTAAACC TACCCAGGCC GGGGAGGGAA CACTGTCTGA GGCCCTGCTG CAGCTCCAGT TCGACGACGA GGATCTGGGA
AGTCCGACAC CGGGGAGGAC GGGGATTTGG ATGGGTCCGG CCCCTCCCTT GTGACAGACT CCGGGACGAC GTCGAGGTCA AGCTGCTGCT CCTAGACCCT

A L L G    N S T      D P A      V F T D    L A S      V D N      S E F Q    Q L L      N Q G      I P V A
GCACTGCTGG GCAATAGCAC CGACCCCGCC GTGTTTACCG ACCTGGCCTC CGTGGACAAC AGCGAGTTCC AGCAGCTCCT CAACCAGGGC ATCCCTGTCG
CGTGACGACC CGTTATCGTG GCTGGGGCGG CACAAATGGC TGGACCGGAG GCACCTGTTG TCGCTCAAGG TCGTCGAGGA GTTGGTCCCG TAGGGACAGC

* P H T    T E P      M L M E    Y P E      A I T      R L V T    G A Q      R P P      D P A P    A P L *
CCCCACACAC CACCGAGCCC ATGCTGATGG AATACCCCGA GGCCATCACC AGACTGGTCA CAGGCGCCCA GAGGCCTCCA GATCCAGCAC CAGCTCCACT
GGGGTGTGTG GTGGCTCGGG TACGACTACC TTATGGGGCT CCGGTAGTGG TCTGACCAGT GTCCGCGGGT CTCCGGAGGT CTAGGTCGTC GTCGAGGTGA

* G A P    G L P N    G L L      S G D      E D F S    S I A      D M D      F S A L    L S Q      I S S
GGGAGCCCCT GGCCTGCCTA ATGGGCTGCT GTCTGGCGAC GAGGACTTCT CCAGCATTGC CGACATGGAC TTCAGCGCCC TGCTGTCCCA GATCAGCAGC
CCCTCGGGGA CCGGACGGAT TACCCGACGA CAGACCGCTG CTCCTGAAGA GGTCGTAACG GCTGTACCTG AAGTCGCGGG ACGACAGGGT CTAGTCGTCG
```

FIG. 9C

HEA4 Nucleotide (SEQ ID NO: and Amino Acid Sequence

```
                         M V    S K L S    Q L Q      T E L      L A A L    L E S      G L S      K E A L    I Q A *
                      ATGGTG TCCAAGCTGT CCCAGCTGCA GACAGAACTG CTGGCAGCAC TGCTGGAAAG CGGCCTGAGC AAAGAGGCCC TGATTCAGGC
                      TACCAC AGGTTCGACA GGGTCGACGT CTGTCTTGAC GACCGTCGTG ACGACCTTTC GCCGGACTCG TTTCTCCGGG ACTAAGTCCG

* L G E    P G P Y    L L A      G E G      P L D K    G E S      C G G      G R G E    L A E      L P N
ACTCGGCGAA CCTGGACCTT ATCTGCTCGC TGGCGAAGGC CCTCTGGATA AGGGCGAGAG CTGTGGCGGA GGAAGAGGAG AGCTGGCCGA GCTGCCTAAC
TGAGCCGCTT GGACCTGGAA TAGACGAGCG ACCGCTTCCG GGAGACCTAT TCCCGCTCTC GACACCGCCT CCTTCTCCTC TCGACCGGCT CGACGGATTG

G L G E    T R G      S E D      E T D D    D G E      D F T      P P I L    K E L      E N L      S P E E
GGCCTGGGCG AGACAAGAGG CAGCGAGGAC GAGACAGACG ACGACGGCGA GGACTTCACC CCCCCCATCC TGAAAGAGCT GGAAAACCTG AGCCCCGAGG
CCGGACCCGC TCTGTTCTCC GTCGCTCCTG CTCTGTCTGC TGCTGCCGCT CCTGAAGTGG GGGGGGTAGG ACTTTCTCGA CCTTTTGGAC TCGGGGCTCC

* A A H    Q K A      V V E T    L L Q      E D P      W R V A    K M V      K S Y      L Q Q H    N I P *
AAGCCGCCCA CCAGAAAGCC GTGGTGGAGA CACTGCTGCA GGAAGATCCC TGGCGGGTCG CCAAGATGGT CAAGAGCTAC CTGCAGCAGC ACAACATCCC
TTCGGCGGGT GGTCTTTCGG CACCACCTCT GTGACGACGT CCTTCTAGGG ACCGCCCAGC GGTTCTACCA GTTCTCGATG GACGTCGTCG TGTTGTAGGG

* Q R E    V V D T    T G L      N Q S      H L S Q    H L N      K G T      P M K T    Q K R      A A L
CCAGCGGGAG GTGGTGGACA CCACCGGCCT GAACCAGAGC CACCTGAGCC AGCACCTGAA CAAGGGCACC CCCATGAAAA CCCAGAAGAG AGCCGCCCTG
GGTCGCCCTC CACCACCTGT GGTGGCCGGA CTTGGTCTCG GTGGACTCGG TCGTGGACTT GTTCCCGTGG GGGTACTTTT GGGTCTTCTC TCGGCGGGAC

Y T W Y    V R K      Q R E      V A Q Q    F T H      A G Q      G G L I    E E P      T G D      E L P T
TACACTTGGT ACGTGCGGAA GCAGAGAGAG GTGGCCCAGC AGTTTACACA CGCCGGCCAG GGCGGCCTGA TCGAGGAACC TACCGGCGAC GAGCTGCCCA
ATGTGAACCA TGCACGCCTT CGTCTCTCTC CACCGGGTCG TCAAATGTGT GCGGCCGGTC CCGCCGGACT AGCTCCTTGG ATGGCCGCTG CTCGACGGGT

* K K G    R R N      R F K W    G P A      S Q Q      I L F Q    A Y E      R Q K      N P S K    E E R *
CCAAGAAGGG CAGACGGAAC CGGTTTAAGT GGGGCCCTGC ATCTCAGCAG ATCCTGTTCC AGGCCTACGA GCGGCAGAAG AACCCCAGCA AAGAGGAACG
GGTTCTTCCC GTCTGCCTTG GCCAAATTCA CCCCGGGACG TAGAGTCGTC TAGGACAAGG TCCGGATGCT CGCCGTCTTC TTGGGGTCGT TTCTCCTTGC

* E T L    V E E C    N R A      E C I      Q R G V    S P S      Q A Q      G L G S    N L V      T E V
GGAGACACTG GTGGAAGAGT GCAACCGGGC CGAGTGCATC CAGAGAGGCG TGAGCCCTTC TCAGGCTCAG GGCCTCGGCA GCAATCTGGT CACCGAAGTG
CCTCTGTGAC CACCTTCTCA CGTTGGCCCG GCTCACGTAG GTCTCTCCGC ACTCGGGAAG AGTCCGAGTC CCGGAGCCGT CGTTAGACCA GTGGCTTCAC

R V Y N    W F A      N R R      K E E A    F R H      K L S      A G D M    R A A      N L W      P S P L
CGGGTGTACA ATTGGTTCGC CAACCGGCGG AAAGAGGAAG CCTTCCGGCA CAAGCTGTCT GCTGGCGATA TGAGAGCCGC CAACCTGTGG CCCAGCCCCC
GCCCACATGT TAACCAAGCG GTTGGCCGCC TTTCTCCTTC GGAAGGCCGT GTTCGACAGA CGACCGCTAT ACTCTCGGCG GTTGGACACC GGGTCGGGGG

* M I K    R S K      K N S L    A L S      L T A      D Q M V    S A L      L D A      E P P I    L Y S *
TGATGATCAA GCGGAGCAAG AAGAACAGCC TGGCCCTGAG CCTGACCGCC GATCAGATGG TGTCCGCTCT GCTGGACGCC GAGCCCCCTA TCCTGTACAG
ACTACTAGTT CGCCTCGTTC TTCTTGTCGG ACCGGGACTC GGACTGGCGG CTAGTCTACC ACAGGCGAGA CGACCTGCGG CTCGGGGGAT AGGACATGTC
```

FIG. 10A

```
* E Y D    P T R P    F S E      A S M      M G L L    T N L      A D R      E L V H    M I N      W A K
CGAGTACGAC CCCACCAGAC CCTTCAGCGA GGCCAGCATG ATGGGCCTGC TGACCAACCT GGCCGACCGG GAGCTGGTGC ACATGATCAA CTGGGCCAAG
GCTCATGCTG GGGTGGTCTG GGAAGTCGCT CCGGTCGTAC TACCCGGACG ACTGGTTGGA CCGGCTGGCC CTCGACCACG TGTACTAGTT GACCCGGTTC

R V P G    F V D      L T L      H D Q V    H L L      E C A      W L E I    L M I      G L V      W R S M
CGGGTGCCCG GCTTCGTGGA CCTGACCCTG CACGACCAGG TCCACCTGCT GGAATGTGCC TGGCTGGAAA TCCTGATGAT CGGCCTCGTG TGGAGAAGCA
GCCCACGGGC CGAAGCACCT GGACTGGGAC GTGCTGGTCC AGGTGGACGA CCTTACACGG ACCGACCTTT AGGACTACTA GCCGGAGCAC ACCTCTTCGT

* E H P    V K L      L F A P    N L L      L D R      N Q G K    C V E      G M V      E I F D    M L L *
TGGAACACCC CGTGAAGCTG CTGTTCGCCC CCAACCTGCT CCTGGACCGG AACCAGGGAA AGTGCGTGGA GGGCATGGTG GAGATCTTCG ACATGCTGCT
ACCTTGTGGG GCACTTCGAC GACAAGCGGG GGTTGGACGA GGACCTGGCC TTGGTCCCTT TCACGCACCT CCCGTACCAC CTCTAGAAGC TGTACGACGA

* A T S    S R F R    M M N      L Q G      E E F V    C L K      S I I      L L N S    G V Y      T F L
GGCCACCTCC AGCCGGTTCC GGATGATGAA CCTGCAGGGC GAGGAATTCG TGTGCCTGAA GTCCATCATC CTGCTGAACA GCGGCGTGTA CACCTTCCTG
CCGGTGGAGG TCGGCCAAGG CCTACTACTT GGACGTCCCG CTCCTTAAGC ACACGGACTT CAGGTAGTAG GACGACTTGT CGCCGCACAT GTGGAAGGAC

S S T L    K S L      E E K      D H I H    R V L      D K I      T D T L    I H L      M A K      A G L T
TCATCCACCC TGAAGTCCCT GGAAGAGAAG GACCACATCC ACCGGGTGCT GGACAAGATC ACCGACACCC TGATCCACCT GATGGCCAAG GCTGGCCTGA
AGTAGGTGGG ACTTCAGGGA CCTTCTCTTC CTGGTGTAGG TGGCCCACGA CCTGTTCTAG TGGCTGTGGG ACTAGGTGGA CTACCGGTTC CGACCGGACT

* L Q Q    Q H Q      R L A Q    L L L      I L S      H I R H    M S N      K G M      E H L Y    S M K *
CACTCCAGCA GCAGCACCAG AGACTGGCCC AGCTGCTGCT GATCCTGAGC CACATCCGGC ACATGAGCAA CAAGGGAATG GAACACCTGT ACAGCATGAA
GTGAGGTCGT CGTCGTGGTC TCTGACCGGG TCGACGACGA CTAGGACTCG GTGTAGGCCG TGTACTCGTT GTTCCCTTAC CTTGTGGACA TGTCGTACTT

* C K N    V V P L    Y D L      L L E      A A D A    H R L      H A P      T S R G    G A S      V E E
GTGCACGAAC GTGGTGCCCC TGTACGACCT GCTGCTCGAG GCTGCCGATG CCCACAGACT GCACGCCCCT ACAAGCAGAG GCGGAGCCAG CGTGGAGGAA
CACGTTCTTG CACCACGGGG ACATGCTGGA CGACGAGCTC CGACGGCTAC GGGTGTCTGA CGTGCGGGGA TGTTCGTCTC CGCCTCGGTC GCACCTCCTT

T D Q S    H L A      T A G      S T S S    H S L      Q K Y      Y I T G    E A E      G F P      A T V E
ACCGACCAGT CTCACCTGGC CACCGCCGGC AGCACAAGCA GCCACAGCCT GCAGAAGTAC TACATCACCG GCGAGGCCGA GGGATTCCCT GCCACCGTGG
TGGCTGGTCA GAGTGGACCG GTGGCGGCCG TCGTGTTCGT CGGTGTCGGA CGTCTTCATG ATGTAGTGGC CGCTCCGGCT CCCTAAGGGA CGGTGGCACC

* F Q Y    L P D      T D D R    H R I      E E K      R K R T    Y E T      F K S      I M K K    S P F *
AGTTCCAGTA CCTGCCCGAC ACCGACGACC GGCACCGGAT CGAGGAAAAG CGGAAGCGGA CCTACGAGAC ATTCAAGAGC ATCATGAAGA AGTCCCCCTT
TCAAGGTCAT GGACGGGCTG TGGCTGCTGG CCGTGGCCTA GCTCCTTTTC GCCTTCGCCT GGATGCTCTG TAAGTTCTCG TAGTACTTCT TCAGGGGGAA

* S G P    T D P R    P P P      R R I      A V P S    R S S      A S V      P K P A    P Q P      Y P F
CAGCGGCCCC ACCGATCCCA GACCCCCCCC TAGAAGAATC GCCGTGCCCA GCAGATCTAG CGCCAGCGTG CCCAAGCCTG CCCCCCAGCC CTACCCTTTC
GTCGCCGGGG TGGCTAGGGT CTGGGGGGGG ATCTTCTTAG CGGCACGGGT CGTCTAGATC GCGGTCGCAC GGGTTCGGAC GGGGGGTCGG GATGGGAAAG

T S S L    S T I      N Y D      E F P T    M V F      P S G      Q I S Q    A S A      L A P      A P P Q
ACCAGCAGCC TGAGCACCAT CAACTACGAC GAGTTCCCTA CCATGGTGTT CCCCAGCGGC CAGATCTCTC AGGCCTCTGC TCTGGCACCT GCTCCACCTC
TGGTCGTCGG ACTCGTGGTA GTTGATGCTG CTCAAGGGAT GGTACCACAA GGGGTCGCCG GTCTAGAGAG TCCGGAGACG AGACCGTGGA CGAGGTGGAG
```

FIG. 10B

```
* V L P    Q A P      A P A P    A P A      M V S      A L A Q    A P A      P V P      V L A P    G P P *
AGGTGCTGCC TCAGGCCCCT GCTCCAGCCC CAGCCCCTGC CATGGTGTCT GCACTGGCCC AGGCTCCAGC TCCTGTGCCT GTGCTGGCCC CTGGACCTCC
TCCACGACGG AGTCCGGGGA CGAGGTCGGG GTCGGGGACG GTACCACAGA CGTGACCGGG TCCGAGGTCG AGGACACGGA CACGACCGGG GACCTGGAGG

* Q A V    A P P A    P K P      T Q A      G E G T    L S E      A L L      Q L Q F    D D E      D L G
TCAGGCTGTG GCCCCTCCTG CCCCTAAACC TACCCAGGCC GGGGAGGGAA CACTGTCTGA GGCCCTGCTG CAGCTCCAGT TCGACGACGA GGATCTGGGA
AGTCCGACAC CGGGGAGGAC GGGGATTTGG ATGGGTCCGG CCCCTCCCTT GTGACAGACT CCGGGACGAC GTCGAGGTCA AGCTGCTGCT CCTAGACCCT

A L L G    N S T      D P A      V F T D    L A S      V D N      S E F Q    Q L L      N Q G      I P V A
GCACTGCTGG GCAATAGCAC CGACCCCGCC GTGTTTACCG ACCTGGCCTC CGTGGACAAC AGCGAGTTCC AGCAGCTCCT CAACCAGGGC ATCCCTGTCG
CGTGACGACC CGTTATCGTG GCTGGGGCGG CACAAATGGC TGGACCGGAG GCACCTGTTG TCGCTCAAGG TCGTCGAGGA GTTGGTCCCG TAGGGACAGC

* P H T    T E P      M L M E    Y P E      A I T      R L V T    G A Q      R P P      D P A P    A P L *
CCCCACACAC CACCGAGCCC ATGCTGATGG AATACCCCGA GGCCATCACC AGACTGGTCA CAGGCGCCCA GAGGCCTCCA GATCCAGCAC CAGCTCCACT
GGGGTGTGTG GTGGCTCGGG TACGACTACC TTATGGGGCT CCGGTAGTGG TCTGACCAGT GTCCGCGGGT CTCCGGAGGT CTAGGTCGTG GTCGAGGTGA

* G A P    G L P N    G L L      S G D      E D F S    S I A      D M D      F S A L    L S Q      I S S
GGGAGCCCCT GGCCTGCCTA ATGGGCTGCT GTCTGGCGAC GAGGACTTCT CCAGCATTGC CGACATGGAC TTCAGCGCCC TGCTGTCCCA GATCAGCAGC
CCCTCGGGGA CCGGACGGAT TACCCGACGA CAGACCGCTG CTCCTGAAGA GGTCGTAACG GCTGTACCTG AAGTCGCGGG ACGACAGGGT CTAGTCGTCG
```

FIG. 10C

```
                                                                M L   L L V      T S L L    L C E      L P H
                                                              ATGCT TCTCCTGGTG ACAAGCCTTC TGCTCTGTGA GTTACCACAC
                                                              TACGA AGAGGACCAC TGTTCGGAAG ACGAGACACT CAATGGTGTG

P A F L    L I P      C H P      E C Q P    Q N G      S V T      C F G P    E A D      Q C V      A C A H
CCAGCATTCC TCCTGATCCC ATGCCACCCT GAGTGTCAGC CCCAGAATGG CTCAGTGACC TGTTTTGGAC CGGAGGCTGA CCAGTGTGTG GCCTGTGCCC
GGTCGTAAGG AGGACTAGGG TACGGTGGGA CTCACAGTCG GGGTCTTACC GAGTCACTGG ACAAAACCTG GCCTCCGACT GGTCACACAC CGGACACGGG

* Y K D    P P F      C V A R    C P S      G V K      P D L S    Y M P      I W K      F P D E    E G A *
ACTATAAGGA CCCTCCCTTC TGCGTGGCCC GCTGCCCCAG CGGTGTGAAA CCTGACCTCT CCTACATGCC CATCTGGAAG TTTCCAGATG AGGAGGGCGC
TGATATTCCT GGGAGGGAAG ACGCACCGGG CGACGGGGTC GCCACACTTT GGACTGGAGA GGATGTACGG GTAGACCTTC AAAGGTCTAC TCCTCCCGCG

* C Q P    C P I N    C T H      S C V      D L D D    K G C      P A E      Q R A S    P L T      S I I
ATGCCAGCCT TGCCCCATCA ACTGCACCCA CTCCTGTGTG GACCTGGATG ACAAGGGCTG CCCCGCCGAG CAGAGAGCCA GCCCTCTGAC GTCCATCATC
TACGGTCGGA ACGGGGTAGT TGACGTGGGT GAGGACACAC CTGGACCTAC TGTTCCCGAC GGGGCGGCTC GTCTCTCGGT CGGGAGACTG CAGGTAGTAG

S A V V    G I L      L V V      V L G V    V F G      I L I      *
TCTGCGGTGG TTGGCATTCT GCTGGTCGTG GTCTTGGGGG TGGTCTTTGG GATCCTCATC TGA
AGACGCCACC AACCGTAAGA CGACCAGCAC CAGAACCCCC ACCAGAAACC CTAGGAGTAG ACT
```

FIG. 11

DHFRdm Nucleotide and Amino Acid Sequences

M V G S L N *
ATGGTTG GTTCGCTAAA
TACCAAC CAAGCGATTT

* C I V A V S Q N M G I G K N G D F P W P P L R N E S R Y F Q R M T
CTGCATCGTC GCTGTGTCCC AGAACATGGG CATCGGCAAG AACGGGGACT TCCCCTGGCC ACCGCTCAGG AATGAATCCA GATATTTCCA GAGAATGACC
GACGTAGCAG CGACACAGGG TCTTGTACCC GTAGCCGTTC TTGCCCCTGA AGGGGACCGG TGGCGAGTCC TTACTTAGGT CTATAAAGGT CTCTTACTGG

T T S S V E G K Q N L V I M G K K T W F S I P E K N R P L K G R I N
ACAACCTCTT CAGTAGAAGG TAAACAGAAT CTGGTGATTA TGGGTAAGAA GACCTGGTTC TCCATTCCTG AGAAGAATCG ACCTTTAAAG GGTAGAATTA
TGTTGGAGAA GTCATCTTCC ATTTGTCTTA GACCACTAAT ACCCATTCTT CTGGACCAAG AGGTAAGGAC TCTTCTTAGC TGGAAATTTC CCATCTTAAT

* L V L S R E L K E P P Q G A H F L S R S L D D A L K L T E Q P E L *
ATTTAGTTCT CAGCAGAGAA CTCAAGGAAC CTCCACAAGG AGCTCATTTT CTTTCCAGAA GTCTAGATGA TGCCTTAAAA CTTACTGAAC AACCAGAATT
TAAATCAAGA GTCGTCTCTT GAGTTCCTTG GAGGTGTTCC TCGAGTAAAA GAAAGGTCTT CAGATCTACT ACGGAATTTT GAATGACTTG TTGGTCTTAA

* A N K V D M V W I V G G S S V Y K E A M N H P G H L K L F V T R I
AGCAAATAAA GTAGACATGG TCTGGATAGT TGGTGGCAGT TCTGTTTATA AGGAAGCCAT GAATCACCCA GGCCATCTTA AACTATTTGT GACAAGGATC
TCGTTTATTT CATCTGTACC AGACCTATCA ACCACCGTCA AGACAAATAT TCCTTCGGTA CTTAGTGGGT CCGGTAGAAT TTGATAAACA CTGTTCCTAG

M Q D F E S D T F F P E I D L E K Y K L L P E Y P G V L S D V Q E E
ATGCAAGACT TTGAAAGTGA CACGTTTTTT CCAGAAATTG ATTTGGAGAA ATATAAACTT CTGCCAGAAT ACCCAGGTGT TCTCTCTGAT GTCCAGGAGG
TACGTTCTGA AACTTTCACT GTGCAAAAAA GGTCTTTAAC TAAACCTCTT TATATTTGAA GACGGTCTTA TGGGTCCACA AGAGAGACTA CAGGTCCTCC

* K G I K Y K F E V Y E K N D
AGAAAGGCAT TAAGTACAAA TTTGAAGTAT ATGAGAAGAA TGAT
TCTTTCCGTA ATTCATGTTT AAACTTCATA TACTCTTCTT ACTA

FIG. 12

SEQUENCE LISTING

<160> NUMBER OF SEQ ID NOS: 94

<210> SEQ ID NO 1
<211> LENGTH: 2528
<212> TYPE: DNA
<213> ORGANISM: Artificial Sequence
<220> FEATURE:
<223> OTHER INFORMATION: GMCSFss-Her2scFv-IgG4hinge-CD28tm-41BB-Zeta-T2A-EGFRt

<400> SEQUENCE: 1

```
atgctgctgc tggtgaccag cctgctgctg tgcgagctgc cccaccccgc ctttctgctg     60
atccccgata tccagatgac ccagtccccg agctccctgt ccgcctctgt gggcgatagg    120
gtcaccatca cctgccgtgc cagtcaggat gtgaatactg ctgtagcctg gtatcaacag    180
aaaccaggaa aagctccgaa actactgatt tactcggcat ccttcctcta ctctggagtc    240
ccttctcgct tctctggttc cagatctggg acggatttca ctctgaccat cagcagtctg    300
cagccggaag acttcgcaac ttattactgt cagcaacatt atactactcc tcccacgttc    360
ggacagggta ccaaggtgga gatcaaaggc agtactagcg gcggtggctc cgggggcgga    420
tccggtgggg gcggcagcag cgaggttcag ctggtggagt ctggcggtgg cctggtgcag    480
ccagggggct cactccgttt gtcctgtgca gcttctggct tcaacattaa agacacctat    540
atacactggg tgcgtcaggc cccgggtaag ggcctggaat gggttgcaag gatttatcct    600
acgaatggtt atactagata tgccgatagc gtcaagggcc gtttcactat aagcgcagac    660
acatccaaaa acacagccta cctgcagatg aacagcctgc gtgctgagga cactgccgtc    720
tattattgtt ctagatgggg aggggacggc ttctatgcta tggactactg gggtcaagga    780
accctggtca ccgtctcgag gaatctaagt acggaccgcc ctgccccccct tgccctatgt    840
tctgggtgct ggtggtggtc ggaggcgtgc tggcctgcta cagcctgctg gtcaccgtgg    900
ccttcatcat cttttgggtg aaacggggca gaaagaaact cctgtatata ttcaaacaac    960
catttatgag accagtacaa actactcaag aggaagatgg ctgtagctgc cgatttccag   1020
aagaagaaga aggaggatgt gaactgcggg tgaagttcag cagaagcgcc gacgcccctg   1080
cctaccagca gggccagaat cagctgtaca acgagctgaa cctgggcaga agggaagagt   1140
acgacgtcct ggataagcgg agaggccggg accctgagat gggcggcaag cctcggcgga   1200
agaacccca ggaaggcctg tataacgaac tgcagaaaga caagatggcc gaggcctaca    1260
gcgagatcgg catgaagggc gagcggaggc ggggcaaggg ccacgacggc ctgtatcagg   1320
gcctgtccac cgccaccaag gatacctacg acgccctgca catgcaggcc ctgcccccaa   1380
ggctcgaggg cggcggagag ggcagaggaa gtcttctaac atgcggtgac gtggaggaga   1440
atcccggccc taggatgctt ctcctggtga caagccttct gctctgtgag ttaccacacc   1500
cagcattcct cctgatccca cgcaaagtgt gtaacggaat aggtattggt gaatttaaag   1560
actcactctc cataaatgct acgaatatta aacacttcaa aaactgcacc tccatcagtg   1620
gcgatctcca catcctgccg gtggcattta ggggtgactc cttcacacat actcctcctc   1680
tggatccaca ggaactggat attctgaaaa ccgtaaagga aatcacaggg tttttgctga   1740
ttcaggcttg gcctgaaaac aggacggacc tccatgcctt tgagaaccta gaaatcatac   1800
gcggcaggac caagcaacat ggtcagtttt ctcttgcagt cgtcagcctg aacataacat   1860
ccttgggatt acgctccctc aaggagataa gtgatggaga tgtgataatt tcaggaaaca   1920
aaaatttgtg ctatgcaaat acaataaact ggaaaaaact gtttgggacc tccggtcaga   1980
```

aaaccaaaat tataagcaac agaggtgaaa acagctgcaa ggccacaggc caggtctgcc 2040
atgccttgtg ctcccccgag ggctgctggg gcccggagcc cagggactgc gtctcttgcc 2100
ggaatgtcag ccgaggcagg gaatgcgtgg acaagtgcaa ccttctggag ggtgagccaa 2160
gggagtttgt ggagaactct gagtgcatac agtgccaccc agagtgcctg cctcaggcca 2220
tgaacatcac ctgcacagga cggggaccag acaactgtat ccagtgtgcc cactacattg 2280
acggccccca ctgcgtcaag acctgcccgg caggagtcat gggagaaaac aacaccctgg 2340
tctggaagta cgcagacgcc ggccatgtgt gccacctgtg ccatccaaac tgcacctacg 2400
gatgcactgg gccaggtctt gaaggctgtc caacgaatgg gcctaagatc ccgtccatcg 2460
ccactgggat ggtgggggcc ctcctcttgc tgctggtggt ggccctgggg atcggcctct 2520
tcatgtga 2528

<210> SEQ ID NO 2
<211> LENGTH: 66
<212> TYPE: DNA
<213> ORGANISM: Artificial Sequence
<220> FEATURE:
<223> OTHER INFORMATION: GMCSFRss

<400> SEQUENCE: 2
atgctgctgc tggtgaccag cctgctgctg tgcgagctgc cccaccccgc ctttctgctg 60
atcccc 66

<210> SEQ ID NO 3
<211> LENGTH: 735
<212> TYPE: DNA
<213> ORGANISM: Artificial Sequence
<220> FEATURE:
<223> OTHER INFORMATION: CD19scFv DNA

<400> SEQUENCE: 3
gacatccaga tgacccagac cacctccagc ctgagcgcca gcctgggcga ccgggtgacc 60
atcagctgcc gggccagcca ggacatcagc aagtacctga actggtatca gcagaagccc 120
gacggcaccg tcaagctgct gatctaccac accagccggc tgcacagcgg cgtgcccagc 180
cggtttagcg gcagcggctc cggcaccgac tacagcctga ccatctccaa cctggaacag 240
gaagatatcg ccacctactt ttgccagcag ggcaacacac tgccctacac ctttggcggc 300
ggaacaaagc tggaaatcac cggcagcacc tccggcagcg gcaagcctgg cagcggcgag 360
ggcagcacca agggcgaggt gaagctgcag gaaagcggcc ctggcctggt ggcccccagc 420
cagagcctga gcgtgacctg caccgtgagc ggcgtgagcc tgcccgacta cggcgtgagc 480
tggatccggc agcccccag gaagggcctg gaatggctgg gcgtgatctg gggcagcgag 540
accacctact acaacagcgc cctgaagagc cggctgacca tcatcaagga caacagcaag 600
agccaggtgt tcctgaagat gaacagcctg cagaccgacg acaccgccat ctactactgc 660
gccaagcact actactacgg cggcagctac gccatggact actggggcca gggcaccagc 720
gtgaccgtga gcagc 735

<210> SEQ ID NO 4
<211> LENGTH: 36
<212> TYPE: DNA
<213> ORGANISM: Artificial Sequence
<220> FEATURE:
<223> OTHER INFORMATION: IgG4hinge

<400> SEQUENCE: 4
gaatctaagt acggaccgcc ctgccccccct tgccct 36

<210> SEQ ID NO 5
<211> LENGTH: 84
<212> TYPE: DNA
<213> ORGANISM: Artificial Sequence
<220> FEATURE:
<223> OTHER INFORMATION: CD28 transmembrane domain

<400> SEQUENCE: 5
atgttctggg tgctggtggt ggtcggaggc gtgctggcct gctacagcct gctggtcacc 60
gtggccttca tcatcttttg ggtg 84

<210> SEQ ID NO 6
<211> LENGTH: 126
<212> TYPE: DNA
<213> ORGANISM: Artificial Sequence
<220> FEATURE:
<223> OTHER INFORMATION: DNA encoding 41BB domain

<400> SEQUENCE: 6
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 7
<211> LENGTH: 336
<212> TYPE: DNA
<213> ORGANISM: Artificial Sequence
<220> FEATURE:
<223> OTHER INFORMATION: DNA encoding CD3Zeta domain

<400> SEQUENCE: 7
cgggtgaagt tcagcagaag cgccgacgcc cctgcctacc agcagggcca gaatcagctg 60
tacaacgagc tgaacctggg cagaagggaa gagtacgacg tcctggataa gcggagaggc 120
cgggaccctg agatgggcgg caagcctcgg cggaagaacc cccaggaagg cctgtataac 180
gaactgcaga aagacaagat ggccgaggcc tacagcgaga tcggcatgaa gggcgagcgg 240
aggcggggca agggccacga cggcctgtat cagggcctgt ccaccgccac caaggatacc 300
tacgacgccc tgcacatgca ggccctgccc ccaagg 336

<210> SEQ ID NO 8
<211> LENGTH: 72
<212> TYPE: DNA
<213> ORGANISM: Artificial Sequence
<220> FEATURE:
<223> OTHER INFORMATION: Self cleaving T2A

<400> SEQUENCE: 8
ctcgagggcg gcggagaggg cagaggaagt cttctaacat gcggtgacgt ggaggagaat 60
cccggcccta gg 72

<210> SEQ ID NO 9
<211> LENGTH: 1074
<212> TYPE: DNA
<213> ORGANISM: Artificial Sequence
<220> FEATURE:
<223> OTHER INFORMATION: EGFRt

<400> SEQUENCE: 9
atgcttctcc tggtgacaag ccttctgctc tgtgagttac cacacccagc attcctcctg 60
atcccacgca aagtgtgtaa cggaataggt attggtgaat ttaaagactc actctccata 120
aatgctacga atattaaaca cttcaaaaac tgcacctcca tcagtggcga tctccacatc 180
ctgccggtgg catttagggg tgactccttc acacatactc ctcctctgga tccacaggaa 240
ctggatattc tgaaaaccgt aaaggaaatc acagggtttt tgctgattca ggcttggcct 300
gaaaacagga cggacctcca tgcctttgag aacctagaaa tcatacgcgg caggaccaag 360
caacatggtc agttttctct tgcagtcgtc agcctgaaca taacatcctt gggattacgc 420
tccctcaagg agataagtga tggagatgtg ataatttcag gaaacaaaaa tttgtgctat 480
gcaaatacaa taaactggaa aaaactgttt gggacctccg gtcagaaaac caaaattata 540
agcaacagag gtgaaaacag ctgcaaggcc acaggccagg tctgccatgc cttgtgctcc 600
cccgagggct gctggggccc ggagcccagg gactgcgtct cttgccggaa tgtcagccga 660
ggcagggaat gcgtggacaa gtgcaacctt ctggagggtg agccaaggga gtttgtggag 720
aactctgagt gcatacagtg ccacccagag tgcctgcctc aggccatgaa catcacctgc 780
acaggacggg gaccagacaa ctgtatccag tgtgcccact acattgacgg cccccactgc 840
gtcaagacct gcccggcagg agtcatggga gaaaacaaca ccctggtctg gaagtacgca 900
gacgccggcc atgtgtgcca cctgtgccat ccaaactgca cctacggatg cactgggcca 960
ggtcttgaag gctgtccaac gaatgggcct aagatcccgt ccatcgccac tgggatggtg 1020
ggggccctcc tcttgctgct ggtggtggcc ctggggatcg gcctcttcat gtga 1074

<210> SEQ ID NO 10
<211> LENGTH: 2529
<212> TYPE: DNA
<213> ORGANISM: Artificial Sequence
<220> FEATURE:
<223> OTHER INFORMATION: Protein that has domains linked as such
GMCSFRss - CD19scFv - IgG4hinge - CD28tm - 41BB - CD3Zeta -
T2A - EGFRt

<400> SEQUENCE: 10
atgctgctgc tggtgaccag cctgctgctg tgcgagctgc cccaccccgc ctttctgctg 60
atccccgaca tccagatgac ccagaccacc tccagcctga gcgccagcct gggcgaccgg 120
gtgaccatca gctgccgggc cagccaggac atcagcaagt acctgaactg gtatcagcag 180
aagcccgacg gcaccgtcaa gctgctgatc taccacacca gccggctgca cagcggcgtg 240
cccagccggt ttagcggcag cggctccggc accgactaca gcctgaccat ctccaacctg 300
gaacaggaag atatcgccac ctacttttgc cagcagggca acacactgcc ctacaccttt 360
ggcggcggaa caaagctgga aatcaccggc agcacctccg gcagcggcaa gcctggcagc 420
ggcgagggca gcaccaaggg cgaggtgaag ctgcaggaaa gcggccctgg cctggtggcc 480
cccagccaga gcctgagcgt gacctgcacc gtgagcggcg tgagcctgcc cgactacggc 540
gtgagctgga tccggcagcc ccccaggaag ggcctggaat ggctgggcgt gatctggggc 600
agcgagacca cctactacaa cagcgccctg aagagccggc tgaccatcat caaggacaac 660
agcaagagcc aggtgttcct gaagatgaac agcctgcaga ccgacgacac cgccatctac 720
tactgcgcca agcactacta ctacggcggc agctacgcca tggactactg gggccagggc 780
accagcgtga ccgtgagcag cgagagcaag tacggaccgc cctgcccccc ttgccctatg 840
ttctgggtgc tggtggtggt cggaggcgtg ctggcctgct acagcctgct ggtcaccgtg 900

-continued

```
gccttcatca tcttttgggt gaaacggggc agaaagaaac tcctgtatat attcaaacaa    960
ccatttatga gaccagtaca aactactcaa gaggaagatg gctgtagctg ccgatttcca   1020
gaagaagaag aaggaggatg tgaactgcgg gtgaagttca gcagaagcgc cgacgcccct   1080
gcctaccagc agggccagaa tcagctgtac aacgagctga acctgggcag aagggaagag   1140
tacgacgtcc tggataagcg gagaggccgg gaccctgaga tgggcggcaa gcctcggcgg   1200
aagaaccccc aggaaggcct gtataacgaa ctgcagaaag acaagatggc cgaggcctac   1260
agcgagatcg gcatgaaggg cgagcggagg cggggcaagg gccacgacgg cctgtatcag   1320
ggcctgtcca ccgccaccaa ggatacctac gacgccctgc acatgcaggc cctgccccca   1380
aggctcgagg gcggcggaga gggcagagga agtcttctaa catgcggtga cgtggaggag   1440
aatcccggcc ctaggatgct tctcctggtg acaagccttc tgctctgtga gttaccacac   1500
ccagcattcc tcctgatccc acgcaaagtg tgtaacggaa taggtattgg tgaatttaaa   1560
gactcactct ccataaatgc tacgaatatt aaacacttca aaaactgcac ctccatcagt   1620
ggcgatctcc acatcctgcc ggtggcattt aggggtgact ccttcacaca tactcctcct   1680
ctggatccac aggaactgga tattctgaaa accgtaaagg aaatcacagg gtttttgctg   1740
attcaggctt ggcctgaaaa caggacggac ctccatgcct ttgagaacct agaaatcata   1800
cgcggcagga ccaagcaaca tggtcagttt tctcttgcag tcgtcagcct gaacataaca   1860
tccttgggat tacgctccct caaggagata agtgatggag atgtgataat ttcaggaaac   1920
aaaaatttgt gctatgcaaa tacaataaac tggaaaaaac tgtttgggac ctccggtcag   1980
aaaaccaaaa ttataagcaa cagaggtgaa aacagctgca aggccacagg ccaggtctgc   2040
catgccttgt gctcccccga gggctgctgg ggcccggagc ccagggactg cgtctcttgc   2100
cggaatgtca gccgaggcag ggaatgcgtg gacaagtgca accttctgga gggtgagcca   2160
agggagtttg tggagaactc tgagtgcata cagtgccacc cagagtgcct gcctcaggcc   2220
atgaacatca cctgcacagg acggggacca gacaactgta tccagtgtgc ccactacatt   2280
gacggccccc actgcgtcaa gacctgcccg gcaggagtca tgggagaaaa caacaccctg   2340
gtctggaagt acgcagacgc cggccatgtg tgccacctgt gccatccaaa ctgcacctac   2400
ggatgcactg ggccaggtct tgaaggctgt ccaacgaatg ggcctaagat cccgtccatc   2460
gccactggga tggtgggggc cctcctcttg ctgctggtgg tggccctggg gatcggcctc   2520
ttcatgtga                                                           2529
```

<210> SEQ ID NO 11
<211> LENGTH: 842
<212> TYPE: PRT
<213> ORGANISM: Artificial Sequence
<220> FEATURE:
<223> OTHER INFORMATION: GMCSFRss - CD19scFv - IgG4hinge - CD28tm - 41BB - CD3Zeta - T2A - EGFRt

<400> SEQUENCE: 11

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60
```

```
Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Glu Ser Lys Tyr Gly
            260                 265                 270

Pro Pro Cys Pro Pro Cys Pro Met Phe Trp Val Leu Val Val Val Gly
        275                 280                 285

Gly Val Leu Ala Cys Tyr Ser Leu Leu Val Thr Val Ala Phe Ile Ile
    290                 295                 300

Phe Trp Val Lys Arg Gly Arg Lys Lys Leu Leu Tyr Ile Phe Lys Gln
305                 310                 315                 320

Pro Phe Met Arg Pro Val Gln Thr Thr Gln Glu Glu Asp Gly Cys Ser
                325                 330                 335

Cys Arg Phe Pro Glu Glu Glu Glu Gly Gly Cys Glu Leu Arg Val Lys
            340                 345                 350

Phe Ser Arg Ser Ala Asp Ala Pro Ala Tyr Gln Gln Gly Gln Asn Gln
        355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro Arg Leu Glu Gly
    450                 455                 460

Gly Gly Glu Gly Arg Gly Ser Leu Leu Thr Cys Gly Asp Val Glu Glu
465                 470                 475                 480
```

-continued

```
Asn Pro Gly Pro Arg Met Leu Leu Leu Val Thr Ser Leu Leu Leu Cys
                485                 490                 495

Glu Leu Pro His Pro Ala Phe Leu Leu Ile Pro Arg Lys Val Cys Asn
            500                 505                 510

Gly Ile Gly Ile Gly Glu Phe Lys Asp Ser Leu Ser Ile Asn Ala Thr
        515                 520                 525

Asn Ile Lys His Phe Lys Asn Cys Thr Ser Ile Ser Gly Asp Leu His
    530                 535                 540

Ile Leu Pro Val Ala Phe Arg Gly Asp Ser Phe Thr His Thr Pro Pro
545                 550                 555                 560

Leu Asp Pro Gln Glu Leu Asp Ile Leu Lys Thr Val Lys Glu Ile Thr
                565                 570                 575

Gly Phe Leu Leu Ile Gln Ala Trp Pro Glu Asn Arg Thr Asp Leu His
            580                 585                 590

Ala Phe Glu Asn Leu Glu Ile Ile Arg Gly Arg Thr Lys Gln His Gly
        595                 600                 605

Gln Phe Ser Leu Ala Val Val Ser Leu Asn Ile Thr Ser Leu Gly Leu
    610                 615                 620

Arg Ser Leu Lys Glu Ile Ser Asp Gly Asp Val Ile Ile Ser Gly Asn
625                 630                 635                 640

Lys Asn Leu Cys Tyr Ala Asn Thr Ile Asn Trp Lys Lys Leu Phe Gly
                645                 650                 655

Thr Ser Gly Gln Lys Thr Lys Ile Ile Ser Asn Arg Gly Glu Asn Ser
            660                 665                 670

Cys Lys Ala Thr Gly Gln Val Cys His Ala Leu Cys Ser Pro Glu Gly
        675                 680                 685

Cys Trp Gly Pro Glu Pro Arg Asp Cys Val Ser Cys Arg Asn Val Ser
    690                 695                 700

Arg Gly Arg Glu Cys Val Asp Lys Cys Asn Leu Leu Glu Gly Glu Pro
705                 710                 715                 720

Arg Glu Phe Val Glu Asn Ser Glu Cys Ile Gln Cys His Pro Glu Cys
                725                 730                 735

Leu Pro Gln Ala Met Asn Ile Thr Cys Thr Gly Arg Gly Pro Asp Asn
            740                 745                 750

Cys Ile Gln Cys Ala His Tyr Ile Asp Gly Pro His Cys Val Lys Thr
        755                 760                 765

Cys Pro Ala Gly Val Met Gly Glu Asn Asn Thr Leu Val Trp Lys Tyr
    770                 775                 780

Ala Asp Ala Gly His Val Cys His Leu Cys His Pro Asn Cys Thr Tyr
785                 790                 795                 800

Gly Cys Thr Gly Pro Gly Leu Glu Gly Cys Pro Thr Asn Gly Pro Lys
                805                 810                 815

Ile Pro Ser Ile Ala Thr Gly Met Val Gly Ala Leu Leu Leu Leu Leu
            820                 825                 830

Val Val Ala Leu Gly Ile Gly Leu Phe Met
        835                 840
```

<210> SEQ ID NO 12
<211> LENGTH: 15
<212> TYPE: PRT
<213> ORGANISM: Artificial Sequence
<220> FEATURE:
<223> OTHER INFORMATION: (G4S)3 linker

<400> SEQUENCE: 12

Gly Gly Gly Gly Ser Gly Gly Gly Gly Ser Gly Gly Gly Gly Ser
1 5 10 15

<210> SEQ ID NO 13
<211> LENGTH: 327
<212> TYPE: PRT
<213> ORGANISM: Artificial Sequence
<220> FEATURE:
<223> OTHER INFORMATION: Uniprot P0861 IgG4-Fc

<400> SEQUENCE: 13

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Ser Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Gln Glu Glu Met Thr Lys
225 230 235 240

Asn Gln Val Ser Leu Thr Cys Leu Val Lys Gly Phe Tyr Pro Ser Asp
245 250 255

Ile Ala Val Glu Trp Glu Ser Asn Gly Gln Pro Glu Asn Asn Tyr Lys
260 265 270

Thr Thr Pro Pro Val Leu Asp Ser Asp Gly Ser Phe Phe Leu Tyr Ser
275 280 285

Arg Leu Thr Val Asp Lys Ser Arg Trp Gln Glu Gly Asn Val Phe Ser
290 295 300

Cys Ser Val Met His Glu Ala Leu His Asn His Tyr Thr Gln Lys Ser
305 310 315 320

Leu Ser Leu Ser Leu Gly Lys
325

<210> SEQ ID NO 14
<211> LENGTH: 220
<212> TYPE: PRT
<213> ORGANISM: Artificial Sequence
<220> FEATURE:
<223> OTHER INFORMATION: CD28 transmembrane domain

<400> SEQUENCE: 14

```
Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220
```

<210> SEQ ID NO 15
<211> LENGTH: 240
<212> TYPE: PRT
<213> ORGANISM: Artificial Sequence
<220> FEATURE:
<223> OTHER INFORMATION: 4-1BB domain

<400> SEQUENCE: 15

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95
```

```
Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240


<210> SEQ ID NO 16
<211> LENGTH: 164
<212> TYPE: PRT
<213> ORGANISM: Artificial Sequence
<220> FEATURE:
<223> OTHER INFORMATION: Human CD3 Zeta isoform 3

<400> SEQUENCE: 16

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg


<210> SEQ ID NO 17
<211> LENGTH: 15
<212> TYPE: PRT
<213> ORGANISM: Artificial Sequence
<220> FEATURE:
<223> OTHER INFORMATION: Human IgG1
```

<400> SEQUENCE: 17

Glu Pro Lys Ser Cys Asp Lys Thr His Thr Cys Pro Pro Cys Pro
1 5 10 15

<210> SEQ ID NO 18
<211> LENGTH: 12
<212> TYPE: PRT
<213> ORGANISM: Artificial Sequence
<220> FEATURE:
<223> OTHER INFORMATION: Human IgG2

<400> SEQUENCE: 18

Glu Arg Lys Cys Cys Val Glu Cys Pro Pro Cys Pro
1 5 10

<210> SEQ ID NO 19
<211> LENGTH: 61
<212> TYPE: PRT
<213> ORGANISM: Artificial Sequence
<220> FEATURE:
<223> OTHER INFORMATION: Human IgG3

<400> SEQUENCE: 19

Glu Leu Lys Thr Pro Leu Gly Asp Thr His Thr Cys Pro Arg Cys Pro
1 5 10 15

Glu Pro Lys Ser Cys Asp Thr Pro Pro Pro Cys Pro Arg Cys Pro Glu
20 25 30

Pro Lys Ser Cys Asp Thr Pro Pro Pro Cys Pro Arg Cys Pro Glu Pro
35 40 45

Lys Ser Cys Asp Thr Pro Pro Pro Cys Pro Arg Cys Pro
50 55 60

<210> SEQ ID NO 20
<211> LENGTH: 12
<212> TYPE: PRT
<213> ORGANISM: Artificial Sequence
<220> FEATURE:
<223> OTHER INFORMATION: Human IgG4

<400> SEQUENCE: 20

Glu Ser Lys Tyr Gly Pro Pro Cys Pro Ser Cys Pro
1 5 10

<210> SEQ ID NO 21
<211> LENGTH: 12
<212> TYPE: PRT
<213> ORGANISM: Artificial Sequence
<220> FEATURE:
<223> OTHER INFORMATION: Modified human IgG4

<400> SEQUENCE: 21

Glu Ser Lys Tyr Gly Pro Pro Cys Pro Pro Cys Pro
1 5 10

<210> SEQ ID NO 22
<211> LENGTH: 26
<212> TYPE: DNA
<213> ORGANISM: Artificial Sequence
<220> FEATURE:
<223> OTHER INFORMATION: oJ02649

<400> SEQUENCE: 22
atcaaaagaa tagaccgaga tagggt 26

-continued

<210> SEQ ID NO 23
<211> LENGTH: 26
<212> TYPE: DNA
<213> ORGANISM: Artificial Sequence
<220> FEATURE:
<223> OTHER INFORMATION: oJ02648

<400> SEQUENCE: 23
ccgtaccttt aagaccaatg acttac 26

<210> SEQ ID NO 24
<211> LENGTH: 18
<212> TYPE: DNA
<213> ORGANISM: Artificial Sequence
<220> FEATURE:
<223> OTHER INFORMATION: oJ02650

<400> SEQUENCE: 24
ttgagagttt tcgccccg 18

<210> SEQ ID NO 25
<211> LENGTH: 24
<212> TYPE: DNA
<213> ORGANISM: Artificial Sequence
<220> FEATURE:
<223> OTHER INFORMATION: oJ02651

<400> SEQUENCE: 25
aatagacaga tcgctgagat aggt 24

<210> SEQ ID NO 26
<211> LENGTH: 18
<212> TYPE: DNA
<213> ORGANISM: Artificial Sequence
<220> FEATURE:
<223> OTHER INFORMATION: oJ02652

<400> SEQUENCE: 26
caggtatccg gtaagcgg 18

<210> SEQ ID NO 27
<211> LENGTH: 19
<212> TYPE: DNA
<213> ORGANISM: Artificial Sequence
<220> FEATURE:
<223> OTHER INFORMATION: oJ02653

<400> SEQUENCE: 27
cgaccagcaa ccatagtcc 19

<210> SEQ ID NO 28
<211> LENGTH: 18
<212> TYPE: DNA
<213> ORGANISM: Artificial Sequence
<220> FEATURE:
<223> OTHER INFORMATION: oJ02654

<400> SEQUENCE: 28
tagcggtttg actcacgg 18

<210> SEQ ID NO 29
<211> LENGTH: 20
<212> TYPE: DNA
<213> ORGANISM: Artificial Sequence
<220> FEATURE:
<223> OTHER INFORMATION: oJ02655

<400> SEQUENCE: 29
gcagggagct agaacgattc 20

<210> SEQ ID NO 30
<211> LENGTH: 22
<212> TYPE: DNA
<213> ORGANISM: Artificial Sequence
<220> FEATURE:
<223> OTHER INFORMATION: oJ02656

<400> SEQUENCE: 30
attgtctggt atagtgcagc ag 22

<210> SEQ ID NO 31
<211> LENGTH: 16
<212> TYPE: DNA
<213> ORGANISM: Artificial Sequence
<220> FEATURE:
<223> OTHER INFORMATION: oJ02657

<400> SEQUENCE: 31
tcgcaacggg tttgcc 16

<210> SEQ ID NO 32
<211> LENGTH: 21
<212> TYPE: DNA
<213> ORGANISM: Artificial Sequence
<220> FEATURE:
<223> OTHER INFORMATION: oJ02658

<400> SEQUENCE: 32
aggaagatat cgccacctac t 21

<210> SEQ ID NO 33
<211> LENGTH: 20
<212> TYPE: DNA
<213> ORGANISM: Artificial Sequence
<220> FEATURE:
<223> OTHER INFORMATION: oJ02601

<400> SEQUENCE: 33
cgggtgaagt tcagcagaag 20

<210> SEQ ID NO 34
<211> LENGTH: 20
<212> TYPE: DNA
<213> ORGANISM: Artificial Sequence
<220> FEATURE:
<223> OTHER INFORMATION: oJ02735

<400> SEQUENCE: 34
actgtgtttg ctgacgcaac 20

<210> SEQ ID NO 35
<211> LENGTH: 20
<212> TYPE: DNA
<213> ORGANISM: Artificial Sequence
<220> FEATURE:
<223> OTHER INFORMATION: oJ02715

<400> SEQUENCE: 35
atgcttctcc tggtgacaag 20

<210> SEQ ID NO 36

<211> LENGTH: 9
<212> TYPE: PRT
<213> ORGANISM: Artificial Sequence
<220> FEATURE:
<223> OTHER INFORMATION: Modified Human IgG4 linker

<400> SEQUENCE: 36

Tyr Gly Pro Pro Cys Pro Pro Cys Pro
1               5

<210> SEQ ID NO 37
<211> LENGTH: 10
<212> TYPE: PRT
<213> ORGANISM: Artificial Sequence
<220> FEATURE:
<223> OTHER INFORMATION: Modified Human IgG4

<400> SEQUENCE: 37

Lys Tyr Gly Pro Pro Cys Pro Pro Cys Pro
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Modified Human IgG4

<400> SEQUENCE: 38

Glu Val Val Lys Tyr Gly Pro Pro Cys Pro Pro Cys Pro
1               5                   10

<210> SEQ ID NO 39
<211> LENGTH: 2586
<212> TYPE: DNA
<213> ORGANISM: Artificial Sequence
<220> FEATURE:
<223> OTHER INFORMATION: TamR-tf(HEA3)

<400> SEQUENCE: 39
atggtgtcca agctgtccca gctgcagaca gaactgctgg cagcactgct ggaaagcggc 60
ctgagcaaag aggccctgat tcaggcactc ggcgaacctg gaccttatct gctcgctggc 120
gaaggccctc tggataaggg cgagagctgt ggcggaggaa gaggagagct ggccgagctg 180
cctaacggcc tgggcgagac aagaggcagc gaggacgaga cagacgacga cggcgaggac 240
ttcacccccc ccatcctgaa agagctggaa aacctgagcc ccgaggaagc cgcccaccag 300
aaagccgtgg tggagacact gctgcaggaa gatccctggc gggtcgccaa gatggtcaag 360
agctacctgc agcagcacaa catcccccag cgggaggtgg tggacaccac cggcctgaac 420
cagagccacc tgagccagca cctgaacaag ggcaccccca tgaaaaccca gaagagagcc 480
gccctgtaca cttggtacgt gcggaagcag agagaggtgg cccagcagtt tacacacgcc 540
ggccagggcg gcctgatcga ggaacctacc ggcgacgagc tgcccaccaa gaagggcaga 600
cggacccggt ttaagtgggg ccctgcatct cagcagatcc tgttccaggc ctacgagcgg 660
cagaagaacc ccagcaaaga ggaacgggag acactggtgg aagagtgcaa ccgggccgag 720
tgcatccaga gaggcgtgag cccttctcag gctcagggcc tcggcagcaa tctggtcacc 780
gaagtgcggg tgtacaattg gttcgccaac cggcggaaag aggaagcctt ccggcacaag 840
ctgtctgctg gcgatatgag agccgccaac ctgtggccca gcccccctgat gatcaagcgg 900 agcaagaaga acagcctggc cctgagcctg accgccgatc agatggtgtc cgctctgctg 960

-continued

```
gacgccgagc cccctatcct gtacagcgag tacgacccca ccagaccctt cagcgaggcc   1020

agcatgatgg gcctgctgac caacctggcc gaccgggagc tggtgcacat gatcaactgg   1080

gccaagcggg tgcccggctt cgtggacctg accctgcacg accaggtcca cctgctggaa   1140

tgtgcctggc tggaaatcct gatgatcggc ctcgtgtgga gaagcatgga acaccccggc   1200

aagctgctgt tcgcccccaa cctgctcctg gaccggaacc agggaaagtg cgtggagggc   1260

atggtggaga tcttcgacat gctgctggcc acctccagcc ggttccggat gatgaacctg   1320

cagggcgagg aattcgtgtg cctgaagtcc atcatcctgc tgaacagcgg cgtgtacacc   1380

ttcctgtcat ccaccctgaa gtccctggaa gagaaggacc acatccaccg ggtgctggac   1440

aagatcaccg acaccctgat ccacctgatg gccaaggctg gcctgacact ccagcagcag   1500

caccagagac tggcccagct gctgctgatc ctgagccaca tccggcacat gagcaacaag   1560

cggatggaac acctgtacag catgaagtgc aagaacgtgg tgcccctgta cgacctgctg   1620

ctcgagatgc tggatgccca cagactgcac gcccctacaa gcagaggcgg agccagcgtg   1680

gaggaaaccg accagtctca cctggccacc gccggcagca caagcagcca cagcctgcag   1740

aagtactaca tcaccggcga ggccgaggga ttccctgcca ccgtggagtt ccagtacctg   1800

cccgacaccg acgaccggca ccggatcgag gaaaagcgga agcggaccta cgagacattc   1860

aagagcatca tgaagaagtc cccccttcagc ggccccaccg atcccagacc cccccctaga   1920

agaatcgccg tgcccagcag atctagcgcc agcgtgccca agcctgcccc ccagccctac   1980

cctttcacca gcagcctgag caccatcaac tacgacgagt tccctaccat ggtgttcccc   2040

agcggccaga tctctcaggc ctctgctctg gcacctgctc cacctcaggt gctgcctcag   2100

gcccctgctc cagccccagc ccctgccatg gtgtctgcac tggcccaggc tccagctcct   2160

gtgcctgtgc tggcccctgg acctcctcag gctgtggccc ctcctgcccc taaacctacc   2220

caggccgggg agggaacact gtctgaggcc ctgctgcagc tccagttcga cgacgaggat   2280

ctgggagcac tgctgggcaa tagcaccgac cccgccgtgt ttaccgacct ggcctccgtg   2340

gacaacagcg agttccagca gctcctcaac cagggcatcc ctgtcgcccc acacaccacc   2400

gagcccatgc tgatggaata ccccgaggcc atcaccagac tggtcacagg cgcccagagg   2460

cctccagatc cagcaccagc tccactggga gcccctggcc tgcctaatgg gctgctgtct   2520

ggcgacgagg acttctccag cattgccgac atggacttca gcgccctgct gtcccagatc   2580

agcagc                                                                2586
```

```
<210> SEQ ID NO 40
<211> LENGTH: 862
<212> TYPE: PRT
<213> ORGANISM: Artificial Sequence
<220> FEATURE:
<223> OTHER INFORMATION: TamR-tf(HEA3)

<400> SEQUENCE: 40

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60
```

```
Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480
```

-continued

```
Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Arg Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val Glu Phe Gln Tyr Leu Pro Asp Thr Asp Asp Arg His Arg
        595                 600                 605

Ile Glu Glu Lys Arg Lys Arg Thr Tyr Glu Thr Phe Lys Ser Ile Met
    610                 615                 620

Lys Lys Ser Pro Phe Ser Gly Pro Thr Asp Pro Arg Pro Pro Pro Arg
625                 630                 635                 640

Arg Ile Ala Val Pro Ser Arg Ser Ser Ala Ser Val Pro Lys Pro Ala
                645                 650                 655

Pro Gln Pro Tyr Pro Phe Thr Ser Ser Leu Ser Thr Ile Asn Tyr Asp
            660                 665                 670

Glu Phe Pro Thr Met Val Phe Pro Ser Gly Gln Ile Ser Gln Ala Ser
        675                 680                 685

Ala Leu Ala Pro Ala Pro Pro Gln Val Leu Pro Gln Ala Pro Ala Pro
    690                 695                 700

Ala Pro Ala Pro Ala Met Val Ser Ala Leu Ala Gln Ala Pro Ala Pro
705                 710                 715                 720

Val Pro Val Leu Ala Pro Gly Pro Pro Gln Ala Val Ala Pro Pro Ala
                725                 730                 735

Pro Lys Pro Thr Gln Ala Gly Glu Gly Thr Leu Ser Glu Ala Leu Leu
            740                 745                 750

Gln Leu Gln Phe Asp Asp Glu Asp Leu Gly Ala Leu Leu Gly Asn Ser
        755                 760                 765

Thr Asp Pro Ala Val Phe Thr Asp Leu Ala Ser Val Asp Asn Ser Glu
    770                 775                 780

Phe Gln Gln Leu Leu Asn Gln Gly Ile Pro Val Ala Pro His Thr Thr
785                 790                 795                 800

Glu Pro Met Leu Met Glu Tyr Pro Glu Ala Ile Thr Arg Leu Val Thr
                805                 810                 815

Gly Ala Gln Arg Pro Pro Asp Pro Ala Pro Ala Pro Leu Gly Ala Pro
            820                 825                 830

Gly Leu Pro Asn Gly Leu Leu Ser Gly Asp Glu Asp Phe Ser Ser Ile
        835                 840                 845

Ala Asp Met Asp Phe Ser Ala Leu Leu Ser Gln Ile Ser Ser
    850                 855                 860
```

<210> SEQ ID NO 41
<211> LENGTH: 119
<212> TYPE: DNA
<213> ORGANISM: Artificial Sequence
<220> FEATURE:
<223> OTHER INFORMATION: 7xHBD/mEF1-alpha

<400> SEQUENCE: 41
tagttaataa tctacaatag ttaataatct acaatagtta ataatctaca atagttaata 60
atctacaata gttaataatc tacaatagtt aataatctac aatagttaat aatctacaa 119

<210> SEQ ID NO 42
<211> LENGTH: 2586
<212> TYPE: DNA
<213> ORGANISM: Artificial Sequence
<220> FEATURE:
<223> OTHER INFORMATION: TamR-tf (HEA4)

<400> SEQUENCE: 42
atggtgtcca agctgtccca gctgcagaca gaactgctgg cagcactgct ggaaagcggc 60
ctgagcaaag aggccctgat tcaggcactc ggcgaacctg gaccttatct gctcgctggc 120
gaaggccctc tggataaggg cgagagctgt ggcggaggaa gaggagagct ggccgagctg 180
cctaacggcc tgggcgagac aagaggcagc gaggacgaga cagacgacga cggcgaggac 240
ttcacccccc ccatcctgaa agagctggaa aacctgagcc ccgaggaagc cgcccaccag 300
aaagccgtgg tggagacact gctgcaggaa gatccctggc gggtcgccaa gatggtcaag 360
agctacctgc agcagcacaa catcccccag cgggaggtgg tggacaccac cggcctgaac 420
cagagccacc tgagccagca cctgaacaag ggcacccccca tgaaaaccca gaagagagcc 480
gccctgtaca cttggtacgt gcggaagcag agagaggtgg cccagcagtt tacacacgcc 540
ggccagggcg gcctgatcga ggaacctacc ggcgacgagc tgcccaccaa gaagggcaga 600
cggaaccggt ttaagtgggg ccctgcatct cagcagatcc tgttccaggc ctacgagcgg 660
cagaagaacc ccagcaaaga ggaacgggag acactggtgg aagagtgcaa ccgggccgag 720
tgcatccaga gaggcgtgag cccttctcag gctcagggcc tcggcagcaa tctggtcacc 780
gaagtgcggg tgtacaattg gttcgccaac cggcggaaag aggaagcctt ccggcacaag 840
ctgtctgctg gcgatatgag agccgccaac ctgtggccca gccccctgat gatcaagcgg 900
agcaagaaga acagcctggc cctgagcctg accgccgatc agatggtgtc cgctctgctg 960
gacgccgagc cccctatcct gtacagcgag tacgacccca ccagaccctt cagcgaggcc 1020
agcatgatgg gcctgctgac caacctggcc gaccgggagc tggtgcacat gatcaactgg 1080
gccaagcggg tgcccggctt cgtggacctg accctgcacg accaggtcca cctgctggaa 1140
tgtgcctggc tggaaatcct gatgatcggc ctcgtgtgga gaagcatgga acacccccgtg 1200 aagctgctgt tcgcccccaa cctgctcctg gaccggaacc agggaaagtg cgtggagggc 1260
atggtggaga tcttcgacat gctgctggcc acctccagcc ggttccggat gatgaacctg 1320
cagggcgagg aattcgtgtg cctgaagtcc atcatcctgc tgaacagcgg cgtgtacacc 1380
ttcctgtcat ccaccctgaa gtccctggaa gagaaggacc acatccaccg ggtgctggac 1440
aagatcaccg acaccctgat ccacctgatg gccaaggctg gcctgacact ccagcagcag 1500
caccagagac tggcccagct gctgctgatc ctgagccaca tccggcacat gagcaacaag 1560
ggaatggaac acctgtacag catgaagtgc acgaacgtgg tgcccctgta cgacctgctg 1620
ctcgaggctg ccgatgccca cagactgcac gcccctacaa gcagaggcgg agccagcgtg 1680
gaggaaaccg accagtctca cctggccacc gccggcagca caagcagcca cagcctgcag 1740
aagtactaca tcaccggcga ggccgaggga ttccctgcca ccgtggagtt ccagtacctg 1800
cccgacaccg acgaccggca ccggatcgag gaaaagcgga agcggaccta cgagacattc 1860

-continued

```
aagagcatca tgaagaagtc cccttcagc ggccccaccg atcccagacc cccccctaga   1920

agaatcgccg tgcccagcag atctagcgcc agcgtgccca agcctgcccc ccagccctac   1980

cctttcacca gcagcctgag caccatcaac tacgacgagt tccctaccat ggtgttcccc   2040

agcggccaga tctctcaggc ctctgctctg gcacctgctc cacctcaggt gctgcctcag   2100

gcccctgctc cagccccagc ccctgccatg gtgtctgcac tggcccaggc tccagctcct   2160

gtgcctgtgc tggcccctgg acctcctcag gctgtggccc ctcctgcccc taaacctacc   2220

caggccgggg agggaacact gtctgaggcc ctgctgcagc tccagttcga cgacgaggat   2280

ctgggagcac tgctgggcaa tagcaccgac cccgccgtgt ttaccgacct ggcctccgtg   2340

gacaacagcg agttccagca gctcctcaac cagggcatcc ctgtcgcccc acacaccacc   2400

gagcccatgc tgatggaata ccccgaggcc atcaccagac tggtcacagg cgcccagagg   2460

cctccagatc cagcaccagc tccactggga gcccctggcc tgcctaatgg gctgctgtct   2520

ggcgacgagg acttctccag cattgccgac atggacttca gcgccctgct gtcccagatc   2580

agcagc                                                              2586
```

<210> SEQ ID NO 43
<211> LENGTH: 862
<212> TYPE: PRT
<213> ORGANISM: Artificial Sequence
<220> FEATURE:
<223> OTHER INFORMATION: TamR-tf (HEA4)

<400> SEQUENCE: 43

```
Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220
```

-continued

```
Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Ala Ala
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val Glu Phe Gln Tyr Leu Pro Asp Thr Asp Asp Arg His Arg
        595                 600                 605

Ile Glu Glu Lys Arg Lys Arg Thr Tyr Glu Thr Phe Lys Ser Ile Met
    610                 615                 620

Lys Lys Ser Pro Phe Ser Gly Pro Thr Asp Pro Arg Pro Pro Pro Arg
625                 630                 635                 640
```

-continued

```
Arg Ile Ala Val Pro Ser Arg Ser Ser Ala Ser Val Pro Lys Pro Ala
                645                 650                 655

Pro Gln Pro Tyr Pro Phe Thr Ser Ser Leu Ser Thr Ile Asn Tyr Asp
            660                 665                 670

Glu Phe Pro Thr Met Val Phe Pro Ser Gly Gln Ile Ser Gln Ala Ser
        675                 680                 685

Ala Leu Ala Pro Ala Pro Pro Gln Val Leu Pro Gln Ala Pro Ala Pro
    690                 695                 700

Ala Pro Ala Pro Ala Met Val Ser Ala Leu Ala Gln Ala Pro Ala Pro
705                 710                 715                 720

Val Pro Val Leu Ala Pro Gly Pro Pro Gln Ala Val Ala Pro Pro Ala
                725                 730                 735

Pro Lys Pro Thr Gln Ala Gly Glu Gly Thr Leu Ser Glu Ala Leu Leu
            740                 745                 750

Gln Leu Gln Phe Asp Asp Glu Asp Leu Gly Ala Leu Leu Gly Asn Ser
        755                 760                 765

Thr Asp Pro Ala Val Phe Thr Asp Leu Ala Ser Val Asp Asn Ser Glu
    770                 775                 780

Phe Gln Gln Leu Leu Asn Gln Gly Ile Pro Val Ala Pro His Thr Thr
785                 790                 795                 800

Glu Pro Met Leu Met Glu Tyr Pro Glu Ala Ile Thr Arg Leu Val Thr
                805                 810                 815

Gly Ala Gln Arg Pro Pro Asp Pro Ala Pro Ala Pro Leu Gly Ala Pro
            820                 825                 830

Gly Leu Pro Asn Gly Leu Leu Ser Gly Asp Glu Asp Phe Ser Ser Ile
        835                 840                 845

Ala Asp Met Asp Phe Ser Ala Leu Leu Ser Gln Ile Ser Ser
    850                 855                 860
```

<210> SEQ ID NO 44
<211> LENGTH: 408
<212> TYPE: DNA
<213> ORGANISM: Artificial Sequence
<220> FEATURE:
<223> OTHER INFORMATION: Her2t

<400> SEQUENCE: 44

```
atgcttctcc tggtgacaag ccttctgctc tgtgagttac cacacccagc attcctcctg      60

atcccatgcc accctgagtg tcagccccag aatggctcag tgacctgttt tggaccggag     120

gctgaccagt gtgtggcctg tgcccactat aaggaccctc ccttctgcgt ggcccgctgc     180

cccagcggtg tgaaacctga cctctcctac atgcccatct ggaagtttcc agatgaggag     240

ggcgcatgcc agccttgccc catcaactgc acccactcct gtgtggacct ggatgacaag     300

ggctgccccg ccgagcagag agccagccct ctgacgtcca tcatctctgc ggtggttggc     360

attctgctgg tcgtggtctt gggggtggtc tttgggatcc tcatctga                  408
```

<210> SEQ ID NO 45
<211> LENGTH: 135
<212> TYPE: PRT
<213> ORGANISM: Artificial Sequence
<220> FEATURE:
<223> OTHER INFORMATION: Her2t

<400> SEQUENCE: 45

```
Met Leu Leu Leu Val Thr Ser Leu Leu Leu Cys Glu Leu Pro His Pro
1               5                   10                  15
```

-continued

```
Ala Phe Leu Leu Ile Pro Cys His Pro Glu Cys Gln Pro Gln Asn Gly
            20                  25                  30

Ser Val Thr Cys Phe Gly Pro Glu Ala Asp Gln Cys Val Ala Cys Ala
        35                  40                  45

His Tyr Lys Asp Pro Pro Phe Cys Val Ala Arg Cys Pro Ser Gly Val
    50                  55                  60

Lys Pro Asp Leu Ser Tyr Met Pro Ile Trp Lys Phe Pro Asp Glu Glu
65                  70                  75                  80

Gly Ala Cys Gln Pro Cys Pro Ile Asn Cys Thr His Ser Cys Val Asp
                85                  90                  95

Leu Asp Asp Lys Gly Cys Pro Ala Glu Gln Arg Ala Ser Pro Leu Thr
            100                 105                 110

Ser Ile Ile Ser Ala Val Val Gly Ile Leu Leu Val Val Val Leu Gly
        115                 120                 125

Val Val Phe Gly Ile Leu Ile
    130                 135
```

<210> SEQ ID NO 46
<211> LENGTH: 561
<212> TYPE: DNA
<213> ORGANISM: Artificial Sequence
<220> FEATURE:
<223> OTHER INFORMATION: DHFRdm

<400> SEQUENCE: 46

```
atggttggtt cgctaaactg catcgtcgct gtgtcccaga acatgggcat cggcaagaac      60

ggggacttcc cctggccacc gctcaggaat gaatccagat atttccagag aatgaccaca     120

acctcttcag tagaaggtaa acagaatctg gtgattatgg gtaagaagac ctggttctcc     180

attcctgaga agaatcgacc tttaaagggt agaattaatt tagttctcag cagagaactc     240

aaggaacctc cacaaggagc tcattttctt tccagaagtc tagatgatgc cttaaaactt     300

actgaacaac cagaattagc aaataaagta gacatggtct ggatagttgg tggcagttct     360

gtttataagg aagccatgaa tcacccaggc catcttaaac tatttgtgac aaggatcatg     420

caagactttg aaagtgacac gtttttttcca gaaattgatt tggagaaata taaacttctg    480

ccagaatacc caggtgttct ctctgatgtc caggaggaga aaggcattaa gtacaaattt     540

gaagtatatg agaagaatga t                                               561
```

<210> SEQ ID NO 47
<211> LENGTH: 187
<212> TYPE: PRT
<213> ORGANISM: Artificial Sequence
<220> FEATURE:
<223> OTHER INFORMATION: DHFRdm

<400> SEQUENCE: 47

```
Met Val Gly Ser Leu Asn Cys Ile Val Ala Val Ser Gln Asn Met Gly
1               5                   10                  15

Ile Gly Lys Asn Gly Asp Phe Pro Trp Pro Pro Leu Arg Asn Glu Ser
            20                  25                  30

Arg Tyr Phe Gln Arg Met Thr Thr Thr Ser Ser Val Glu Gly Lys Gln
        35                  40                  45

Asn Leu Val Ile Met Gly Lys Lys Thr Trp Phe Ser Ile Pro Glu Lys
    50                  55                  60

Asn Arg Pro Leu Lys Gly Arg Ile Asn Leu Val Leu Ser Arg Glu Leu
65                  70                  75                  80
```

-continued

```
Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
            100                 105                 110

Val Trp Ile Val Gly Gly Ser Ser Val Tyr Lys Glu Ala Met Asn His
        115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
                165                 170                 175

Lys Tyr Lys Phe Glu Val Tyr Glu Lys Asn Asp
            180                 185
```

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59
<211> LENGTH: 98
<212> TYPE: PRT
<213> ORGANISM: Artificial Sequence
<220> FEATURE:
<223> OTHER INFORMATION: CH3 domain

<400> SEQUENCE: 59

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val
```

<210> SEQ ID NO 60
<211> LENGTH: 12
<212> TYPE: PRT
<213> ORGANISM: Artificial Sequence
<220> FEATURE:
<223> OTHER INFORMATION: Hinge domain

<400> SEQUENCE: 60

```
Glu Ser Lys Tyr Gly Pro Pro Cys Pro Ser Cys Pro
1               5                   10
```

<210> SEQ ID NO 61
<211> LENGTH: 110
<212> TYPE: PRT
<213> ORGANISM: Artificial Sequence
<220> FEATURE:
<223> OTHER INFORMATION: CH2 domain

<400> SEQUENCE: 61

```
Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30
```

```
Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110


<210> SEQ ID NO 62
<211> LENGTH: 107
<212> TYPE: PRT
<213> ORGANISM: Artificial Sequence
<220> FEATURE:
<223> OTHER INFORMATION: CH3 protein domain

<400> SEQUENCE: 62

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105


<210> SEQ ID NO 63

<400> SEQUENCE: 63

000


<210> SEQ ID NO 64
<211> LENGTH: 12
<212> TYPE: PRT
<213> ORGANISM: Artificial Sequence
<220> FEATURE:
<223> OTHER INFORMATION: Signal peptide

<400> SEQUENCE: 64

Met Leu Arg Leu Leu Leu Ala Leu Asn Leu Phe Pro
1               5                   10


<210> SEQ ID NO 65
<211> LENGTH: 134
<212> TYPE: PRT
<213> ORGANISM: Artificial Sequence
<220> FEATURE:
<223> OTHER INFORMATION: Extracellular domain

<400> SEQUENCE: 65

Asn Lys Ile Leu Val Lys Gln Ser Pro Met Leu Val Ala Tyr Asp Asn
1               5                   10                  15
```

```
Ala Val Asn Leu Ser Cys Lys Tyr Ser Tyr Asn Leu Phe Ser Arg Glu
            20                  25                  30

Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
        115                 120                 125

Pro Gly Pro Ser Lys Pro
    130
```

<210> SEQ ID NO 66
<211> LENGTH: 27
<212> TYPE: PRT
<213> ORGANISM: Artificial Sequence
<220> FEATURE:
<223> OTHER INFORMATION: Transmembrane domain

<400> SEQUENCE: 66

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 67
<211> LENGTH: 50
<212> TYPE: PRT
<213> ORGANISM: Artificial Sequence
<220> FEATURE:
<223> OTHER INFORMATION: Intracellular domain

<400> SEQUENCE: 67

```
Thr Val Ala Phe Ile Ile Phe Trp Val Arg Ser Lys Arg Ser Arg Leu
1               5                   10                  15

Leu His Ser Asp Tyr Met Asn Met Thr Pro Arg Arg Pro Gly Pro Thr
            20                  25                  30

Arg Lys His Tyr Gln Pro Tyr Ala Pro Pro Arg Asp Phe Ala Ala Tyr
        35                  40                  45

Arg Ser
    50
```

<210> SEQ ID NO 68

<400> SEQUENCE: 68

000

<210> SEQ ID NO 69
<211> LENGTH: 23
<212> TYPE: PRT
<213> ORGANISM: Artificial Sequence
<220> FEATURE:
<223> OTHER INFORMATION: Signal peptide

<400> SEQUENCE: 69

Met Gly Asn Ser Cys Tyr Asn Ile Val Ala Thr Leu Leu Leu Val Leu
1 5 10 15

Asn Phe Glu Arg Thr Arg Ser
20

<210> SEQ ID NO 70
<211> LENGTH: 166
<212> TYPE: PRT
<213> ORGANISM: Artificial Sequence
<220> FEATURE:
<223> OTHER INFORMATION: Extracellular domain

<400> SEQUENCE: 70

Thr Arg Ser Leu Gln Asp Pro Cys Ser Asn Cys Pro Ala Gly Thr Phe
1 5 10 15

Cys Asp Asn Asn Arg Asn Gln Ile Cys Ser Pro Cys Pro Pro Asn Ser
20 25 30

Phe Ser Ser Ala Gly Gly Gln Arg Thr Cys Asp Ile Cys Arg Gln Cys
35 40 45

Lys Gly Val Phe Arg Thr Arg Lys Glu Cys Ser Ser Thr Ser Asn Ala
50 55 60

Glu Cys Asp Cys Thr Pro Gly Phe His Cys Leu Gly Ala Gly Cys Ser
65 70 75 80

Met Cys Glu Gln Asp Cys Lys Gln Gly Gln Glu Leu Thr Lys Lys Gly
85 90 95

Cys Lys Asp Cys Cys Phe Gly Thr Phe Asn Asp Gln Lys Arg Gly Ile
100 105 110

Cys Arg Pro Trp Thr Asn Cys Ser Leu Asp Gly Lys Ser Val Leu Val
115 120 125

Asn Gly Thr Lys Glu Arg Asp Val Val Cys Gly Pro Ser Pro Ala Asp
130 135 140

Leu Ser Pro Gly Ala Ser Ser Val Thr Pro Pro Ala Pro Ala Arg Glu
145 150 155 160

Pro Gly His Ser Pro Gln
165

<210> SEQ ID NO 71
<211> LENGTH: 27
<212> TYPE: PRT
<213> ORGANISM: Artificial Sequence
<220> FEATURE:
<223> OTHER INFORMATION: Transmembrane domain

<400> SEQUENCE: 71

Ile Ile Ser Phe Phe Leu Ala Leu Thr Ser Thr Ala Leu Leu Phe Leu
1 5 10 15

Leu Phe Phe Leu Thr Leu Arg Phe Ser Val Val
20 25

<210> SEQ ID NO 72
<211> LENGTH: 42
<212> TYPE: PRT
<213> ORGANISM: Artificial Sequence
<220> FEATURE:
<223> OTHER INFORMATION: Intracellular domain

<400> SEQUENCE: 72

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 73
<211> LENGTH: 21
<212> TYPE: PRT
<213> ORGANISM: Artificial Sequence
<220> FEATURE:
<223> OTHER INFORMATION: Signal peptide

<400> SEQUENCE: 73

Met Lys Trp Lys Ala Leu Phe Thr Ala Ala Ile Leu Gln Ala Gln Leu
1               5                   10                  15

Pro Ile Thr Glu Ala
            20

<210> SEQ ID NO 74
<211> LENGTH: 9
<212> TYPE: PRT
<213> ORGANISM: Artificial Sequence
<220> FEATURE:
<223> OTHER INFORMATION: Extracellular domain

<400> SEQUENCE: 74

Gln Ser Phe Gly Leu Leu Asp Pro Lys
1               5

<210> SEQ ID NO 75
<211> LENGTH: 21
<212> TYPE: PRT
<213> ORGANISM: Artificial Sequence
<220> FEATURE:
<223> OTHER INFORMATION: Transmembrane domain

<400> SEQUENCE: 75

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 76
<211> LENGTH: 113
<212> TYPE: PRT
<213> ORGANISM: Artificial Sequence
<220> FEATURE:
<223> OTHER INFORMATION: Intracellular domain

<400> SEQUENCE: 76

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

```
Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg


<210> SEQ ID NO 77
<211> LENGTH: 29
<212> TYPE: PRT
<213> ORGANISM: Artificial Sequence
<220> FEATURE:
<223> OTHER INFORMATION: ITAM I

<400> SEQUENCE: 77

Ala Pro Ala Tyr Gln Gln Gly Gln Asn Gln Leu Tyr Asn Glu Leu Asn
1               5                   10                  15

Leu Gly Arg Arg Glu Glu Tyr Asp Val Leu Asp Lys Arg
            20                  25


<210> SEQ ID NO 78
<211> LENGTH: 29
<212> TYPE: PRT
<213> ORGANISM: Artificial Sequence
<220> FEATURE:
<223> OTHER INFORMATION: ITAM 2

<400> SEQUENCE: 78

Pro Gln Arg Arg Lys Asn Pro Gln Glu Gly Leu Tyr Asn Glu Leu Gln
1               5                   10                  15

Lys Asp Lys Met Ala Glu Ala Tyr Ser Glu Ile Gly Met
            20                  25


<210> SEQ ID NO 79
<211> LENGTH: 29
<212> TYPE: PRT
<213> ORGANISM: Artificial Sequence
<220> FEATURE:
<223> OTHER INFORMATION: ITAM 3

<400> SEQUENCE: 79

Glu Arg Arg Arg Gly Lys Gly His Asp Gly Leu Tyr Gln Gly Leu Ser
1               5                   10                  15

Thr Ala Thr Lys Asp Thr Tyr Asp Ala Leu His Met Gln
            20                  25


<210> SEQ ID NO 80
<211> LENGTH: 66
<212> TYPE: DNA
<213> ORGANISM: Artificial Sequence
<220> FEATURE:
<223> OTHER INFORMATION: Leader

<400> SEQUENCE: 80

atgcttctcc tggtgacaag ccttctgctc tgtgagttac cacacccagc attcctcctg     60

atccca                                                                66


<210> SEQ ID NO 81
<211> LENGTH: 734
<212> TYPE: DNA
<213> ORGANISM: Artificial Sequence
<220> FEATURE:
```

<223> OTHER INFORMATION: Her2scFV

<400> SEQUENCE: 81
gatatccaga tgacccagtc cccgagctcc ctgtccgcct ctgtgggcga tagggtcacc 60
atcacctgcc gtgccagtca ggatgtgaat actgctgtag cctggtatca acagaaacca 120
ggaaaagctc cgaaactact gatttactcg gcatccttcc tctactctgg agtcccttct 180
cgcttctctg gttccagatc tgggacggat ttcactctga ccatcagcag tctgcagccg 240
gaagacttcg caacttatta ctgtcagcaa cattatacta ctcctcccac gttcggacag 300
ggtaccaagg tggagatcaa aggcagtact agcggcggtg gctccggggg cggatccggt 360
gggggcggca gcagcgaggt tcagctggtg gagtctggcg gtggcctggt gcagccaggg 420
ggctcactcc gtttgtcctg tgcagcttct ggcttcaaca ttaaagacac ctatatacac 480
tgggtgcgtc aggccccggg taagggcctg gaatgggttg caaggattta tcctacgaat 540
ggttatacta gatatgccga tagcgtcaag ggccgtttca ctataagcgc agacacatcc 600
aaaaacacag cctacctgca gatgaacagc ctgcgtgctg aggacactgc cgtctattat 660
tgttctagat ggggagggga cggcttctat gctatggact actggggtca aggaaccctg 720
gtcaccgtct cgag 734

<210> SEQ ID NO 82
<211> LENGTH: 36
<212> TYPE: DNA
<213> ORGANISM: Artificial Sequence
<220> FEATURE:
<223> OTHER INFORMATION: Hinge spacer

<400> SEQUENCE: 82
gagagcaagt acggaccgcc ctgcccccct tgccct 36

<210> SEQ ID NO 83
<211> LENGTH: 84
<212> TYPE: DNA
<213> ORGANISM: Artificial Sequence
<220> FEATURE:
<223> OTHER INFORMATION: CD28tm

<400> SEQUENCE: 83
atgttctggg tgctggtggt ggtcggaggc gtgctggcct gctacagcct gctggtcacc 60
gtggccttca tcatcttttg ggtg 84

<210> SEQ ID NO 84
<211> LENGTH: 126
<212> TYPE: DNA
<213> ORGANISM: Artificial Sequence
<220> FEATURE:
<223> OTHER INFORMATION: 4-1BB

<400> SEQUENCE: 84
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 85
<211> LENGTH: 336
<212> TYPE: DNA
<213> ORGANISM: Artificial Sequence
<220> FEATURE:
<223> OTHER INFORMATION: CD3 zeta

<400> SEQUENCE: 85
cgggtgaagt tcagcagaag cgccgacgcc cctgcctacc agcagggcca gaatcagctg 60
tacaacgagc tgaacctggg cagaagggaa gagtacgacg tcctggataa gcggagaggc 120
cgggaccctg agatgggcgg caagcctcgg cggaagaacc cccaggaagg cctgtataac 180
gaactgcaga aagacaagat ggccgaggcc tacagcgaga tcggcatgaa gggcgagcgg 240
aggcggggca agggccacga cggcctgtat cagggcctgt ccaccgccac caaggatacc 300
tacgacgccc tgcacatgca ggccctgccc ccaagg 336

<210> SEQ ID NO 86
<211> LENGTH: 72
<212> TYPE: DNA
<213> ORGANISM: Artificial Sequence
<220> FEATURE:
<223> OTHER INFORMATION: T2A

<400> SEQUENCE: 86
ctcgagggcg gcggagaggg cagaggaagt cttctaacat gcggtgacgt ggaggagaat 60
cccggcccta gg 72

<210> SEQ ID NO 87
<211> LENGTH: 1074
<212> TYPE: DNA
<213> ORGANISM: Artificial Sequence
<220> FEATURE:
<223> OTHER INFORMATION: tEGFR

<400> SEQUENCE: 87
atgcttctcc tggtgacaag ccttctgctc tgtgagttac cacacccagc attcctcctg 60
atcccacgca aagtgtgtaa cggaataggt attggtgaat ttaaagactc actctccata 120
aatgctacga atattaaaca cttcaaaaac tgcacctcca tcagtggcga tctccacatc 180
ctgccggtgg catttagggg tgactccttc acacatactc ctcctctgga tccacaggaa 240
ctggatattc tgaaaaccgt aaaggaaatc acagggtttt tgctgattca ggcttggcct 300
gaaaacagga cggacctcca tgcctttgag aacctagaaa tcatacgcgg caggaccaag 360
caacatggtc agttttctct tgcagtcgtc agcctgaaca taacatcctt gggattacgc 420
tccctcaagg agataagtga tggagatgtg ataatttcag gaaacaaaaa tttgtgctat 480
gcaaatacaa taaactggaa aaaactgttt gggacctccg gtcagaaaac caaaattata 540
agcaacagag gtgaaaacag ctgcaaggcc acaggccagg tctgccatgc cttgtgctcc 600
cccgagggct gctggggccc ggagcccagg gactgcgtct cttgccggaa tgtcagccga 660
ggcagggaat gcgtggacaa gtgcaacctt ctggagggtg agccaaggga gtttgtggag 720
aactctgagt gcatacagtg ccacccagag tgcctgcctc aggccatgaa catcacctgc 780
acaggacggg gaccagacaa ctgtatccag tgtgcccact acattgacgg cccccactgc 840
gtcaagacct gcccggcagg agtcatggga gaaaacaaca ccctggtctg gaagtacgca 900
gacgccggcc atgtgtgcca cctgtgccat ccaaactgca cctacggatg cactgggcca 960
ggtcttgaag gctgtccaac gaatgggcct aagatcccgt ccatcgccac tgggatggtg 1020
ggggccctcc tcttgctgct ggtggtggcc ctggggatcg gcctcttcat gtga 1074

<210> SEQ ID NO 88
<211> LENGTH: 11
<212> TYPE: PRT

<213> ORGANISM: Artificial Sequence
<220> FEATURE:
<223> OTHER INFORMATION: Humanized ScFv comprising a variable light chain comprising a CDRL1 sequence

<400> SEQUENCE: 88

Arg Ala Ser Gln Asp Ile Ser Lys Tyr Leu Asn
1 5 10

<210> SEQ ID NO 89
<211> LENGTH: 7
<212> TYPE: PRT
<213> ORGANISM: Artificial Sequence
<220> FEATURE:
<223> OTHER INFORMATION: CDRL2

<400> SEQUENCE: 89

Ser Arg Leu His Ser Gly Val
1 5

<210> SEQ ID NO 90
<211> LENGTH: 9
<212> TYPE: PRT
<213> ORGANISM: Artificial Sequence
<220> FEATURE:
<223> OTHER INFORMATION: CDRL3

<400> SEQUENCE: 90

Gly Asn Thr Leu Pro Tyr Thr Phe Gly
1 5

<210> SEQ ID NO 91
<211> LENGTH: 5
<212> TYPE: PRT
<213> ORGANISM: Artificial Sequence
<220> FEATURE:
<223> OTHER INFORMATION: CDRH1

<400> SEQUENCE: 91

Asp Tyr Gly Val Ser
1 5

<210> SEQ ID NO 92
<211> LENGTH: 16
<212> TYPE: PRT
<213> ORGANISM: Artificial Sequence
<220> FEATURE:
<223> OTHER INFORMATION: CDRH2

<400> SEQUENCE: 92

Val Ile Trp Gly Ser Glu Thr Thr Tyr Tyr Asn Ser Ala Leu Lys Ser
1 5 10 15

<210> SEQ ID NO 93
<211> LENGTH: 7
<212> TYPE: PRT
<213> ORGANISM: Artificial Sequence
<220> FEATURE:
<223> OTHER INFORMATION: CDRH3

<400> SEQUENCE: 93

Tyr Ala Met Asp Tyr Trp Gly
1 5

<210> SEQ ID NO 94
<211> LENGTH: 18
<212> TYPE: PRT

-continued

```
<213> ORGANISM: Artificial Sequence
<220> FEATURE:
<223> OTHER INFORMATION: Flexible linker between the VH and VL chains in
      the scFv

<400> SEQUENCE: 94

Gly Ser Thr Ser Gly Ser Gly Lys Pro Gly Ser Gly Glu Gly Ser Thr
1               5                   10                  15

Lys Gly
```

DRUG REGULATED TRANSGENE EXPRESSION

CROSS-REFERENCE TO RELATED APPLICATIONS

This application is a continuation of U.S. application Ser. No. 16/287,074 filed Feb. 27, 2019 now U.S. Pat. No. 11,155,616 issued Oct. 26, 2021 which is a continuation of U.S. application Ser. No. 15/302,415 filed Oct. 6, 2016 now U.S. Pat. No. 10,266,592 issued Apr. 23, 2019 which is a U.S. National Phase Application of PCT International Application Number PCT/US2015/024947, filed on Apr. 8, 2015, designating the United States of America and published in the English language, which claims the benefit of priority to U.S. Prov. App. No. 62/058,973, filed Oct. 2, 2014, U.S. Prov. App. No. 61/977,751, filed Apr. 10, 2014, U.S. Prov. App. No. 61/986,479, filed Apr. 30, 2014, U.S. Prov. App. No. 62/089,730 filed Dec. 9, 2014, U.S. Prov. App. No. 62/090,845, filed Dec. 11, 2014, and U.S. Prov. App. No. 62/088,363, filed Dec. 5, 2014. The entire disclosures of the aforementioned applications are expressly incorporated by reference in their entireties.

REFERENCE TO SEQUENCE LISTING

The present application is being filed along with a Sequence Listing in electronic format. The Sequence Listing is provided as a file entitled SCRI053C2SEQLIST.TXT, created Sep. 3, 2024, which is approximately 73,360 bytes in size. The information in the electronic format of the Sequence Listing is incorporated herein by reference in its entirety.

BACKGROUND OF THE INVENTION

The adoptive transfer of human T lymphocytes that are engineered by gene transfer to express chimeric antigen receptors (CARs) specific for surface molecules expressed on tumor cells has the potential to effectively treat cancer. Chimeric receptors are synthetic receptors that include an extracellular ligand binding domain, most commonly a single chain variable fragment of a monoclonal antibody (scFv) linked to intracellular signaling components, most commonly CD3ζ alone or combined with one or more costimulatory domains. Much of the research in the design of chimeric receptors has focused on defining scFvs and other ligand binding elements that target malignant cells without causing serious toxicity to essential normal tissues, and on defining the optimal composition of intracellular signaling modules to activate T cell effector functions.

Although, T cell (CAR-T) adoptive therapy clinical trials (chimeric antigen receptor expressing T cells) are demonstrating potent anti-tumor activity, it is apparent that significant toxicities can arise, for example, engraftment-induced cytokine storm, tumor lysis syndromes and ongoing B cell cytopenias, each of which are attributable to unregulated functional outputs of constitutively expressed CARs. Such toxicities can in some context threaten to limit the applicability of CAR-T cell adoptive therapy. Clinical trials using transgene-modified adoptive T cell immunotherapies have only tested T cells that constitutively express the transgene, or are always in the "ON" state, contributing in large part to transgene associated side-effects. Suicide gene-mediated elimination of CAR-T cells can ameliorate such toxicities; however, this approach risks premature attenuation of anti-tumor activity and significantly impacts curative potential.

Current small molecule-regulated transgene expression technologies rely on a variety of drug inputs including macrolides, ecdysones and rapamycin analogs. Clinical applicability of these systems is limited due to toxic off target effects, unfavorable biodistribution and pharmacodynamics profiles, limited output dynamic range, and/or limited availability as FDA-approved commercially available pharmaceuticals. Furthermore, many of these systems use chimeric transcriptional regulators built from xenogeneic components, thus introducing the complication of immunogenicity when applying these systems to human therapeutics.

There is a need to identify methods for determining elements of chimeric receptor design that are important for therapeutic activity and cell populations to genetically modify and adoptively transfer that will provide enhanced survival and efficacy in vivo while minimizing adverse side effects. There is also a need for expression systems and methods for modulating cells for use in cell therapy, such as for modulating expression of recombinant antigen receptors such as CARs and/or other molecules expressed by such cells, such as to improve therapeutic activity, enhanced survival and/or efficacy in vivo and/or minimize adverse side effects.

SUMMARY OF THE INVENTION

One aspect of the disclosure includes a genetic system to deliver drug-regulated transgene expression in cells. In an alternative, regulated transgene expression is targeted to cells, such as lymphocytes designed for use in adoptive immunotherapy. This system provides rigorous safety attributes to chimeric antigen receptor (CAR) redirected adoptive therapeutic strategies without sacrificing curative intent that permits real-time clinician control of CAR expression in vivo. By engineering vectors that enable drug responsive transcriptional control of CAR expression, the activity of CARs and other cell mediators can be turned "ON" and "OFF" in vivo, based on a clinician prescribed pharmaceutical drug input that exhibits clinically permissive pharmacokinetics, tissue distribution, and partitioning between the extracellular space and cytosol of lymphocytes. The genetic system provides for drug regulated transgene expression to enforce a functional "OFF" state in the absence of the drug and a functional "ON" state transgene expression in the presence of the drug.

One alternative of such a drug is tamoxifen. Tamoxifen is an estrogen antagonist/partial agonist that is an FDA-approved and commercially available drug. It is taken orally and can be administered on a daily basis over an extended period of time. Tamoxifen has a proven safety record, favorable pharmacokinetic profile, excellent tissue distribution and a low partition coefficient between the extracellular space and cytosol. Other drugs can be selected based on safety record, favorable pharmacokinetic profile, and excellent tissue distribution, a low partition coefficient between the extracellular space and cytosol, and/or low toxicities.

In some alternatives, the system employs a synthetic transcriptional regulator, which, in the presence of tamoxifen, binds a synthetic promoter upstream of a transgene to induce expression. The tamoxifen regulated transcription factor ("TamR-tf", also designated "HEA3") is a chimeric transcription factor composed of human subunits including the N-terminal DNA binding domain of Hepatocyte Nuclear Factor 1-alpha (HNF-1a) fused in frame to the mutant tamoxifen-specific ligand binding domain of the estrogen receptor ligand binding domain (ER-LBD), that is in turn fused to the p65 activation domain of NF-κB (p65). An exemplary amino acid sequence is provided in FIGS. 9A, 9B, and 9C and is identified as SEQ ID NO: 40. The mutant tamoxifen-specific ligand binding domain of the estrogen receptor ligand binding domain (ER-LBD) is found at amino acids 282-595 of the TamR-tf and has a mutation at position 521. The p65 activation domain of NF-κB (p65) is found at amino acids 596-862 of SEQ ID NO: 40. Further changes can be made to the transcriptional activator to increase the properties of the transcription factor including, without limitation, altering one or more amino acids in the estrogen receptor ligand binding domain to increase the affinity of the factor for estrogen analogs and altering one or more amino acids in the p65 transactivating domain.

In the absence of tamoxifen, TamR-tf is excluded from the nucleus by binding of cytosolic heat-shock protein 90 (HSP90) to the tamoxifen binding active site and transgene expression is in the "OFF" state. Nanomolar concentrations of cytosolic tamoxifen actively out competes HSP90 for ER-LBD binding, resulting in TamR-tf translocation to the nucleus. Upon nuclear translocation, TamR-tf is readily available to bind its restricted synthetic promoter (e.g. 7×HBD/EF1αp). In the presence of tamoxifen, binding of TamR-tf to 7×HBD/EF1αp promoter induces the "ON" state of transgene expression. In some alternatives, this transcriptional regulator can be modified to provide for a varying level of control of transgene expression. Amino acid substitutions in the LBD of TamR-tf permit selective responsiveness to tamoxifen and its metabolites, where 4-hydroxy tamoxifen (4-OHT) is the most pharmacologically active metabolite, in regards to TamR-tf activity, while lacking interaction with endogenous estrogen.

In one aspect, the present disclosure relates to methods and compositions to confer and/or augment immune responses mediated by cellular immunotherapy, such as, by adoptively transferring tumor-specific, genetically modified subsets of CD8+ or CD4+ T cells alone, or in combination. The disclosure provides for chimeric receptor nucleic acids, and vectors and host cells including such nucleic acids. The nucleic acid sequence that encodes the chimeric receptor links together a number of modular components that can be excised and replaced with other components in order to customize the chimeric receptor for efficient T cell activation and recognition of a specific target molecule or an epitope on the target molecule and provide for regulated transcription as described herein.

In some alternatives, a system for inducible expression of a chimeric antigen receptor comprises: a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain; and a second nucleic acid comprising a second promoter operably linked to nucleic acid coding for a transcriptional activator for the inducible promoter. In some alternatives, the drug is tamoxifen and/or its metabolites. In some alternatives, the spacer is optimized for increased T cell proliferation and/or cytokine production in response to the ligand as compared to a reference chimeric receptor. In some alternatives, the second promoter is constitutive or inducible.

In some alternatives, a system for inducible expression of a chimeric antigen receptor comprises: a first nucleic acid comprising a first promoter inducible by a drug, wherein the first nucleic acid is operably linked to a polynucleotide coding for a cytokine, a chemokine, a polypeptide that regulates apoptosis and/or a polypeptide that modulates checkpoint signaling; and a second nucleic acid comprising a second promoter operably linked to a nucleic acid coding for a transcriptional activator for the inducible promoter. In some alternatives, the second promoter is constitutive or inducible. In an exemplary alternative, the second nucleic acid further comprises a polynucleotide coding for a chimeric antigen receptor, under the control of a constitutive promoter. In some alternatives, the drug is tamoxifen and/or its metabolites.

In another aspect, the present disclosure provides compositions to confer and/or augment immune responses mediated by cellular immunotherapy, such as by adoptively transferring tumor-specific, subset specific genetically modified CD4+ T cells, wherein the CD4+ T cells confer and/or augment the ability of CD8+ T cells to sustain anti-tumor reactivity and increase and/or maximize tumor-specific proliferation. In some alternatives, the CD4+ cells are genetically modified to express a chimeric receptor nucleic acid and/or chimeric receptor polypeptide under the control of a regulated promoter, as described herein.

In another aspect, the present disclosure provides compositions to confer and/or augment immune responses mediated by cellular immunotherapy, such as by adoptively transferring tumor-specific, subset specific genetically modified T cells. In some alternatives, the cells are precursor T cells. In some alternatives, the cells are hematopoietic stem cells. In some alternatives, the cells are CD8+ T cells. In some alternatives, the CD8+ T cells express a chimeric receptor nucleic acid and/or chimeric receptor polypeptide under the control of a regulated promoter, as described herein.

Some alternatives concern methods of performing cellular immunotherapy in a subject having a disease or disorder by administering to the subject a genetically modified T lymphocyte cell preparation that provides a cellular immune response and administering a drug that induces a transgene in the genetically modified T lymphocyte cells. In some alternatives, the genetically modified T lymphocyte cell preparation comprises precursor T cells. In some alternatives, the genetically modified T lymphocyte cell preparation comprises hematopoietic stem cells. In some alternatives, the genetically modified CD8+ and genetically modified CD4+ cell population are co-administered. In some alternatives, the drug is tamoxifen and/or its metabolites. In some alternatives, the T cells are autologous or allogeneic T cells. Various modifications of the above method are possible. For example, the chimeric receptor that is expressed by the CD4+ T cell and the CD8+ T cell can be the same or different.

In some alternatives, a system for inducible expression of a chimeric antigen receptor is provided, wherein the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain; and b) a second nucleic acid comprising a second promoter operably linked to nucleic acid coding for a transcriptional activator for the inducible promoter. In some alternatives, the drug is tamoxifen and/or its metabolites. In some alternatives, the second promoter is inducible. In some alternatives, the second promoter is constitutive. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, the spacer is optimized for increased T cell proliferation and/or cytokine production in response to the ligand as compared to a reference chimeric receptor.

In some alternatives, a system for inducible expression of a chimeric antigen receptor is provided, wherein the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized a polynucleotide coding for a transmembrane domain; and d) a polynucleotide coding for an intracellular signaling domain and b) a second nucleic acid comprising a second promoter operably linked to nucleic acid coding for a transcriptional activator for the inducible promoter. In some alternatives, the second promoter is constitutive or inducible. In some alternatives, the drug is tamoxifen and/or its metabolites. In some alternatives, the second nucleic acid further comprises a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the drug is tamoxifen and/or its metabolites. In some alternatives, the first promoter is in opposite orientation to the second promoter. In some alternatives, the ligand binding domain is an antibody fragment. In some alternatives, the ligand binding domain is single chain variable fragment. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the spacer is optimized for increased T cell proliferation and/or cytokine production in response to the ligand as compared to a reference chimeric receptor. In some alternatives, the second promoter is inducible. In some alternatives, the second promoter is constitutive.

In some alternatives, a chimeric receptor polypeptide is provided, wherein the chimeric receptor polypeptide is coded for by a system. In some alternatives, the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain; and b) a second nucleic acid comprising a second promoter operably linked to nucleic acid coding for a transcriptional activator for the inducible promoter. In some alternatives, the second promoter is constitutive or inducible. In some alternatives, the drug is tamoxifen and/or its metabolites. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, the second promoter is an inducible promoter. In some alternatives, the spacer is optimized for increased T cell proliferation and/or cytokine production in response to the ligand as compared to a reference chimeric receptor.

In some alternatives, a system for inducible expression of chimeric antigen receptor is provided, wherein the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling and b) a second nucleic acid comprising a second promoter operably linked to nucleic acid coding for a transcriptional activator for the inducible promoter. In some alternatives, the second promoter is constitutive or inducible. In some alternatives, the second nucleic acid further comprises a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the first promoter is in opposite orientation to the second promoter. In some alternatives, the ligand binding domain is an antibody fragment, preferably a binding domain thereof. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling; and b) a second nucleic acid comprising a second promoter operably linked to nucleic acid coding for a transcriptional activator for the inducible promoter. In some alternatives, the second promoter is constitutive or inducible. In some alternatives, the drug is tamoxifen and/or its metabolites. In some alternatives, the second nucleic acid further comprises a polynucleotide coding for chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain. In some alternatives, the first promoter is in opposite orientation to the second promoter. In some alternatives, the ligand binding domain is an antibody fragment, preferably a binding fragment thereof. In some alternatives, the ligand binding domain is single chain variable fragment. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the spacer is optimized for increased T cell proliferation and/or cytokine production in response to the ligand as compared to a reference chimeric receptor.

In some alternatives, a host cell is provided, wherein the host cell comprises a system. In some alternatives, the system comprises a) a first nucleic acid comprising a first promoter inducible by a drug, wherein the first nucleic acid is operably linked to a polynucleotide coding for a chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain; and b) a second nucleic acid comprising a second promoter operably linked to nucleic acid coding for a transcriptional activator for the inducible promoter. In some alternatives, the second promoter is constitutive or inducible. In some alternatives, the drug is tamoxifen and/or its metabolites. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, the second nucleic acid further comprises a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the first promoter is in opposite orientation to the second promoter. In some alternatives, the ligand binding domain is an antibody fragment, preferably a binding fragment thereof. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling; and b) a second nucleic acid comprising a second promoter operably linked to nucleic acid coding for a transcriptional activator for the inducible promoter. In some alternatives, the second promoter is constitutive or inducible. In some alternatives, the second nucleic acid further comprises a polynucleotide coding for chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the first promoter is in opposite orientation to the second promoter. In some alternatives, the ligand binding domain is an antibody fragment, preferably a binding fragment thereof. In some alternatives, the ligand binding domain is single chain variable fragment. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the spacer is optimized for increased T cell proliferation and/or cytokine production in response to the ligand as compared to a reference chimeric receptor. In some alternatives, the host cell is precursor T cell. In some alternatives, the precursor T cell is a hematopoietic stem cell.

In some alternatives, a composition is provided, wherein the composition comprises a host cell in a pharmaceutically acceptable excipient. In some alternatives, the host cell comprises a system. In some alternatives, the system comprises a) a first nucleic acid comprising a first promoter inducible by a drug, wherein the first nucleic acid is operably linked to a polynucleotide coding for a chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain; and b) a second nucleic acid comprising a second promoter operably linked to nucleic acid coding for a transcriptional activator for the inducible promoter. In some alternatives, the second promoter is constitutive or inducible. In some alternatives, the drug is tamoxifen and/or its metabolites. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, the second nucleic acid further comprises a polynucleotide coding for a chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain. In some alternatives, the first promoter is in opposite orientation to the second promoter. In some alternatives, the ligand binding domain is an antibody fragment. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling; and b) a second nucleic acid comprising a second promoter operably linked to nucleic acid coding for a transcriptional activator for the inducible promoter. In some alternatives, the second promoter is constitutive or inducible. In some alternatives, the second nucleic acid further comprises a polynucleotide coding for chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the first promoter is in opposite orientation to the second promoter. In some alternatives, the ligand binding domain is an antibody fragment, preferably a binding fragment thereof. In some alternatives, the ligand binding domain is single chain variable fragment. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the host cell is precursor T cell. In some alternatives, the precursor T cell is a hematopoietic stem cell. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells and further comprises another host cell wherein the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the host cell is precursor T cell. In some alternatives, the precursor T cell is a hematopoietic stem cell. In some alternatives, the spacer is optimized for increased T cell proliferation and/or cytokine production in response to the ligand as compared to a reference chimeric receptor. In some alternatives, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells or the host cell is a CD4+T helper lymphocyte cell that is selected from the group consisting of naïve CD4+ T cells, central memory CD4+ T cells, effector memory CD4+ T cells, and bulk CD4+ T cells and a second host cell, wherein the second host cell is a precursor T cell or a hematopoietic stem cell.

In some alternatives, an in vitro method for preparing a host cell is provided wherein the method comprises a) providing a system and b) introducing the system into a separate isolated T lymphocyte population and expanding each T lymphocyte population in vitro. In some alternatives, the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain; and b) a second nucleic acid comprising a second promoter operably linked to nucleic acid coding for a transcriptional activator for the inducible promoter. In some alternatives, the second promoter is constitutive or inducible. In some alternatives, the drug is tamoxifen and/or its metabolites. In some alternatives, the second promoter is constitutive or inducible. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, the second nucleic acid further comprises a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain. In some alternatives, the first promoter is in opposite orientation to the second promoter. In some alternatives, the ligand binding domain is an antibody fragment, preferably a binding fragment thereof. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling; and b) a second nucleic acid comprising a second promoter operably linked to nucleic acid coding for a transcriptional activator for the inducible promoter. In some alternatives, the second promoter is constitutive or inducible. In some alternatives, the second nucleic acid further comprises a polynucleotide coding for chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain. In some alternatives, the first promoter is in opposite orientation to the second promoter. In some alternatives, the ligand binding domain is an antibody fragment, preferably a binding fragment thereof. In some alternatives, the ligand binding domain is single chain variable fragment. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, wherein the T lymphocytes are expanded, the method further comprises culturing the cells in the presence of anti-CD3 and/or anti CD28, and at least one homeostatic cytokine until the cells expand sufficiently for use as a cell infusion. In some alternatives, the lymphocyte is CD8+ or CD4+. In some alternatives, the spacer is optimized for increased T cell proliferation and/or cytokine production in response to the ligand as compared to a reference chimeric receptor. In some alternatives, the host cell is precursor T cell. In some alternatives, the precursor T cell is a hematopoietic stem cell.

In some alternatives, a use of a host cell or a composition in combination with a drug that induces expression of a transgene in the host cell or composition for the treatment of cancer or a viral infection is provided. In some alternatives, the host cell comprises a system. In some alternatives, the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain; and b) a second nucleic acid comprising a second promoter operably linked to nucleic acid coding for a transcriptional activator for the inducible promoter. In some alternatives, the second promoter is constitutive or inducible. In some alternatives, the drug is tamoxifen and/or its metabolites. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, the second nucleic acid further comprises a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the first promoter is in opposite orientation to the second promoter. In some alternatives, the ligand binding domain is an antibody fragment. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling; and b) a second nucleic acid comprising a second promoter operably linked to nucleic acid coding for a transcriptional activator for the inducible promoter. In some alternatives, the second promoter is constitutive or inducible. In some alternatives, the second nucleic acid further comprises a polynucleotide coding for chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the first promoter is in opposite orientation to the second promoter. In some alternatives, the ligand binding domain is an antibody fragment, preferably a binding fragment thereof. In some alternatives, the ligand binding domain is single chain variable fragment. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the cells are precursor T cells. In some alternatives, the cells are hematopoietic stem cells. In some alternatives, the composition comprises a host cell in a pharmaceutically acceptable excipient. In some alternatives, the host cell comprises a system. In some alternatives, the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and b) a second nucleic acid comprising a second promoter operably linked to nucleic acid coding for a transcriptional activator for the inducible promoter. In some alternatives, the second promoter is constitutive or inducible. In some alternatives, the drug is tamoxifen and/or its metabolites. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, the second nucleic acid further comprises a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the first promoter is in opposite orientation to the second promoter. In some alternatives, the ligand binding domain is an antibody fragment, preferably a binding fragment thereof. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling; and b) a second nucleic acid comprising a second promoter operably linked to nucleic acid coding for a transcriptional activator for the inducible promoter. In some alternatives, the second promoter is constitutive or inducible. In some alternatives, the second nucleic acid further comprises a polynucleotide coding for a chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the first promoter is in opposite orientation to the second promoter. In some alternatives, the ligand binding domain is an antibody fragment, preferably a binding fragment thereof. In some alternatives, the ligand binding domain is single chain variable fragment. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells and another host cell wherein the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the cancer is a solid tumor or hematologic malignancy. In some alternatives, the solid tumor is selected from the group consisting of a breast cancer, brain cancer, lung cancer, colon cancer, renal cancer, pancreatic cancer, prostate cancer, and ovarian cancer. In some alternatives, the spacer is optimized for increased T cell proliferation and/or cytokine production in response to the ligand as compared to a reference chimeric receptor. In some alternatives, the host cell is precursor T cell. In some alternatives, the precursor T cell is a hematopoietic stem cell. In some alternatives, the host cell is precursor T cell. In some alternatives, the precursor T cell is a hematopoietic stem cell. In some alternatives, the spacer is optimized for increased T cell proliferation and/or cytokine production in response to the ligand as compared to a reference chimeric receptor. In some alternatives, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells or the host cell is a CD4+T helper lymphocyte cell that is selected from the group consisting of naïve CD4+ T cells, central memory CD4+ T cells, effector memory CD4+ T cells, and bulk CD4+ T cells and a second host cell, wherein the second host cell is a precursor T cell or a hematopoietic stem cell.

In some alternatives, a method of performing cellular immunotherapy in a subject having cancer or a viral infection is provided wherein the method comprises administering a composition or a host cell to the subject and administering a drug that induces expression of a transgene in the composition or the host cells. In some alternatives, the host cell comprises a system. In some alternatives, the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain; and b) a second nucleic acid comprising a second promoter operably linked to nucleic acid coding for a transcriptional activator for the inducible promoter. In some alternatives, the second promoter is constitutive or inducible. In some alternatives, the drug is tamoxifen and/or its metabolites. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, the second nucleic acid further comprises a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the first promoter is in opposite orientation to the second promoter. In some alternatives, the ligand binding domain is an antibody fragment, preferably a binding fragment thereof. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling; and b) a second nucleic acid comprising a second promoter operably linked to nucleic acid coding for a transcriptional activator for the inducible promoter. In some alternatives, the second promoter is constitutive or inducible. In some alternatives, the second nucleic acid further comprises a polynucleotide coding for a chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain. In some alternatives, the first promoter is in opposite orientation to the second promoter. In some alternatives, the ligand binding domain is an antibody fragment, preferably a binding fragment thereof. In some alternatives, the ligand binding domain is single chain variable fragment. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell in a pharmaceutically acceptable excipient. In some alternatives, the host cell comprises a system. In some alternatives, the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and b) a second nucleic acid comprising a second promoter operably linked to nucleic acid coding for a transcriptional activator for the inducible promoter. In some alternatives, the second promoter is constitutive or inducible. In some alternatives, the drug is tamoxifen and/or its metabolites. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, the second nucleic acid further comprises a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the first promoter is in opposite orientation to the second promoter. In some alternatives, the ligand binding domain is an antibody fragment, preferably a binding fragment thereof. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling; and b) a second nucleic acid comprising a second promoter operably linked to nucleic acid coding for a transcriptional activator for the inducible promoter. In some alternatives, the second promoter is constitutive or inducible. In some alternatives, the second nucleic acid further comprises a polynucleotide coding for a chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the first promoter is in opposite orientation to the second promoter. In some alternatives, the ligand binding domain is an antibody fragment, preferably a binding fragment thereof. In some alternatives, the ligand binding domain is single chain variable fragment. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells and another host cell wherein the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the host cell is precursor T cell. In some alternatives, the precursor T cell is a hematopoietic stem cell. In some alternatives, the spacer is optimized for increased T cell proliferation and/or cytokine production in response to the ligand as compared to a reference chimeric receptor. In some alternatives, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells or the host cell is a CD4+T helper lymphocyte cell that is selected from the group consisting of naïve CD4+ T cells, central memory CD4+ T cells, effector memory CD4+ T cells, and bulk CD4+ T cells and a second host cell, wherein the second host cell is a precursor T cell or a hematopoietic stem cell. In some alternatives, the cancer is selected from a solid tumor or hematologic malignancy. In some alternatives, the solid tumor is selected from the group consisting of a breast cancer, brain cancer, lung cancer, colon cancer, renal cancer, pancreatic cancer, prostate cancer, and ovarian cancer. In some alternatives, the spacer is optimized for increased T cell proliferation and/or cytokine production in response to the ligand as compared to a reference chimeric receptor. In some alternatives, the host cell is a precursor T cell. In some alternatives, the precursor T cell is a hematopoietic stem cell. In some alternatives, the isolated T lymphocyte population comprises precursor T cells. In some alternatives, the precursor T cells are hematopoietic stem cells. In some alternatives, the administering of the drug is performed after administering of the composition or host cells, wherein administering is performed 1 day, 2 days, 3 days, 4 days, 5 days, 6 days, 7 days, 2 weeks, 4 weeks or two months, or any time in between any two values of time listed.

BRIEF DESCRIPTION OF THE DRAWINGS

FIG. 4D shows construct A, which comprises the constitutive promoter EF1αp linked to TamR-tf (HEA3) linked to EGFRt, and construct B comprising a synthetic promoter 7×HBD/mE1b linked to a polynucleotide coding for ZsGreen.

FIG. 9A, FIG. 9B, and FIG. 9C depict a single HEA3 nucleotide sequence (SEQ ID NO:39) and amino acid sequence (SEQ ID NO:40).

FIG. 10A, FIG. 10B, and FIG. 10C depict a single HEA4 nucleotide sequence (SEQ ID NO:42) and amino acid sequence (SEQ ID NO:43).

FIG. 11 depicts a HER2t nucleotide sequence (SEQ ID NO:44) and amino acid sequence (SEQ ID NO:45).

FIG. 12 depicts a DHFRdm nucleotide sequence (SEQ ID NO:46) and amino acid sequence (SEQ ID NO:47).

DETAILED DESCRIPTION

Definitions

Figure 1A:
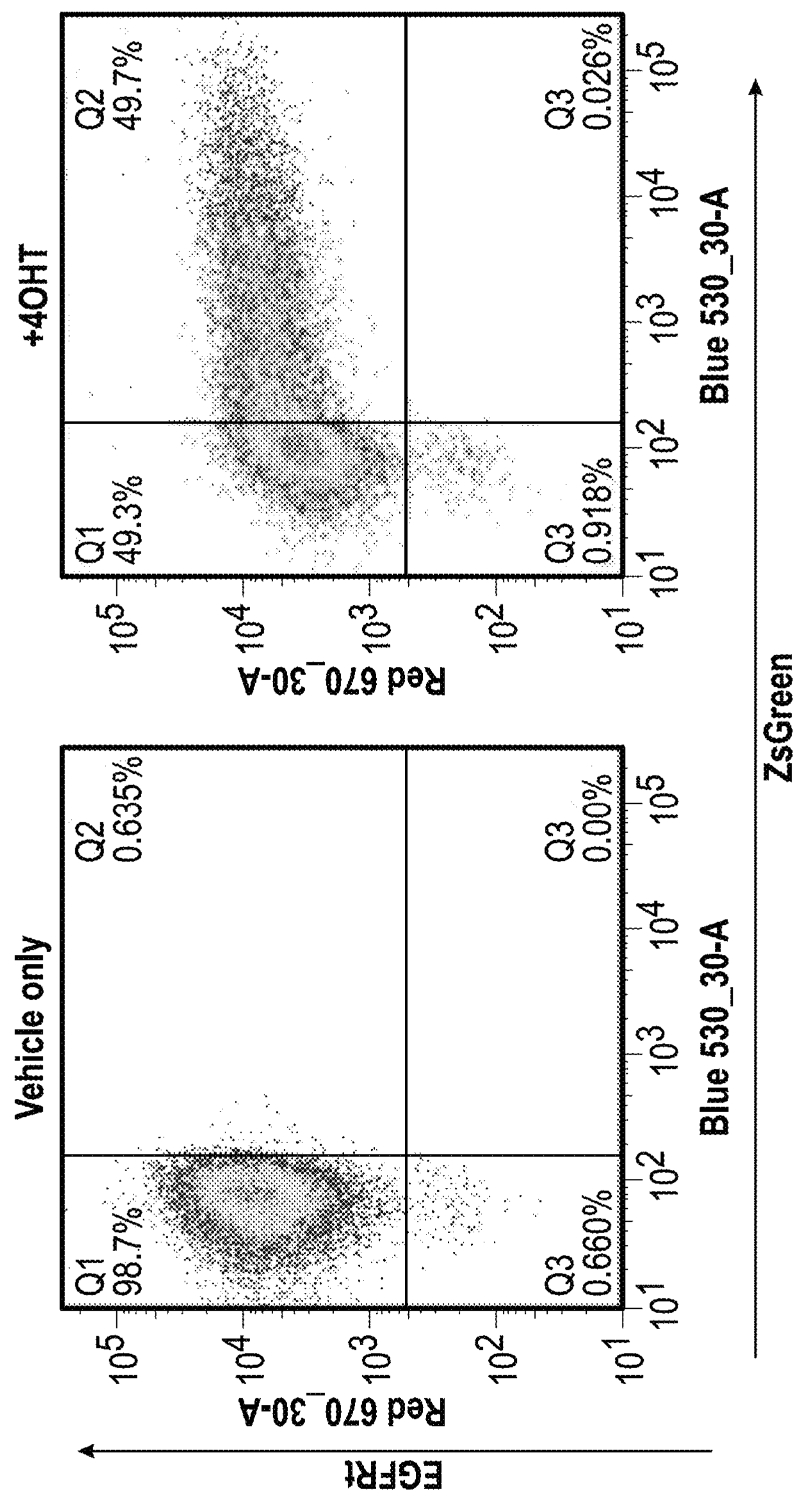
FIG. 1A shows the expression of ZsGreen and EGFRt as determined by flow cytometry in Jurkat cells transduced with a dual plasmid lentiviral construct including constructs A and B in the presence or absence of 4 hydroxy tamoxifen (4OHT). The results show the expression of EGFRt in the presence or absence of 4-OHT indicating the cells carry construct A. The results also show that the cells carry construct B as expression of ZsGreen is induced in the presence of 4-OHT.

Unless defined otherwise, all technical and scientific terms used herein have the same meaning as commonly understood by one of ordinary skill in the art to which the invention pertains.

"About" as used herein when referring to a measurable value is meant to encompass variations of +20% or +10%, more preferably +5%, even more preferably +1%, and still more preferably +0.1% from the specified value.

Antigen" or "Ag" as used herein refers to a molecule that provokes an immune response. This immune response can involve either antibody production, or the activation of specific immunologically-competent cells, or both. It is readily apparent that an antigen can be generated synthesized, produced recombinantly or can be derived from a biological sample. Such a biological sample can include, but is not limited to a tissue sample, a tumor sample, a cell or a biological fluid such, for example, blood, plasma or ascites fluid.

"Anti-tumor effect" as used herein, refers to a biological effect, which can be manifested by a decrease in tumor volume, a decrease in the number of tumor cells, a decrease in the number of metastases, an increase in life expectancy, or a decrease of various physiological symptoms associated with the cancerous condition. An "anti-tumor effect" can also be manifested by a decrease in recurrence or an increase in the time before recurrence.

"Chimeric receptor" as used herein refers to a synthetically designed receptor comprising a ligand binding domain of an antibody or other protein sequence that binds to a molecule associated with the disease or disorder and is linked via a spacer domain to one or more intracellular signaling domains of a T cell or other receptors, such as a costimulatory domain. Chimeric receptor can also be referred to as artificial T cell receptors, chimeric T cell receptors, chimeric immunoreceptors, and chimeric antigen receptors (CARs). These CARs are engineered receptors that can graft an arbitrary specificity onto an immune receptor cell. The term Chimeric antigen receptors or "CARs" are also considered by some investigators to include the antibody or antibody fragment, the spacer, signaling domain, and transmembrane region. However, due to the surprising effects of modifying the different components or domains of the CAR described herein, such as the epitope binding region (for example, antibody fragment, scFv, or portion thereof), spacer, transmembrane domain, and/or signaling domain), the components of the CAR are frequently distinguished throughout this disclosure in terms of independent elements. The variation of the different elements of the CAR can, for example, lead to stronger binding affinity for a specific epitope or antigen. "Co-stimulatory domain," as the term is used herein refers to a signaling moiety that provides to T cells a signal which, in addition to the primary signal provided by for instance the CD3 zeta chain of the TCR/CD3 complex, mediates a T cell response, including, but not limited to, activation, proliferation, differentiation, cytokine secretion, and the like. A co-stimulatory domain can include all or a portion of, but is not limited to, CD27, CD28, 4-1BB, OX40, CD30, CD40, ICOS, lymphocyte function-associated antigen-1 (LFA-1), CD2, CD7, LIGHT, NKG2C, B7-H3, or a ligand that specifically binds with CD83. In some alternatives, the co-stimulatory domain is an intracellular signaling domain that interacts with other intracellular mediators to mediate a cell response including activation, proliferation, differentiation and cytokine secretion, and the like. "Coding for" are used herein refers to the property of specific sequences of nucleotides in a polynucleotide, such as a gene, a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system. A "nucleic acid sequence coding for a polypeptide" includes all nucleotide sequences that are degenerate versions of each other and that code for the same amino acid sequence.

"Conditional" or "Inducible" as used herein refer to the nucleic acid construct that includes a promoter that provides for gene expression in the presence of an inducer and does not substantially provide for gene expression in the absence of the inducer.

"Constitutive" as used herein refer to the nucleic acid construct that includes a promoter that is constitutive providing for expression of a polypeptide that is continuously produced.

"Specific" or "Specificity" can refer to the characteristic of a ligand for the binding partner or alternatively, the binding partner for the ligand, and can include complementary shape, charge and hydrophobic specificity for binding. Specificity for binding can include stereospecificity, regioselectivity and chemoselectivity. In some alternatives, a method of making a nucleic acid encoding a chimeric antigen receptor is provided such that a nucleic acid encoding a chimeric antigen receptor is generated.

"Regulate" or "modulate" as described herein, refers to the act of controlling a biological process, or to exert a modifying or controlling influence on a biological or cellular process or pathway. In some alternatives, a system for inducible expression of a chimeric antigen receptor is provided, wherein the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte, a polynucleotide coding for a polypeptide spacer, wherein the spacer is optimized, a polynucleotide coding for a transmembrane domain, and d) a polynucleotide coding for an intracellular signaling domain, and b) a second nucleic acid comprising a second promoter operably linked to nucleic acid coding for a transcriptional activator for the inducible promoter. In some alternatives, modulation comprises modulation of cellular differentiation and apoptosis. In some alternatives, modulation comprises modulation of cellular proliferation by regulation of activity of proteins. In some alternatives, the proteins are cell cycle regulators and transcription factors. In some alternatives, the cell cycle regulators are cyclin D1, p21, p27 and/or cdc25A. In some alternatives, the transcription factors are c-Myc.

"Cytotoxic T lymphocyte" (CTL) as used herein refers to a T lymphocyte that expresses CD8 on the surface thereof (e.g., a $CD8^+$ T cell). In some alternatives such cells are preferably "memory" T cells ($T_M$ cells) that are antigen-experienced.

"Central memory" T cell (or "$T_{CM}$") as used herein refers to an antigen experienced CTL that expresses CD62L, CCR-7 and/or CD45RO on the surface thereof, and does not express or has decreased expression of CD45RA, as compared to naive cells. In some alternatives, central memory cells are positive for expression of CD62L, CCR7, CD28, CD127, CD45RO, and/or CD95, and may have decreased expression of CD54RA, as compared to naïve cells. "Effector memory" T cell (or "TEM") as used herein refers to an antigen experienced T cell that does not express or has decreased expression of CD62L on the surface thereof, as compared to central memory cells, and does not express or has a decreased expression of CD45RA, as compared to naïve cell. In some alternatives, effector memory cells are negative for expression of CD62L and/or CCR7, as compared to naïve cells or central memory cells, and may have variable expression of CD28 and/or CD45RA.

"Naïve" T cells as used herein refers to a non-antigen experienced T lymphocyte that expresses CD62L and/or CD45RA, and does not express CD45RO−, as compared to central or effector memory cells. In some alternatives, naïve CD8+ T lymphocytes are characterized by the expression of phenotypic markers of naïve T cells including CD62L, CCR7, CD28, CD127, and/or CD45RA.

"Effector" "$T_E$" T cells as used herein refers to antigen experienced cytotoxic T lymphocyte cells that do not express or have decreased expression of CD62L, CCR7, and/or CD28, and are positive for granzyme B and/or perforin, as compared to central memory or naïve T cells.

"Enriched" and "depleted" as used herein to describe amounts of cell types in a mixture refers to the subjecting of the mixture of the cells to a process or step, which results in an increase in the number of the "enriched" type and a decrease in the number of the "depleted" cells. Thus, depending upon the source of the original population of cells subjected to the enriching process, a mixture or composition may contain 60, 70, 80, 90, 95, or 99 percent or more (in number or count) of the "enriched" cells and/or 40, 30, 20, 10, 5 or 1 percent or less (in number or count) of the "depleted" cells.

"Epitope" as used herein refers to a part of an antigen or molecule that is recognized by the immune system including antibodies, T cells, and/or B cells. Epitopes usually have at least 7 amino acids and can be linear or conformational.

"Isolated," when used to describe the various polypeptides disclosed herein, means polypeptide or nucleic acid that has been identified and separated and/or recovered from a component of its natural environment. Preferably, the isolated polypeptide or nucleic acid is free of association with all components with which it is naturally associated. Contaminant components of its natural environment are materials that would typically interfere with diagnostic or therapeutic uses for the polypeptide or nucleic acid, and can include enzymes, hormones, and other proteinaceous or non-proteinaceous solutes.

"Intracellular signaling domain" as used herein refers to all or a portion of one or more domains of a molecule (here the chimeric receptor molecule) that provides for activation of a lymphocyte. Intracellular domains of such molecules mediate a signal by interacting with cellular mediators to result in proliferation, differentiation, activation and other effector functions. In some alternatives, such molecules include all or portions of CD28, CD3, or 4-1BB, or combinations thereof.

"Ligand" as used herein refers to a substance that binds specifically to another substance to form a complex. Examples of ligands include epitopes on antigens, molecules that bind to receptors, substrates, inhibitors, hormones, and/or activators. "Ligand binding domain" as used herein refers to substance or portion of a substance that binds to a ligand. Examples of ligand binding domains include antigen binding portions of antibodies, extracellular domains of receptors, and/or active sites of enzymes. "Operably linked" as used herein refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Percent (%) amino acid sequence identity" with respect to the chimeric receptor polypeptide sequences identified herein is defined as the percentage of amino acid residues in a candidate sequence that are identical with the amino acid residues in the reference sequence for each of the ligand binding domain, spacer, transmembrane domain, and/or the lymphocyte activating domain, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, % amino acid sequence identity values generated using the WU-BLAST-2 computer program [Altschul et al., Methods in Enzymology, 266:460-480 (1996)] uses several search parameters, most of which are set to the default values. Those that are not set to default values (i.e., the adjustable parameters) are set with the following values: overlap span=1, overlap fraction=0.125, word threshold (T)=11 and scoring matrix=BLOSUM62. A % amino acid sequence identity value is determined by dividing (a) the number of matching identical amino acid residues between the each or all of the polypeptide amino acid sequence of the reference chimeric receptor sequence provided in Table 2 and the comparison amino acid sequence of interest as determined by WU-BLAST-2 by (b) the total number of amino acid residues of the polypeptide of interest. In some alternatives, the percent sequence identity of amino acids or nucleic acids are determined by computer software.

"Chimeric receptor variant polynucleotide" or "chimeric receptor variant nucleic acid sequence" as used herein refers to a polypeptide-encoding nucleic acid molecule as defined below having at least 80%, 85%, 90%, or 95% nucleic acid sequence identity (or a percentage nucleic acid sequence identity within a range defined by any two of the aforementioned percentages) with the polynucleotide acid sequence shown in Table 1 or a specifically derived fragment thereof, such as polynucleotide coding for an antigen binding domain, a polynucleotide encoding a spacer domain, a polynucleotide coding for a transmembrane domain and/or a polynucleotide coding for a lymphocyte stimulatory domain. Ordinarily, a chimeric receptor variant of polynucleotide or fragment thereof will have at least 80% nucleic acid sequence identity, more preferably at least 81% nucleic acid sequence identity, more preferably at least 82% nucleic acid sequence identity, more preferably at least 83% nucleic acid sequence identity, more preferably at least 84% nucleic acid sequence identity, more preferably at least 85% nucleic acid sequence identity, more preferably at least 86% nucleic acid sequence identity, more preferably at least 87% nucleic acid sequence identity, more preferably at least 88% nucleic acid sequence identity, more preferably at least 89% nucleic acid sequence identity, more preferably at least 90% nucleic acid sequence identity, more preferably at least 91% nucleic acid sequence identity, more preferably at least 92% nucleic acid sequence identity, more preferably at least 93% nucleic acid sequence identity, more preferably at least 94% nucleic acid sequence identity, more preferably at least 95% nucleic acid sequence identity, more preferably at least 96% nucleic acid sequence identity, more preferably at least 97% nucleic acid sequence identity, more preferably at least 98% nucleic acid sequence identity and yet more preferably at least 99% nucleic acid sequence identity with the nucleic acid sequence as shown in Table or a derived fragment thereof. Variants do not encompass the native nucleotide sequence. In this regard, due to the degeneracy of the genetic code, one of ordinary skill in the art will immediately recognize that a large number of chimeric receptor variant polynucleotides having at least 80% nucleic acid sequence identity to the nucleotide sequence of Table 1 will encode a polypeptide having an amino acid sequence which is identical to the amino acid sequence of Table 2.

"Substantially purified" refers to a molecule that has 10%, 9%, 8%, 7%, 6%, 5%, 4%, 3%, 2%, or 1% or less other molecule types or other cell types. A substantially purified cell also refers to a cell, which has been separated from other cell types with which it is normally associated in its naturally occurring state. In some instances, a population of substantially purified cells refers to a homogenous population of cells.

"Not substantially found" when used in reference the presence of a tumor antigen or other molecules on normal cells refers to the percentage of a normal cell type that has the antigen or molecule, and/or the density of the antigen on the cells. In some alternatives, not substantially found means that the antigen or molecule is found on less than 50% of normal cell type and/or at a 50% less density as compared to the amount of cells or antigen found on a tumor cell or other diseased cell.

"T cells" or "T lymphocytes" as used herein can be from any mammalian, preferably primate, species, including monkeys, dogs, and humans. In some alternatives the T cells are allogeneic (from the same species but different donor) as the recipient subject; in some alternatives the T cells are autologous (the donor and the recipient are the same); in some alternatives the T cells arc syngeneic (the donor and the recipients are different but are identical twins).

"Vector" or "construct" is a nucleic acid used to introduce heterologous nucleic acids into a cell that has regulatory elements to provide expression of the heterologous nucleic acids in the cell. Vectors include but are not limited to plasmid, minicircles, yeast, and viral genomes. In some alternatives, the vectors are plasmid, minicircles, yeast, or viral genomes.

"Apoptosis" as described herein, refers to the process of programmed cell death (PCD) that can occur in multicellular organisms. Biochemical events lead to characteristic cell changes (morphology) and death. These changes include blebbing, cell shrinkage, nuclear fragmentation, chromatin condensation, and chromosomal DNA fragmentation. In apoptosis, a cell initiates intracellular apoptotic signaling in response to a stress, which can bring about cell suicide. The binding of nuclear receptors by glucocorticoids, heat, radiation, nutrient deprivation, viral infection, hypoxia and increased intracellular calcium concentration, for example, by damage to the membrane, can all trigger the release of intracellular apoptotic signals by a damaged cell. A number of cellular components, such as poly ADP ribose polymerase, can also help regulate apoptosis.

Before the actual process of cell death is precipitated by enzymes, apoptotic signals must cause regulatory proteins to initiate the apoptosis pathway. This step allows apoptotic signals to cause cell death, or the process to be stopped, should the cell no longer need to die. Several proteins are involved, but two main methods of regulation have been identified: targeting mitochondria functionality, or directly transducing the signal via adaptor proteins to the apoptotic mechanisms. Another extrinsic pathway for initiation identified in several toxin studies is an increase in calcium concentration within a cell caused by drug activity, which also can cause apoptosis via a calcium binding protease calpain.

Apoptosis can be regulated by many factors. These factors can include but are not limited to genes that can express IL-2, IL-15, Chemokine receptors, Bcl2, CA-Akt, dn-TGF-betaRIII, dn-SHP1/2, and/or PD-1CD28 chimeras. IL-15 regulates T and natural killer cell activation and proliferation. In rodent lymphocytes, IL15 was shown to prevent apoptosis by inducing an apoptosis inhibitor, BCL2L1/BCL-X (L). In humans with celiac disease, IL-15 similarly suppresses apoptosis in T-lymphocytes by inducing Bcl-2 and/or BCL-xL. Bcl-2 (B-cell lymphoma 2), encoded in humans by the BCL2 gene, is the founding member of the Bcl-2 family of regulator proteins that regulate cell death (apoptosis), by either inducing (pro-apoptotic) it or inhibiting it (anti-apoptotic). Bcl-2 is specifically considered as an important anti-apoptotic protein and is, thus classified as an oncogene. Protein kinase B (PKB), also known as Akt, is a serine/threonine-specific protein kinase that plays a key role in multiple cellular processes such as glucose metabolism, apoptosis, cell proliferation, transcription and cell migration. In some alternatives, a system for inducible expression of chimeric antigen receptor is provided, wherein the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling and b) a second nucleic acid comprising a second constitutive or inducible promoter operably linked to nucleic acid coding for a transcriptional activator for the inducible promoter. In some alternatives, the polypeptide that regulates apoptosis or modulates checkpoint signaling comprises IL-2, IL-15, Chemokine receptors, Bcl2, CA-Akt, dn-TGFbetaRIII, dn-SHP1/2 or PD-1CD28 chimeras.

"Checkpoint signaling" as described herein, blocks the cell cycle at specific transition points, checkpoints to ensure that the events of the cell cycle take please in the correct order. Checkpoint signaling can also be activated. By way of example and not of limitation, checkpoint signaling can occur by damage to the DNA so that the cell cycle does not have to proceed until the damage is repaired. "Cell cycle checkpoints" are control mechanisms in eukaryotic cells which ensure proper division of the cell. Each checkpoint serves as a potential halting point along the cell cycle, during which the conditions of the cell are assessed, with progression through the various phases of the cell cycle occurring when favorable conditions are met. Currently, there are three known checkpoints: the G1 checkpoint, also known as the restriction or start checkpoint; the G2/M checkpoint; and the metaphase checkpoint, also known as the spindle checkpoint. The biochemical pathways that restrain cell cycle transition and/or induce cell death after stress are known as cell cycle checkpoints. These checkpoints maintain the fidelity of DNA replication, repair, and division. Polypeptides that can regulate checkpoint signaling can include but are not limited to p53, p107, p130, and transcriptional repressor Rb.

"Negative checkpoint regulators" as described herein, refers to factors that can restrict the ability of T-cell responses to effectively attack tumors. They are also referred to as negative checkpoint signaling. In some alternatives, a system for inducible expression of chimeric antigen receptor is provided, wherein the system comprises a) a first nucleic acid comprising a first promoter inducible by a drug, wherein the first nucleic acid is operably linked to a polynucleotide coding for a cytokine, a chemokine receptor, a polypeptide that inhibits regulates apoptosis, or a polypeptide that modulates checkpoint signaling and b) a second nucleic acid comprising a second constitutive or inducible promoter operably linked to nucleic acid coding for a transcriptional activator for the inducible promoter. In some alternatives, the polypeptide that modulates checkpoint signaling inhibits negative checkpoint regulators. In some alternatives, the negative checkpoint regulator comprises VISTA, LAG-3 and/or TIM3.

In another example, cell cycle inhibitors mediating the growth inhibitory cues of upstream signaling pathways, the cyclin-CDK inhibitors of the Cip/Kip family p21Cip1, p27Kip1, and p57Kip2 have emerged as multifaceted proteins with functions beyond cell cycle regulation. In addition to regulating the cell cycle, Cip/Kip proteins can also play important roles in apoptosis, transcriptional regulation, cell fate determination, cell migration and cytoskeletal dynamics. A complex phosphorylation network modulates Cip/Kip protein functions by altering their subcellular localization, protein-protein interactions, and stability. These functions are essential for the maintenance of normal cell and tissue homeostasis, in processes ranging from embryonic development to tumor suppression. In some alternatives, a system for inducible expression of chimeric antigen receptor is provided, wherein the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling and b) a second nucleic acid comprising a second constitutive or inducible promoter operably linked to nucleic acid coding for a transcriptional activator for the inducible promoter. In some alternatives, the polypeptide modulates checkpoint signaling. In some alternatives, the polypeptide that modulates checkpoint signaling inhibits negative checkpoint regulators. In some alternatives, the negative checkpoint regulator comprises VISTA, LAG-3 and/or TIM3.

"T cell precursors" as described herein refers to lymphoid precursor cells that can migrate to the thymus and become T cell precursors, which do not express a T cell receptor. All T cells originate from hematopoietic stem cells in the bone marrow. Hematopoietic progenitors (lymphoid progenitor cells) from hematopoietic stem cells populate the thymus and expand by cell division to generate a large population of immature thymocytes. The earliest thymocytes express neither CD4 nor CD8, and are therefore classed as double-negative (CD4 CD8) cells. As they progress through their development, they become double-positive thymocytes (CD4 CD8), and finally mature to single-positive (CD4 CD8 or CD4 CD8) thymocytes that are then released from the thymus to peripheral tissues.

About 98% of thymocytes die during the development processes in the thymus by failing either positive selection or negative selection, whereas the other 2% survive and leave the thymus to become mature immunocompetent T cells.

The double negative (DN) stage of the precursor T cell is focused on producing a functional β-chain whereas the double positive (DP) stage is focused on producing a functional α-chain, ultimately producing a functional αβ T cell receptor. As the developing thymocyte progresses through the four DN stages (DN1, DN2, DN3, and DN4), the T cell expresses an invariant α-chain but rearranges the β-chain locus. If the rearranged β-chain successfully pairs with the invariant α-chain, signals are produced which cease rearrangement of the β-chain (and silence the alternate allele) and result in proliferation of the cell. Although these signals require this pre-TCR at the cell surface, they are dependent on ligand binding to the pre-TCR. These thymocytes will then express both CD4 and CD8 and progresses to the double positive (DP) stage where selection of the α-chain takes place. If a rearranged β-chain does not lead to any signaling (e.g. as a result of an inability to pair with the invariant α-chain), the cell may die by neglect (lack of signaling).

"Hematopoietic stem cells" or "HSC" as described herein, are precursor cells that can give rise to myeloid cells such as, for example, macrophages, monocytes, macrophages, neutrophils, basophils, eosinophils, erythrocytes, megakaryocytes/platelets, dendritic cells and lymphoid lineages (such as, for example, T-cells, B-cells, NK-cells). HSCs have a heterogeneous population in which three classes of stem cells exist, which are distinguished by their ratio of lymphoid to myeloid progeny in the blood (L/M).

This disclosure provides for a system that has an inducible component for expression of transgenes and a constitutive component for expression of transgenes. The system can be tailored to provide for regulated expression of one or more transgenes to provide for functional characteristics in the transduced cells.

In some alternatives, a transgene under the control of the inducible promoter is a chimeric antigen receptor (CAR). The inducible promoter provides for the capacity to terminate CAR expression in cells while providing for reactivation of the cells at a later date (e.g. in the case of relapse). In addition, the cycling of CAR T cells through on and off periods can minimize exhaustion and/or anergy due to chronic stimulation of the T cell receptors.

The design of the vectors also provides for additional transgenes that can enhance one or more functional characteristics of transduced cells, such as enhanced tumor potency, survival and proliferation of transduced cells. In some alternatives, these transgenes are under the control of an inducible promoter. Such transgenes include, without limitation, genes that promote survival and proliferation, genes that prevent apoptosis, and genes that that regulate checkpoint signaling. Such genes include genes encoding IL-2, IL-15, Chemokine receptors, Bcl2, CA-Akt, dn-TGF-betaRIII, dn-SHP1/2, and/or PD-1CD28 chimeras. In some alternatives, the transgenes are genes encoding IL-2, IL-15, Chemokine receptors, Bcl2, CA-Akt, dn-TGFbetaRIII, dn-SHP1/2, and/or PD-1CD28 chimeras. In some alternatives, the gene that modulates checkpoint signaling, encodes a polypeptide that inhibits negative checkpoint regulators. In some alternatives, the negative checkpoint regulator comprises VISTA, LAG-3 and/or TIM3.

The disclosure provides for a system comprising first and second nucleic acids, and vectors and host cells including such nucleic acids. Each of the first and second nucleic acids comprise a number of modular components that can be excised and replaced with other components in order to customize the system for a specific target cell. In some alternatives, the first nucleic acid includes an inducible promoter for control of the expression of the genes (e.g polynucleotide coding for a chimeric antigen receptor) in an on and off manner as needed. In other alternatives, the second nucleic acid comprises a constitutive promoter that provides for expression of a transcriptional activator. In some alternatives, the gene encodes for a chimeric antigen receptor.

Inducible System.

The disclosure provides a system useful for providing regulated expression of transgenes in cells. Such transgenes include, without limitation, T cell receptors, affinity matured T cell receptors, chimeric antigen receptors, chemokine receptors, cytokines, genes that inhibit apoptosis, and/or genes that modulate checkpoint signaling. In some alternatives, the polypeptide that modulates checkpoint signaling inhibits negative checkpoint regulators. In some alternatives, the negative checkpoint regulator comprises VISTA, LAG-3 and/or TIM3. In some alternatives, the system contains a number of modular components that provide for easy substitution of elements of the nucleic acid. In some alternatives of the system, the system provides regulation of expression of transgenes in cells. In some alternatives, the transgenes code for T cell receptors, affinity matured T cell receptors, chimeric antigen receptors, chemokine receptors, cytokines, genes that regulate apoptosis, and/or genes that modulate checkpoint signaling. In some alternatives, the gene that modulates checkpoint signaling encodes a polypeptide inhibits negative checkpoint regulators. In some alternatives, the negative checkpoint regulator comprises VISTA, LAG-3 and/or TIM3.

In some alternatives, a system for inducible expression of chimeric antigen receptor comprises: a first nucleic acid comprising a first promoter inducible by a drug, wherein the first nucleic acid is operably linked to a polynucleotide coding for a chimeric antigen receptor, the chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain; and a second nucleic acid comprising a second promoter operably linked to nucleic acid coding for a transcriptional modulator for the inducible promoter. In some alternatives, the second promoter is constitutive or inducible.

In some alternatives, a polynucleotide coding for a chimeric antigen receptor comprises a polynucleotide coding for a ligand binding domain, wherein the target molecule is a tumor specific antigen, a polynucleotide coding for a polypeptide spacer wherein the spacer is optimized; a polynucleotide coding for a transmembrane domain; and a polynucleotide coding for an intracellular signaling domain. In some alternatives, an expression vector comprises a first and/or second nucleic acid, as described herein. Polypeptides encoded by all of or a portion of the chimeric receptor nucleic acids are also included herein.

In other alternatives, a first nucleic acid comprises a first promoter inducible by a drug, wherein the first nucleic acid is operably linked to a polynucleotide coding for a gene that promotes cell survival and proliferation, a gene that regulates apoptosis, and/or a gene that modulates checkpoint signaling. Such genes include genes encoding IL-2, IL-15, Chemokine receptors, Bcl2, CA-Akt, dn-TGFbetaRIII, dn-SHP1/2, and/or PD-1CD28 chimeras. In some alternatives, the gene that modulates checkpoint signaling encodes a polypeptide that inhibits negative checkpoint regulators. In some alternatives, the negative checkpoint regulator comprises VISTA, LAG-3 and/or TIM3.

Inducible Promoters.

A system comprises a first nucleic acid comprising a first promoter inducible by a drug. By utilizing an inducible promoter, transgene expression can be turned on and off in order to avoid toxic side effects and/or to allow the cells to rest during remission. Although several inducible promoter systems are known, clinical applicability of these systems is limited due to toxic off target effects, unfavorable biodistribution and pharmacodynamics profiles, limited output dynamic range, and/or limited availability as FDA-approved commercially available pharmaceuticals. Furthermore, many of these systems use chimeric transcriptional regulators built from xenogeneic components, thus introducing the complication of immunogenicity when applying these systems to human therapeutics.

In some alternatives, a first promoter is inducible by a drug. The drug is selected based on safety record, favorable pharmacokinetic profile, tissue distribution, a low partition coefficient between the extracellular space and cytosol, low immunogenicity, low toxicities, and/or high expression in lymphocytes. In a specific alternative, a drug is selected that is FDA approved, provides for transgene expression in lymphocytes, does not activate other undesirable gene expression, and induces a promoter that does not contain any xenogeneic components. In some alternatives, the inducible promoter is activated by a transcriptional activator that interacts with a drug. The transcriptional activator is activated or able to bind to and activate the inducible promoter in the presence of the drug.

A specific alternative of a drug is a drug that binds to an estrogen receptor ligand binding domain of a transcriptional activator. In some alternatives, the drug includes tamoxifen, its metabolites, analogs, and pharmaceutically acceptable salts and/or hydrates or solvates thereof.

Tamoxifen, CAS RN: 10540-29-1, is also known as 2-(4-((1Z)-1,2-diphenyl-1-butenyl) phenoxy)-N,N-dimethyl-ethanamine, or (Z)-2-(para-(1,2-Diphenyl-1-butenyl) phenoxy)-N,N-dimethylamine (IUPAC), and has a molecular formula of $C_{26}H_{29}NO$, M.W. 371.52. Tamoxifen is a Selective Estrogen Receptor Modulator with tissue-specific activities. Tamoxifen acts as an anti-estrogen (inhibiting agent) agent in the mammary tissue, but as an estrogen (stimulating agent) in cholesterol metabolism, bone density, and cell proliferation in the endometrium. Tamoxifen is frequently administered orally as a pharmaceutically acceptable salt. For example, Tamoxifen citrate (RN 54965-24-1, M.W. 563.643) is indicated for treatment of metastatic breast cancer, and as an adjuvant for the treatment of breast cancer in women following mastectomy axillary dissection, and breast irradiation. Tamoxifen citrate is also indicated to reduce incidence of breast cancer in women at high risk for breast cancer.

Metabolites of tamoxifen in rat, mouse and human breast cancer patients, including major metabolites N-desmethyltamoxifen (RN 31750-48-8, M.W. 357.494) and 4-hydroxytamoxifen (4-OHT) (RN 68392-35-8, M.W. 387.52, Afimoxifene), are disclosed in Robinson et al., Metabolites, pharmacodynamics, and pharmacokinetics of tamoxifen in rats and mice compared to the breast cancer patient. Drug Metab Dispos January 1991 19:36-43, which is incorporated by reference herein in its entirety. Additional cytochrome P-450 metabolites are disclosed in Crewe et al., 2002, including cis-4-hydroxytamoxifen (RN 174592, M.W. 387.52; Afimoxifene, E-isomer), and 4'-hydroxytamoxifen ((Z)-4-(1-(4-(2-(dimethylamino) ethoxy)phenyl)-1-phenylbut-1-en-2-yl) phenol). See Crewe et al., 2002, Metabolism of Tamoxifen by recombinant human cytochrome P-450 enzymes: Formation of the 4-hydroxy, 4'-hydroxy and N-desmethyl metabolites and isomerization of trans-4-hydroxytamoxifen, Drug Metab Dispos, 30 (8): 869-874, FIG. 1, which is incorporated herein by reference.

Compounds with structural similarity to tamoxifen include, but are not limited to, cis-tamoxifen (RN 13002-65-8, M.W. 371.521), 4-methyltamoxifen (RN 73717-95-5, M.W. 385.548), N-desmethyltamoxifen (RN 31750-48-8, M.W. 357.494), (Z)-desethyl methyl tamoxifen (RN 15917-50-7, M.W. 357.494), (E)-desethyl methyl tamoxifen (RN 31750-45-5, M.W. 357.494), trans-4-hydoxytamoxifen (RN 68047 June 3, M.W. 387.52), Afimoxifene (RN 68392-35-8, M.W. 387.52, 4-hydroxytamoxifen), Afimoxifene, E-isomer (RN 174592-47-3, M.W. 387.52), 4-chlorotamoxifen (RN 77588-46-6, M.W. 405.966), 4-fluorotamoxifen (RN 73617-96-6, M.W. 389.511), Toremifene (RN 89778-26-7, M.W. 405.966), desethyl tamoxifen (RN 19957-51-8, M.W. 343.47), (E)-desethyl tamoxifen (RN 97151 October 5, M.W. 343.47), (Z)-desethyl tamoxifen (RN 97151 November 6, M.W. 343.47), Miproxifene (RN 129612-87-9, M.W. 429.6), 2-(p-(beta-ethyl-alpha-phenylstyryl) phenoxy)triethylamine (RN 749-86-0, M.W. 399.575), Droloxifene (RN 82413-20-5, M.W. 387.52), 4-iodo-tamoxifen (RN 116057-68-2, M.W. 497.413), dihydrotamoxifen (RN 109640-20-2, M.W. 373.537), (E)-N,N-dimethyl-2-(4-(1-(2-methylphenyl)-2-phenyl-1-butenyl) phenoxy) ethanamine (RN 97150-96-4, M.W. 385.548), or 4-hydroxytoremifene (RN 110503-62-3, M.W. 421.965); and/or pharmaceutically acceptable salts and/or hydrates or solvates thereof.

For example, citrate salts of tamoxifen, or citrate salts of compounds with structural similarity to tamoxifen, include, but are not limited to tamoxifen citrate (RN 54965-24-1, M.W. 563.64), 2-(p-(1,2-diphenyl-1-butenyl) phenoxy)-N,N-dimethylethylamine citrate (RN 7244-97-5, 563.64), (E)-tamoxifen citrate (RN 76487-65-5, M.W. 563.64), Toremifene citrate (RN 89778-27-8, M.W. 598.088), Droloxifene citrate (RN 97752-20-0, M.W. 579.64), 2-(p-(1,2-bis(p-methoxyphenyl)-1-butenyl) phenoxy)triethylamine citrate (RN 42920-39-8, M.W. 651.748), 2-(4-(1,2-diphenylethenyl) phenoxy)-N,N-diethyl-ethanamine 2-hydroxy-1,2,3-propanetricarboxylate (RN 40297-42-5, M.W. 563.643), 2-(p-(alpha-phenylstyryl) phenoxy)triethylamine citrate (RN 102433-95-4, M.W. 563.64), 2-(p-(2-(p-methoxyphenyl)-1-phenyl-1-butenyl) phenoxy)triethylamine citrate (1:1) (RN 42824-34-0, M.W. 637.72), 2-(p-(1-(p-methoxyphenyl)-2-phenylpropenyl) phenoxy)triethylamine citrate (RN 13554-24-0, M.W. 607.696), 2-(p-(alpha-(p-methoxyphenyl) styryl) phenoxy)triethylamine citrate monohydrate (RN 13542-71-7, M.W. 593.669), 2-(p-(p-methoxy-alpha-phenylphenethyl) phenoxy)triethylamine citrate (RN 16421-72-0, M.W. 595.685), alpha-(p-(2-(diethylamino) ethoxy)phenyl)-beta-ethyl-p-methoxy-alpha-phenylphenethyl alcohol citrate (1:1) (RN 35263-93-5, M.W. 639.737), 1-(p-(2-(diethylamino) ethoxy)phenyl)-2-(p-methoxyphenyl)-1-phenylethanol citrate (M.W. 611.68), alpha-p-(2-(diethylamino) ethoxy)phenyl)-beta-ethyl-alpha-(p-hydroxyphenyl)-p-methoxyphenethyl alcohol citrate (RN 35263-96-8, M.W. 655.737), and/or 2-(p-(p-methoxy-alpha-methylphenethyl) phenoxy)-triethylamine citrate (RN 15624-34-7, M.W. 533.614).

In some alternatives, an affective amount of the drug for inducing expression is an amount that provides for an increase in transgene expression over uninduced and/or basal level of expression. In some alternatives, this amount can be readily determined using known dosages and pharmacokinetic profile of the drug.

In some alternatives, the inducible promoter has a low level of basal activity. When a lentiviral vector is used, the level of basal activity in uninduced cells is 20%, 15%, 10%, 5%, 4%, 3%, 2%, 1% or less, as compared to when cells are induced to express the gene. The level of basal activity can be determined by measuring the amount of the expression of the transgene (e.g. marker gene) in the absence of the inducer (e.g. drug) using flow cytometry.

In some alternatives, the inducible promoter provides for a high level of induced activity, as compared to uninduced or basal activity. In some alternatives, the level of activity in the induced state is 2, 4, 6, 8, or 10 fold or greater than the activity level in the uninduced state. In some alternatives, transgene expression under control of the inducible promoter is turned off in the absence of a transactivator in less than 10, 8, 6, 4, 2, or 1 days excluding 0 days.

In some alternatives, an inducible promoter can be designed and/or modified to provide for a low level of basal activity, a high level of inducibility, and/or a short time for reversibility. In some alternatives, the inducible promoter is the 7×HBD/mE1b promoter. An exemplary sequence for the promoter is found in Table 12 (SEQ ID NO: 41) For example, in the 7×HBD/mE1b promoter, mutations can be made to enhance the binding of the transcriptional activator.

In some alternatives, the system employs a synthetic transcriptional activator which, in the presence of the drug (e.g. tamoxifen), binds a synthetic promoter upstream of a transgene to induce expression. In some alternatives, the transcriptional activator is TamR-tf (HEA3). The tamoxifen regulated transcription factor ("TamR-tf", also designated "HEA3") is a chimeric transcription factor composed of human subunits including the N-terminal DNA binding domain of Hepatocyte Nuclear Factor 1-alpha (HNF-la) (e.g. amino acids 1-281 of SEQ ID NO: 40) fused in frame to the mutant tamoxifen-specific ligand binding domain of the estrogen receptor ligand binding domain (ER-LBD), that is in turn fused to the p65 activation domain of NF-κB (p65). An exemplary amino acid sequence is provided in FIGS. 9A, 9B, and 9C and is identified as SEQ ID NO: 40. The mutant tamoxifen-specific ligand binding domain of the estrogen receptor ligand binding domain (ER-LBD) is found at amino acids 282-595 of the TamR-tf and has a mutation at position 521. The p65 activation domain of NF-κB (p65 or TAD) is found at amino acids 596 to 862.

In some alternatives, a system for inducible expression of a chimeric antigen receptor is provided, wherein the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain; and b) a second nucleic acid comprising a second promoter operably linked to nucleic acid coding for a transcriptional activator for the inducible promoter. In some alternatives, the drug is tamoxifen and/or its metabolites. In some alternatives, the second promoter is constitutive or inducible. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, a system for inducible expression of chimeric antigen receptor is provided, wherein the system comprises a) a first nucleic acid comprising a first promoter inducible by a drug operably linked to a polynucleotide coding for a cytokine, a chemokine receptor, a polypeptide that regulates apoptosis, or a polypeptide that modulates checkpoint signaling; and b) a second nucleic acid comprising a second promoter operably linked to nucleic acid coding for a transcriptional activator for the inducible promoter. In some alternatives, the polypeptide that modulates checkpoint signaling inhibits negative checkpoint regulators. In some alternatives, the negative checkpoint regulator comprises VISTA, LAG-3 and/or TIM3. In some alternatives, the second promoter is constitutive or inducible. In some alternatives, the second nucleic acid further comprises a polynucleotide coding for chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the first promoter is in opposite orientation to the second promoter. In some alternatives, the ligand binding domain is an antibody fragment, preferably a binding fragment thereof. In some alternatives, the ligand binding domain is single chain variable fragment. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the system employs a synthetic transcriptional activator which, in the presence of a drug binds a synthetic promoter upstream of a transgene to induce expression. In some alternatives, the transcriptional activator is TamR-tf (HEA3). In some alternatives, the drug is tamoxifen.

Additional changes can be made to the transcriptional activator to increase the properties of the transcription factor including, without limitation, altering one or more amino acids in the estrogen receptor ligand binding domain and/or altering one or more amino acids in the p65 transactivating domain. Altering amino acids in the estrogen receptor binding domain can provide for more specific binding of the drug to the transcriptional activator. An example of a transcriptional activator with altered amino acid sequence in the ER-LBD is shown in FIGS. 10A, 10B, and 10C (SEQ ID NO:43). Mutations are made at amino acid position 400, 543, and 544 of SEQ ID NO: 40. The transcriptional activator with altered sequence has increased affinity for tamoxifen or 4-OHT. Altering amino acids in the p65 transactivating domain can provide for increased expression of the transgene in the absence of activation of the transduced cells.

In the absence of tamoxifen, TamR-tf is excluded from the nucleus by binding of cytosolic heat-shock protein 90 (HSP90) to the tamoxifen binding active site and transgene expression is in the "OFF" state. Nanomolar concentrations of cytosolic tamoxifen actively outcompete HSP90 for ER-LBD binding, resulting in TamR-tf translocation to the nucleus. Upon nuclear translocation, TamR-tf is readily available to bind its restricted synthetic promoter. In the presence of tamoxifen, binding of TamR-tf to 7×HBD/EF1αp promoter induces the "ON" state of transgene expression. In some alternatives, this transcriptional regulator can be modified to provide for varying level of control of transgene expression. Amino acid substitutions in the LBD of TamR-tf (HEA-3) permit selective responsiveness to tamoxifen and its metabolites, where 4-hydroxy tamoxifen (4-OHT) is the most pharmacologically active metabolite, in regards to TamR-tf (HEA-3) activity, while lacking interaction with endogenous estrogen.

In some alternatives, the inducible promoter functions in a lentiviral construct and/or in lymphocytes.

Chimeric Antigen Receptors.

A system for expression of chimeric antigen receptor comprises: a first nucleic acid comprising a first promoter inducible by a drug, wherein the first nucleic acid is operably linked to a polynucleotide coding for a chimeric antigen receptor, the chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain. In other alternatives, another polynucleotide coding for a chimeric antigen receptor is under the control of a constitutive promoter. In some alternatives, the drug is tamoxifen.

Ligand Binding Domain.

In some alternatives, the chimeric receptor nucleic acid comprises a polynucleotide coding for a ligand binding domain. In some alternatives, the ligand binding domain specifically binds to a tumor or viral specific antigen and said ligand binding domain may be humanized. In some alternatives, a ligand binding domain, includes without limitation, receptors or portions thereof, small peptides, peptidomimetics, substrates, cytokines, and the like. In some alternatives, the ligand binding domain is an antibody or fragment thereof, preferably a binding fragment thereof, any of which may be humanized. A nucleic acid sequence coding for an antibody or antibody fragment can readily be determined. In a specific alternative, the polynucleotide codes for a single chain Fv that specifically binds CD19. In other specific alternatives, the polynucleotide codes for a single chain Fv that specifically binds HER2, CE7, hB7H3, or EGFR and, optionally, said polynucleotide encodes a humanized version thereof. The sequences of these antibodies and binding domains thereof are known to or can readily be determined by those of skill in the art.

Tumor antigens are proteins that are produced by tumor cells that elicit an immune response. The selection of the ligand binding domain of the invention will depend on the type of cancer to be treated, and can target tumor antigens or other tumor cell surface molecules. A tumor sample from a subject can be characterized for the presence of certain biomarkers or cell surface markers. For example, breast cancer cells from a subject can be positive or negative for each of Her2Neu, Estrogen receptor, and/or the Progesterone receptor. A tumor antigen or cell surface molecule is selected that is found on the individual subject's tumor cells. Tumor antigens and cell surface molecules are well known in the art and include, for example, carcinoembryonic antigen (CEA), prostate specific antigen, PSMA, Her2/neu, estrogen receptor, progesterone receptor, ephrinB2, CD19, CD20, CD22, CD23, CD123, CS-1, CE7, hB7H3, ROR1, mesothelin, c-Met, GD-2, and/or MAGE A3 TCR. In some alternatives, a target molecule is a cell surface molecule that is found on tumor cells and is not substantially found on normal tissues, or restricted in its expression to non-vital normal tissues.

In one alternative, the target molecule on the tumor comprises one or more epitopes associated with a malignant tumor. Malignant tumors express a number of proteins that can serve as target antigens for T cell receptor or chimeric receptor mediated recognition. Other target molecules belong to the group of cell transformation-related molecules such as the oncogene HER-2/Neu/ErbB2. In some alternatives, the tumor antigen is selectively expressed or overexpressed on the tumor cells as compared to control cells of the same tissue type. In other alternatives, the tumor antigen is a cell surface polypeptide.

Once a tumor cell surface molecule that might be targeted with a chimeric receptor is identified, an epitope of the target molecule is selected and characterized. Antibodies that specifically bind a tumor cell surface molecule can be prepared using methods of obtaining monoclonal antibodies, methods of phage display, methods to generate human or humanized antibodies, or methods using a transgenic animal or plant engineered to produce human antibodies. Phage display libraries of partially or fully synthetic antibodies are available and can be screened for an antibody or fragment thereof that can bind to the target molecule. Phage display libraries of human antibodies are also available. In some alternatives, antibodies specifically bind to a tumor cell surface molecule and do not cross react with nonspecific components such as bovine serum albumin or other unrelated antigens. Once identified, the amino acid sequence or polynucleotide sequence coding for the antibody can be isolated and/or determined.

Antibodies or antigen binding fragments include all or a portion of polyclonal antibodies, a monoclonal antibody, a human antibody, a humanized antibody, a synthetic antibody, a chimeric antibody, a bispecific antibody, a minibody, and a linear antibody. “Antibody fragments” comprise a portion of an intact antibody, preferably the antigen binding or variable region of the intact antibody and can readily be prepared. Examples of antibody fragments include Fab, Fab', $F(ab')_2$, and Fv fragments; diabodies; linear antibodies; single-chain antibody molecules; and multispecific antibodies formed from antibody fragments. In some alternatives the antibody fragments are Fab, Fab', $F(ab')_2$, and Fv fragments; diabodies; linear antibodies; single-chain antibody molecules; or multispecific antibodies formed from antibody fragments. Any of such aforementioned antibodies or antibody fragments can be humanized and used with the compositions and methods described herein.

In some alternatives, a number of different antibodies that bind to a particular tumor cell surface molecules can be isolated and characterized. In some alternatives, the antibodies are characterized based on epitope specificity of the targeted molecule. In addition, in some cases, antibodies that bind to the same epitope can be selected based on the affinity of the antibody for that epitope. In some alternatives, an antibody has an affinity of at least 1 mM, and preferably <50 nM. In some alternatives, the antibody has an affinity of 50 nM, 100 nM, 200 nM, 300 nM 400 nM, 500 nM, 1 uM, 100 μM, 200 μM, 300 μM, 400 uM, 500 μM, 600 μM, 700 μM, 800 μM, 900 uM or 1 mM or an affinity within a range defined by any two of the aforementioned values. In some alternatives, an antibody is selected that has a higher affinity for the epitope, as compared to other antibodies. For example, an antibody is selected that has at least a 2 fold, at least a 5 fold, at least a 10 fold, at least a 20 fold, at least a 30 fold, at least a 40 fold, or at least a 50 fold greater affinity than a reference antibody that binds to the same epitope or an affinity that is greater than a reference antibody within a range defined by any two of the aforementioned values.

In some alternatives, target molecules are CD19, CD20, CD22, CD23, CE7, hB7H3, EGFR, CD123, CS-1, ROR1, mesothelin, Her2, c-Met, PSMA, GD-2, or MAGE A3 TCR or combinations thereof. In some alternatives, the antibody or binding fragment there of specific for these target molecules is humanized.

In specific alternatives, the target antigen is CD19. A number of antibodies specific for CD19 are known to those of skill in the art and can be readily characterized for sequence, epitope binding, and affinity. In a specific alternative, the chimeric receptor construct includes a scFV sequence from a FMC63 antibody. In other alternatives, the scFV is a human or humanized ScFv comprising a variable light chain comprising a CDRL1 sequence of RASQDISKYLN (SEQ ID NO: 88), CDRL2 sequence of SRLHSGV (SEQ ID NO: 89), and a CDRL3 sequence of GNTLPYTFG (SEQ ID NO: 90). In other alternatives, the scFV is a human or humanized ScFv comprising a variable heavy chain comprising CDRH1 sequence of DYGVS (SEQ ID NO: 91), CDRH2 sequence of VIWGSETTYYNSALKS (SEQ ID NO: 92), and a CDRH3 sequence of YAMDYWG (SEQ ID NO: 93). The disclosure also contemplates variable regions that have at least 90%, 91%, 92%, 93%, 94%, 95%, 96%, 97%, 98%, or 99% amino acid sequence identity to that of the scFv for FMC63 and that have at least the same affinity for CD19.

In some alternatives, CDR regions are found within antibody regions as numbered by Kabat as follows: for the light chain; CDRL1 amino acids 24-34; CDRL2 amino acids 50-56; CDRL3 at amino acids 89-97; for the heavy chain at CDRH1 at amino acids 31-35; CDRH2 at amino acids 50-65; and for CDRH3 at amino acids 95-102. CDR regions in antibodies can be readily determined.

In specific alternatives, the target antigen is Her2. A number of antibodies specific for Her2 are known to those of skill in the art and can be readily characterized for sequence, epitope binding, and affinity. In a specific alternative, the chimeric receptor construct includes a scFV sequence from a Herceptin antibody. In other alternatives, the scFV is a human or humanized ScFv comprising a variable light chain comprising a CDRL1 sequence, CDRL2 sequence and a CDRL3 sequence of the Herceptin antibody. In other alternatives, the scFV is a human or humanized ScFv comprising a variable heavy chain comprising CDRH1 sequence, CDRH2, and a CDRH3 sequence of Herceptin. The CDR sequences can readily be determined from the amino acid sequence of Herceptin. The disclosure also contemplates variable regions that have at least 90%, 91%, 92%, 93%, 94%, 95%, 96%, 97%, 98%, or 99% amino acid sequence identity to that of the scFv for Herceptin and that have at least the same affinity for Her2.

“Humanized antibodies,” as described herein, refers to antibodies from non-human species whose protein sequences have been modified to increase their similarity to antibody variants produced naturally in humans. The process of “humanization” can be applied to monoclonal antibodies developed for administration to humans (for example, antibodies developed as anti-cancer drugs). Humanization can be desirable when the process of developing a specific antibody involves utilization of a non-human immune system (such as that in mice). The protein sequences of antibodies produced in this way are partially distinct from homologous antibodies occurring naturally in humans, and are therefore potentially immunogenic when administered to human patients. Humanized antibodies are distinct from chimeric antibodies, in that they have the protein sequences made more similar to human antibodies but can carry a larger stretch of non-human protein. A derivative of a humanized antibody can refer to a segment of an antibody or sequence that is derived from a humanized antibody. In some alternatives, the ligand binding domain comprises a humanized antibody or portion thereof. In some alternatives, the ligand binding domain comprises a scFv. In some alternatives, the scFv is a humanized scFv.

Humanization can be desirable in some alternatives for reducing the immunogenicity of monoclonal antibodies that are derived from xenogeneic sources, such as, for example, rodents. Humanization is also desirable in some alternatives so as to improve the interaction of the antibody or a fragment thereof with the human immune system. Due to the development of hybridoma technology, a large number of xenogeneic antibodies are highly immunogenic in humans, which can ultimately limit their clinical applications especially when administration may need to be repeated. Additionally, they can be rapidly removed from the circulation and can cause systemic inflammatory effects as well. Therefore humanization strategies are desirable in some alternatives to circumvent these situations. Techniques for antibody humanization are known to those skilled in the art.

In some alternatives, a polynucleotide coding for a ligand binding domain is operably linked to a polynucleotide coding for a spacer region. In some alternatives, the polynucleotide coding for a ligand binding domain can also have one or more restriction enzyme sites at the 5' and/or 3' ends of the coding sequence in order to provide for easy excision and replacement of the polynucleotide with another polynucleotide coding for a ligand binding domain coding for a different antigen or that has different binding characteristics.

For example, a restriction site, NheI, is encoded upstream of the leader sequence; and a 3' RsrII located within the hinge region allows subcloning of any desirable scFv into a chimeric receptor vector. In some alternatives, the polynucleotide is codon optimized for expression in mammalian cells.

In some alternatives, the polynucleotide coding for a ligand binding domain is operably linked to a signal peptide. In some alternatives, the signal peptide is a signal peptide for granulocyte colony stimulating factor. Polynucleotides coding for other signal peptides such as CD8 alpha can be utilized. In some alternatives, the polynucleotide codes for CD8 alpha.

In some alternatives, the polynucleotide coding for a ligand binding domain is operably linked to a promoter. A promoter is selected that provides for expression of the chimeric antigen receptor in a mammalian cell. In a specific alternative, the promoter is an inducible promoter.

A specific alternative of a polynucleotide coding for a ligand binding domain is shown in Table 1 as the scFv from an antibody that specifically binds CD19, such as FMC63. A polynucleotide encoding for a flexible linker including the amino acids GSTSGSGKPGSGEGSTKG (SEQ ID NO: 94) separates the VH and VL chains in the scFV. The amino acid sequence of the scFv including the linker is shown in Table 2. (SEQ ID NO: 11) Other CD19-targeting antibodies such as SJ25C1 and HD37 are known. (SJ25C1: Bejcek et al. Cancer Res 2005, PMID 7538901; HD37: Pezutto et al. JI 1987, PMID 2437199).

Spacer.

In some alternatives, the chimeric receptor nucleic acid comprises a polynucleotide coding for a spacer region. Typically a spacer region is found between the ligand binding domain and the transmembrane domain of the chimeric receptor. In some alternatives, a spacer region provides for flexibility of the ligand binding domain and allows for high expression levels in lymphocytes. A CD19-specific chimeric receptor having a spacer domain of 229 amino acids had less antitumor activity than a CD19-specific chimeric receptor with a short spacer region comprised of the modified IgG4 hinge only. In some alternatives, the spacer is optimized for increased T cell proliferation and/or cytokine production in response to the ligand as compared to a reference chimeric receptor.

In some alternatives, a spacer region has at least 10 to 229 amino acids, 10 to 200 amino acids, 10 to 175 amino acids, 10 to 150 amino acids, 10 to 125 amino acids, 10 to 100 amino acids, 10 to 75 amino acids, 10 to 50 amino acids, 10 to 40 amino acids, 10 to 30 amino acids, 10 to 20 amino acids, or 10 to 15 amino acids, or a length within a range defined by any two of the aforementioned lengths. In some alternatives, a spacer region has 12 amino acids or less, 119 amino acids or less, or 229 amino acids or less but greater than 1 or 2 amino acids. In some alternatives, the spacer is optimized for increased T cell proliferation and/or cytokine production in response to the ligand as compared to a reference chimeric receptor.

In some alternatives, the spacer region is derived from a hinge region of an immunoglobulin like molecule. In some alternatives, a spacer region comprises all or a portion of the hinge region from a human IgG1, human IgG2, a human IgG3, or a human IgG4, and can contain one or more amino acid substitutions. Exemplary sequences of the hinge regions are provided in Table 8. In some alternatives, a portion of the hinge region includes the upper hinge amino acids found between the variable heavy chain and the core, and the core hinge amino acids including a polyproline region. In some alternatives, the spacer is optimized for increased T cell proliferation and/or cytokine production in response to the ligand as compared to a reference chimeric receptor.

In some alternatives, hinge region sequences can be modified in one or more amino acids in order to avoid undesirable structural interactions such as dimerization. In a specific alternative, the spacer region comprises a portion of a modified human hinge region from IgG4, for example, as shown in Table 2 or Table 8 (SEQ ID NO: 21). A representative of a polynucleotide coding for a portion of a modified IgG4 hinge region is provided in Table 1. (SEQ ID NO: 4). In some alternatives, a hinge region can have at least 90%, 91%, 92%, 93%, 94%, 95%, 96%, 97%, 98%, or 99% sequence identity with a hinge region amino acid sequence identified in Table 2 or Table 8, or any other percent sequence identity between any two of the percent sequence identities listed. In a specific alternative, a portion of a human hinge region from IgG4 has an amino acid substitution in the core amino acids from CPSP to CPPC.

In some alternatives, all or a portion of the hinge region is combined with one or more domains of a constant region of an immunoglobulin. For example, a portion of a hinge region can be combined with all or a portion of a CH2 or CH3 domain or variant thereof. In some alternatives, the spacer region does not include the 47-48 amino acid hinge region sequence from CD8alpha or the spacer region consisting of an extracellular portion of the CD28 molecule.

In some alternatives, a short spacer region has 12 amino acids or less and comprises all or a portion of a IgG4 hinge region sequence or variant thereof, an intermediate spacer region has 119 amino acids or less and comprises all or a portion of a IgG4 hinge region sequence and a CH3 region or variant thereof, and a long spacer has 229 amino acids or less and comprises all or a portion of a IgG4 hinge region sequence, a CH2 region, and a CH3 region or variant thereof. In some alternatives, a short spacer region has 1, 2, 3, 4, 5, 6, 7, 8, 9, 10, 11 or 12 amino acids or a size within a range defined by any two of the aforementioned amino acid lengths. In some alternatives, a medium spacer region has 13, 20, 30, 40, 50, 60, 70, 80, 90, 100, 110 or 119 amino acids or a size within a range defined by any two of the aforementioned amino acid lengths. In some alternatives, a spacer region has 120, 130, 140, 150, 160, 170, 180, 190, 200, 210 or 219 amino acids or a size within a range defined by any two of the aforementioned amino acid lengths.

A polynucleotide coding for a spacer region can be readily prepared by synthetic or recombinant methods from the amino acid sequence. In some alternatives, a polynucleotide coding for a spacer region is operably linked to a polynucleotide coding for a transmembrane region. In some alternatives, the polynucleotide coding for the spacer region can also have one or more restriction enzyme sites at the 5' and/or 3' ends of the coding sequence in order to provide for easy excision and replacement of the polynucleotide with another polynucleotide coding for a different spacer region. In some alternatives, the polynucleotide coding for the spacer region is codon optimized for expression in mammalian cells.

In an alternative, the spacer region is a hinge region sequence from IgG1, IgG2, IgG3, or IgG4 or a portion thereof, a hinge region sequence from IgG1, IgG2, IgG3, or IgG4 in combination with all or a portion of a CH2 region or variant thereof, a hinge region sequence from IgG1, IgG2, IgG3, or IgG4 in combination with all or a portion of a CH3 region or variant thereof, and a hinge region sequence from IgG1, IgG2, IgG3, or IgG4 in combination with all or a portion of a CH2 region or variant thereof, and/or a CH3 region or variant thereof. In some alternatives, a short spacer region is a modified IgG4 hinge sequence (SEQ ID NO: 4) having 12 amino acids or less but greater than one or two amino acids, an intermediate sequence is a IgG4 hinge sequence with a CH3 sequence having 119 amino acids or less but greater than one or two amino acids (SEQ ID NO: 62); or a IgG4 hinge sequence with a CH2 and CH3 region having 229 amino acids or less but greater than one or two amino acids (SEQ ID NO: 50).

Transmembrane Domain.

In some alternatives, the chimeric receptor nucleic acid comprises a polynucleotide coding for a transmembrane domain. The transmembrane domain provides for anchoring of the chimeric receptor in the membrane.

In an alternative, the transmembrane domain that naturally is associated with one of the domains in the chimeric receptor is used. In some cases, the transmembrane domain can be selected or modified by amino acid substitution to avoid binding of such domains to the transmembrane domains of the same or different surface membrane proteins to minimize interactions with other members of the receptor complex.

The transmembrane domain can be derived either from a natural or a synthetic source. When the source is natural, the domain can be derived from any membrane-bound or transmembrane protein.

Transmembrane regions comprise at least the transmembrane region(s) of) the alpha, beta or zeta chain of the T-cell receptor, CD28, CD3, CD45, CD4, CD8, CD9, CD16, CD22; CD33, CD37, CD64, CD80, CD86, CD134, CD137 and/or CD154. In a specific alternative, the transmembrane domain comprises the amino acid sequence of the CD28 transmembrane domain as shown in Table 2. A representative polynucleotide sequence coding for the CD28 transmembrane domain is shown in Table 1 (SEQ ID NO: 5).

A transmembrane domain can be synthetic or a variant of a naturally occurring transmembrane domain. In some alternatives, synthetic or variant transmembrane domains comprise predominantly hydrophobic residues such as leucine and valine. In some alternatives, a transmembrane domain can have at least 80%, 85%, 90%, 95%, or 100% amino acid sequence identity with a transmembrane domain as shown in Table 2 or Table 6 or an amino acid sequence identity within a range defined by any two of the aforementioned values. Variant transmembrane domains preferably have a hydrophobic score of at least 50 as calculated by Kyte Doolittle.

A polynucleotide coding for a transmembrane domain can be readily prepared by synthetic or recombinant methods. In some alternatives, a polynucleotide coding for a transmembrane domain is operably linked to a polynucleotide coding for an intracellular signaling region. In some alternatives, the polynucleotide coding for a transmembrane domain can also have one or more restriction enzyme sites at the 5' and/or 3' ends of the coding sequence in order to provide for easy excision and replacement of the polynucleotide coding for a transmembrane domain with another polynucleotide coding for a different transmembrane domain. In some alternatives, the polynucleotide coding for a transmembrane domain is codon optimized for expression in mammalian cells. In some alternatives, the mammalian cells are human cells.

Intracellular Signaling Domain.

In some alternatives, the chimeric receptor nucleic acid comprises a polynucleotide coding for an intracellular signaling domain. The intracellular signaling domain provides for activation of one function of the transduced cell expressing the chimeric receptor upon binding to the ligand expressed on tumor cells. In some alternatives, the intracellular signaling domain contains one or more intracellular signaling domains. In some alternatives, the intracellular signaling domain is a portion of and/or a variant of an intracellular signaling domain that provides for activation of at least one function of the transduced cell.

Examples of intracellular signaling domains for use in a chimeric receptor of the disclosure include the cytoplasmic sequences of the CD3 zeta chain, and/or co-receptors that act in concert to initiate signal transduction following chimeric receptor engagement, as well as any derivative or variant of these sequences and any synthetic sequence that has the same functional capability. T cell activation can be said to be mediated by two distinct classes of cytoplasmic signaling sequence: those that initiate antigen-dependent primary activation and provide a T cell receptor like signal (primary cytoplasmic signaling sequences) and those that act in an antigen-independent manner to provide a secondary or co-stimulatory signal (secondary cytoplasmic signaling sequences). Primary cytoplasmic signaling sequences that act in a stimulatory manner can contain signaling motifs which are known as receptor tyrosine-based activation motifs or ITAMs. Examples of ITAM containing primary cytoplasmic signaling sequences include those derived from CD3 zeta, FcR gamma, CD3 gamma, CD3 delta, CD3 epsilon, CD5, CD22, CD79a, CD79b, and/or CD66d. In some alternatives, the primary signaling intracellular domain can have at least 80%, 85%, 90%, or 95% sequence identity to CD3zeta having a sequence provided in Table 2 or at least a percent sequence identity that is within a range defined by any two of the percent sequence identities listed. In some alternatives of the variants, of CD3 zeta retain at least one, two, three or all ITAM regions as shown in Table 7.

In a preferred alternative, the intracellular signaling domain of the chimeric receptor can be designed to comprise the CD3-zeta signaling domain by itself or combined with any other desired cytoplasmic domain(s). For example, the intracellular signaling domain of the chimeric receptor can comprise a CD3zeta chain and a costimulatory signaling region.

The costimulatory signaling region refers to a portion of the chimeric receptor comprising the intracellular domain of a costimulatory molecule. A costimulatory molecule is a cell surface molecule other than an antigen receptor or their ligands that is required for a response of lymphocytes to an antigen. Examples of such molecules include CD27, CD28, 4-1BB (CD 137), OX40, CD30, CD40, lymphocyte function-associated antigen-1 (LFA-1), CD2, CD7, LIGHT, NKG2C, B7-H3, zeta chain associated protein kinase (ZAP70), and/or a ligand that specifically binds with CD83. In some alternatives, the costimulatory signaling domain can have at least 80%, 85%, 90%, or 95% amino acid sequence identity to the intracellular domain of CD28 as shown in Table 5 or to 4-1BB having a sequence provided in Table 2 or at least a percent sequence identity that is within a range defined by any two of the percent sequence identities listed. In an alternative, a variant of the CD28 intracellular domain comprises an amino acid substitution at positions 186-187, wherein LL is substituted with GG.

The intracellular signaling sequences of the chimeric receptor can be linked to each other in a random or specified order. In some alternatives, a short oligo- or polypeptide linker, preferably between 2 and 10 amino acids in length can form the linkage. In one alternative, the intracellular signaling domains comprises all or a portion of the signaling domain of CD3-zeta or variant thereof and all or a portion of the signaling domain of CD28 or a variant thereof. In another alternative, the intracellular signaling domain comprises all or a portion of the signaling domain of CD3-zeta or variant thereof and all or a portion of the signaling domain of 4-1BB or variant thereof. In yet another alternative, the intracellular signaling domain comprises all or a portion of the signaling domain of CD3-zeta or variant thereof, all or a portion of the signaling domain of CD28 or variant thereof, and all or a portion of the signaling domain of 4-1BB or variant thereof. In a specific alternative, the amino acid sequence of the intracellular signaling domain comprising a variant of CD3zeta and a portion of the 4-1BB intracellular signaling domain is provided in Table 2. A representative nucleic acid sequence is provided in Table 1 (SEQ ID NO: 6; SEQ ID NO: 7). In some alternatives, the nucleic acid sequence comprises the sequence set forth in SEQ ID NO: 6. In some alternatives, the nucleic acid sequence comprises the sequence set forth in SEQ ID NO: 7.

In an alternative, a polynucleotide coding for an intracellular signaling domain comprises a 4-1BB intracellular domain linked to a portion of a CD3zeta domain. In other alternatives, a 4-1BB intracellular domain and a CD28 intracellular domain are linked to a portion of a CD3 zeta domain.

A polynucleotide coding for an intracellular signaling domain can be readily prepared by synthetic or recombinant methods from the amino acid sequence. In some alternatives, the polynucleotide coding for an intracellular signaling domain can also have one or more restriction enzyme sites at the 5' and/or 3' ends of the coding sequence in order to provide for easy excision and replacement of the polynucleotide coding for an intracellular signaling domain with another polynucleotide coding for a different intracellular signaling domain. In some alternatives, the polynucleotide coding for an intracellular signaling domain is codon optimized for expression in mammalian cells. In some alternatives, the mammalian cells are human cells.

Marker Sequences.

In some alternatives, the system further comprises one or more marker sequences under the control of an inducible promoter. A marker sequence can provide for selection of transduced cells, and/or identification of transduced cells. In some alternatives, the marker sequence is for a selection of transduced cells and/or identification of transduced cells. In some alternatives, the marker sequence is operably linked to a polynucleotide sequence coding for a linker sequence. In some alternatives, the linker sequence is a cleavable linker sequence. In some alternatives, the linker is a cleavable T2A linker.

A number of different marker sequences can be employed. Typically a marker sequence has a functional characteristic that allows for selection of transduced cells and/or detection of transduced cells. In some alternatives, the marker sequence is compatible with transduction of human lymphocytes. In some alternatives, the marker sequence allows for selection of transduced cells and/or detection of transduced cells.

The positive selectable marker can be a gene, which upon being introduced into the host cell, expresses a dominant phenotype permitting positive selection of cells carrying the gene. Genes of this type are known in the art, and include, inter alia, hygromycin-B phosphotransferase gene (hph) which confers resistance to hygromycin B, the amino glycoside phosphotransferase gene (neo or aph) from Tn5, which codes for resistance to the antibiotic G418, the dihydrofolate reductase (DHFR) gene, which provides resistance to methotrexate, DHFR dm (exemplary polynucleotide and amino acid sequences in FIG. 12, SEQ ID NO: 46 and SEQ ID NO: 47, the pac gene that provides resistance to puromycin, Sh ble gene which inactivates zeocin, the adenosine deaminase gene (ADA), and the multi-drug resistance (MDR) gene. Transduced cells cultured in the presence of these agents will survive and be selected.

In an alternative, a first nucleic acid further comprises a polynucleotide coding for a marker sequence. In an alternative, the marker sequence is a truncated epidermal growth factor receptor as shown in Table 2. An exemplary polynucleotide for the truncated epidermal growth factor receptor is shown in Table 1. (SEQ ID NO: 9). In some alternatives, the marker sequence is a truncated Her2 sequence. An exemplary polynucleotide and amino acid for the truncated Her2 sequences is shown in FIG. 11 and provided by SEQ ID NO: 44 and SEQ ID NO: 45, respectively.

In some alternatives, the polynucleotide coding for the marker sequence is operably linked to a polynucleotide coding for a linker sequence. In a specific alternative, the linker sequence is a cleavable linker sequence T2A, as shown in Table 2. An exemplary polynucleotide sequence coding for the T2A linker is provided in Table 1. (SEQ ID NO:8).

A polynucleotide coding for marker sequence can be readily prepared by synthetic or recombinant methods from the amino acid sequence. In some alternatives, a polynucleotide coding for a marker sequence is operably linked to a polynucleotide coding for an intracellular signaling domain. In some alternatives, the polynucleotide coding for a marker sequence can also have one or more restriction enzyme sites at the 5' and/or 3' ends of the coding sequence in order to provide for easy excision and replacement of the polynucleotide coding for a marker sequence with another polynucleotide coding for a different marker sequence. In some alternatives, the polynucleotide coding for a marker sequence is codon optimized for expression in mammalian cells, preferably humans.

In some alternatives, two or more marker sequences can be employed. In some alternatives, a first marker sequence is under control of a constitutive promoter and provides for an indication that the transduced cell is expressing the transgene. In other alternatives, a second marker sequence is under the control of the inducible promoter and provides an indication that the transgene expression has been induced. In some alternatives, the marker under the control of the inducible promoter can be used to select for cells in which noninduced or basal expression is much lower than in other cells by selecting cells that have a lower expression of the marker sequence under the control of the inducible promoter and expand those cells for further applications.

Other Genetic Components Under Control of Inducible Promoter.

In some alternatives, the first nucleic acid comprises a polynucleotide sequence coding for genes that promote survival and proliferation, genes that prevent apoptosis, and/or genes that inhibit negative checkpoint signaling under the control of an inducible promoter. Such genes include genes encoding IL-2, IL-15, Chemokine receptors, Bcl2, CA-Akt, dn-TGFbetaRIII, dn-SHP1/2, and/or PD-1CD28 chimeras. These genes are also placed under the control of an inducible promoter as described herein. In some alternatives, the genes encode IL-2, IL-15, Chemokine receptors, Bcl2, CA-Akt, dn-TGFbetaRIII, dn-SHP1/2, and/or PD-1CD28 chimeras. In some alternatives, the gene that modulates checkpoint signaling encodes a polypeptide that inhibits negative checkpoint regulators. In some alternatives, the negative checkpoint regulator comprises VISTA, LAG-3 and/or TIM3.

In some alternatives, a first nucleic acid comprises a first inducible promoter linked to a polynucleotide coding for a cytokine or chemokine receptor. Chemokines, also referred to as chemotactic cytokines, are a group of structurally related proteins that regulate cell trafficking of lymphocytes. In some alternatives, the chemokines are homeostatic or inflammatory. Chemokine receptors include CCR2, CCR7, or CCR15. Cytokines include interleukins such as IL2, IL-12, IL-7, and/or Il-15, interferons, such as interferon 8, tumor necrosis factor, and a TLR4 agonist. In some alternatives, the chemokine receptors comprise CCR2, CCR7, and/or CCR15. In some alternatives, the chemokine receptors include CCR2, CCR7, or CCR15. In some alternatives, the cytokines include interleukins, wherein the interleukins are IL2, IL-12, IL-7 and/or Il-15 or interferons, wherein the interferons comprise interferon 8, tumor necrosis factor, or a TLR4 agonist.

In some alternatives, a first nucleic acid comprises a first inducible promoter linked to a polynucleotide coding for a polypeptide that regulates apoptosis. In some alternatives, genes that inhibit apoptosis include, for example, Bcl2, and/or CA-Akt. In some alternatives, the polypeptide is Bcl2 or CA-Akt.

In some alternatives, a first nucleic acid comprises a first inducible promoter linked to a polynucleotide coding for a polypeptide that modulates checkpoint signaling. Such genes include dn-TGFbetaRIII, dn-SHP1/2, and/or PD-1CD28 chimeras. In some alternatives, the polypeptide is dn-TGFbetaRIII, dn-SHP1/2, and/or PD-1CD28 chimeras. In some alternatives, the polypeptide that modulates checkpoint signaling inhibits negative checkpoint regulators. In some alternatives, the negative checkpoint regulator comprises VISTA, LAG-3 and/or TIM3.

Exemplary sequences for polynucleotides encoding these genes are found at:

| Gene | A.A. Accession | A.A. gI | N.A. Accession | N.A. gI |
|---|---|---|---|---|
| CCR2 | P41597 | 1168965 | NM_001123041 | 183979979 |
| CCR7 | P32248 | 1352335 | NM_001838 | 299473754 |
| IL-2 | AAH70338 | 47682793 | BC070338 | 47682792 |
| IL-12 | AAD16432 | 4323579 | AF101062 | 4323578 |
| IL-7 | AAC63047 | 386824 | NM_000880 | 315467865 |
| IL-15 | CAG46804 | 49456967 | CR542007 | 49456966 |
| IFN-g | EAW97180 | 119617586 | EAW97180 | 119617586 |
| TNF | NP_000585 | 25952111 | NM_000594 | 395132451 |
| Bcl2 | AAH27258 | 20072668 | BC027258 | 20072667 |
| CA-Akt | NP_001014432 | 62241015 | NM_001014432 | 62241014 |
| TGFbeta Receptor III | Q03167 | 311033535 | NM_003243 | 307574689 |
| SHP1 | NP_002822 | 18104989 | NM_002831 | 166064064 |
| SHP2 | Q06124 | 84028248 | NM_002834 | 33356176 |
| PD-1 | NP_001129245 | 209413749 | NM_001135773 | 209413748 |
| CD28 | AAA51945 | 180092 | NM_006139 | 340545506 |

Any number of nucleic acids can be placed under the control of an inducible promoter including those coding for chimeric antigen receptor, a marker sequences, a cytokine, a chemokine, an inhibitor of apoptosis, and/or an inhibitor of negative checkpoint signaling. In some alternatives, one or more inducible promoters can be utilized to provide for an adequate expression level of each of the nucleic acids. In some alternatives, constructs can be prepared with a gene such as a cytokine under the control of an inducible promoter and a construct comprising a chimeric antigen receptor under the control of a constitutive promoter. Such constructs are useful to provide for cell survival and proliferation of transduced cells, for example lymphocytes expressing a chimeric antigen receptor.

Constitutive Promoter Systems.

In other alternatives, a system comprises a second nucleic acid that comprises a constitutive promoter or a second inducible promoter linked to a transcriptional activator. In other alternatives, a system comprises a second nucleic acid that comprises a promoter linked to a transcriptional activator. In some alternatives, the promoter is a constitutive promoter or an inducible promoter. In some alternatives, a constitutive promoter includes EF1α promoter, actin promoter, the myosin promoter, the hemoglobin promoter, and the creatine kinase promoter. In some alternatives, viral promoters such as the CMV promoter are excluded. In some alternatives, the constitutive promoter can be linked to one or more of a polynucleotide coding for marker, or a chimeric antigen receptor as described herein.

Constitutive Promoters.

A constitutive promoter provides for continuous gene expression of the gene under the control of the promoter. In some alternatives, the constitutive promoter is a promoter that provides for gene expression in a lentiviral construct and/or in lymphocytes. In some alternatives, the promoter is not derived from a xenogenic source such as a plant or a virus.

In a specific alternative, the constitutive promoter comprises EF1α promoter, actin promoter, the myosin promoter, the hemoglobin promoter, and/or the creatine kinase promoter. In some alternatives, viral promoters such as the CMV promoter are excluded.

Transcriptional Activators.

In some alternatives, the constitutive promoter is operably linked to a transcriptional activator. In some alternatives, the transcriptional activator activates an inducible promoter in the presence of the inducer (e.g. drug).

In some alternatives, an inducible promoter is induced in the presence of a transcriptional activator. In some alternatives, the transcriptional activator preferentially binds to the promoter in the presence of the drug. In some alternatives, the transcriptional activator is TamR-tf (HEA3). Modification of the transcriptional activator can be made in the amino acid sequence that can affect the ability of activator to bind to the drug, the promoter, or both. For example, binding in the ER ligand binding domain would affect the binding of the drug to the transcriptional activator.

In some alternatives, the system employs a synthetic transcriptional activator which, in the presence of the drug (e.g. tamoxifen), binds a synthetic promoter upstream of a transgene to induce expression. In some alternatives, the transcriptional activator is TamR-tf (HEA3). The tamoxifen regulated transcription factor ("TamR-tf", also designated "HEA3") is a chimeric transcription factor composed of human subunits including the N-terminal DNA binding domain of Hepatocyte Nuclear Factor 1-alpha (HNF-1a) (e.g. amino acids 1-281 of SEQ ID NO: 40) fused in frame to the mutant tamoxifen-specific ligand binding domain of the estrogen receptor ligand binding domain (ER-LBD), that is in turn fused to the p65 activation domain of NF-κB (p65). An exemplary amino acid sequence is provided in FIGS. 9A, 9B and 9C and is identified as SEQ ID NO: 40. The mutant tamoxifen-specific ligand binding domain of the estrogen receptor ligand binding domain (ER-LBD) is found at amino acids 282-595 of the TamR-tf and has a mutation at position 521. The p65 activation domain of NF-κB (p65 or TAD) is found at amino acids 596 to 862.

Additional changes can be made to the transcriptional activator to increase the properties of the transcription factor including, without limitation, altering one or more amino acids in the estrogen receptor ligand binding domain and/or altering one or more amino acids in the p65 transactivating domain. Altering amino acids in the estrogen receptor binding domain can provide for more specific binding of the drug to the transcriptional activator. An example of a transcriptional activator with altered sequence in the ER-LBD is shown in FIGS. 10A, 10B and 10C (SEQ ID NO:43). Mutations are made at amino acid position 400, 543, and 544 of SEQ ID NO: 40. The transcriptional activator with altered sequence has increased affinity for tamoxifen or 4-OHT. Altering amino acids in the p65 transactivating domain can provide for increased expression of the transgene in the absence of activation of the transduced cells.

Marker.

In some alternatives, the constitutive promoter is operably linked to a polynucleotide coding for a marker polypeptide. Such marker polypeptides are described herein, and include EGFRt, Her2t, and/or DHFRdm.

Chimeric Antigen Receptor.

In some alternatives, the constitutive promoter is operably linked to a polynucleotide coding for a chimeric antigen receptor. In some alternatives, the chimeric antigen receptor comprises a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain. In some alternatives, the spacer is optimized to provide for increased T cell proliferation and/or cytokine production in response to the ligand as compared to a reference chimeric receptor. Examples of chimeric antigen receptors are described herein.

Vectors.

A variety of vector combinations can be constructed to provide for efficiency of transduction and transgene expression. In some alternatives, the vector is a dual packaged or single (all in one) viral vector. In other alternatives, the vectors can include a combination of viral vectors and plasmid vectors. Other viral vectors include foamy virus, adenoviral vectors, retroviral vectors, and lentiviral vectors. In some alternatives, the vector is a lentiviral vector. In some alternatives, the vector is a foamy viral vector, adenoviral vectors, retroviral vectors or lentiviral vectors.

In some alternatives, a plasmid vector or a viral vector comprises a first nucleic acid comprising an inducible promoter linked to a polynucleotide coding for a chimeric antigen receptor. In some alternatives, a plasmid vector or viral vector comprises a first nucleic acid sequence comprising a polynucleotide coding for a gene that enhances cell survival or proliferation, a gene that regulates apoptosis, and/or a gene that modulates checkpoint signaling. In some alternatives, the modulation of checkpoint signaling inhibits negative checkpoint regulators. In some alternatives, the negative checkpoint regulator comprises VISTA, LAG-3 and/or TIM3. Such polynucleotides code for a cytokine, or a chemokine receptor. In some alternatives, a plasmid vector or a viral vector comprises a first nucleic acid comprising an inducible promoter linked to a polynucleotide coding for a marker sequence. Marker sequences are described herein. In some alternatives, the marker sequence is compatible with transduction of human lymphocytes. In some alternatives, the marker sequence allows for selection of transduced cells and/or detection of transduced cells. In some alternatives, the marker is a gene that can include inter alia, hygromycin-B phosphotransferase gene (hph), which confers resistance to hygromycin B, the amino glycoside phosphotransferase gene (neo or aph) from Tn5, which codes for resistance to the antibiotic G418, the dihydrofolate reductase (DHFR) gene, which provides resistance to methotrexate, DHFR dm (exemplary polynucleotide and amino acid sequences in FIG. 12, SEQ ID NO:46 and SEQ ID NO:47, the pac gene that provides resistance to puromycin, Sh ble gene, which inactivates zeocin, the adenosine deaminase gene (ADA), and/or the multi-drug resistance (MDR) gene. A first nucleic acid can include a number of different polynucleotide sequences all under the control of the inducible promoter. For example, a polynucleotide coding for a chimeric antigenic receptor can be linked to a polynucleotide coding for a marker polypeptide and/or a polynucleotide coding for cytokine or chemokine receptor.

In some alternatives, a lentiviral vector comprises a second nucleic acid comprising a constitutive promoter linked to a nucleic acid sequence coding for transcriptional activator that binds to drug and activates expression of an inducible promoter. In some alternatives, a lentiviral vector with a constitutive promoter can also include a nucleic acid sequence including a marker gene, piggyback transposase, and/or a polynucleotide coding for a chimeric antigen receptor. Each element of the nucleic acid can be separated from one another with a sequence such as a T2A self-cleaving sequence. In some alternatives, the elements of the nucleic acid are separated from one another with a sequence self-cleaving sequence. In some alternatives, the self-cleaving sequence is T2A.

In other alternatives, the heterogeneous (heterogeneous to the vector, e.g. lentiviral vector) nucleic acid sequence is limited by the amount of additional genetic components that can be packaged in the vector. In some alternatives, a construct contains at least two genes heterogenous to the viral vector. In some alternatives, the construct contains no more than 4 genes heterogenous to the viral vector. The number of genes heterogenous to the viral vector that can be packaged in the vector can be determined by detecting the expression of one or more transgenes, and selecting vector constructs that provide for transduction of at least 10% of the cells and/or detectable expression levels of the transgene in at least 10% of the cells.

In some alternatives, a lentivirus is a dual packaged virus. A dual packaged virus contains at least one conditional construct comprising an inducible promoter operably linked to a polynucleotide coding for a chimeric antigen receptor. Optionally the conditional construct comprises a marker gene, a nucleic acid for a cytokine, a nucleic acid for a chemokine receptor. In some alternatives, a dual packaged lentivirus contains a constitutive construct comprising a constitutive promoter. In an alternative, the constitutive construct comprises a constitutive promoter linked to a transcriptional activator for the inducible promoter. In some alternatives, the constitutive construct also includes a marker gene and/or a polynucleotide encoding a cytokine or chemokine. In some alternatives of a system with two constructs, each construct can be packaged in a separate viral vector and the viral vectors can be mixed together for transduction in a cell population.

When the constitutive and conditional constructs both contain a marker gene, the marker gene on each construct is the same or different from one another. In some alternatives, when the constitutive and conditional constructs both contain a polynucleotide coding for a chimeric antigen receptor, the chimeric antigen receptor can be targeted to the same antigen but have different ligand binding domains, can be targeted to the same antigen but different epitopes, or can be targeted to different antigens.

In some alternatives, the vector is a minicircle. Minicircles are episomal DNA vectors that are produced as circular expression cassettes devoid of any bacterial plasmid DNA backbone. Their smaller molecular size enables more efficient transfections and offers sustained expression over a period of weeks as compared to standard plasmid vectors that only work for a few days. In some alternatives, a minicircle contains a drug inducible promoter linked to a polynucleotide coding for a chimeric antigen receptor. In some alternatives, the inducible promoter can be linked to chemokine receptor, a marker gene, and/or a cytokine. One or more minicircles can be employed. In some alternatives, a minicircle comprises an inducible promoter linked to a polynucleotide coding for a first chimeric antigen receptor, another minicircle comprises an inducible promoter linked to a polynucleotide coding for a second and different chimeric antigen receptor, and/or a minicircle comprises an inducible promoter linked to a polynucleotide coding for a chemokine receptor, a chimeric antigen receptor, and a marker gene. Each element of the constructs is separated by a nucleic acid, such as that coding for a self-cleaving T2A sequence. In some alternatives, each element of the constructs is separated by a nucleic acid, such as that coding for a self-cleaving T2A sequence. In some alternatives each minicircle differs from one another in the chimeric antigen receptor including but not limited to the spacer length and sequence, the intracellular signaling domain, and/or the marker sequence. The minicircle vector can be used with a constitutive lentivirus vector coding for a transcriptional activator for the inducible promoter. In some alternatives, the minicircle vector is used with a constitutive lentivirus vector coding for a transcriptional activator for the inducible promoter.

In some alternatives, the vector is a piggy bac transposon. The PiggyBac (PB) transposon is a mobile genetic element that efficiently transposes between vectors and chromosomes via a "cut and paste" mechanism. During transposition, the PB transposase recognizes transposon-specific inverted terminal repeat sequences (ITRs) located on both ends of the transposon vector and efficiently moves the contents from the original sites and efficiently integrates them into TTAA chromosomal sites. The powerful activity of the PiggyBac transposon system enables genes of interest between the two ITRs in the PB vector to be easily mobilized into target genomes.

In some alternatives, a PB contains a drug inducible promoter linked to a polynucleotide coding for a chimeric antigen receptor. In some alternatives, the inducible promoter can be linked to chemokine receptor, a marker gene, and/or a cytokine. One or more PB transposons can be employed. In some alternatives, a PB comprises an inducible promoter linked to a polynucleotide coding for a first chimeric antigen receptor, another PB comprises an inducible promoter linked to a polynucleotide coding for a second and different chimeric antigen receptor, and/or a PB comprises an inducible promoter linked to a polynucleotide coding for a chemokine receptor, a chimeric antigen receptor, and a marker gene. Each element of the constructs is separated by a nucleic acid, such as that coding for a self-cleaving T2A sequence. In some alternatives each PB differs from one another in the chimeric antigen receptor including but not limited to the spacer length and sequence, the intracellular signaling domain, and/or the marker sequence. The PB vector can be used with a constitutive lentivirus vector coding for a transcriptional activator for the inducible promoter and constitutive vector comprising the piggyback transposase linked to a constitutive promoter.

In some alternatives, a first nucleic acid comprising a first promoter inducible by a drug, wherein the first nucleic acid is operably linked to a polynucleotide coding for chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain; and a second nucleic acid comprising a second constitutive or inducible promoter operably linked to nucleic acid coding for a transcriptional activator for the inducible promoter. In some alternatives, the first and second nucleic acid are in a single lentivirus vector. In some alternatives, the spacer is optimized for increased T cell proliferation and/or cytokine production in response to the ligand as compared to a reference chimeric receptor.

In some alternatives, the first nucleic acid further comprises a marker gene. In some alternatives, the second nucleic acid further comprises polynucleotide coding for a second and different chimeric antigen receptor. The first and second chimeric antigen receptor can differ from one another in the ligand binding domain, the target antigen, an epitope of the target antigen, the spacer domain in length and sequence (short medium or long), and in the intracellular signaling domains.

In some alternatives, in a single lentivirus construct the first and second nucleic acids can be separated by a genomic insulator nucleic acid such as the sea urchin insulator chromatin domain. In other alternatives, the inducible promoter of the first nucleic acid and the constitutive promoter of the second nucleic acid are in opposite orientation.

One or more of these vectors can be used in conjunction with one another to transduce target cells and provide for inducible expression of a chimeric antigen receptor.

Host Cells and Compositions: T Lymphocyte Populations.

The compositions described herein provide for genetically modified host cells with the vectors and/or constructs as described herein. In some alternatives, the host cells are CD4+ and/or CD8+T lymphocytes.

T lymphocytes can be collected in accordance with known techniques and enriched or depleted by known techniques such as affinity binding to antibodies such as flow cytometry and/or immunomagnetic selection. After enrichment and/or depletion steps, in vitro expansion of the desired T lymphocytes can be carried out in accordance with known techniques or variations thereof that will be apparent to those skilled in the art. In some alternatives, the T cells are autologous T cells obtained from the patient.

For example, the desired T cell population or subpopulation can be expanded by adding an initial T lymphocyte population to a culture medium in vitro, and then adding to the culture medium feeder cells, such as non-dividing peripheral blood mononuclear cells (PBMC), (e.g., such that the resulting population of cells contains at least 5, 10, 20, or 40 or more PBMC feeder cells for each T lymphocyte in the initial population to be expanded); and incubating the culture (e.g. for a time sufficient to expand the numbers of T cells). The non-dividing feeder cells can comprise gamma-irradiated PBMC feeder cells. In some alternatives, the PBMC are irradiated with gamma rays in the range of 3000 to 3600 rads to prevent cell division. In some alternatives, the PBMC are irradiated with gamma rays of 3000, 3100, 3200, 3300, 3400, 3500 or 3600 rads or any value of rads between any two endpoints of any of the listed values to prevent cell division. The order of addition of the T cells and feeder cells to the culture media can be reversed if desired. The culture can typically be incubated under conditions of temperature and the like that are suitable for the growth of T lymphocytes. For the growth of human T lymphocytes, for example, the temperature will generally be at least 25 degrees Celsius, preferably at least 30 degrees, more preferably 37 degrees. In some alternatives, the temperature for the growth of human T lymphocytes is 22, 24, 26, 28, 30, 32, 34, 36, 37 degrees Celsius or any other temperature between any two endpoints of any of the listed values.

The T lymphocytes expanded include CD8 cytotoxic T lymphocytes (CTL) and CD4 helper T lymphocytes that can be specific for an antigen present on a human tumor or a pathogen. In some alternatives, the cells include precursor T cells. In some alternatives, the cells are hematopoietic stem cells.

In some alternatives, the expansion method can further comprise adding non-dividing EBV-transformed lymphoblastoid cells (LCL) as feeder cells. LCL can be irradiated with gamma rays in the range of 6000 to 10,000 rads. In some alternatives, the LCL are irradiated with gamma rays in of 6000, 6500, 7000, 7500, 8000, 8500, 9000, 9500 or 10,000 rads or any amount of rads between two endpoints of any of the listed values. The LCL feeder cells can be provided in any suitable amount, such as a ratio of LCL feeder cells to initial T lymphocytes of at least 10:1.

In some alternatives, the expansion method can further comprise adding anti-CD3 and/or anti CD28 antibody to the culture medium (e.g., at a concentration of at least 0.5 ng/ml). In some alternatives, the expansion method can further comprise adding IL-2 and/or IL-15 to the culture medium (e.g., wherein the concentration of IL-2 is at least 10 units/ml).

After isolation of T lymphocytes both cytotoxic and helper T lymphocytes can be sorted into naïve, memory, and effector T cell subpopulations either before or after expansion.

CD8+ cells can be obtained by using standard methods. In some alternatives, CD8+ cells are further sorted into naïve, central memory, and effector memory cells by identifying cell surface antigens that are associated with each of those types of CD8+ cells. In some alternatives, memory T cells are present in both CD62L+ and CD62L-subsets of CD8+ peripheral blood lymphocytes. PBMC are sorted into CD62L-CD8+ and CD62L+CD8+ fractions after staining with anti-CD8 and anti-CD62L antibodies. In some alternatives, the expression of phenotypic markers of central memory $T_{CM}$ include CD45RO, CD62L, CCR7, CD28, CD3, and/or CD127 and are negative or low for granzyme B. In some alternatives, central memory T cells are CD45RO+, CD62L+, and/or CD8+ T cells. In some alternatives, effector $T_E$ are negative for CD62L, CCR7, CD28, and/or CD127, and positive for granzyme B and/or perforin. In some alternatives, naïve CD8+T lymphocytes are characterized by the expression of phenotypic markers of naïve T cells including CD62L, CCR7, CD28, CD3, CD127, and/or CD45RA.

CD4+T helper cells are sorted into naïve, central memory, and effector cells by identifying cell populations that have cell surface antigens. CD4+ lymphocytes can be obtained by standard methods. In some alternatives, naïve CD4+T lymphocytes are CD45RO−, CD45RA+, CD62L+, and/or CD4+ T cells. In some alternatives, central memory CD4+ cells are CD62L+ and/or CD45RO+. In some alternatives, effector CD4+ cells are CD62L- and/or CD45RO−.

Whether a cell or cell population is positive for a particular cell surface marker can be determined by flow cytometry using staining with a specific antibody for the surface marker and an isotype matched control antibody. A cell population negative for a marker refers to the absence of significant staining of the cell population with the specific antibody above the isotype control, positive refers to uniform staining of the cell population above the isotype control. In some alternatives, a decrease in expression of one or markers refers to loss of 1 log 10 in the mean fluorescence intensity and/or decrease of percentage of cells that exhibit the marker of at least 20% of the cells, 25% of-the cells, 30% of the cells, 35% of the cells, 40% of the cells, 45% of the cells, 50% of the cells, 55% of the cells, 60% of the cells, 65% of the cells, 70% of the cells, 75% of the cells, 80% of the cells, 85% of the cells, 90% of the cell, 95% of the cells, and 100% of the cells or any % between 20 and 100% when compared to a reference cell population. In some alternatives, a cell population positive for one or markers refers to a percentage of cells that exhibit the marker of at least 50% of the cells, 55% of the cells, 60% of the cells, 65% of the cells, 70% of the cells, 75% of the cells, 80% of the cells, 85% of the cells, 90% of the cell, 95% of the cells, or 100% of the cells or any % between 50 and 100% when compared to a reference cell population.

Whether a cell or cell population is positive for a particular cell surface marker can be determined by flow cytometry using staining with a specific antibody for the surface marker and an isotype matched control antibody. A cell population negative for a marker refers to the absence of significant staining of the cell population with the specific antibody above the isotype control, positive refers to uniform staining of the cell population above the isotype control. In some alternatives, a decrease in expression of one or markers refers to loss of 1 log 10 in the mean fluorescence intensity and/or decrease of percentage of cells that exhibit the marker of at least 20% of the cells, 25% of-the cells, 30% of the cells, 35% of the cells, 40% of the cells, 45% of the cells, 50% of the cells, 55% of the cells, 60% of the cells, 65% of the cells, 70% of the cells, 75% of the cells, 80% of the cells, 85% of the cells, 90% of the cell, 95% of the cells, and 100% of the cells or any % between 20 and 100% when compared to a reference cell population. In some alternatives, an increase refers to an increase in mean fluorescence intensity and/or to an increase in the number of cells in a cell population that are positive for one or a given marker, such as a population in which s refers to a percentage of cells that exhibit the marker of at least 50% of the cells, 55% of the cells, 60% of the cells, 65% of the cells, 70% of the cells, 75% of the cells, 80% of the cells, 85% of the cells, 90% of the cell, 95% of the cells, or 100% of the cells or any % between 50 and 100% exhibit the marker, e.g., when compared to a reference cell population.

In some alternatives, populations of CD4+ and CD8+ that are antigen specific can be obtained by stimulating naïve or antigen specific T lymphocytes with antigen. For example, antigen-specific T cell lines or clones can be generated to Cytomegalovirus antigens by isolating T cells from infected subjects and stimulating the cells in vitro with the same antigen. Naïve T cells can also be used. Any number of antigens from tumor cells can be utilized as targets to elicit T cell responses. In some alternatives, the adoptive cellular immunotherapy compositions are useful in the treatment of a disease or disorder including a solid tumor, hematologic malignancy, breast cancer or melanoma.

Modification of T Lymphocyte Populations.

In some alternatives it can be desired to introduce functional genes into the T cells to be used in immunotherapy in accordance with the present disclosure. For example, the introduced gene or genes can improve the efficacy of therapy by promoting the viability and/or function of transferred T cells; or they can provide a genetic marker to permit selection and/or evaluation of in vivo survival or migration; or they can incorporate functions that improve the safety of immunotherapy, for example, by making the cell susceptible to controlled expression of the transgene. This can be carried out in accordance with known techniques that will be apparent to those skilled in the art based upon the present disclosure.

In some alternatives, T cells are modified with a vector coding for drug inducible chimeric receptors as described herein. In some alternatives, cells are modified with a vector comprising a polynucleotide coding for a chimeric antigen receptor under control of an inducible promoter. In other alternatives, cells are modified with a vector comprising a polynucleotide coding for a cytokine, chemokine receptor, a gene that regulates apoptosis, or a gene that modulates checkpoint signaling under the control of an inducible promoter. In some alternatives, the T cells are obtained from the subject to be treated, in other alternatives, the lymphocytes are obtained from allogeneic human donors, preferably healthy human donors. In some alternatives, the modulation of checkpoint signaling inhibits negative checkpoint regulators. In some alternatives, the negative checkpoint regulator comprises VISTA, LAG-3 and/or TIM3.

Chimeric receptors can be constructed with a specificity for any cell surface marker by utilizing antigen binding fragments or antibody variable domains of, for example, antibody molecules. The antigen binding molecules can be linked to one or more cell signaling modules. In some alternatives, cell signaling modules include CD3 transmembrane domains, CD3 intracellular signaling domains, and/or CD28 transmembrane domains. In some alternatives, the intracellular signaling domain comprises a CD28 transmembrane and signaling domain linked to a CD3 zeta intracellular domain. In some alternatives, a chimeric receptor can also include a transduction marker such as tEGFR.

In some alternatives, the same or a different chimeric receptor can be introduced into each of population of CD4+ and/or CD8+T lymphocytes. In some alternatives, the chimeric receptor in each of these populations has a ligand binding domain that specifically binds to the same ligand on the tumor or infected cell or a different antigen or epitope. The cellular signaling modules can differ. In some alternatives, the intracellular signaling domain of the CD8+ cytotoxic T cells is the same as the intracellular signaling domain of the CD4+ helper T cells. In other alternatives, the intracellular signaling domain of the CD8+ cytotoxic T cells is different than the intracellular signaling domain of the CD4+ helper T cells.

In some alternatives each of the CD4 or CD8 T lymphocytes can be sorted into naïve, central memory, effector memory or effector cells prior to transduction, as described herein. In some alternatives, each of the CD4 or CD8 T lymphocytes can be sorted into naïve, central memory, effector memory, or effector cells after transduction.

As described herein, in some alternatives, naïve CD4+ cells are CD45RO−, CD45RA+, CD62L+, and/or CD4+ positive T cells. In some alternatives, central memory CD4+ cells are CD62L positive and/or CD45RO positive. In some alternatives, effector CD4+ cells are CD62L negative and/or CD45RO positive. Each of these populations can be independently modified with a chimeric receptor.

As described, in some alternatives, memory T cells are present in both CD62L+ and CD62L-subsets of CD8+ peripheral blood lymphocytes. PBMC are sorted into CD62L-CD8+ and CD62L+CD8+ fractions after staining with anti-CD8 and anti-CD62L antibodies. In some alternatives, the expression of phenotypic markers of central memory T cells (TCM) include CD62L, CCR7, CD28, CD3, and/or CD127 and are negative or low for granzyme B. In some alternatives, central memory T cells are CD45RO+, CD62L+, and/or CD8+ T cells. In some alternatives, effector T cells ($T_E$) are negative for CD62L, CCR7, CD28, and/or CD127, and positive for granzyme B and/or perforin. In some alternatives, naïve CD8+T lymphocytes are characterized by CD8+, CD62L+, CD45RO+, CCR7+, CD28+ CD127+, and/or CD45RO+. Each of these populations can be independently modified with a chimeric receptor.

Various transduction techniques have been developed which utilize recombinant infectious virus particles for gene delivery. This represents a currently preferred approach to the transduction of T lymphocytes of the present invention. The viral vectors, which have been used in this way include virus vectors derived from simian virus 40, adenoviruses, adeno-associated virus (AAV), lentiviral vectors, and/or retroviruses. Thus, gene transfer and expression methods are numerous but essentially function to introduce and express genetic material in mammalian cells. Several of the above techniques have been used to transduce hematopoietic or lymphoid cells, including calcium phosphate transfection, protoplast fusion, electroporation, and infection with recombinant adenovirus, adeno-associated virus and retrovirus vectors. Primary T lymphocytes have been successfully transduced by electroporation and by retroviral or lentiviral infection.

Retroviral and lentiviral vectors provide a highly efficient method for gene transfer into eukaryotic cells. Moreover, retroviral or lentiviral integration takes place in a controlled fashion and results in the stable integration of one or a few copies of the new genetic information per cell.

It is contemplated that overexpression of a stimulatory factor (for example, a lymphokine or a cytokine) can be toxic to the treated individual. Therefore, it is within the scope of the invention to include gene segments that cause the T cells of the invention to be susceptible to negative selection in vivo. By “negative selection” is meant that the infused cell can be eliminated as a result of a change in the in vivo condition of the individual. The negative selectable phenotype can result from the insertion of a gene that confers sensitivity to an administered agent, for example, a compound. Negative selectable genes are known in the art, and include, inter alia the following: the Herpes simplex virus type I thymidine kinase (HSV-I TK) gene, which confers ganciclovir sensitivity; the cellular hypoxanthine phosphribosyltransferase (HPRT) gene, the cellular adenine phosphoribosyltransferase (APRT) gene, and bacterial cytosine deaminase.

In some alternatives it can be useful to include in the T cells a positive marker that enables the selection of cells of the negative selectable phenotype in vitro. The positive selectable marker can be a gene that upon being introduced into the host cell expresses a dominant phenotype permitting positive selection of cells carrying the gene. Genes of this type are known in the art, and include, inter alia, hygromycin-B phosphotransferase gene (hph), which confers resistance to hygromycin B, the amino glycoside phosphotransferase gene (neo or aph) from Tn5, which codes for resistance to the antibiotic G418, the dihydrofolate reductase (DHFR) gene, the adenosine deaminase gene (ADA), and/or the multi-drug resistance (MDR) gene.

A variety of methods can be employed for transducing T lymphocytes, as is well known in the art. In some alternatives, transduction is carried out using lentiviral vectors.

In some alternatives, CD4+ and CD8+ cells each can separately be modified with an expression vector encoding a chimeric receptor to form defined populations. In some alternatives, cells can be separately modified with a vector comprising a polynucleotide under the control of a constitutive promoter and a vector comprising a polynucleotide coding for a cytokine or chemokine receptor under control of an inducible promoter.

In some alternatives, these cells are then further sorted into subpopulations of naïve, central memory and effector cells as described above, by sorting for cell surface antigens unique to each of those cell populations. In addition, CD4+ or CD8+ cell populations can be selected by their cytokine profile or proliferative activities. For example, CD4+T lymphocytes that have enhanced production of cytokines such as IL-2, IL-4, IL-10, TNFα, and/or IFNγ, as compared to sham transduced cells or transduced CD8+ cells when stimulated with antigen can be selected. In other alternatives, naïve or central memory CD4+ T cells that have enhanced production of IL-2 and/or TNFα are selected. Likewise, CD8+ cells that have enhanced IFNγ production are selected, as compared to sham transduced CD8+ cells.

In some alternatives, CD4+ and CD8+ cells are selected that are cytotoxic for antigen bearing cells. In some alternatives, CD4+ are expected to be weakly cytotoxic as compared to CD8+ cells. In a preferred alternative, transduced lymphocytes, such as CD8+ central memory cells, are selected that provide for tumor cell killing in vivo using an animal model established for the particular type of cancer.

In yet other alternatives, transduced chimeric receptor expressing T cells are selected that can persist in vivo using an animal model established for the particular type of cancer. In some alternatives, transduced chimeric receptor CD8+ central memory cells with a short spacer region have been shown to persist in vivo after introduction into the animal for 3 days or more, 10 days or more, 20 days or more, 30 days or more, 40 days or more, or 50 days or more.

The disclosure contemplates that combinations of CD4+ and CD8+ T cells will be utilized in the compositions. In one alternative, combinations of chimeric receptor transduced CD4+ cells can be combined with chimeric receptor transduced CD8+ cells of the same ligand specificity or combined with CD8 T cells that are specific for a distinct tumor ligand. In other alternatives, chimeric receptor transduced CD8+ cells are combined with chimeric receptor transduced CD4+ cells specific for a different ligand expressed on the tumor. In yet another alternative, chimeric receptor modified CD4+ and CD8+ cells are combined. In some alternatives CD8+ and CD4+ cells can be combined in different ratios for example, a 1:1 ratio of CD8+ and CD4+, a ratio of 10:1 of CD8+ to CD4+, or a ratio of 100:1 of CD8+ to CD4+, or any other ratio of CD8+ to CD4+ that is between any of the listed ratios. In some alternatives, the combined population is tested for cell proliferation in vitro and/or in vivo, and the ratio of cells that provides for proliferation of cells is selected.

After transduction and/or selection for chimeric receptor bearing cells, the cell populations are preferably expanded in vitro until a sufficient number of cells are obtained to provide for at least one infusion into a human subject, typically around 10+ cells/kg to $10^9$ cells/kg In some alternatives, the transduced cells are cultured in the presence of antigen bearing cells, anti CD3, anti CD28, and IL 2, IL-7, IL 15, or IL-21 or combinations thereof.

In some alternatives, CD4+ and CD8+ cells that proliferate in response to cytokine stimulation, antigen or tumor targets in vitro or in vivo are selected. For example, CD4+ or CD8+ transduced cells that proliferate vigorously when stimulated with antiCD3 and/or anti-CD28 are selected. In some alternatives, stimulation of transduced cells provides for enhanced transgene expression in the presence of an inducer (e.g. drug) of those trans genes under the control of an inducible promoter.

Each of the subpopulations of CD4+ and CD8+ cells can be combined with one another. In a specific alternative, modified naïve or central memory CD4+ cells are combined with modified central memory CD8+ T cells to provide a synergistic cytotoxic effect on antigen bearing cells, such as tumor cells.

Compositions.

The disclosure provides for an adoptive cellular immunotherapy composition comprising a genetically modified T lymphocyte cell preparation as described herein. In some alternatives, the T lymphocyte cell preparation comprises CD4+ T cells that have a chimeric receptor comprising an extracellular antibody variable domain specific for a ligand associated with the disease or disorder, a spacer region, a transmembrane domain, and an intracellular signaling domain of a T cell receptor or other receptors under the control of a drug inducible promoter as described herein. In other alternatives, an adoptive cellular immunotherapy composition further comprises a chimeric receptor modified tumor-specific CD8+ cytotoxic T lymphocyte cell preparation that provides a cellular immune response, wherein the cytotoxic T lymphocyte cell preparation comprises CD8+ T cells that have a chimeric receptor comprising an extracellular single chain antibody specific for a ligand associated with the disease or disorder, a spacer region, a transmembrane domain, and an intracellular signaling domain of a T cell receptor under the control of a drug inducible promoter as described herein. In some alternatives, the chimeric receptor modified T cell population of the disclosure can persist in vivo for at least 3 days or longer. In an alternative, each of these populations can be combined with one another or other cell types to provide a composition.

In some alternatives, the CD4+T helper lymphocyte cell is naïve CD4+ T cells, central memory CD4+ T cells, effector memory CD4+ T cells, or bulk CD4+ T cells. In some alternatives, CD4+ helper lymphocyte cell is a naïve CD4+ T cell, wherein the naïve CD4+ T cell comprises a CD45RO−, CD45RA+, and/or is a CD62L+CD4+ T cell.

In some alternatives, the CD8+T cytotoxic lymphocyte cell is a naïve CD8+ T cell, central memory CD8+ T cell, effector memory CD8+ T cell and/or bulk CD8+ T cell. In some alternatives, the CD8+ cytotoxic T lymphocyte cell is a central memory T cell, wherein the central memory T cell comprises a CD45RO+, CD62L+, and/or CD8+ T cell. In yet other alternatives, the CD8+ cytotoxic T lymphocyte cell is a central memory T cell and the CD4+ helper T lymphocyte cell is a naïve or central memory CD4+ T cell.

In some alternatives, the compositions comprise T cell precursors. In some alternatives, the compositions comprise hematopoietic stem cells. In some alternatives, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells or a CD4+T helper lymphocyte cell that is selected from the group consisting of naïve CD4+ T cells, central memory CD4+ T cells, effector memory CD4+ T cells, and bulk CD4+ T cells and a second host cell, wherein the second host cell is a precursor T cell. In some alternatives, the precursor T cell is a hematopoietic stem cell.

Methods.

The disclosure provides methods of making adoptive immunotherapy compositions and uses or methods of using these compositions for performing cellular immunotherapy in a subject having a disease or disorder. In some alternatives, a method of manufacturing the compositions comprises obtaining a modified naïve or central memory CD4+T helper cell, wherein the modified helper T lymphocyte cell preparation comprises CD4+ T cells that have a chimeric receptor comprising a ligand binding domain specific for a tumor cell surface molecule, a spacer domain, a transmembrane domain, and an intracellular signaling domain under control of an inducible promoter as described herein. In other alternatives, CD4+ cells have a cytokine or chemokine receptor under the control of an inducible promoter.

In another alternative, a method further comprises obtaining a modified CD8+ central memory T cell, wherein the modified central memory CD8 T lymphocyte cell preparation comprises CD8+ cells that have a chimeric receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte, a spacer domain, a transmembrane domain, and an intracellular signaling domain under control of the inducible promoter as described herein. In other alternatives, CD4+ cells have a cytokine or chemokine receptor under the control of an inducible promoter.

The drug inducible promoter in both modified CD4+ T cells and modified CD8+ cytotoxic T cells can be the same or different. In some alternatives, in one population of cells the promoter linked to the chimeric antigen receptor is a constitutive promoter and in the other population it is an inducible promoter. For example, modified CD4+ T cells that have a chimeric receptor comprising a ligand binding domain specific for a tumor cell surface molecule, a spacer domain, a transmembrane domain, and an intracellular signaling domain under control of an constitutive promoter, while the CD8+ cytotoxic T cell comprises CD8+ cells that have a chimeric receptor comprising a ligand binding domain specific for a tumor cell surface molecule, a spacer domain, a transmembrane domain, and an intracellular signaling domain under control of the inducible promoter.

In some alternatives, the polynucleotide can code for a chimeric antigen receptor that differs in the CD4+ versus the CD8+ cell population. The difference between the two constructs can include the specificity or affinity of the ligand binding domain for an antigen or epitope, the length and sequence of the spacer region, and the intracellular signaling components.

The preparation of the CD4+ and CD8+ cells that are modified with a chimeric receptor is described throughout this disclosure. Antigen specific T lymphocytes can be obtained from a patient having the disease or disorder or can be prepared by in vitro stimulation of T lymphocytes in the presence of antigen. Subpopulations of CD4+ and/or CD8+T lymphocytes that are not selected for antigen specificity can also be isolated as described herein and combined in the methods of manufacturing.

In some alternatives, the combination of cell populations can be evaluated for uniformity of cell surface makers, the ability to proliferate through at least two generations, to have a uniform cell differentiation status. Quality control can be performed by co-culturing a cell line expressing the target ligand with chimeric receptor modified T cells and the drug that induces expression of the chimeric antigen receptor to determine if the chimeric receptor modified T cells recognize the cell line using cytotoxicity, proliferation, or cytokine production assays in the presence of the inducer that are known in the field. Cell differentiation status and cell surface markers on the chimeric receptor modified T cells can be determined by flow cytometry. In some alternatives, the markers and cell differentiation status on the CD8+ cells include CD3, CD8, CD62L, CD28, CD27, CD69, CD25, PD-1, CTLA-4, CD45RO, and/or CD45RA. In some alternatives, the markers and the cell differentiation status on the CD4+ cells include CD3, CD4, CD62L, CD28, CD27, CD69, CD25, PD-1, CTLA-4 CD45RO, and/or CD45RA.

In some alternatives, the chimeric receptor modified T cells as described herein are able to persist in vivo for at least 3 days, or at least 10 days. In some alternatives, the chimeric receptor modified T cells as described herein, can proliferate in vivo through at least 2, or at least 3 generations as determined by CFSE dye dilution. Proliferation and persistence of the chimeric receptor modified T cells can be determined by using an animal model of the disease or disorder and administering the cells and determining persistence and/or proliferative capacity of the transferred cells. In other alternatives, proliferation and activation can be tested in vitro by going through multiple cycles of activation with antigen bearing cells.

The disclosure also provides methods of performing cellular immunotherapy in a subject having a disease or disorder comprising: administering a composition of lymphocytes expressing a chimeric receptor under the control of a drug inducible promoter as described herein, and administering the drug.

In some alternatives, the drug is tamoxifen, variants, derivatives, pharmaceutical salts, solvates, and hydrates thereof as described herein. In some alternatives, the drug is delivered prior to, at the same time as the composition, or at later time points after the composition has been administered.

In some alternatives, the drug is administered with the composition, and if a toxic effect of the composition is observed the drug is withdrawn until the toxic effects diminish. After the symptoms of toxicity diminish, the drug is administered again. In some alternatives, a drug can be administered again once symptoms of toxicity diminish.

In some alternatives, the drug is administered with the composition but once the subject has a decrease in the tumor load or cancer cells, the drug is withdrawn for a period of time to allow the modified cells to rest and if there is no activity of the modified cells, the modified cells are not needed because of remission of the cancer.

In other alternatives, a method comprises administering to the subject a genetically modified cytotoxic T lymphocyte cell preparation that provides a cellular immune response, wherein the cytotoxic T lymphocyte cell preparation comprises CD8+ T cells that have a chimeric receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte, a spacer domain, a transmembrane domain, and an intracellular signaling domain under the control of a drug inducible promoter as described herein, and/or a genetically modified helper T lymphocyte cell preparation that elicits direct tumor recognition and augments the genetically modified cytotoxic T lymphocyte cell preparations ability to mediate a cellular immune response, wherein the helper T lymphocyte cell preparation comprises CD4+ T cells that have a chimeric receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte, a spacer domain, a transmembrane domain, and an intracellular signaling domain under control of a constitutive or drug inducible promoter as described herein and administering the drug that induces the inducible promoter. In some alternatives, the administering of the drug is performed after administering of the composition or host cells, wherein administering is performed 1 day, 2 days, 3 days, 4 days, 5 days, 6 days, 7 days, 2 weeks, 4 weeks or two months, or any time in between any two values of time listed.

In other alternatives, a method comprises administering to the subject a genetically modified cytotoxic T lymphocyte cell preparation that provides a cellular immune response, wherein the cytotoxic T lymphocyte cell preparation comprises CD8+ T cells that have a chimeric receptor comprising a ligand binding domain specific for a tumor cell surface molecule, a spacer domain, a transmembrane domain, and an intracellular signaling domain under the control of a constitutive promoter as described herein, and/or a genetically modified helper T lymphocyte cell preparation that elicits direct tumor recognition and augments the genetically modified cytotoxic T lymphocyte cell preparations ability to mediate a cellular immune response, wherein the helper T lymphocyte cell preparation comprises CD4+ T cells that have a chimeric receptor comprising a ligand binding domain specific for a tumor cell surface molecule, a spacer domain, a transmembrane domain, and an intracellular signaling domain under control of a constitutive or drug inducible promoter as described herein and administering the drug that induces the inducible promoter. In some alternatives, the tumor specific molecule is a tumor surface molecule.

In other alternatives, a method comprises administering to the subject a genetically modified cytotoxic T lymphocyte cell preparation that provides a cellular immune response, wherein the cytotoxic T lymphocyte cell preparation comprises CD8+ T cells that express a cytokine, chemokine receptor, a polypeptide that regulates apoptosis, and/or a polypeptide that modulates checkpoint signaling under the control of an inducible promoter as described herein, and/or a genetically modified helper T lymphocyte cell preparation that elicits direct tumor recognition and augments the genetically modified cytotoxic T lymphocyte cell preparations ability to mediate a cellular immune response, wherein the helper T lymphocyte cell preparation comprises CD4+ T cells that express a cytokine, chemokine receptor, a polypeptide that regulates apoptosis, and/or a polypeptide that modulates checkpoint signaling under control of a constitutive or drug inducible promoter as described herein and administering the drug that induces the inducible promoter. In some alternatives, one or more of the cell populations expresses a chimeric antigen receptor under the control of a constitutive promoter. In some alternatives, the modulation of checkpoint signaling inhibits negative checkpoint regulators. In some alternatives, the negative checkpoint regulator comprises VISTA, LAG-3 and/or TIM3.

An effective amount of the drug for induction is an amount of the drug that provides for induction of the chimeric antigen receptor in at least 5%, at least 10%, at least 20%, at least 30%, at least 40%, at least 50%, at least 60%, at least 70%, at least 80%, at least 90%, at least 100% or any number in between any of the listed percent values of the transduced cells.

Another alternative describes a method of performing cellular immunotherapy in a subject having a disease or disorder comprising: analyzing a biological sample of the subject for the presence of a target molecule associated with the disease or disorder and administering the adoptive immunotherapy compositions described herein and administering the drug that induces the inducible promoter, wherein the chimeric receptor specifically binds to the target molecule.

Subjects that can be treated by the present invention are, in general, human and other primate subjects, such as monkeys and apes for veterinary medicine purposes. The subjects can be male or female and can be any suitable age, including infant, juvenile, adolescent, adult, and geriatric subjects.

The methods are useful in the treatment or inhibition of, for example, hematologic malignancy, melanoma, breast cancer, brain cancer, and other epithelial malignancies or solid tumors. In some alternatives, the molecule associated with the disease or disorder is an orphan tyrosine kinase receptor ROR1, Her2, EGFR, CE7, hB7H3, CD19, CD20, CD22, mesothelin, CEA, or a hepatitis B surface antigen.

Subjects that can be addressed using the methods described herein include subjects identified or selected as having cancer, including but not limited to colon, lung, liver, breast, renal, prostate, ovarian, skin (including melanoma), bone, and brain cancer, etc. Such identification and/or selection can be made by clinical or diagnostic evaluation. In some alternatives the tumor associated antigens or molecules are known, such as melanoma, breast cancer, brain cancer, squamous cell carcinoma, colon cancer, leukemia, myeloma, and/or prostate cancer. In other alternatives the tumor associated molecules can be targeted with genetically modified T cells expressing an engineered chimeric receptor. Examples include but are not limited to B cell lymphoma, breast cancer, brain cancer, prostate cancer, and/or leukemia.

Cells prepared as described above can be utilized in methods and compositions for adoptive immunotherapy in accordance with known techniques, or variations thereof that will be apparent to those skilled in the art based on the instant disclosure.

In some alternatives, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin, fetal bovine serum or other human serum components.

In some alternatives, a treatment or inhibitory effective amount of cells in the composition is a transduced CD4 or CD8 cell or at least 2 cell subsets (for example, 1 CD8+ central memory T cell subset and 1 CD4+ helper T cell subset) or is more typically greater than $10^2$ cells, and up to $10^6$, up to and including $10^8$ or $10^9$ cells and can be more than $10^{10}$ cells. The number of cells will depend upon the ultimate use for which the composition is intended as will the type of cells included therein. For example, if cells that are specific for a particular antigen are desired, then the population will contain greater than 70%, generally greater than 80%, 85% and 90-95% of such cells. For uses provided herein, the cells are generally in a volume of a liter or less, can be 500 mls or less, even 250 mls or 100 mls or less or a volume in between any two listed volume values. Hence the density of the desired cells is typically greater than 10+ cells/ml and generally is greater than $10^7$ cells/ml, generally $10^8$ cells/ml or greater. The clinically relevant number of immune cells can be apportioned into multiple infusions that cumulatively equal or exceed $10^6$, $10^7$, $10^8$, $10^8$, $10^9$, $10^{10}$ or $10^{11}$ cells or any amount of cells defined between any two endpoints of any of the listed values.

In some alternatives, the lymphocytes of the invention can be used to confer immunity to individuals. By "immunity" is meant a lessening of one or more physical symptoms associated with a response to infection by a pathogen, or to a tumor, to which the lymphocyte response is directed. The amount of cells administered is usually in the range present in normal individuals with immunity to the pathogen. Thus, the cells are usually administered by infusion, with each infusion in a range of from 2 cells, up to at least $10^6$ to $3\times10^{10}$ cells, preferably in the range of at least $10^7$ to $10^9$ cells. The T cells can be administered by a single infusion, or by multiple infusions over a range of time. However, since different individuals are expected to vary in responsiveness, the type and amount of cells infused, as well as the number of infusions and the time range over which multiple infusions are given are determined by the attending physician, and can be determined by routine examination. The generation of sufficient levels of T lymphocytes (including cytotoxic T lymphocytes and/or helper T lymphocytes) is readily achievable using the rapid expansion method of the present invention, as exemplified herein.

In some alternatives, a composition as described herein is administered to an identified or selected subject, such as a subject identified or selected as having melanoma, breast cancer, brain cancer, squamous cell carcinoma, colon cancer, leukemia, myeloma, and/or prostate cancer, intravenously, intraperitoneally, intratumorly, into the bone marrow, into the lymph node, and/or into cerebrospinal fluid. In some alternatives, the chimeric receptor engineered compositions are delivered to the site of the tumor. Alternatively, the compositions as described herein can be combined with a compound that targets the cells to the tumor or the immune system compartments and avoid sites such as the lung.

In some alternatives, the compositions as described herein are administered with chemotherapeutic agents and/or immunosuppressants. In an alternative, a patient is first administered a chemotherapeutic agent that inhibits or destroys other immune cells followed by the compositions described herein. In some cases, chemotherapy can be avoided entirely.

In some alternatives, a method comprising administering the modified T cells as described herein in combination with the inducer (e.g. inducible drug) until the tumor burden is diminished. Once the tumor burden is diminished, the inducer drug can be withdrawn in order to switch the expression of the chimeric antigen receptor off and decrease the number of T cell expressing the receptor. In other alternatives, the inducer drug can be administered at different time in order to switch the expression of the chimeric antigen receptor on in the event of a relapse or increase in tumor growth.

In other alternatives, the inducer drug can be given for a period of time of days, weeks, or months, and then withdrawn for days, weeks or months, followed by re-administration of the inducer drug for days, weeks or months to allow for cycling of the expression of the chimeric antigen receptor to avoid anergy or nonresponsiveness due to chronic stimulation of the cells.

Vector Construction and Preparation of Dual Packaged Lentivirus.

An inducible lentiviral vector encoding 7×HBD/mE1b-CD19t-her2t-T2A-epHIV7) was constructed. CD19t specific chimeric receptors were constructed using: (1) the VL and VH chain segments of the CD19-specific mAb FMC63 (SEQ ID NO: 3), linked by a (G+S) 3 linker (SEQ ID NO: 12) peptide (VL-linker-VH); (2) a spacer domain derived from IgG4-Fc Hinge only (12 AA encoded by (SEQ ID NO: 4)). Spacers contained a S→P substitution within the Hinge domain located at position 108 of the native IgG4-Fc protein; the 27 AA transmembrane domain of human CD28 (Uniprot Database: P10747, (SEQ ID NO: 14)); (4) a signaling module comprising either (i) the 41 AA cytoplasmic domain of human CD28 with an LL→GG substitution located at position 186-187 of the native CD28 protein (SEQ ID NO: 14); and/or (ii) the 42 AA cytoplasmic domain of human 4-1BB (Uniprot Database: Q07011, (SEQ ID NO: 15)); linked to (iii) the 112 AA cytoplasmic domain of isoform 3 of human CD3ζ (Uniprot Database: P20963, (SEQ ID NO: 16)).

The nucleic acid sequences coding for the CD19t were linked with sequences coding for Her2t (SEQ Id NO: 44); and the self-cleaving T2A sequence (SEQ ID NO: 8).

A conditional lentiviral vector encoding 7×HBD/mEF1ap-ZsGreen-epHIV7 was constructed. The synthetic promoter 7×HBD/mEF1ap was constructed by combining seven minimal hepatocyte nuclear family-1 (HNF-1) binding sites cloned from the human albumin promoter and the huEF1α promoter TATA box and has a sequence of (SEQ ID NO: 41). In this way, only in the presence of tamoxifen does binding of HEA-3 to 7×HBD/EF Imp promoter induce the "ON" state of transgene expression.

A conditional lentiviral vector encoding 7×HBD/mEF1ap-CD19t-T2A-DHFRdm_epHIV7 was constructed. CD19t specific chimeric receptors were constructed using: (1) the VL and VH chain segments of the CD19-specific mAb FMC63 (SEQ ID NO: 3), linked by a (G+S) 3 linker (SEQ ID NO: 12) peptide (VL-linker-VH); (2) a spacer domain derived from IgG4-Fc Hinge only (12 AA encoded by (SEQ ID NO: 4)). Spacers contained a S→P substitution within the Hinge domain located at position 108 of the native IgG4-Fc protein; the 27 AA transmembrane domain of human CD28 (Uniprot Database: P10747, (SEQ ID NO: 14)); (4) a signaling module comprising either (i) the 41 AA cytoplasmic domain of human CD28 with an LL→GG substitution located at position 186-187 of the native CD28 protein (SEQ ID NO: 14); and/or (ii) the 42 AA cytoplasmic domain of human 4-1BB (Uniprot Database: Q07011, (SEQ ID NO: 15)); linked to (iii) the 112 AA cytoplasmic domain of isoform 3 of human CD3ζ (Uniprot Database: P20963, (SEQ ID NO: 16)).

The nucleic acid sequences coding for the CD19t were linked with sequences coding for the self-cleaving T2A sequence (SEQ ID NO: 8); and DHFRdm (SEQ ID NO: 46)

The transcriptional regulator, HEA-3, is a chimeric transcription factor composed of human subunits including the N-terminal DNA binding domain of Hepatocyte Nuclear Factor 1-alpha (HNF-1α) fused in frame to the mutant tamoxifen-specific ligand binding domain of the estrogen receptor ligand binding domain (ER-LBD), that is in turn fused to the p65 activation domain of NF-κB (p65). In the absence of tamoxifen, HEA-3 is excluded from the nucleus by binding of cytosolic heat-shock protein 90 (HSP90) to the tamoxifen binding active site and transgene expression is in the "OFF" state. Nanomolar concentrations of cytosolic tamoxifen actively outcompete HSP90 for ER-LBD binding, resulting in HEA-3 translocation to the nucleus. Upon nuclear translocation, HEA-3 is readily available to bind its restricted synthetic promoter. Transcriptional responsiveness to HEA-3 in the presence of tamoxifen is achieved when transgenes are placed behind an HEA-3 responsive synthetic promoter (7×HBD/EF1mp).

A constitutive construct was constructed with a constitutive promoter EF-1 a linked to a polynucleotide coding for a transcriptional activator HEA3 (SEQ ID NO: 39) and a marker sequence EGFRt (SEQ ID NO: 9).

Human codon-optimized nucleotide sequences encoding each transgene were synthesized (LifeTechnologies, Carlsbad, CA) and cloned into the epHIV7 lentiviral vector using NheI and Not1 restriction sites. The epHIV7 lentiviral vector had been derived from the pHIV7 vector by replacing the cytomegalovirus promoter of pHIV7 with an EF-1 promoter.

The inducible CD19 chimeric receptor-encoding and the constitutive lentivirus was produced in 293T cells co-transfected with the lentiviral vector and the packaging vectors pCHGP-2, pCMV-Rev2 and pCMV-G using Calphos transfection reagent (Clontech). Medium was changed 16 hours after transfection, and lentivirus collected after 24, 48 and 72 hours.

Generation of Jurkat T-Cell Lines Expressing the CD19 Chimeric Receptors and ZsGreen when Induced with Tamoxifen.

Jurkat cells were transduced with lentiviral supernatant (MOl=3) supplemented with 1 μg/mL polybrene (Millipore) on day 3 after activation by centrifugation at 2,100 rpm for 45 minutes at 32° C. T cells were expanded in RPMI, 10% human serum, 2 mM L-glutamine and 1% penicillin-streptomycin (CTL medium), supplemented with recombinant human (rh) IL-2 to a final concentration of 50 U/mL every 48 hours.

Additional Alternatives

In some alternatives, system for inducible expression of a chimeric antigen receptor is provided, wherein the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized a polynucleotide coding for a transmembrane domain; and d) a polynucleotide coding for an intracellular signaling domain; and b) a second nucleic acid comprising a second promoter operably linked to nucleic acid coding for a transcriptional activator for the inducible promoter. In some alternatives, the spacer is optimized for increased T cell proliferation and/or cytokine production in response to the ligand as compared to a reference chimeric receptor. In some alternatives, the drug is tamoxifen and/or its metabolites. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker.

In some alternatives, a system for inducible expression of chimeric antigen receptor comprises: a first nucleic acid comprising a first promoter inducible by a drug, wherein the first nucleic acid is operably linked to a polynucleotide coding for a cytokine, a chemokine, a polypeptide that regulates apoptosis and/or a polypeptide that modulates checkpoint signaling; and a second nucleic acid comprising a second promoter operably linked to a nucleic acid coding for a transcriptional activator for the inducible promoter. In some alternatives, the second promoter is constitutive or inducible. In an exemplary alternative, the second nucleic acid further comprises a polynucleotide coding for a chimeric antigen receptor, under the control of a constitutive promoter.

In another aspect, the present disclosure provides compositions to confer and/or augment immune responses mediated by cellular immunotherapy, such as by adoptively transferring tumor-specific, subset specific genetically modified CD4+ T cells, wherein the CD4+ T cells confer and/or augment the ability of CD8+ T cells to sustain anti-tumor reactivity and increase and/or maximize tumor-specific proliferation. In some alternatives, the CD4+ cells are genetically modified to express a chimeric receptor nucleic acid and/or chimeric receptor polypeptide under the control of a regulated promoter as described herein.

In another aspect, the present disclosure provides compositions to confer and/or augment immune responses mediated by cellular immunotherapy, such as by adoptively transferring tumor-specific, subset specific genetically modified CD8+ T cells. In some alternatives, the CD8+ T cells express a chimeric receptor nucleic acid and/or chimeric receptor polypeptide under the control of a regulated promoter, as described herein.

In one alternative, the present invention provides a method of performing cellular immunotherapy in a subject having a disease or disorder by administering to the subject a genetically modified T lymphocyte cell preparation that provides a cellular immune response and administering a drug that induces a transgene in the genetically modified T lymphocyte cells.

In some alternatives, the genetically modified CD8+ and genetically modified CD4+ cell population are co-administered. In some alternatives, the T cells are autologous or allogeneic T cells. Various modifications of the above method are possible. For example, the chimeric receptor that is expressed by the CD4+ T cell and the CD8+ T cell can be the same or different.

In some alternatives, a system for inducible expression of a chimeric antigen receptor is provided, wherein the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain; and b) a second nucleic acid comprising a second promoter operably linked to nucleic acid coding for a transcriptional activator for the inducible promoter. In some alternatives, the second promoter is constitutive or inducible. In some alternatives, the drug is tamoxifen and/or its metabolites. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, the spacer is optimized for increased T cell proliferation and/or cytokine production in response to the ligand as compared to a reference chimeric receptor.

In some alternatives, a system for inducible expression of chimeric antigen receptor is provided, wherein the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling; and b) a second nucleic acid comprising a second promoter operably linked to nucleic acid coding for a transcriptional activator for the inducible promoter. In some alternatives, the polypeptide that modulates checkpoint signaling inhibits negative checkpoint regulators. In some alternatives, the negative checkpoint regulator comprises VISTA, LAG-3 and/or TIM3. In some alternatives, the second nucleic acid further comprises a polynucleotide coding for chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the spacer is optimized for increased T cell proliferation and/or cytokine production in response to the ligand as compared to a reference chimeric receptor; a polynucleotide coding for a transmembrane domain. In some alternatives, the first promoter is in opposite orientation to the second promoter. In some alternatives, the ligand binding domain is an antibody fragment. In some alternatives, the ligand binding domain is single chain variable fragment. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the second promoter is an inducible promoter or a constitutive promoter.

In some alternatives, a chimeric receptor polypeptide is provided, wherein the chimeric receptor polypeptide is coded for by a system. In some alternatives, the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte, a polynucleotide coding for a polypeptide spacer, wherein the spacer is optimized; a polynucleotide coding for a transmembrane domain, and d) a polynucleotide coding for an intracellular signaling domain, and b) a second nucleic acid comprising a second promoter operably linked to nucleic acid coding for a transcriptional activator for the inducible promoter. In some alternatives, the drug is tamoxifen and/or its metabolites. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling and b) a second nucleic acid comprising a second promoter operably linked to nucleic acid coding for a transcriptional activator for the inducible promoter. In some alternatives, the polypeptide that modulates checkpoint signaling inhibits negative checkpoint regulators. In some alternatives, the negative checkpoint regulator comprises VISTA, LAG-3 and/or TIM3. In some alternatives, the second nucleic acid further comprises a polynucleotide coding for chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain. In some alternatives, the spacer is optimized for increased T cell proliferation and/or cytokine production in response to the ligand as compared to a reference chimeric receptor. In some alternatives, the first promoter is in opposite orientation to the second promoter. In some alternatives, the ligand binding domain is an antibody fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or combinations thereof. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling; and b) a second nucleic acid comprising a second constitutive or inducible promoter operably linked to nucleic acid coding for a transcriptional activator for the inducible promoter. In some alternatives, the polypeptide that modulates checkpoint signaling inhibits negative checkpoint regulators. In some alternatives, the negative checkpoint regulator comprises VISTA, LAG-3 and/or TIM3. In some alternatives, the second nucleic acid further comprises a polynucleotide coding for chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the spacer is optimized for increased T cell proliferation and/or cytokine production in response to the ligand as compared to a reference chimeric receptor; a polynucleotide coding for a transmembrane domain. In some alternatives, the first promoter is in opposite orientation to the second promoter. In some alternatives, the ligand binding domain is an antibody fragment. In some alternatives, the ligand binding domain is single chain variable fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or combinations thereof. In some alternatives, the spacer is optimized for increased T cell proliferation and/or cytokine production in response to the ligand as compared to a reference chimeric receptor. In some alternatives, the second promoter is an inducible promoter. In some alternatives, the second promoter is constitutive promoter.

In some alternatives, a host cell is provided, wherein the host cell comprises a system. In some alternatives, the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte, a polynucleotide coding for a polypeptide spacer, wherein the spacer is optimized; a polynucleotide coding for a transmembrane domain, and d) a polynucleotide coding for an intracellular signaling domain, and b) a second nucleic acid comprising a second promoter operably linked to nucleic acid coding for a transcriptional activator for the inducible promoter. In some alternatives, the drug is tamoxifen and/or its metabolites. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling and b) a second nucleic acid comprising a second promoter operably linked to nucleic acid coding for a transcriptional activator for the inducible promoter. In some alternatives, the polypeptide that modulates checkpoint signaling inhibits negative checkpoint regulators. In some alternatives, the negative checkpoint regulator comprises VISTA, LAG-3 and/or TIM3. In some alternatives, the second nucleic acid further comprises a polynucleotide coding for chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain. In some alternatives, the spacer is optimized for increased T cell proliferation and/or cytokine production in response to the ligand as compared to a reference chimeric receptor. In some alternatives, the first promoter is in opposite orientation to the second promoter. In some alternatives, the ligand binding domain is an antibody fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or combinations thereof. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling; and b) a second nucleic acid comprising a second constitutive or inducible promoter operably linked to nucleic acid coding for a transcriptional activator for the inducible promoter. In some alternatives, the polypeptide that modulates checkpoint signaling inhibits negative checkpoint regulators. In some alternatives, the negative checkpoint regulator comprises VISTA, LAG-3 and/or TIM3. In some alternatives, the second nucleic acid further comprises a polynucleotide coding for chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the spacer is optimized for increased T cell proliferation and/or cytokine production in response to the ligand as compared to a reference chimeric receptor; a polynucleotide coding for a transmembrane domain. In some alternatives, the first promoter is in opposite orientation to the second promoter. In some alternatives, the ligand binding domain is an antibody fragment. In some alternatives, the ligand binding domain is single chain variable fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or combinations thereof. In some alternatives, the spacer is optimized for increased T cell proliferation and/or cytokine production in response to the ligand as compared to a reference chimeric receptor. In some alternatives, the second promoter is an inducible promoter. In some alternatives, the second promoter is constitutive promoter. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or combinations thereof. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the spacer is optimized for increased T cell proliferation and/or cytokine production in response to the ligand as compared to a reference chimeric receptor. In some alternatives, the host cell is a precursor T cell. In some alternatives, the precursor T cell is a hematopoietic stem cell.

In some alternatives, a composition is provided, wherein the composition comprises a host cell in a pharmaceutically acceptable excipient. In some alternatives, the host cell comprises a system. In some alternatives, the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte, a polynucleotide coding for a polypeptide spacer, wherein the spacer is optimized; a polynucleotide coding for a transmembrane domain, and d) a polynucleotide coding for an intracellular signaling domain, and b) a second nucleic acid comprising a second promoter operably linked to nucleic acid coding for a transcriptional activator for the inducible promoter. In some alternatives, the drug is tamoxifen and/or its metabolites. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling and b) a second nucleic acid comprising a second promoter operably linked to nucleic acid coding for a transcriptional activator for the inducible promoter. In some alternatives, the polypeptide that modulates checkpoint signaling inhibits negative checkpoint regulators. In some alternatives, the negative checkpoint regulator comprises VISTA, LAG-3 and/or TIM3. In some alternatives, the second nucleic acid further comprises a polynucleotide coding for chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain. In some alternatives, the spacer is optimized for increased T cell proliferation and/or cytokine production in response to the ligand as compared to a reference chimeric receptor. In some alternatives, the first promoter is in opposite orientation to the second promoter. In some alternatives, the ligand binding domain is an antibody fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or combinations thereof. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling; and b) a second nucleic acid comprising a second constitutive or inducible promoter operably linked to nucleic acid coding for a transcriptional activator for the inducible promoter. In some alternatives, the polypeptide that modulates checkpoint signaling inhibits negative checkpoint regulators. In some alternatives, the negative checkpoint regulator comprises VISTA, LAG-3 and/or TIM3. In some alternatives, the second nucleic acid further comprises a polynucleotide coding for chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the spacer is optimized for increased T cell proliferation and/or cytokine production in response to the ligand as compared to a reference chimeric receptor; a polynucleotide coding for a transmembrane domain. In some alternatives, the first promoter is in opposite orientation to the second promoter. In some alternatives, the ligand binding domain is an antibody fragment. In some alternatives, the ligand binding domain is single chain variable fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or combinations thereof. In some alternatives, the spacer is optimized for increased T cell proliferation and/or cytokine production in response to the ligand as compared to a reference chimeric receptor. In some alternatives, the second promoter is an inducible promoter. In some alternatives, the second promoter is constitutive promoter. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells and further comprises another host cell wherein the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells or a CD4+T helper lymphocyte cell that is selected from the group consisting of naïve CD4+ T cells, central memory CD4+ T cells, effector memory CD4+ T cells, and bulk CD4+ T cells and a second host cell, wherein the second host cell is a precursor T cell. In some alternatives, the precursor T cell is a hematopoietic stem cell.

In some alternatives, an in vitro method for preparing a host cell is provided wherein the method comprises a) providing a system and b) introducing the system into a separate isolated T lymphocyte population and expanding each T lymphocyte population in vitro. In some alternatives, the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte, a polynucleotide coding for a polypeptide spacer, wherein the spacer is optimized; a polynucleotide coding for a transmembrane domain, and d) a polynucleotide coding for an intracellular signaling domain, and b) a second nucleic acid comprising a second promoter operably linked to nucleic acid coding for a transcriptional activator for the inducible promoter. In some alternatives, the drug is tamoxifen and/or its metabolites. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling and b) a second nucleic acid comprising a second promoter operably linked to nucleic acid coding for a transcriptional activator for the inducible promoter. In some alternatives, the polypeptide that modulates checkpoint signaling inhibits negative checkpoint regulators. In some alternatives, the negative checkpoint regulator comprises VISTA, LAG-3 and/or TIM3. In some alternatives, the second nucleic acid further comprises a polynucleotide coding for chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain. In some alternatives, the spacer is optimized for increased T cell proliferation and/or cytokine production in response to the ligand as compared to a reference chimeric receptor. In some alternatives, the first promoter is in opposite orientation to the second promoter. In some alternatives, the ligand binding domain is an antibody fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or combinations thereof. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling; and b) a second nucleic acid comprising a second constitutive or inducible promoter operably linked to nucleic acid coding for a transcriptional activator for the inducible promoter. In some alternatives, the polypeptide that modulates checkpoint signaling inhibits negative checkpoint regulators. In some alternatives, the negative checkpoint regulator comprises VISTA, LAG-3 and/or TIM3. In some alternatives, the second nucleic acid further comprises a polynucleotide coding for chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the spacer is optimized for increased T cell proliferation and/or cytokine production in response to the ligand as compared to a reference chimeric receptor; a polynucleotide coding for a transmembrane domain. In some alternatives, the first promoter is in opposite orientation to the second promoter. In some alternatives, the ligand binding domain is an antibody fragment. In some alternatives, the ligand binding domain is single chain variable fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or combinations thereof. In some alternatives, the spacer is optimized for increased T cell proliferation and/or cytokine production in response to the ligand as compared to a reference chimeric receptor. In some alternatives, the second promoter is an inducible promoter. In some alternatives, the second promoter is constitutive promoter. In some alternatives, wherein the T lymphocytes are expanded, the method further comprises culturing the cells in the presence of anti-CD3 and/or anti CD28, and at least one homeostatic cytokine until the cells expand sufficiently for use as a cell infusion. In some alternatives, the lymphocyte is CD8+ or CD4+. In some alternatives, the cells are precursor T cells. In some alternatives, the cells are hematopoietic stem cells. In some alternatives, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells or a CD4+T helper lymphocyte cell that is selected from the group consisting of naïve CD4+ T cells, central memory CD4+ T cells, effector memory CD4+ T cells, and bulk CD4+ T cells and a second host cell, wherein the second host cell is a precursor T cell. In some alternatives, the precursor T cell is a hematopoietic stem cell.

In some alternatives, a use of a host cell or a composition in combination with a drug that induces expression of a transgene in the host cell or composition for the treatment of cancer or a viral infection is provided. In some alternatives, the host cell comprises a system. In some alternatives, the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte, a polynucleotide coding for a polypeptide spacer, wherein the spacer is optimized; a polynucleotide coding for a transmembrane domain, and d) a polynucleotide coding for an intracellular signaling domain, and b) a second nucleic acid comprising a second promoter operably linked to nucleic acid coding for a transcriptional activator for the inducible promoter. In some alternatives, the drug is tamoxifen and/or its metabolites. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling and b) a second nucleic acid comprising a second promoter operably linked to nucleic acid coding for a transcriptional activator for the inducible promoter. In some alternatives, the polypeptide that modulates checkpoint signaling inhibits negative checkpoint regulators. In some alternatives, the negative checkpoint regulator comprises VISTA, LAG-3 and/or TIM3. In some alternatives, the second nucleic acid further comprises a polynucleotide coding for chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain. In some alternatives, the spacer is optimized for increased T cell proliferation and/or cytokine production in response to the ligand as compared to a reference chimeric receptor. In some alternatives, the first promoter is in opposite orientation to the second promoter. In some alternatives, the ligand binding domain is an antibody fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or combinations thereof. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling; and b) a second nucleic acid comprising a second constitutive or inducible promoter operably linked to nucleic acid coding for a transcriptional activator for the inducible promoter. In some alternatives, the polypeptide that modulates checkpoint signaling inhibits negative checkpoint regulators. In some alternatives, the negative checkpoint regulator comprises VISTA, LAG-3 and/or TIM3. In some alternatives, the second nucleic acid further comprises a polynucleotide coding for chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the spacer is optimized for increased T cell proliferation and/or cytokine production in response to the ligand as compared to a reference chimeric receptor; a polynucleotide coding for a transmembrane domain. In some alternatives, the first promoter is in opposite orientation to the second promoter. In some alternatives, the ligand binding domain is an antibody fragment. In some alternatives, the ligand binding domain is single chain variable fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or combinations thereof. In some alternatives, the spacer is optimized for increased T cell proliferation and/or cytokine production in response to the ligand as compared to a reference chimeric receptor. In some alternatives, the second promoter is an inducible promoter. In some alternatives, the second promoter is constitutive promoter. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+T cells, effector memory CD4+ T cells, and bulk CD4+ T cells. In some alternatives, the composition comprises a host cell in a pharmaceutically acceptable excipient. In some alternatives, the host cell comprises a system. In some alternatives, the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain; and b) a second nucleic acid comprising a second promoter operably linked to nucleic acid coding for a transcriptional activator for the inducible promoter. In some alternatives, the second promoter is constitutive or inducible. In some alternatives, the drug is tamoxifen and/or its metabolites. In some alternatives, the first promoter comprises a nucleic acid sequence of SEQ ID NO:41. In some alternatives, the second promoter is a constitutive promoter. In some alternatives, the second promoter is the EF1αp. In some alternatives, the transcriptional activator comprises a sequence of SEQ ID NO:40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, the second nucleic acid further comprises a polynucleotide coding for chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain. In some alternatives, the first promoter is in opposite orientation to the second promoter. In some alternatives, the ligand binding domain is an antibody fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or combinations thereof. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling; and b) a second nucleic acid comprising a second promoter operably linked to nucleic acid coding for a transcriptional activator for the inducible promoter. In some alternatives, the second promoter is constitutive or inducible. In some alternatives, the second nucleic acid further comprises a polynucleotide coding for chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain. In some alternatives, the first promoter is in opposite orientation to the second promoter. In some alternatives, the ligand binding domain is an antibody fragment. In some alternatives, the ligand binding domain is single chain variable fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or combinations thereof. In some alternatives, the host cell is a precursor T cell. In some alternatives, the precursor T cell is a hematopoietic stem cell. In some alternatives, the isolated T lymphocyte population comprises precursor T cells. In some alternatives, the precursor T cells are hematopoietic stem cells. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells and another host cell wherein the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the cancer is a solid tumor or hematologic malignancy. In some alternatives, the solid tumor is selected from the group consisting of a breast cancer, brain cancer, lung cancer, colon cancer, renal cancer, pancreatic cancer, prostate cancer, and ovarian cancer. In some alternatives, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells or a CD4+T helper lymphocyte cell that is selected from the group consisting of naïve CD4+ T cells, central memory CD4+ T cells, effector memory CD4+ T cells, and bulk CD4+ T cells and a second host cell, wherein the second host cell is a precursor T cell. In some alternatives, the precursor T cell is a hematopoietic stem cell.

In some alternatives, a method of performing cellular immunotherapy in a subject having cancer or a viral infection is provided wherein the method comprises administering a composition or a host cell to the subject and administering a drug that induces expression of a transgene in the composition or the host cells. In some alternatives, the host cell comprises a system. In some alternatives, the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte, a polynucleotide coding for a polypeptide spacer, wherein the spacer is optimized; a polynucleotide coding for a transmembrane domain, and d) a polynucleotide coding for an intracellular signaling domain, and b) a second nucleic acid comprising a second promoter operably linked to nucleic acid coding for a transcriptional activator for the inducible promoter. In some alternatives, the drug is tamoxifen and/or its metabolites. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling and b) a second nucleic acid comprising a second promoter operably linked to nucleic acid coding for a transcriptional activator for the inducible promoter. In some alternatives, the polypeptide that modulates checkpoint signaling inhibits negative checkpoint regulators. In some alternatives, the negative checkpoint regulator comprises VISTA, LAG-3 and/or TIM3. In some alternatives, the second nucleic acid further comprises a polynucleotide coding for chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain. In some alternatives, the spacer is optimized for increased T cell proliferation and/or cytokine production in response to the ligand as compared to a reference chimeric receptor. In some alternatives, the first promoter is in opposite orientation to the second promoter. In some alternatives, the ligand binding domain is an antibody fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or combinations thereof. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling; and b) a second nucleic acid comprising a second constitutive or inducible promoter operably linked to nucleic acid coding for a transcriptional activator for the inducible promoter. In some alternatives, the polypeptide that modulates checkpoint signaling inhibits negative checkpoint regulators. In some alternatives, the negative checkpoint regulator comprises VISTA, LAG-3 and/or TIM3. In some alternatives, the second nucleic acid further comprises a polynucleotide coding for chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and d) a polynucleotide coding for an intracellular signaling domain. In some alternatives, the spacer is optimized for increased T cell proliferation and/or cytokine production in response to the ligand as compared to a reference chimeric receptor; a polynucleotide coding for a transmembrane domain. In some alternatives, the first promoter is in opposite orientation to the second promoter. In some alternatives, the ligand binding domain is an antibody fragment. In some alternatives, the ligand binding domain is single chain variable fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or combinations thereof. In some alternatives, the spacer is optimized for increased T cell proliferation and/or cytokine production in response to the ligand as compared to a reference chimeric receptor. In some alternatives, the second promoter is an inducible promoter. In some alternatives, the second promoter is constitutive promoter. In some alternatives, the host cell is a precursor T cell. In some alternatives, the host cell is a hematopoietic stem cell. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell in a pharmaceutically acceptable excipient. In some alternatives, the host cell comprises a system. In some alternatives, the system comprises a) a first nucleic acid comprising a first promoter inducible by a drug, wherein the first nucleic acid is operably linked to a polynucleotide coding for a chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain; and b) a second nucleic acid comprising a second promoter operably linked to nucleic acid coding for a transcriptional activator for the inducible promoter. In some alternatives, the second promoter is constitutive or inducible. In some alternatives, the drug is tamoxifen and/or its metabolites. In some alternatives, the first promoter comprises a nucleic acid sequence of SEQ ID NO: 41. In some alternatives, the second promoter is a constitutive promoter. In some alternatives, the second promoter is the EF1αp. In some alternatives, the transcriptional activator comprises a sequence of SEQ ID NO: 40. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, the second nucleic acid further comprises a polynucleotide coding for chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain. In some alternatives, the first promoter is in opposite orientation to the second promoter. In some alternatives, the ligand binding domain is an antibody fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or combinations thereof. In some alternatives, the system comprises a) a first nucleic acid comprising a first promoter inducible by a drug, wherein the first nucleic acid is operably linked to a polynucleotide coding for a cytokine, a chemokine receptor, a polypeptide that regulates apoptosis, or a polypeptide that modulates checkpoint signaling; and b) a second nucleic acid comprising a second promoter operably linked to nucleic acid coding for a transcriptional activator for the inducible promoter. In some alternatives, the second promoter is constitutive or inducible. In some alternatives, the polypeptide that modulates checkpoint signaling inhibits negative checkpoint regulators. In some alternatives, the negative checkpoint regulator comprises VISTA, LAG-3 and/or TIM3. In some alternatives, the second nucleic acid further comprises a polynucleotide coding for chimeric antigen receptor comprising a ligand binding domain, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and d) a polynucleotide coding for an intracellular signaling domain. In some alternatives, the first promoter is in opposite orientation to the second promoter. In some alternatives, the ligand binding domain is an antibody fragment. In some alternatives, the ligand binding domain is single chain variable fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or combinations thereof. In some alternatives, the host cell is a precursor T cell. In some alternatives, the host cell is a hematopoietic stem cell. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells and another host cell wherein the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the cancer is selected from a solid tumor or hematologic malignancy. In some alternatives, the solid tumor is selected from the group consisting of a breast cancer, brain cancer, lung cancer, colon cancer, renal cancer, pancreatic cancer, prostate cancer, and ovarian cancer. In some alternatives, the host cell is a precursor T cell. In some alternatives, the precursor T cell is a hematopoietic stem cell. In some alternatives, the isolated T lymphocyte population comprises precursor T cells. In some alternatives, the precursor T cells are hematopoietic stem cells. In some alternatives, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells or a CD4+T helper lymphocyte cell that is selected from the group consisting of naïve CD4+ T cells, central memory CD4+ T cells, effector memory CD4+ T cells, and bulk CD4+ T cells and a second host cell, wherein the second host cell is a precursor T cell. In some alternatives, the precursor T cell is a hematopoietic stem cell.

More Alternatives

In some alternatives, a system for inducible expression of a chimeric antigen receptor, the system is provided, wherein the system comprises a) a first nucleic acid comprising a first promoter, which is an inducible promoter, operably linked to a polynucleotide coding for a chimeric antigen receptor and b) a second nucleic acid comprising a second promoter operably linked to a polynucleotide coding for a transcriptional activator, which is capable of activating transcription from the first promoter in the presence of a drug or metabolite thereof. In some alternatives, a system for inducible expression is provided, wherein the system comprises a) an inducible promoter, b) a polynucleotide coding for a chimeric antigen receptor and c) a polynucleotide coding for a transcriptional activator, which transcriptional activator is capable of activating transcription from the inducible promoter in the presence of a drug or metabolite thereof. In some alternatives, the polynucleotide coding for the chimeric receptor is operably linked to the inducible promoter. In some alternatives, the system further comprises further comprising a polynucleotide encoding a recombinant protein, which polynucleotide is operably linked to the inducible promoter. In some alternatives, the drug or metabolite thereof comprises: (i) a drug tolerated when administered to a human subject daily or weekly, or a metabolite thereof; (ii) a molecule that specifically binds to a human receptor, optionally the estrogen receptor, or a metabolite thereof; and/or (iii) tamoxifen and/or a metabolite or analog of tamoxifen. In some alternatives, the transcriptional activator comprises: (a) a DNA-binding domain; (b) a ligand-binding domain that specifically binds to the drug or metabolite thereof; and (c) a transactivation domain, optionally linked and/or fused in that order. In some alternatives of the system, (a) the DNA-binding domain comprises DNA binding sites not present in a protein naturally expressed in a lymphocyte or not present in a protein naturally expressed in a T cell; and/or (b) the drug or metabolite is the molecule that specifically binds to the human receptor, optionally estrogen receptor, or metabolite thereof, and the binding between the drug or metabolite and the ligand-binding domain is selective for the ligand-binding domain over the human receptor, whereby binding by the ligand-binding domain to the drug or metabolite is greater, optionally at least 1.5, 2, 3, or 4 times as strong, as the binding by the human receptor; and/or (c) the transactivation domain comprises a p65 transactivation domain or functional variant thereof; and/or (d) the first promoter comprises one or more binding sites for the DNA binding domain. In some alternatives, the first promoter does not comprise another binding site for any human DNA binding domain other than a DNA-binding domain or domains present in the transcriptional activator; and/or wherein the first promoter is a synthetic chimeric promoter and/or the transcriptional activator is a synthetic chimeric transcriptional activator; and/or wherein the DNA binding domain comprises a DNA binding domain present in a hepatocyte nuclear factor, which is optionally HNF1-alpha or HNF1-beta. In some alternatives of the system, the first promoter comprises the nucleic acid sequence of SEQ ID NO: 41. In some alternatives, the second promoter is a constitutive promoter. In some alternatives, the second promoter is or comprises an EF1α promoter or functional portion thereof. In some alternatives, the transcriptional activator comprises a polypeptide having the sequence of SEQ ID NO: 40. In some alternatives, the first nucleic acid is comprised within a first vector, which is further comprised by the system and the second nucleic acid is comprised within a second vector, which is further comprised by the system. In some alternatives, the first nucleic acid and the second nucleic acid or the first promoter, polynucleotide encoding the chimeric antigen receptor, second promoter, and polynucleotide encoding the transactivator, are comprised within a vector, which is further comprised by the system. In some alternatives of the system, the system is comprised in a single viral packaging vector. In some alternatives, the viral vector is a lentiviral vector. In some alternatives, the first nucleic acid further comprises a nucleic acid sequence coding for a selectable marker or wherein the system further comprises a selectable marker operably linked to the first promoter. In some alternatives, the second nucleic acid further comprises a nucleic acid coding for a selectable marker or wherein the system further comprises a selectable marker operably linked to the second promoter.

In some alternatives, a system for inducible expression is provided, wherein the system comprises a) a first nucleic acid comprising a first promoter, which is an inducible promoter and is operably linked to a polynucleotide coding for a cytokine, a chemokine receptor, a polypeptide than inhibits apoptosis, or a polypeptide that inhibits negative checkpoint signaling and b) a second nucleic acid comprising a second promoter, which is a constitutive or inducible promoter, operably linked to a polynucleotide coding for a transcriptional activator capable of inducing transcription from the first promoter in the presence of a drug or metabolite or analog thereof. In some alternatives, the second nucleic acid further comprises a polynucleotide coding for a recombinant antigen receptor, which optionally is a chimeric antigen receptor. In some alternatives, the chimeric antigen receptor comprises a a) ligand binding domain, which binds to a ligand that is optionally a tumor specific molecule, viral molecule, or any other molecule expressed on a target cell population that is suitable to mediate recognition and elimination by a lymphocyte b) a polypeptide spacer, wherein the spacer optionally provides for increased T cell proliferation and/or cytokine production in response to the ligand as compared to a reference chimeric receptor, c) a transmembrane domain and d) an intracellular signaling domain. In some alternatives, the first promoter is in opposite orientation to the second promoter. In some alternatives, the ligand binding domain is an antibody fragment. In some alternatives, the ligand binding domain is single chain variable fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, MAGE A3 TCR and combinations thereof.

In some alternatives, a chimeric receptor polypeptide encoded by the system is provided. In some alternatives, the system comprises a) a first nucleic acid comprising a first promoter, which is an inducible promoter, operably linked to a polynucleotide coding for a chimeric antigen receptor and b) a second nucleic acid comprising a second promoter operably linked to a polynucleotide coding for a transcriptional activator, which is capable of activating transcription from the first promoter in the presence of a drug or metabolite thereof. In some alternatives, a system for inducible expression is provided, wherein the system comprises a) an inducible promoter, b) a polynucleotide coding for a chimeric antigen receptor and c) a polynucleotide coding for a transcriptional activator, which transcriptional activator is capable of activating transcription from the inducible promoter in the presence of a drug or metabolite thereof. In some alternatives, the polynucleotide coding for the chimeric receptor is operably linked to the inducible promoter. In some alternatives, the system further comprises further comprising a polynucleotide encoding a recombinant protein, which polynucleotide is operably linked to the inducible promoter. In some alternatives, the drug or metabolite thereof comprises: (i) a drug tolerated when administered to a human subject daily or weekly, or a metabolite thereof; (ii) a molecule that specifically binds to a human receptor, optionally the estrogen receptor, or a metabolite thereof; and/or (iii) tamoxifen and/or a metabolite or analog of tamoxifen. In some alternatives, the transcriptional activator comprises: (a) a DNA-binding domain; (b) a ligand-binding domain that specifically binds to the drug or metabolite thereof; and (c) a transactivation domain, optionally linked and/or fused in that order. In some alternatives of the system, (a) the DNA-binding domain comprises DNA binding sites not present in a protein naturally expressed in a lymphocyte or not present in a protein naturally expressed in a T cell; and/or (b) the drug or metabolite is the molecule that specifically binds to the human receptor, optionally estrogen receptor, or metabolite thereof, and the binding between the drug or metabolite and the ligand-binding domain is selective for the ligand-binding domain over the human receptor, whereby binding by the ligand-binding domain to the drug or metabolite is greater, optionally at least 1.5, 2, 3, or 4 times as strong, as the binding by the human receptor; and/or (c) the transactivation domain comprises a p65 transactivation domain or functional variant thereof; and/or (d) the first promoter comprises one or more binding sites for the DNA binding domain. In some alternatives, the first promoter does not comprise another binding site for any human DNA binding domain other than a DNA-binding domain or domains present in the transcriptional activator; and/or wherein the first promoter is a synthetic chimeric promoter and/or the transcriptional activator is a synthetic chimeric transcriptional activator; and/or wherein the DNA binding domain comprises a DNA binding domain present in a hepatocyte nuclear factor, which is optionally HNF1-alpha or HNF1-beta. The system of any of claims 1-8, wherein the first promoter comprises the nucleic acid sequence of SEQ ID NO: 41. In some alternatives, the second promoter is a constitutive promoter. In some alternatives, the second promoter is or comprises an EF1α promoter or functional portion thereof. In some alternatives, the transcriptional activator comprises a polypeptide having the sequence of SEQ ID NO: 40. In some alternatives, the first nucleic acid is comprised within a first vector, which is further comprised by the system and the second nucleic acid is comprised within a second vector, which is further comprised by the system. In some alternatives, the first nucleic acid and the second nucleic acid or the first promoter, polynucleotide encoding the chimeric antigen receptor, second promoter, and polynucleotide encoding the transactivator, are comprised within a vector, which is further comprised by the system. In some alternatives of the system, the system is comprised in a single viral packaging vector. In some alternatives, the viral vector is a lentiviral vector. In some alternatives, the first nucleic acid further comprises a nucleic acid sequence coding for a selectable marker or wherein the system further comprises a selectable marker operably linked to the first promoter. In some alternatives, the second nucleic acid further comprises a nucleic acid coding for a selectable marker or wherein the system further comprises a selectable marker operably linked to the second promoter. In some alternatives, the system comprises a) a first nucleic acid comprising a first promoter, which is an inducible promoter and is operably linked to a polynucleotide coding for a cytokine, a chemokine receptor, a polypeptide than inhibits apoptosis, or a polypeptide that inhibits negative checkpoint signaling and b) a second nucleic acid comprising a second promoter, which is a constitutive or inducible promoter, operably linked to a polynucleotide coding for a transcriptional activator capable of inducing transcription from the first promoter in the presence of a drug or metabolite or analog thereof. In some alternatives, the second nucleic acid further comprises a polynucleotide coding for a recombinant antigen receptor, which optionally is a chimeric antigen receptor. In some alternatives, the chimeric antigen receptor comprises a a) ligand binding domain, which binds to a ligand that is optionally a tumor specific molecule, viral molecule, or any other molecule expressed on a target cell population that is suitable to mediate recognition and elimination by a lymphocyte b) a polypeptide spacer, wherein the spacer optionally provides for increased T cell proliferation and/or cytokine production in response to the ligand as compared to a reference chimeric receptor, c) a transmembrane domain and d) an intracellular signaling domain. In some alternatives, the first promoter is in opposite orientation to the second promoter. In some alternatives, the ligand binding domain is an antibody fragment. In some alternatives, the ligand binding domain is single chain variable fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR and combinations thereof.

In some alternatives, a host cell comprising a system or viral packaging vector is provided. In some alternatives, the system comprises a) a first nucleic acid comprising a first promoter, which is an inducible promoter, operably linked to a polynucleotide coding for a chimeric antigen receptor and b) a second nucleic acid comprising a second promoter operably linked to a polynucleotide coding for a transcriptional activator, which is capable of activating transcription from the first promoter in the presence of a drug or metabolite thereof. In some alternatives, a system for inducible expression is provided, wherein the system comprises a) an inducible promoter, b) a polynucleotide coding for a chimeric antigen receptor and c) a polynucleotide coding for a transcriptional activator, which transcriptional activator is capable of activating transcription from the inducible promoter in the presence of a drug or metabolite thereof. In some alternatives, the polynucleotide coding for the chimeric receptor is operably linked to the inducible promoter. In some alternatives, the system further comprises further comprising a polynucleotide encoding a recombinant protein, which polynucleotide is operably linked to the inducible promoter. In some alternatives, the drug or metabolite thereof comprises: (i) a drug tolerated when administered to a human subject daily or weekly, or a metabolite thereof; (ii) a molecule that specifically binds to a human receptor, optionally the estrogen receptor, or a metabolite thereof; and/or (iii) tamoxifen and/or a metabolite or analog of tamoxifen. In some alternatives, the transcriptional activator comprises: (a) a DNA-binding domain; (b) a ligand-binding domain that specifically binds to the drug or metabolite thereof; and (c) a transactivation domain, optionally linked and/or fused in that order. In some alternatives of the system, (a) the DNA-binding domain comprises DNA binding sites not present in a protein naturally expressed in a lymphocyte or not present in a protein naturally expressed in a T cell; and/or (b) the drug or metabolite is the molecule that specifically binds to the human receptor, optionally estrogen receptor, or metabolite thereof, and the binding between the drug or metabolite and the ligand-binding domain is selective for the ligand-binding domain over the human receptor, whereby binding by the ligand-binding domain to the drug or metabolite is greater, optionally at least 1.5, 2, 3, or 4 times as strong, as the binding by the human receptor; and/or (c) the transactivation domain comprises a p65 transactivation domain or functional variant thereof; and/or (d) the first promoter comprises one or more binding sites for the DNA binding domain. In some alternatives, the first promoter does not comprise another binding site for any human DNA binding domain other than a DNA-binding domain or domains present in the transcriptional activator; and/or wherein the first promoter is a synthetic chimeric promoter and/or the transcriptional activator is a synthetic chimeric transcriptional activator; and/or wherein the DNA binding domain comprises a DNA binding domain present in a hepatocyte nuclear factor, which is optionally HNF1-alpha or HNF1-beta. In some alternatives, the first promoter comprises the nucleic acid sequence of SEQ ID NO: 41. In some alternatives, the second promoter is a constitutive promoter. In some alternatives, the second promoter is or comprises an EF1α promoter or functional portion thereof. In some alternatives, the transcriptional activator comprises a polypeptide having the sequence of SEQ ID NO: 40. In some alternatives, the first nucleic acid is comprised within a first vector, which is further comprised by the system and the second nucleic acid is comprised within a second vector, which is further comprised by the system. In some alternatives, the first nucleic acid and the second nucleic acid or the first promoter, polynucleotide encoding the chimeric antigen receptor, second promoter, and polynucleotide encoding the transactivator, are comprised within a vector, which is further comprised by the system. In some alternatives, the system described above is comprised in a single viral packaging vector. In some such alternatives, viral vector is a lentiviral vector. In some alternatives, the first nucleic acid further comprises a nucleic acid sequence coding for a selectable marker or wherein the system further comprises a selectable marker operably linked to the first promoter. In some alternatives, the second nucleic acid further comprises a nucleic acid coding for a selectable marker or wherein the system further comprises a selectable marker operably linked to the second promoter. In some alternatives, the system comprises a) a first nucleic acid comprising a first promoter, which is an inducible promoter and is operably linked to a polynucleotide coding for a cytokine, a chemokine receptor, a polypeptide than inhibits apoptosis, or a polypeptide that inhibits negative checkpoint signaling and b) a second nucleic acid comprising a second promoter, which is a constitutive or inducible promoter, operably linked to a polynucleotide coding for a transcriptional activator capable of inducing transcription from the first promoter in the presence of a drug or metabolite or analog thereof. In some alternatives, the second nucleic acid further comprises a polynucleotide coding for a recombinant antigen receptor, which optionally is a chimeric antigen receptor. In some alternatives, the chimeric antigen receptor comprises a a) ligand binding domain, which binds to a ligand that is optionally a tumor specific molecule, viral molecule, or any other molecule expressed on a target cell population that is suitable to mediate recognition and elimination by a lymphocyte b) a polypeptide spacer, wherein the spacer optionally provides for increased T cell proliferation and/or cytokine production in response to the ligand as compared to a reference chimeric receptor, c) a transmembrane domain and d) an intracellular signaling domain. In some alternatives, the first promoter is in opposite orientation to the second promoter. In some alternatives, the ligand binding domain is an antibody fragment. In some alternatives, the ligand binding domain is single chain variable fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR and combinations thereof.

In some alternatives, a host cell is provided, wherein the host cell is a primary human lymphocyte, wherein the host cell comprises a) a nucleic acid comprising a first promoter, which is an inducible synthetic promoter containing a binding site for a DNA binding domain not naturally present in the primary human lymphocyte and b) a polynucleotide coding for a transcriptional activator, the transcriptional activator comprising i) the DNA binding domain, wherein the DNA binding domain does not specifically bind to a DNA sequence naturally present in the primary human lymphocyte; ii) a domain that specifically binds to a drug or metabolite thereof and does not bind or does not bind with as great a degree of affinity to any molecule naturally present in the primary human lymphocyte and iii) a transactivation domain, wherein the transcriptional activator is capable of inducing transcription from the first promoter in the presence of the drug or metabolite thereof and/or upon binding of the drug or metabolite thereof to the domain in (ii). In some alternatives, the cell further comprises a polynucleotide encoding a chimeric antigen receptor, which optionally is operably linked to the first promoter. In some alternatives, In some alternatives, the cell further comprises a second promoter, which is operably linked to the polynucleotide encoding the transcriptional activator, wherein the second promoter is optionally constitutive. In some alternatives, the host cell is a CD8+T cytotoxic lymphocyte cell selected from the group consisting of naïve CD8+ T cells, central memory CD8+ T cells, effector memory CD8+ T cells and bulk CD8+ T cell. In some alternatives, the host cell is a CD4+T helper lymphocyte cell that is selected from the group consisting of naïve CD4+ T cells, central memory CD4+ T cells, effector memory CD4+ T cells, and bulk CD4+ T cells.

In some alternatives, a composition is provided, wherein the composition comprises a host cell in a pharmaceutically acceptable excipient. In some alternatives, the host cell the host cell is a primary human lymphocyte, wherein the host cell comprises a) a nucleic acid comprising a first promoter, which is an inducible synthetic promoter containing a binding site for a DNA binding domain not naturally present in the primary human lymphocyte and b) a polynucleotide coding for a transcriptional activator, the transcriptional activator comprising i) the DNA binding domain, wherein the DNA binding domain does not specifically bind to a DNA sequence naturally present in the primary human lymphocyte; ii) a domain that specifically binds to a drug or metabolite thereof and does not bind or does not bind with as great a degree of affinity to any molecule naturally present in the primary human lymphocyte and iii) a transactivation domain, wherein the transcriptional activator is capable of inducing transcription from the first promoter in the presence of the drug or metabolite thereof and/or upon binding of the drug or metabolite thereof to the domain in (ii). In some alternatives, the cell further comprises a polynucleotide encoding a chimeric antigen receptor, which optionally is operably linked to the first promoter. In some alternatives, In some alternatives, the cell further comprises a second promoter, which is operably linked to the polynucleotide encoding the transcriptional activator, wherein the second promoter is optionally constitutive. In some alternatives, the host cell is a CD8+T cytotoxic lymphocyte cell selected from the group consisting of naïve CD8+ T cells, central memory CD8+ T cells, effector memory CD8+ T cells and bulk CD8+ T cell. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a CD8+T cytotoxic lymphocyte cell selected from the group consisting of naïve CD8+ T cells, central memory CD8+ T cells, effector memory CD8+ T cells and bulk CD8+ T cell and a CD4+T helper lymphocyte cell that is selected from the group consisting of naïve CD4+ T cells, central memory CD4+ T cells, effector memory CD4+ T cells, and bulk CD4+ T cells.

In some alternatives, an in vitro method for preparing a host cell is provided and comprises introducing a system into a separate isolated T lymphocyte population and expanding each T lymphocyte population in vitro. In some alternatives, the host cell the host cell is a primary human lymphocyte, wherein the host cell comprises a) a nucleic acid comprising a first promoter, which is an inducible synthetic promoter containing a binding site for a DNA binding domain not naturally present in the primary human lymphocyte and b) a polynucleotide coding for a transcriptional activator, the transcriptional activator comprising i) the DNA binding domain, wherein the DNA binding domain does not specifically bind to a DNA sequence naturally present in the primary human lymphocyte; ii) a domain that specifically binds to a drug or metabolite thereof and does not bind or does not bind with as great a degree of affinity to any molecule naturally present in the primary human lymphocyte and iii) a transactivation domain, wherein the transcriptional activator is capable of inducing transcription from the first promoter in the presence of the drug or metabolite thereof and/or upon binding of the drug or metabolite thereof to the domain in (ii). In some alternatives, the cell further comprises a polynucleotide encoding a chimeric antigen receptor, which optionally is operably linked to the first promoter. In some alternatives, In some alternatives, the cell further comprises a second promoter, which is operably linked to the polynucleotide encoding the transcriptional activator, wherein the second promoter is optionally constitutive. In some alternatives, the host cell is a CD8+T cytotoxic lymphocyte cell selected from the group consisting of naïve CD8+ T cells, central memory CD8+ T cells, effector memory CD8+ T cells and bulk CD8+ T cell. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the system comprises a) a first nucleic acid comprising a first promoter, which is an inducible promoter, operably linked to a polynucleotide coding for a chimeric antigen receptor and b) a second nucleic acid comprising a second promoter operably linked to a polynucleotide coding for a transcriptional activator, which is capable of activating transcription from the first promoter in the presence of a drug or metabolite thereof. In some alternatives, a system for inducible expression is provided, wherein the system comprises a) an inducible promoter, b) a polynucleotide coding for a chimeric antigen receptor and c) a polynucleotide coding for a transcriptional activator, which transcriptional activator is capable of activating transcription from the inducible promoter in the presence of a drug or metabolite thereof. In some alternatives, the polynucleotide coding for the chimeric receptor is operably linked to the inducible promoter. In some alternatives, the system further comprises further comprising a polynucleotide encoding a recombinant protein, which polynucleotide is operably linked to the inducible promoter. In some alternatives, the drug or metabolite thereof comprises: (i) a drug tolerated when administered to a human subject daily or weekly, or a metabolite thereof; (ii) a molecule that specifically binds to a human receptor, optionally the estrogen receptor, or a metabolite thereof; and/or (iii) tamoxifen and/or a metabolite or analog of tamoxifen. In some alternatives, the transcriptional activator comprises: (a) a DNA-binding domain; (b) a ligand-binding domain that specifically binds to the drug or metabolite thereof; and (c) a transactivation domain, optionally linked and/or fused in that order. In some alternatives of the system, (a) the DNA-binding domain comprises DNA binding sites not present in a protein naturally expressed in a lymphocyte or not present in a protein naturally expressed in a T cell; and/or (b) the drug or metabolite is the molecule that specifically binds to the human receptor, optionally estrogen receptor, or metabolite thereof, and the binding between the drug or metabolite and the ligand-binding domain is selective for the ligand-binding domain over the human receptor, whereby binding by the ligand-binding domain to the drug or metabolite is greater, optionally at least 1.5, 2, 3, or 4 times as strong, as the binding by the human receptor; and/or (c) the transactivation domain comprises a p65 transactivation domain or functional variant thereof; and/or (d) the first promoter comprises one or more binding sites for the DNA binding domain. In some alternatives, the first promoter does not comprise another binding site for any human DNA binding domain other than a DNA-binding domain or domains present in the transcriptional activator; and/or wherein the first promoter is a synthetic chimeric promoter and/or the transcriptional activator is a synthetic chimeric transcriptional activator; and/or wherein the DNA binding domain comprises a DNA binding domain present in a hepatocyte nuclear factor, which is optionally HNF 1-alpha or HNF1-beta. In some alternatives, the first promoter comprises the nucleic acid sequence of SEQ ID NO: 41. In some alternatives, the second promoter is a constitutive promoter. In some alternatives, the second promoter is or comprises an EF1α promoter or functional portion thereof. In some alternatives, the transcriptional activator comprises a polypeptide having the sequence of SEQ ID NO: 40. In some alternatives, the first nucleic acid is comprised within a first vector, which is further comprised by the system and the second nucleic acid is comprised within a second vector, which is further comprised by the system. In some alternatives, the first nucleic acid and the second nucleic acid or the first promoter, polynucleotide encoding the chimeric antigen receptor, second promoter, and polynucleotide encoding the transactivator, are comprised within a vector, which is further comprised by the system. In some alternatives, the system is comprised in a single viral packaging vector. In some alternatives, the viral vector is a lentiviral vector. In some alternatives, the first nucleic acid further comprises a nucleic acid sequence coding for a selectable marker or wherein the system further comprises a selectable marker operably linked to the first promoter. In some alternatives, the second nucleic acid further comprises a nucleic acid coding for a selectable marker or wherein the system further comprises a selectable marker operably linked to the second promoter. In some alternatives, the system comprises a) a first nucleic acid comprising a first promoter, which is an inducible promoter and is operably linked to a polynucleotide coding for a cytokine, a chemokine receptor, a polypeptide than inhibits apoptosis, or a polypeptide that inhibits negative checkpoint signaling and b) a second nucleic acid comprising a second promoter, which is a constitutive or inducible promoter, operably linked to a polynucleotide coding for a transcriptional activator capable of inducing transcription from the first promoter in the presence of a drug or metabolite or analog thereof. In some alternatives, the second nucleic acid further comprises a polynucleotide coding for a recombinant antigen receptor, which optionally is a chimeric antigen receptor. In some alternatives, the chimeric antigen receptor comprises a a) ligand binding domain, which binds to a ligand that is optionally a tumor specific molecule, viral molecule, or any other molecule expressed on a target cell population that is suitable to mediate recognition and elimination by a lymphocyte b) a polypeptide spacer, wherein the spacer optionally provides for increased T cell proliferation and/or cytokine production in response to the ligand as compared to a reference chimeric receptor, c) a transmembrane domain and d) an intracellular signaling domain. In some alternatives, the first promoter is in opposite orientation to the second promoter. In some alternatives, the ligand binding domain is an antibody fragment. In some alternatives, the ligand binding domain is single chain variable fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, MAGE A3 TCR and combinations thereof. In some alternatives, the T lymphocytes in the population are expanded and wherein the method further comprises culturing the cells in the presence of anti-CD3 and/or anti CD28, and at least one homeostatic cytokine until the cells expand sufficiently for use as a cell infusion. In some alternatives, culturing in the presence of anti-CD3 and/or anti CD28, and at least one homeostatic cytokine can be performed before or after the introduction of the system.

In some alternatives, a use of the host cell or a composition in combination with the drug or a metabolite thereof for the treatment of cancer or a viral infection is provided. In some alternatives, the host cell is a primary human lymphocyte, wherein the host cell comprises a) a nucleic acid comprising a first promoter, which is an inducible synthetic promoter containing a binding site for a DNA binding domain not naturally present in the primary human lymphocyte and b) a polynucleotide coding for a transcriptional activator, the transcriptional activator comprising i) the DNA binding domain, wherein the DNA binding domain does not specifically bind to a DNA sequence naturally present in the primary human lymphocyte; ii) a domain that specifically binds to a drug or metabolite thereof and does not bind or does not bind with as great a degree of affinity to any molecule naturally present in the primary human lymphocyte and iii) a transactivation domain, wherein the transcriptional activator is capable of inducing transcription from the first promoter in the presence of the drug or metabolite thereof and/or upon binding of the drug or metabolite thereof to the domain in (ii). In some alternatives, the cell further comprises a polynucleotide encoding a chimeric antigen receptor, which optionally is operably linked to the first promoter. In some alternatives, In some alternatives, the cell further comprises a second promoter, which is operably linked to the polynucleotide encoding the transcriptional activator, wherein the second promoter is optionally constitutive. In some alternatives, the host cell is a CD8+T cytotoxic lymphocyte cell selected from the group consisting of naïve CD8+ T cells, central memory CD8+ T cells, effector memory CD8+ T cells and bulk CD8+ T cell. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell in a pharmaceutically acceptable excipient. In some alternatives, the host cell the host cell is a primary human lymphocyte, wherein the host cell comprises a) a nucleic acid comprising a first promoter, which is an inducible synthetic promoter containing a binding site for a DNA binding domain not naturally present in the primary human lymphocyte and b) a polynucleotide coding for a transcriptional activator, the transcriptional activator comprising i) the DNA binding domain, wherein the DNA binding domain does not specifically bind to a DNA sequence naturally present in the primary human lymphocyte; ii) a domain that specifically binds to a drug or metabolite thereof and does not bind or does not bind with as great a degree of affinity to any molecule naturally present in the primary human lymphocyte and iii) a transactivation domain, wherein the transcriptional activator is capable of inducing transcription from the first promoter in the presence of the drug or metabolite thereof and/or upon binding of the drug or metabolite thereof to the domain in (ii). In some alternatives, the cell further comprises a polynucleotide encoding a chimeric antigen receptor, which optionally is operably linked to the first promoter. In some alternatives, the cell further comprises a second promoter, which is operably linked to the polynucleotide encoding the transcriptional activator, wherein the second promoter is optionally constitutive. In some alternatives, the host cell is a CD8+T cytotoxic lymphocyte cell selected from the group consisting of naïve CD8+ T cells, central memory CD8+ T cells, effector memory CD8+ T cells and bulk CD8+ T cell. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a CD8+T cytotoxic lymphocyte cell selected from the group consisting of naïve CD8+ T cells, central memory CD8+ T cells, effector memory CD8+ T cells and bulk CD8+ T cell and a CD4+T helper lymphocyte cell that is selected from the group consisting of naïve CD4+ T cells, central memory CD4+ T cells, effector memory CD4+ T cells, and bulk CD4+ T cells.

In some alternatives, a cell and a drug for use in treatment or inhibition of cancer or a viral infection is provided, wherein the cell comprises: (a) a polynucleotide encoding a chimeric antigen receptor that specifically binds to an antigen associated with the cancer or the viral infection, (b) an inducible synthetic promoter, and (c) a transcriptional activator containing a DNA binding domain that specifically binds to the synthetic promoter and a domain that specifically binds to the drug or a metabolite thereof and is capable of inducing transcription from the synthetic promoter in the presence of the drug or a metabolite thereof. In some alternatives, the cancer is a solid tumor or hematologic malignancy. In some alternatives, the solid tumor is selected from the group consisting of a breast cancer, lung cancer, colon cancer, renal cancer, pancreatic cancer, prostate cancer, and ovarian cancer.

In some alternatives, a method of performing cellular immunotherapy in a subject having cancer or a viral infection is provided wherein the method comprises administering a composition or a host cell to the subject and administering the drug or metabolite thereof, thereby inducing expression from the promoter. In some alternatives, the host cell is a primary human lymphocyte, wherein the host cell comprises a) a nucleic acid comprising a first promoter, which is an inducible synthetic promoter containing a binding site for a DNA binding domain not naturally present in the primary human lymphocyte and b) a polynucleotide coding for a transcriptional activator, the transcriptional activator comprising i) the DNA binding domain, wherein the DNA binding domain does not specifically bind to a DNA sequence naturally present in the primary human lymphocyte; ii) a domain that specifically binds to a drug or metabolite thereof and does not bind or does not bind with as great a degree of affinity to any molecule naturally present in the primary human lymphocyte and iii) a transactivation domain, wherein the transcriptional activator is capable of inducing transcription from the first promoter in the presence of the drug or metabolite thereof and/or upon binding of the drug or metabolite thereof to the domain in (ii). In some alternatives, the cell further comprises a polynucleotide encoding a chimeric antigen receptor, which optionally is operably linked to the first promoter. In some alternatives, In some alternatives, the cell further comprises a second promoter, which is operably linked to the polynucleotide encoding the transcriptional activator, wherein the second promoter is optionally constitutive. In some alternatives, the host cell is a CD8+T cytotoxic lymphocyte cell selected from the group consisting of naïve CD8+ T cells, central memory CD8+ T cells, effector memory CD8+ T cells and bulk CD8+ T cell. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell in a pharmaceutically acceptable excipient. In some alternatives, the host cell the host cell is a primary human lymphocyte, wherein the host cell comprises a) a nucleic acid comprising a first promoter, which is an inducible synthetic promoter containing a binding site for a DNA binding domain not naturally present in the primary human lymphocyte and b) a polynucleotide coding for a transcriptional activator, the transcriptional activator comprising i) the DNA binding domain, wherein the DNA binding domain does not specifically bind to a DNA sequence naturally present in the primary human lymphocyte; ii) a domain that specifically binds to a drug or metabolite thereof and does not bind or does not bind with as great a degree of affinity to any molecule naturally present in the primary human lymphocyte and iii) a transactivation domain, wherein the transcriptional activator is capable of inducing transcription from the first promoter in the presence of the drug or metabolite thereof and/or upon binding of the drug or metabolite thereof to the domain in (ii). In some alternatives, the cell further comprises a polynucleotide encoding a chimeric antigen receptor, which optionally is operably linked to the first promoter. In some alternatives, the cell further comprises a second promoter, which is operably linked to the polynucleotide encoding the transcriptional activator, wherein the second promoter is optionally constitutive. In some alternatives, the host cell is a CD8+T cytotoxic lymphocyte cell selected from the group consisting of naïve CD8+ T cells, central memory CD8+ T cells, effector memory CD8+ T cells and bulk CD8+ T cell. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a CD8+T cytotoxic lymphocyte cell selected from the group consisting of naïve CD8+ T cells, central memory CD8+ T cells, effector memory CD8+ T cells and bulk CD8+ T cell and a CD4+T helper lymphocyte cell that is selected from the group consisting of naïve CD4+ T cells, central memory CD4+ T cells, effector memory CD4+ T cells, and bulk CD4+ T cells. In some alternatives, the cancer is selected from a solid tumor or hematologic malignancy. In some alternatives, the solid tumor is selected from the group consisting of a breast cancer, lung cancer, colon cancer, renal cancer, pancreatic cancer, prostate cancer, and ovarian cancer.

Another aspect of the disclosure includes a genetic system to deliver drug-regulated transgene expression in cells, such as drug-regulated expression of a recombinant protein such as a recombinant antigen receptor and/or a molecule expressed by a cell expressing a recombinant antigen receptor. In an alternative, regulated transgene expression is engineered into and/or contained within cells, such as lymphocytes, for example, for use in adoptive cell therapy, such as adoptive immunotherapy. Such systems provide rigorous safety attributes to cell therapies, such as chimeric antigen receptor (CAR) adoptive therapeutic strategies, generally without sacrificing curative intent. In some aspects, such features permit real-time clinician control of recombinant protein expression, e.g., CAR expression, in vivo. By engineering vectors that enable drug responsive transcriptional control of recombinant gene, e.g., CAR, expression, the activity of the recombinant gene, e.g., CARs, and/or other cell mediators can be turned "ON" and "OFF" in vivo, for example, based on a clinician prescribed pharmaceutical drug input that exhibits clinically permissive pharmacokinetics, tissue distribution, and partitioning between the extracellular space and cytosol of lymphocytes. The genetic system provides for drug regulated transgene expression to enforce a functional "OFF" state in the absence of the drug and a functional "ON" state transgene expression in the presence of the drug.

One alternative of such a drug is tamoxifen. Tamoxifen is an estrogen antagonist/partial agonist that is an FDA-approved and commercially available drug. It is taken orally and can be administered on a daily basis over an extended period of time. Tamoxifen has a proven safety record, favorable pharmacokinetic profile, excellent tissue distribution and a low partition coefficient between the extracellular space and cytosol. Functional analogs of tamoxifen also may be used. Other drugs can be selected, for example, based on safety record, favorable pharmacokinetic profile, excellent tissue distribution, a low partition coefficient between the extracellular space and cytosol, and/or low toxicities.

In some alternatives, the system employs a synthetic transcriptional regulator, e.g., synthetic transcriptional activator, which, in the presence of tamoxifen, can be induced to bind to a synthetic promoter operably linked to, e.g., upstream of, a transgene, to induce expression from the promoter, e.g., of the transgene. In some alternatives provided herein, the transcriptional activator is regulated by a drug or metabolite thereof, such as a tamoxifen-regulated transcriptional activator or transcription factor, which may be regulated, e.g., induced, by tamoxifen or an analog or metabolite thereof. Exemplary tamoxifen-regulated transcription factors are chimeric transcription factors, such as those comprising a DNA binding domain specific for a synthetic promoter of the system, a domain that specifically binds tamoxifen and/or metabolite(s) thereof, for example, with affinity higher than the affinity of the domain for a natural molecule such as estrogen, and a transactivating domain, such as a strong transactivating domain. One tamoxifen regulated transcription factor ("TamR-tf", also designated "HEA3") is a chimeric transcription factor composed of human subunits including the N-terminal DNA binding domain of Hepatocyte Nuclear Factor 1-alpha (HNF-la) fused in frame to a mutant (G521R) tamoxifen-specific form of an estrogen receptor ligand binding domain (ER-LBD), which binds to tamoxifen metabolites with high affinity as compared to estrogen, which is in turn fused to the p65 activation domain of NF-κB (p65). An exemplary amino acid sequence of a TamR-tf is provided in FIGS. 9A, 9B, and 9C and is identified as SEQ ID NO: 40. In this sequence, the mutant tamoxifen-specific form of the ligand binding domain of the estrogen receptor ligand binding domain (ER-LBD) is found at amino acids 282-595 of the TamR-tf and has a mutation at position 521, as compared to wild-type estrogen receptor ligand binding domain. The p65 activation domain of NF-κB (p65) is found at amino acids 596-862 of SEQ ID NO: 40. Changes can be made to the transcriptional activator, for example, to increase the properties of the transcription factor including, without limitation, altering one or more amino acids in the estrogen receptor ligand binding domain to increase the affinity of the factor for estrogen analogs and altering one or more amino acids in the p65 transactivating domain. In some alternatives, changes are made to the transcriptional activator that result in an altered transcription factor which retains or substantially retains one or more functions of tamR-tf, such as tamoxifen-specific binding and/or the same or substantially the same or at least the same specificity for tamoxifen or metabolite as compared to any natural molecule, at least the same or about the same specific DNA binding function, and/or the same or at least the same degree of transactivation activity.

In the absence of tamoxifen, the transcriptional activator, e.g., TamR-tf, is generally excluded from the nucleus by binding of cytosolic heat-shock protein 90 (HSP90) to the tamoxifen-binding active site, resulting in the expression of a transgene operably linked to the tamR-tf-inducible promoter being in the "OFF" state. Nanomolar concentrations of cytosolic tamoxifen actively out-compete HSP90 for ER-LBD binding, resulting in TamR-tf translocation to the nucleus. Upon nuclear translocation, TamR-tf is readily available to bind to a restricted synthetic promoter (e.g. 7×HBD/EF1αp). In the presence of tamoxifen, binding of TamR-tf to the synthetic promoter, e.g., the 7×HBD/EF1αp promoter, induces the "ON" state of expression for a transgene operably linked to the synthetic promoter. In some alternatives, this transcriptional regulator can be modified to provide for a varying level of control of transgene expression. Amino acid substitutions in the LBD of TamR-tf permit selective responsiveness to tamoxifen and its metabolites, where 4-hydroxy tamoxifen (4-OHT) is the most pharmacologically active metabolite, in regards to TamR-tf activity, while lacking interaction with endogenous estrogen. In some alternatives, a system for inducible expression of chimeric antigen receptor is provided, wherein the system comprises: a first nucleic acid comprising a first promoter inducible by a drug operably linked to a polynucleotide, such as one coding for a chimeric antigen receptor, the chimeric antigen receptor optionally comprising a ligand binding domain, wherein the ligand binding domain binds to a ligand, wherein the ligand is a tumor specific molecule, viral molecule, or any other molecule expressed on a target cell population that is suitable to mediate recognition and elimination by a lymphocyte, a polypeptide spacer, wherein the spacer optionally provides for increased T cell proliferation and/or cytokine production in response to the ligand as compared to a reference chimeric receptor, a transmembrane domain, and an intracellular signaling domain. In some alternatives, the system further includes a second nucleic acid encoding a transcriptional modulator for the inducible promoter, which is capable of modulating, e.g., activating, transcription from the first promoter, such as in the presence of the drug or metabolite thereof; typically the system comprises a second constitutive or inducible promoter operably linked to a nucleic acid coding for the transcriptional modulator.

In some alternatives of the inducible system, the first promoter is operably linked to a polynucleotide coding for a gene that promotes cell survival and proliferation, a gene that prevents apoptosis, and/or a gene that that inhibits negative checkpoint signaling. Such genes include genes encoding IL-2, IL-15, Chemokine receptors, Bcl2, CA-Akt, dn-TGFbetaRIII, dn-SHP1/2, and/or PD-1CD28 chimeras.

In some alternatives, the system employs a synthetic transcriptional activator which, in the presence of the drug (e.g. tamoxifen) or a metabolite thereof, such as following administration of the drug, is induced to bind a synthetic promoter upstream of a transgene to induce expression. In some alternatives, the transcriptional activator is TamR-tf (HEA3) or other tamoxifen-inducible transcriptional activator with analogous domains. The tamoxifen regulated transcription factor ("TamR-tf", also designated "HEA3") is a chimeric transcription factor composed of human subunits including the N-terminal DNA binding domain of Hepatocyte Nuclear Factor 1-alpha (HNF-1α) (e.g. amino acids 1-281 of SEQ ID NO: 40) fused in frame to the mutant tamoxifen-specific ligand binding domain of the estrogen receptor ligand binding domain (ER-LBD), that is in turn fused to the p65 activation domain of NF-κB (p65).

In some alternatives of the compositions herein, the CD4+T helper lymphocyte cell is naïve CD4+ T cells, central memory CD4+ T cells, effector memory CD4+ T cells, or bulk CD4+ T cells. In some alternatives, CD4+ helper lymphocyte cell is a naïve CD4+ T cell, wherein the naïve CD4+ T cell comprises a CD45RO−, CD45RA+, and/or is a CD62L+CD4+ T cell. In some alternatives, at least 20, 30, 40, 50, 60, 70, 80, 90, 95, 99, or 100% of the cells in the composition are CD4+; in some alternatives, at least 20, 30, 40, 50, 60, 70, 80, 90, 95, 99, or 100% of the cells in the composition or the CD4+ cells in the composition are naïve CD4+ T cells, central memory CD4+ T cells, effector memory CD4+ T cells, or bulk CD4+ T cells.

In some alternatives of the compositions herein, the CD8+T cytotoxic lymphocyte cell is a naïve CD8+ T cell, central memory CD8+ T cell, effector memory CD8+ T cell and/or bulk CD8+ T cell. In some alternatives, the CD8+ cytotoxic T lymphocyte cell is a central memory T cell, wherein the central memory T cell comprises a CD45RO+, CD62L+, and/or CD8+ T cell. In yet other alternatives, the CD8+ cytotoxic T lymphocyte cell is a central memory T cell and the CD4+ helper T lymphocyte cell is a naïve or central memory CD4+ T cell. In some alternatives, at least 20, 30, 40, 50, 60, 70, 80, 90, 95, 99, or 100% of the cells in the composition are CD8+; in some alternatives, at least 20, 30, 40, 50, 60, 70, 80, 90, 95, 99, or 100% of the cells in the composition or the CD8+ cells in the composition are naïve CD8+ T cells, central memory CD8+ T cells, effector memory CD8+ T cells, or bulk CD8+ T cells. In some embodiments, at least 20, 30, 40, 50, 60, 70, 80, 90, 95, 99, or 100% of the cells in the composition, and/or of the CD4+ and/or CD8+ cells in the composition, express the transgene or recombinant molecule, such as the CAR, and/or contain the expression system.

Additionally provided are methods of making compositions including adoptive immunotherapy compositions, such as those containing the systems, and uses or methods of using these compositions, such as for performing cellular immunotherapy in a subject having a disease or disorder.

In some alternatives, a method of manufacturing the compositions comprises obtaining generating a modified naïve or naïve-derived or central memory or central memory-derived CD4+T helper cell or population containing the same, wherein the modified helper T lymphocyte cell preparation comprises CD4+ T cells that have a chimeric receptor, such as one comprising a ligand binding domain specific for a tumor cell surface molecule, a spacer domain, a transmembrane domain, and an intracellular signaling domain under control of an inducible promoter as described herein. In other some alternatives, CD4+ cells have a cytokine or chemokine receptor under the control of an inducible promoter.

In some alternatives of the methods described herein, the T-cells are administered with other T-cells that are non-CAR expressing, and/or produce Tam-inducible proteins. In some alternatives, the transcriptional activator for the CAR comprises a DNA-binding domain, a tamofexin/metabolite binding domain, or a transactivation domain. In some alternatives, one or more, generally all, of the domains from the synthetic transcriptional activator is or are derived from human proteins, such as human or substantially human domains. Such features can reduce immunogenicity of the constructs upon administration to human subjects, for example, in cell therapy.

Expression in Jurkat Cells.

The "ON" and "OFF" state of Jurkat T cells expressing TamR ZsGreen was studied.

Constructs.

In some alternatives, this system involves two components: 1) constitutive expression of HEA-3 linked to a single transgene or set of transgenes by T2A skip-linker domains and 2) conditional expression of a transgene that is under control of the HEA-3 restricted synthetic promoter 7×HBD/mEF1ap whereby induction of the transgene occurs in response to tamoxifen. Depending on the desired use of TamRLV genetic control, a combination of delivery systems and vector compositions can be used. Construction of constructs is described above.

An alternative of the TamR-LV system allows for constitutive HEA3 expression and inducible expression of either ZsGreen or chimeric antigen receptors, permitting kinetic analysis and biological effect controlled in an "ON" and "OFF" manner by the presence or absence of tamoxifen. For this, two constructs were used: 1) HEA-3 is driven by the human EF1a promoter and linked to the constructed truncated EGFR (EGFRt) transmembrane marker protein by a T2A skip-linker sequence and cloned into a third generation epHIV7 self-inactivating lentivirus packaging plasmid (construct A). (See FIGS. 9A, 9B and 9C; SEQ ID NO: 39; Table 1: SEQ ID NO: 8 and SEQ ID NO: 9) and 2) 7×HBD/mEF1ap controls tamoxifen-dependent expression of ZsGreen cloned into pcDNA3.1 (−) which was engineered to lack the commercially used CMV promoter (construct B) (See Table 12; SEQ ID NO: 41). ZsGreen1 is a human codon-optimized ZsGreen variant that encodes the brightest commercially available green fluorescent protein. (Available from Clontech).

Methods.

Jurkat cells were transduced at a MOI of 5 with lentivirus packaging constructs described above in which a dual packaging approach in which each plasmid is co-transfected into 293T cells during lentiviral production. This construct utilized molar ratio of 1:2 of construct A to construct B. Construct A encodes the chimeric transcription factor HEA3 linked via a ribosomal cleavage sequence, T2A, to the tracking and selection marker EGFRt. Construct B encodes the synthetic, HEA3-responsive promoter, 7×HBD/mE1b which regulates expression of the transgene ZsGreen-DR1, a short half-life green fluorescent reporter gene.

Figure 1B:
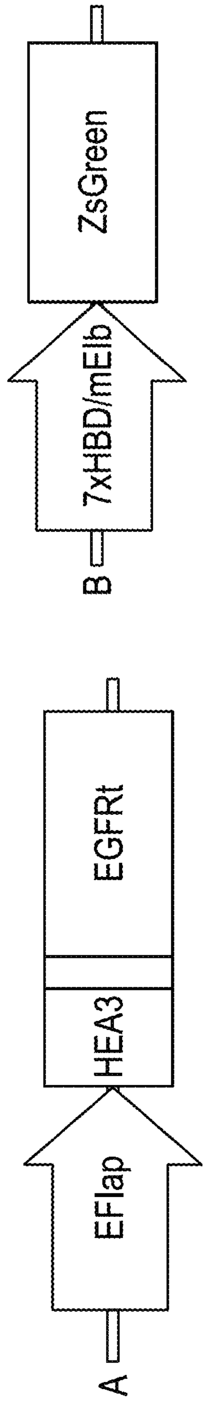
FIG. 1B shows construct A, which comprises the constitutive promoter EF1αp linked to TamR-tf (HEA3) linked to EGFRt, and construct B comprising a synthetic promoter 7×HBD/mE1b linked to a polynucleotide coding for ZsGreen.

After transduction, cells were expanded in culture, enriched for EGFRt expression utilizing Miltenyi magnetic bead selection, to a purity >99%. After further expansion in culture, cells were harvested and treated with Ethanol (Vehicle) as a negative control or 500 nM 4-hydroxytamoxifen (4OHT) for 24 hours, and then were harvested, stained with Erbitux-biotin followed by SA-APC, and analyzed for APC expression and ZsGreen expression via flow cytometry. The results are shown in FIG. 1.

Dose Response.

Figure 2:
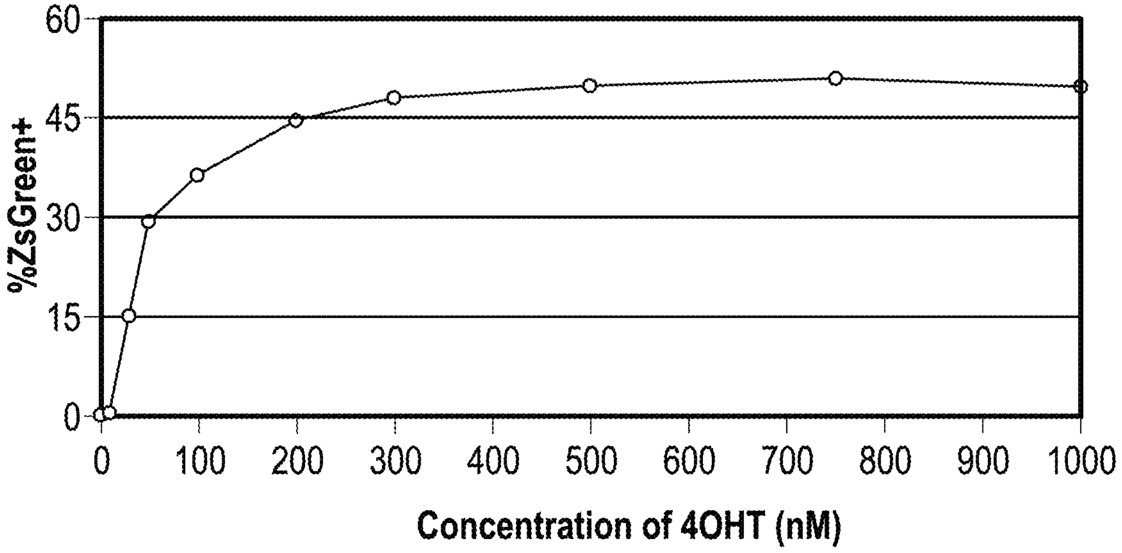
FIG. 2 shows the expression of ZsGreen in transduced Jurkat cells contacted with different doses of 4-OHT ranging from 50 to 1000 nM.

Cells were harvested and were then subjected to treatment with 40HT with concentrations ranging from 0 nM-1000 nM, as indicated. Samples were harvested, washed, and stained with EGFRt-biotin, followed by strepavidin-APC, and then analyzed by flow cytometry for ZsGreen expression. The results are shown in FIG. 2.

On and Off Rate Kinetics.

Figure 3:
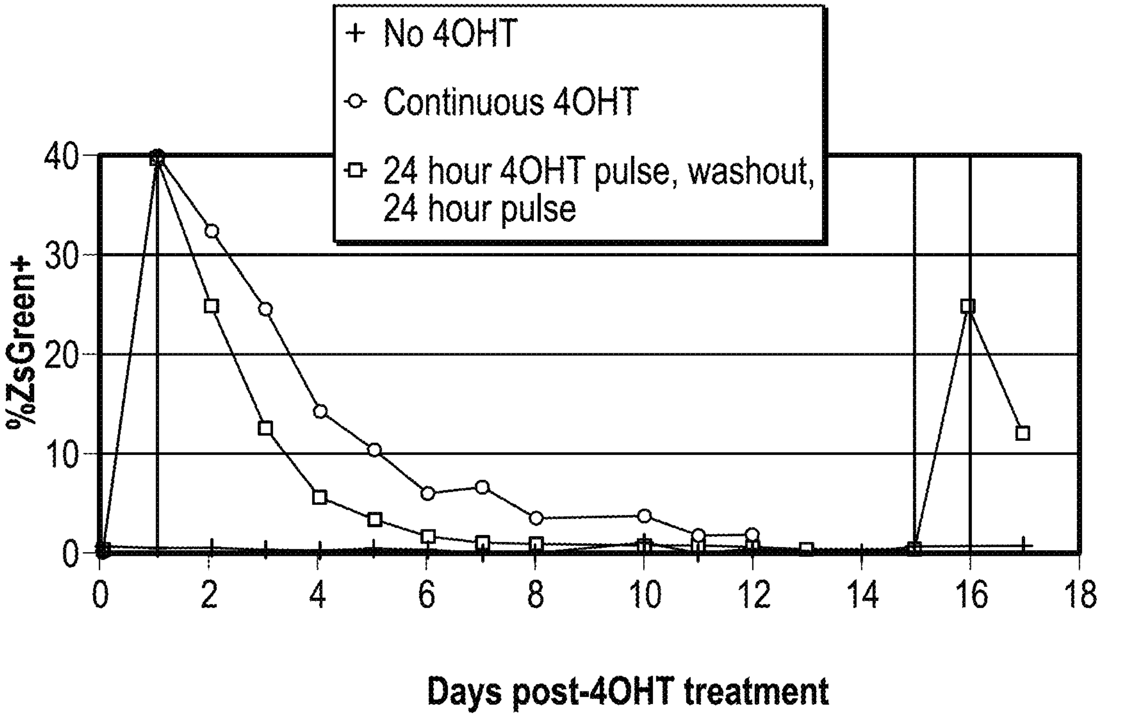
FIG. 3 shows the on and off rate kinetics of expression of ZsGreen in transduced Jurkat cells with a single 48 hour treatment of 4-OHT followed by a washout (o) and transduced Jurkat cells with a 24 hour treatment of 4-OHT followed by washout and then a re-stimulation with 4-OHT at day 15 (■).
Figure 4A:
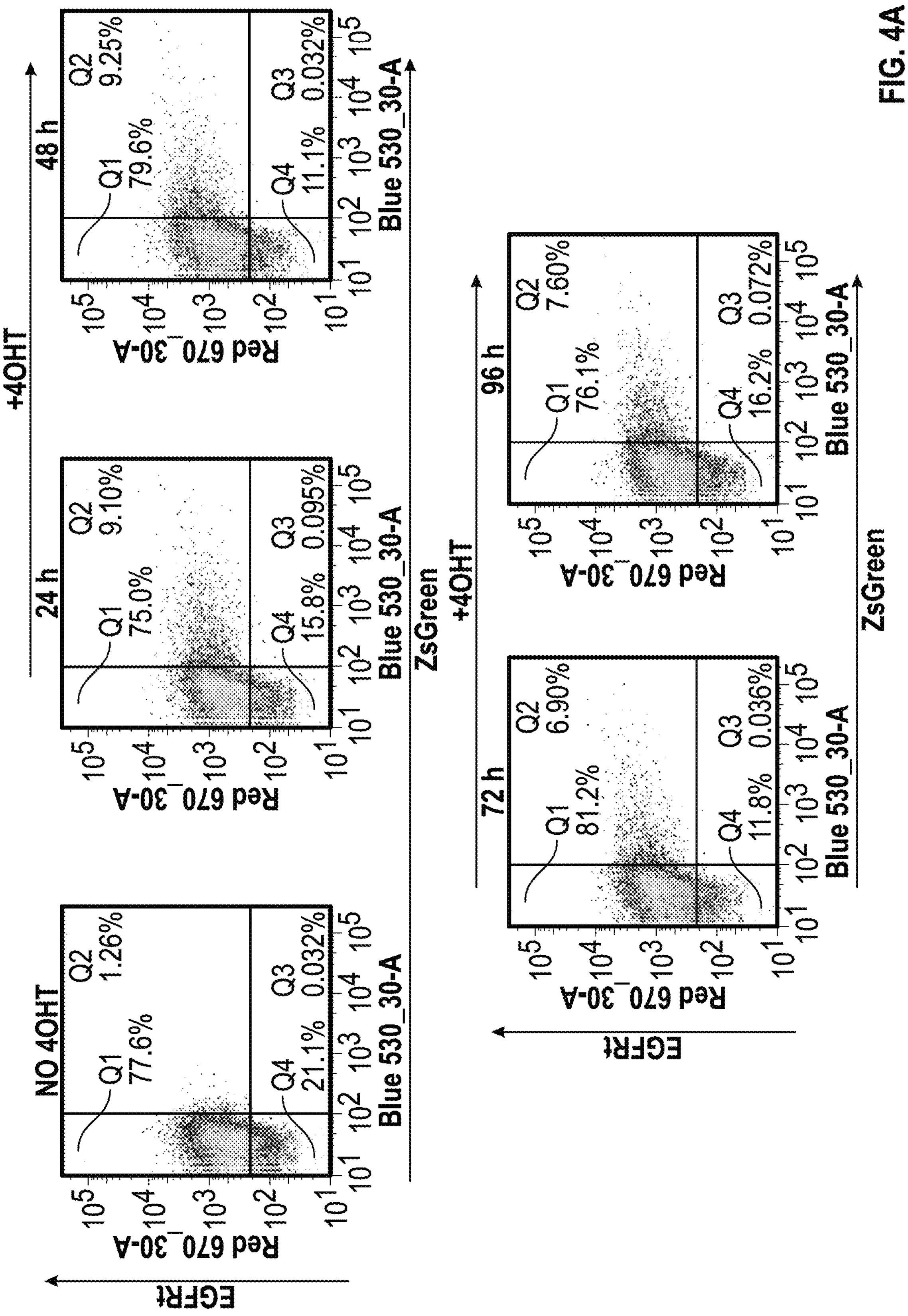
FIG. 4A-D shows the expression of ZsGreen in CD4 central memory cells transduced with dual package lentiviral constructs A and B. Cells were divided into 3 treatment groups, 4OHT alone (FIG. 4A), 4OHT combined with CD3/CD28 bead co-treatment (FIG. 4B) or 40HT alone for 48 hours, followed by addition of CD3/CD28 beads (FIG. 4C). Expression of ZsGreen was monitored over 96 hours.
Figure 4B:
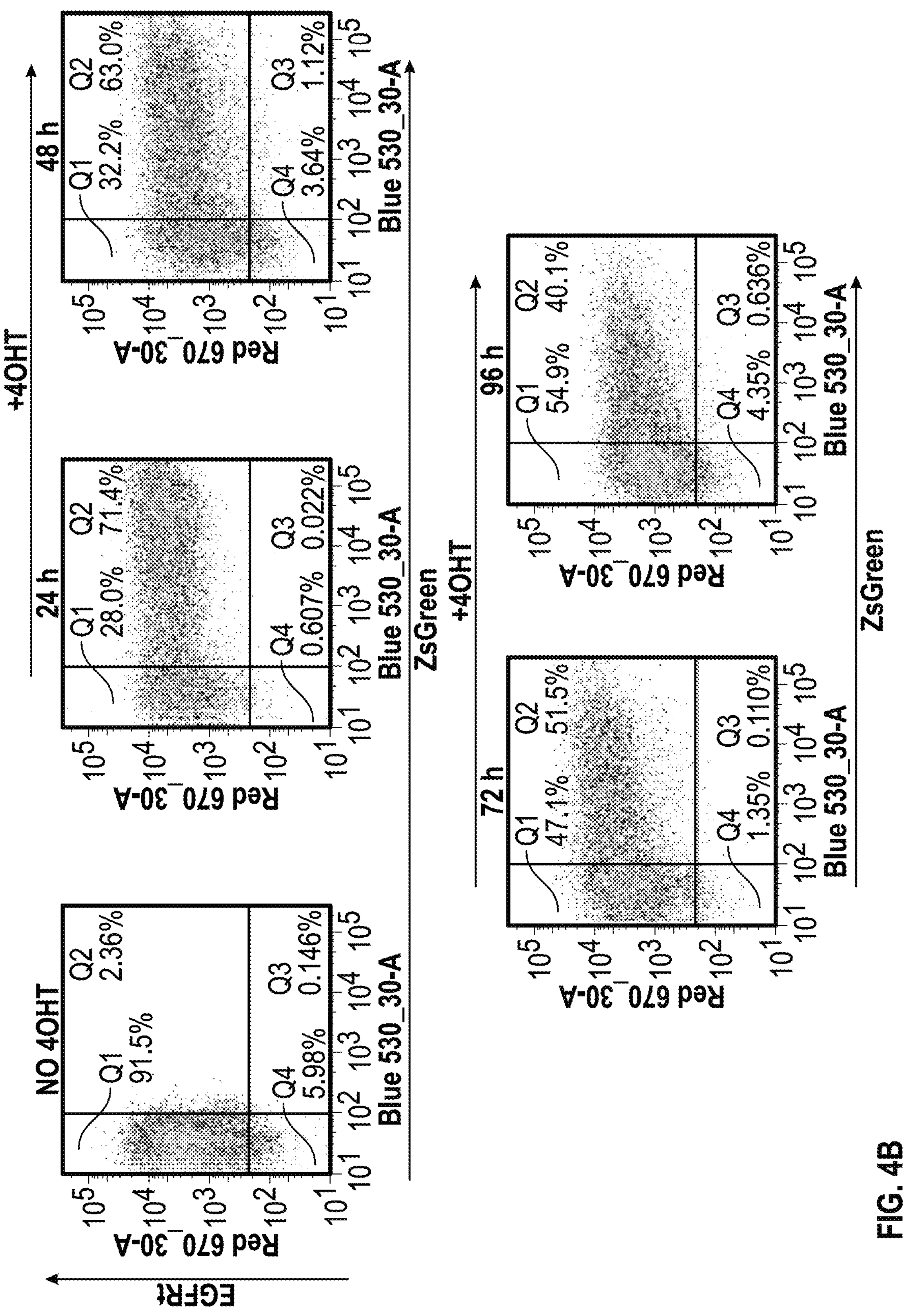
Figure 4C:
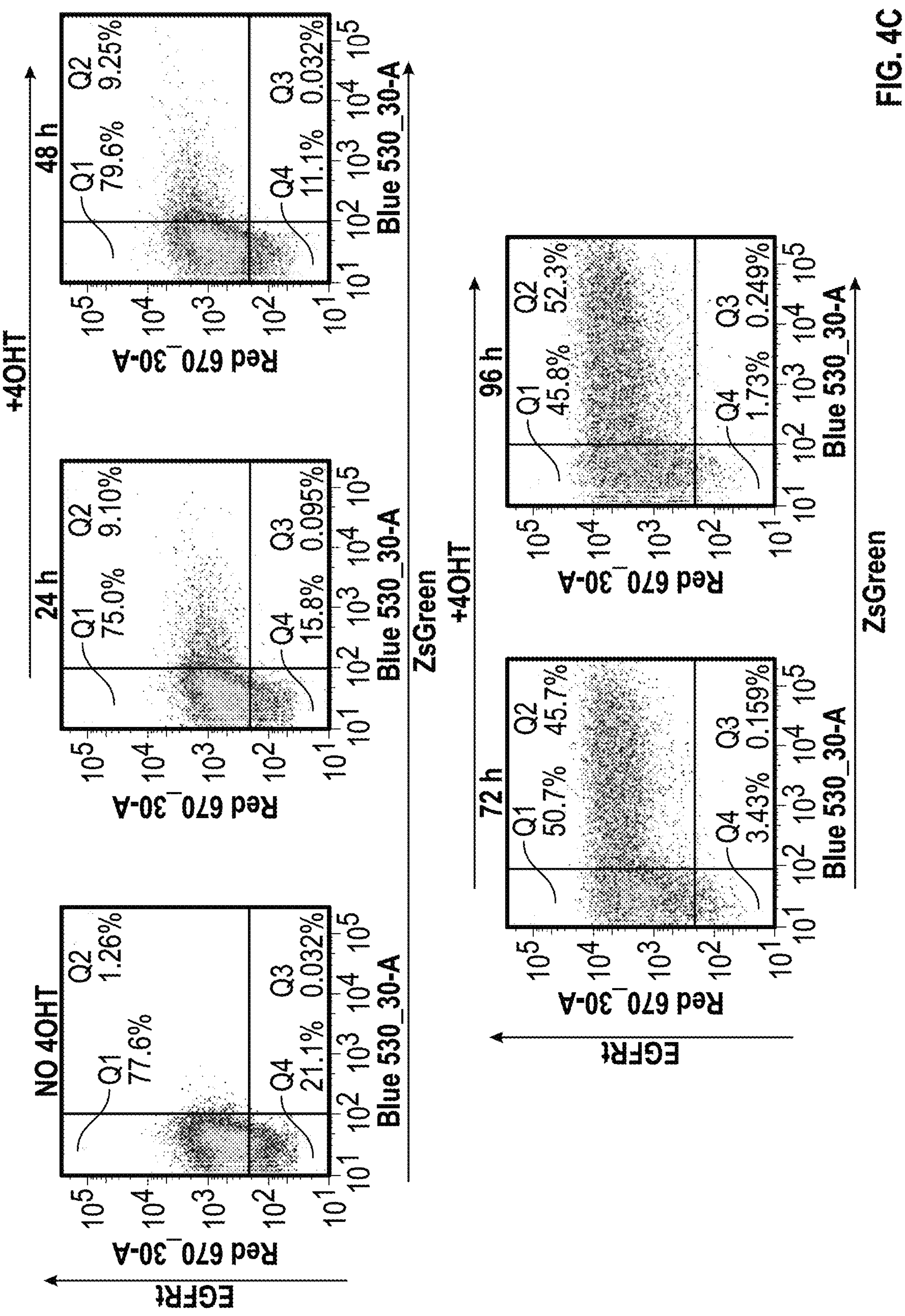
Figure 4D:
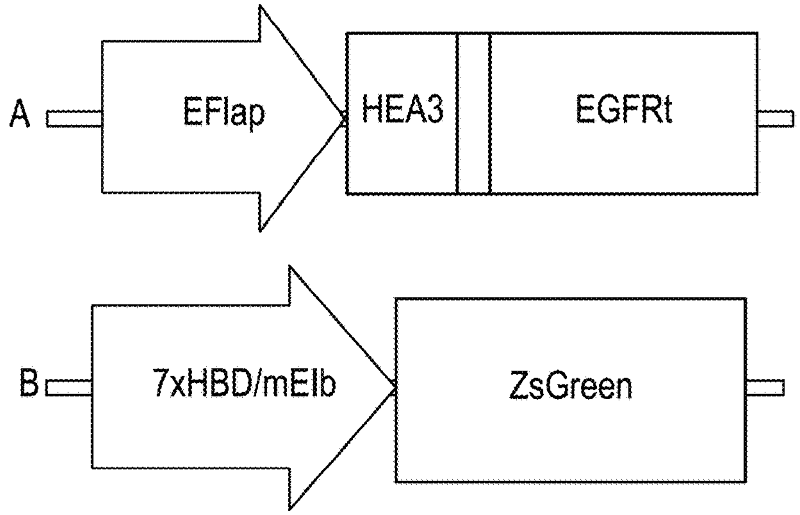

The population was subjected to 500 nM 4OHT stimulation for 48 hours, and then sorted for ZsGreen+cells utilizing FACS, yielding a >99% ZsGreen+population on immediate post-sort analysis. Cells were subsequently expanded in culture for 3 weeks, and then prepared for kinetic studies. Cells were divided into 3 treatment groups: (1) no 4OHT (2) 200 nM 4OHT (added every 48 hours) (3) 24 hour 200 nM 4OHT, followed by washout 1× in PBS, then culture in 4OHT free media for 14 days, followed by a 24 hour re-stimulation with 200 nm 4OHT, and then washout in 1×PBS. At each time point, samples were harvested and analyzed via flow cytometry for ZsGreen expression. Results are shown in FIG. 3 and are presented as % ZsGreen+.

Results

The results in FIG. 1 show that in the presence of 4-hydroxy tamoxifen (4-OHT), about 50% of the cells express ZsGreen, indicating these cells have both constructs A and B and that 4-OHT induced expression of construct B. The results of the dose response curve show that a concentration of 200 nM or greater of 4-OHT was effective to induce expression of the transgene in transduced cells. (FIG. 2). The results in FIG. 3 show that as the 4-OHT is washed out of the culture, the Zs Green expression drops off to less than 10% of the max ZsGReen activity within 5 days. When 4-OHT is added back, ZsGreen activity returns to about 100% max activity within 2 days.

Discussion

These experiments show that human T Jurkat cells can be transduced with a dual packaged lentivirus with a constitutive component and an inducible component. Expression of the ZsGreen gene is induced in the presence of 4-OHT in a dose responsive manner. In addition, washing out of 4-OHT from the cell culture resulted in a decrease in expression of ZsGreen that could be re-stimulated by addition of 4-OHT back to the cells.

Expression in Primary CD4 Central Memory Cells and CD8 Central Memory Cells.

"ON" and "OFF" state of CD4 and CD8 Central memory T cells expressing TamR ZsGreen was studied.

Constructs.

In some alternatives, this system involves two components: 1) constitutive expression of HEA-3 linked to a single transgene or set of transgenes by T2A skip-linker domains (construct A) (See FIGS. 9A, 9B and 9C; SEQ ID NO: 39; Table 1 SEQ ID NO: 8 and SEQ ID NO: 9) and 2) conditional expression of a transgene that is under control of the HEA-3 restricted synthetic promoter 7×HBD/mEF1ap whereby induction of the transgene occurs in response to tamoxifen (construct B) (See Table 12; SEQ ID NO: 41). Depending on the desired use of TamRLV genetic control a combination of delivery systems and vector compositions can be used. Constructs were prepared as described above.

Methods

CD4 central memory cells were obtained from peripheral blood by selecting cells through flow cytometry for markers CD4, and CD62L and negative for CD45RO. Cells were cultured with anti-CD3/anti-CD28 beads for 3 days.

CD8 central memory cells were obtained from peripheral blood by selecting cells through flow cytometry for markers CD8, and CD62L and negative for CD45RO. Cells were cultured with anti-CD3/anti-CD28 beads for 3 days.

After 3 days, CD4 or CD8 central memory cells were transduced at a MOI of 5 with lentivirus packaging constructs described above in which a dual packaging approach in which each plasmid is co-transfected into 293T cells during lentiviral production. This construct utilized molar ratio of 1:2 of construct A to construct B. Construct A encodes the chimeric transcription factor HEA3 linked via a ribosomal cleavage sequence, T2A, to the tracking and selection marker EGFRt. Construct B encodes the synthetic, HEA3-responsive promoter, 7×HBD/mE1b which regulates expression of the transgene ZsGreen-DR1, a short half-life green fluorescent reporter gene.

Figure 5A:
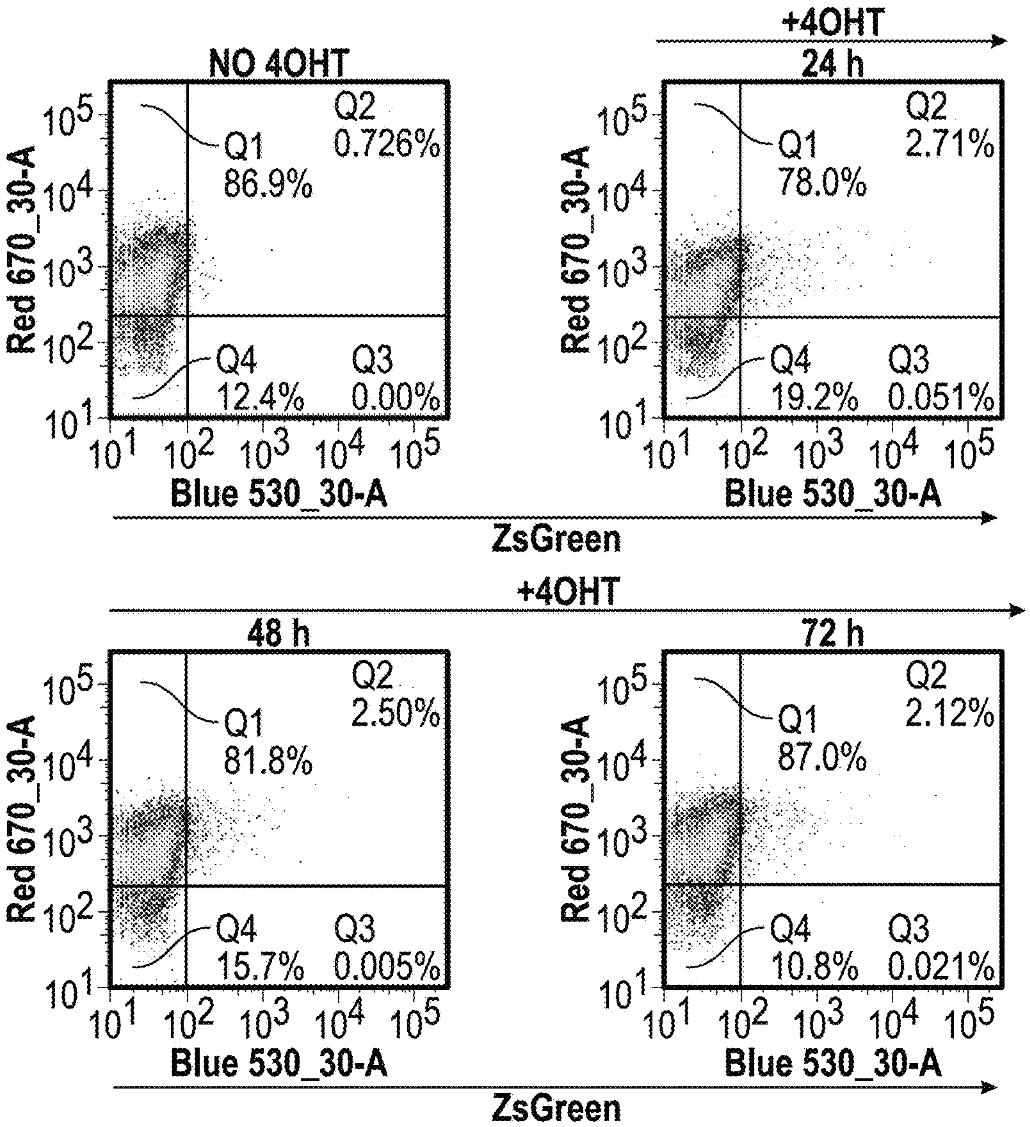
FIGS. 5A-C shows the expression of ZsGreen in CD8 central memory cells transduced with dual package lentiviral constructs A and B as shown in FIG. 4. Cells were divided into 3 treatment groups, 4OHT alone (FIG. 5A), 4OHT combined with CD3/CD28 bead co-treatment (FIG. 5B) or 40HT alone for 48 hours, followed by addition of CD3/CD28 beads (FIG. 5C). Expression of ZsGreen was monitored over 72 hours.
Figure 5B:
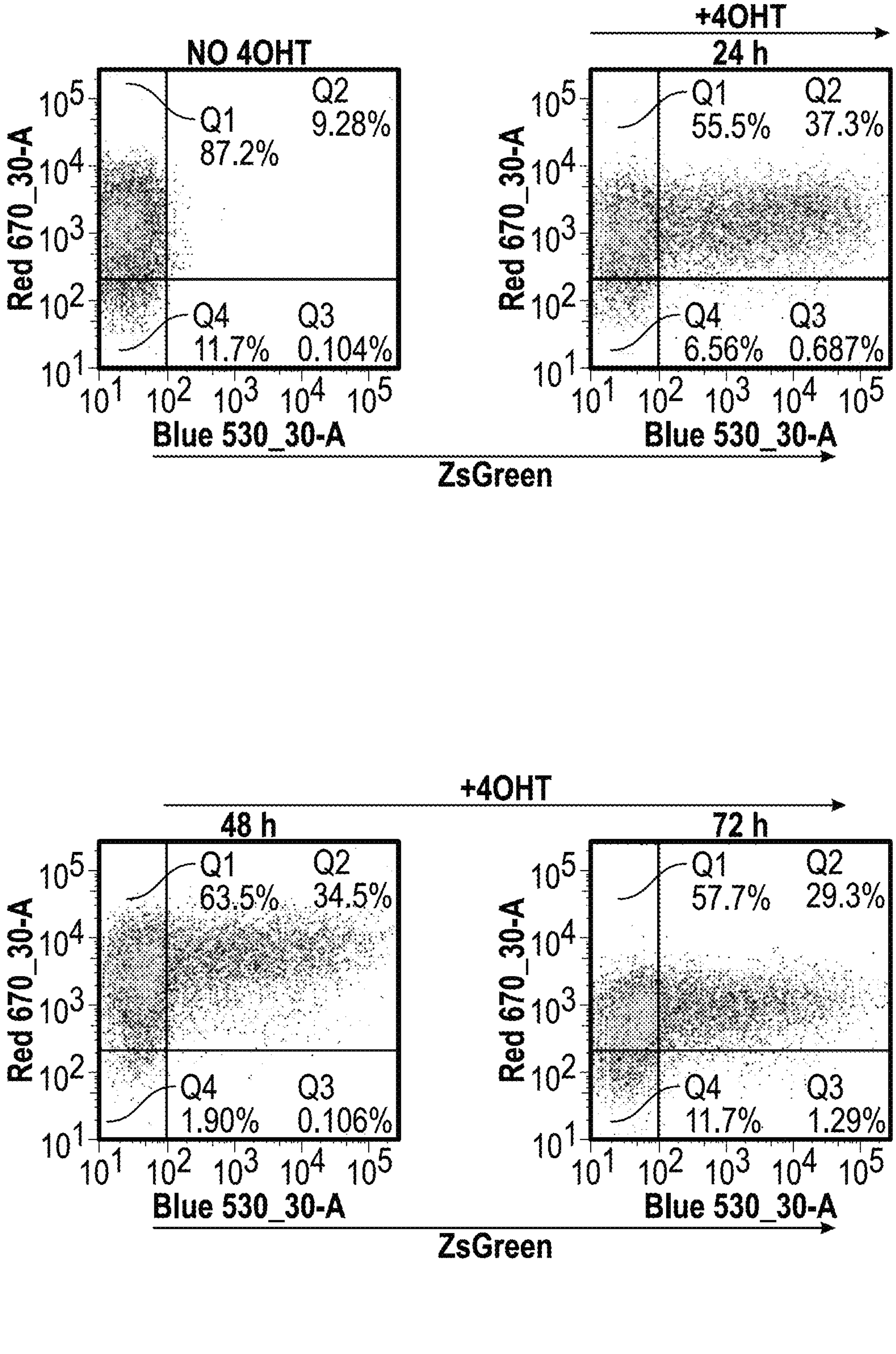
Figure 5C:
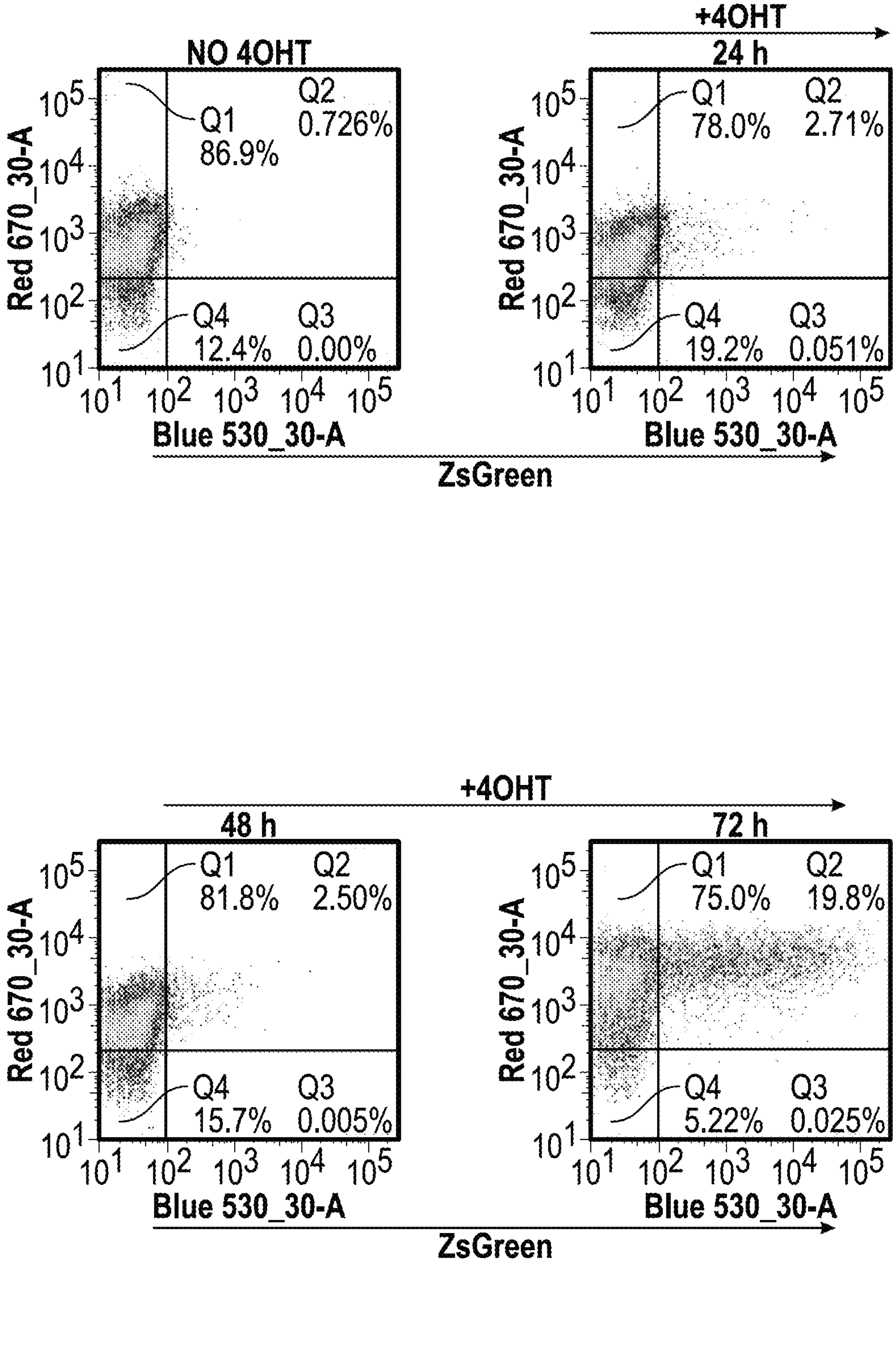

On day 21 after transduction, cells were enriched for EGFRt, and subsequently expanded with feeder cells, IL2, and IL15. Following expansion, cells were divided into 3 treatment groups, 4OHT alone (A), 4OHT combined with CD3/CD28 bead cotreatment (B) or 40HT alone for 48 hours, followed by addition of CD3/CD28 beads (C). Corresponding samples without 4OHT were also obtained for comparison. All samples were harvested at indicated time points following 4OHT treatment, stained with EGFRt-biotin antibody, followed by SA-APC, and analyzed for flow cytometry. The results are shown in FIG. 4 (CD4 central memory) and FIG. 5 (CD8 central memory).

Results

The results show that the CD4 cells transduced with the dual plasmid vector required the presence of activation stimulus in order to express the ZsGreen even in the presence of tamoxifen. See FIG. 4B. About 70% of the primary transduced CD4 cells in the presence of tamoxifen and antiCD3/anti-CD28 beads expressed ZsGreen. Gene expression was seen when activation occurred after a 48 hour treatment with tamoxifen. See FIG. 4C.

The results show that the CD8 cells transduced with the dual plasmid vector also required the presence of activation stimulus in order to express the ZsGreen even in the presence of tamoxifen. See FIG. 5B. About 37% of the primary transduced CD8 cells in the presence of tamoxifen and antiCD3/anti-CD28 beads expressed ZsGreen. Gene expression was seen when activation occurred after a 48 hour treatment with tamoxifen. See FIG. 5C.

These results show that primary central memory T cells transduced with an inducible construct can express the transgene in the presence of the inducer upon activation with antiCD3/CD28 cells. However, nonactivated cells expressing the transgene can be readily isolated using immunomagnetic or flow cytometry sorting.

Construction of TamR—CD19CAR LV.

Construction of the vector was accomplished by dual packaging of transfer plasmids housing constructs as described above at a plasmid molar ratio of 1:1. (See FIGS. 6C and 7C) Construct A under the constitutive EF-1alpha promoter encodes TamR-tf (HEA3) linked via a ribosomal cleavage sequence, T2A, to the tracking and selection marker EGFRt. (See FIGS. 9A, 9B and 9C; SEQ ID NO: 39, Table 1: SEQ ID NO: 8 and SEQ ID NO: 9) Construct B contains the 7×HBD/mE1b promoter with downstream transgene cDNA including CD19CAR linked via 2a cleavage sequence to Her2t, a tracking and selection marker. (See Table 12; SEQ ID NO: 41; Table 2 SEQ ID NO: 10; FIG. 11; SEQ ID NO: 44). Another construct was prepared adding an additional selective marker DHFRdm (See FIG. 12; SEQ ID NO: 46).

Figure 6A:
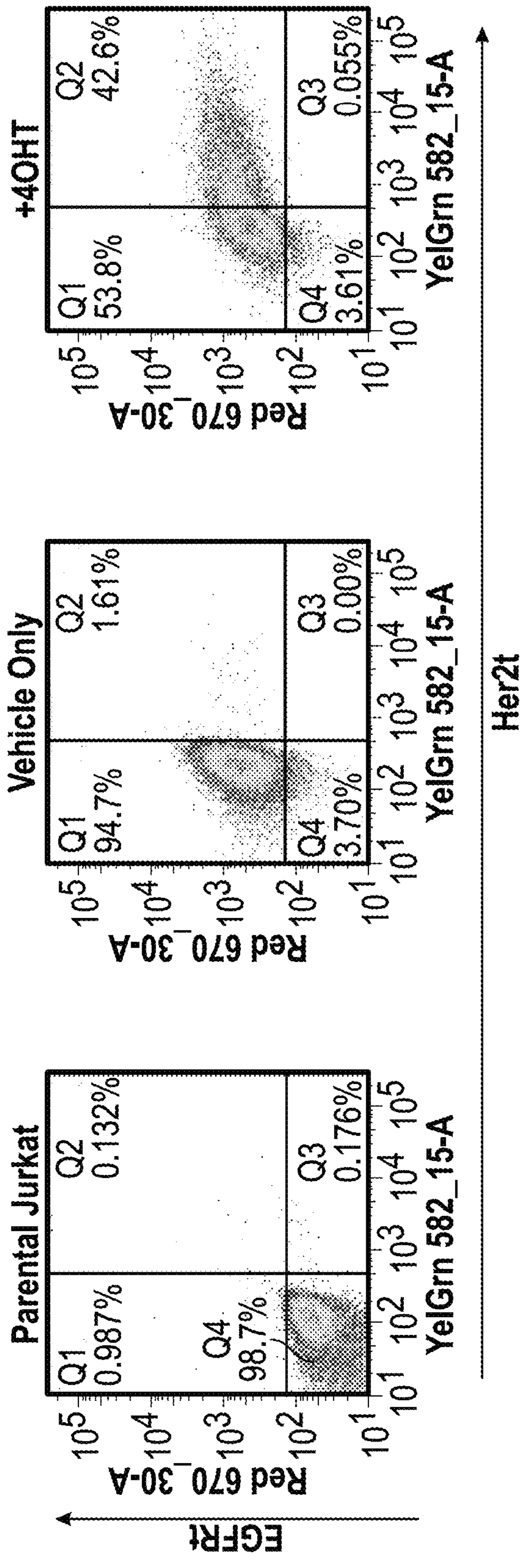
FIG. 6A shows expression of EGFRt and Her2t in Human Jurkat T cells transduced with constructs A and B as shown in FIG. 6C. Expression of EGFRt and Her2t were monitored in the presence or absence of 4OHT. Samples were stained with EGFRt-APC antibody and Herceptin-biotin, followed by SA-PE.
Figure 6B:
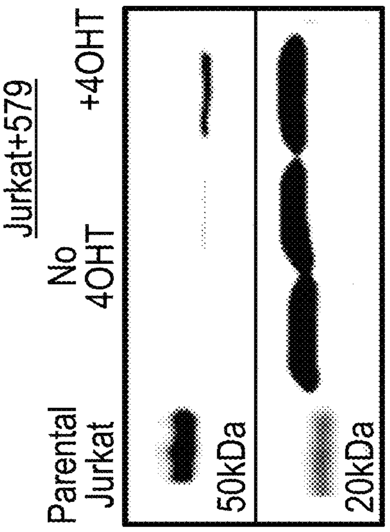
FIG. 6B shows a western blot of parental Jurkat cells and transduced CD19CAR transduced cells stained with mouse antiCD247 which recognizes the intracellular CD3 zeta chain on CD19 CAR (about 48 kDA), the endogenous CD3 zeta chain has migrates at 23 kDA. The endogenous CD3 zeta chain was detected in all of the cells. The CD19 CAR CD3 zeta chain was only detected in transduced Jurkat cells exposed to 4-OHT.

Human Jurkat cells were transduced at a MOI of 2, then were expanded in culture, and selected for EGFRt+ cells via magnetic bead selection. After further expansion, cells were either treated with vehicle alone (EtOH) or 500 nM 4OHT, and harvested for flow cytometry. Samples were stained with EGFRt-APC antibody and Herceptin-biotin, followed by SA PE. Samples were also prepared for western blot, the primary antibody used is an anti-CD247 mouse mAb which recognizes the intracellular CD3 zeta chain on the CD19CAR (~48 kDa). The endogenous CD3 zeta migrates at ~23 kDa. The results are shown in FIG. 6.

Jurkat T Cells Transduced with TamR CD19CAR LV Containing a Selective Marker.

Construction of TamR CD19CAR LV was done through dual packaging of constructs A and B. Construct A contains HEA3 linked via a ribosomal cleavage sequence, T2A, to the tracking and selection marker EGFRt. Construct B contains the 7×HBD/mE1b promoter with downstream transgene consisting of CD19CAR linked via 2a cleavage sequence to Her2t, a tracking and selection marker, linked via another 2a cleavage sequence (P2A) to DHFRdm, a methotrexate selection gene.

Figure 7A:
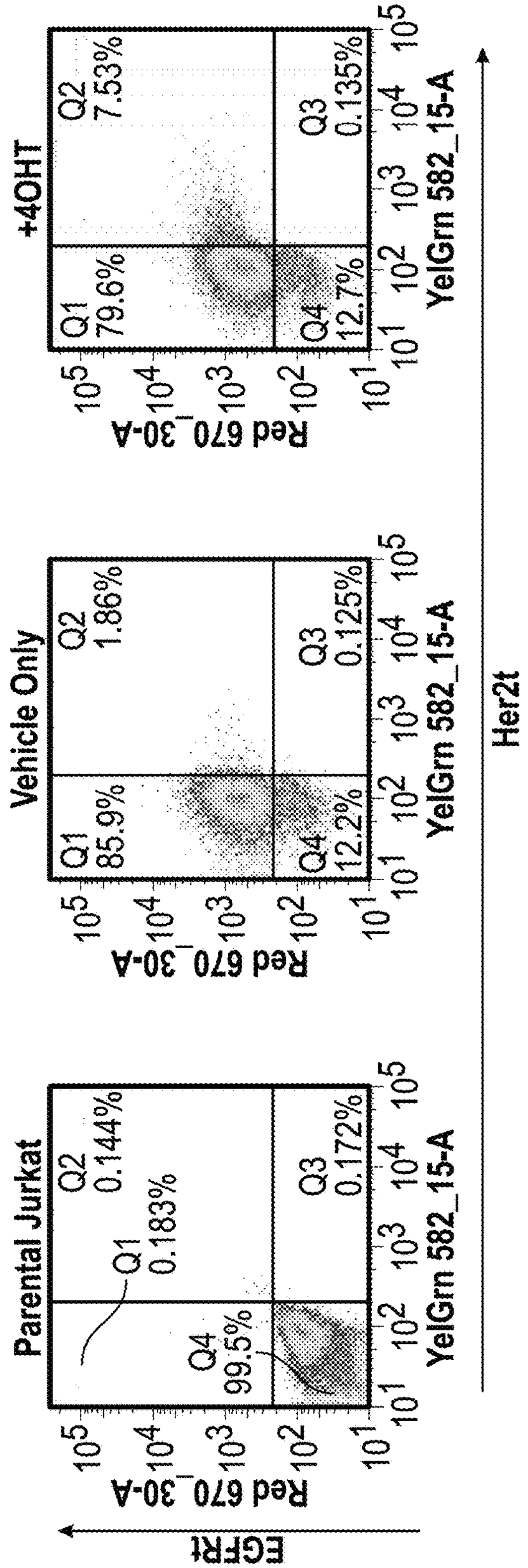
FIG. 7A shows expression of EGFRt and Her2t in Human Jurkat T cells transduced with TamR CD19CAR LV including an additional selective marker, DHFRdm in the presence or absence of 4OHT. Expression of EGFRt and Her2t were monitored in the presence or absence of 4OHT. Samples were stained with EGFRt-APC antibody and Herceptin-biotin, followed by SA-PE.

Cells were transduced with TamR CD19CAR LV at a MOI of 1, expanded in culture, selected for EGFRt via magnetic bead selection. Following further expansion cells were treated with vector alone (EtOH) or 500 nM 4OHT, and harvested for flow cytometry, (upper panel). FIG. 7. Samples were stained with EGFRt-APC antibody and Herceptin-biotin, followed by SA-PE. Parental (untransduced Jurkat) is shown for comparison. Samples were also prepared for western blot, the primary antibody used is an anti-CD247 mouse mAb which recognizes the intracellular CD3 zeta chain on the CD19CAR (~48 kDa). The endogenous CD3 zeta migrates at ~23 kDa.

Results

Figure 6C:
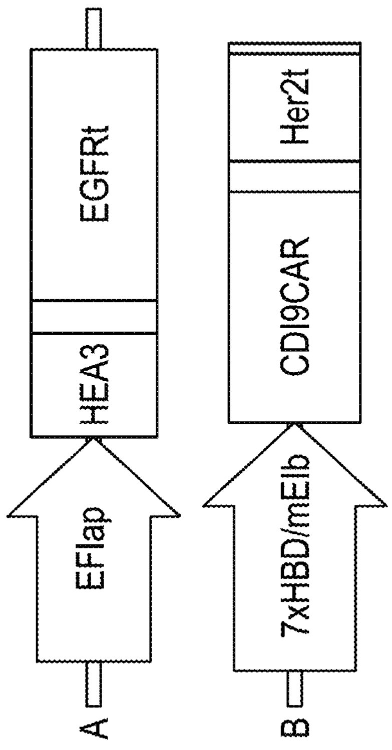
FIG. 6C shows construct A, which comprises the constitutive promoter EF1αp linked to TamR-tf (HEA3) linked to EGFRt, and construct B comprising a synthetic promoter 7×HBD/mE1b linked to a polynucleotide coding for CD19CAR linked to a polynucleotide coding for Her2t.

The results show that EGFRt is detected in 94.6% of cells transduced with a construct not including the additional selective marker DHFRdm. See FIG. 6B. FIG. 6C shows that in the presence of tamoxifen, about 42.6% of the cells transduced with a construct not including DHFRdm expressed both EGFRt and Her2t. The cells expressing both markers expressed the CD3zeta chain as part of the CAR construct (48 kDa) as detected in Western blot. See FIG. 6B.

Figure 7B:
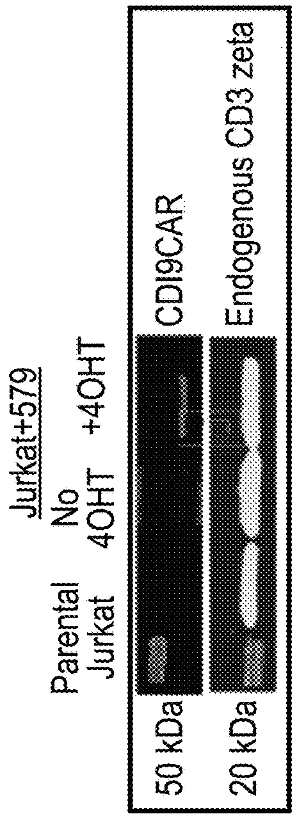
FIG. 7B shows a western blot of parental Jurkat cells and transduced CD19CAR transduced cells stained with mouse antiCD247 which recognizes the intracellular CD3 zeta chain on CD19 CAR (about 48 kDA), the endogenous CD3 zeta chain has migrates at 23 kDA. The endogenous CD3 zeta chain was detected in all of the cells. The CD19 CAR CD3 zeta chain was only detected in transduced Jurkat cells exposed to 4-OHT.
Figure 7C:
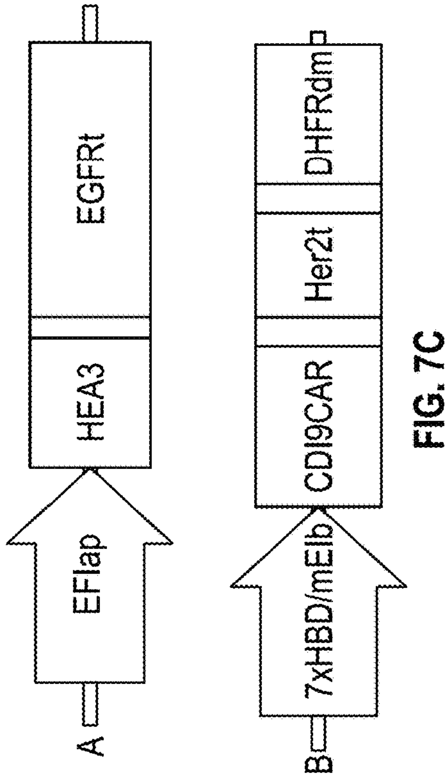
FIG. 7C shows construct A, which comprises the constitutive promoter EF1αp linked to TamR-tf (HEA3) linked to EGFRt, and construct B comprising a synthetic promoter 7×HBD/mE1b linked to a polynucleotide coding for CD19CAR linked to a polynucleotide coding for Her2t linked to a polynucleotide coding for DHFRdm.

FIG. 7 shows that 85.9% Jurkat cells transduced with a construct including another 2a cleavage sequence (P2A) to DHFRdm in the absence of tamoxifen express EGFRt. In the presence of tamoxifen, about 7.5% of the cells expressed both EGFRt and Her2t. The cells expressing both markers expressed the CD3zeta chain as part of the CAR construct (48 kDa) as detected in Western blot. See FIG. 7B.

Inducible expression of CD19 CAR is shown in transduced Jurkat cells. Induction can be measured by detecting expression of the marker Her2t as well as detecting expression of CD19CAR using western blot. Adding an additional selectable marker, DHFRdm, to the inducible construct did not improve inducible gene expression.

TamR CD19CAR LV Transduced Human CD4 TCM T Cells.

Figures 8A, 8B:
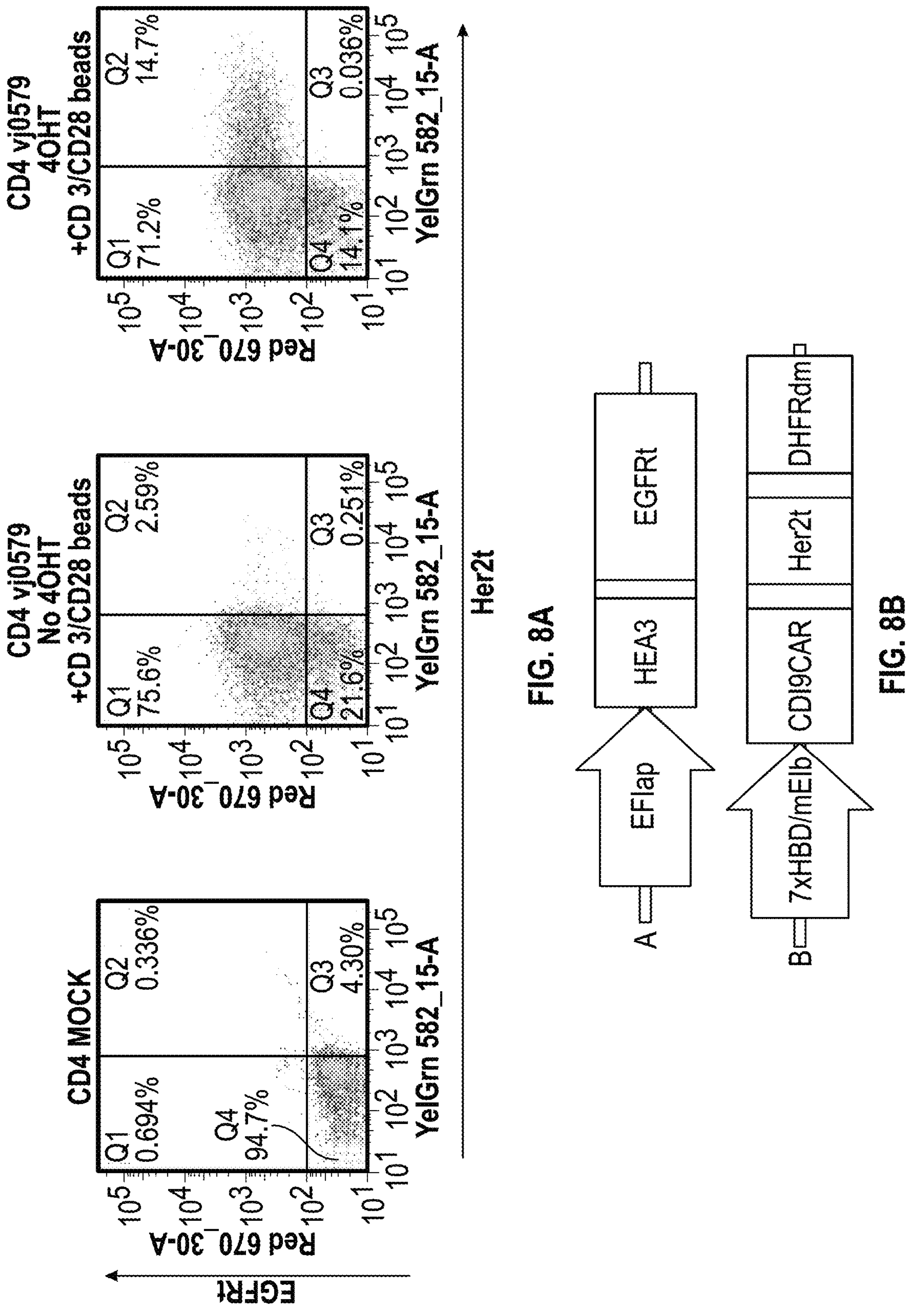
FIG. 8A shows expression of EGFRt and Her2t in Human CD4 central memory T cells transduced with TamR CD19CAR LV including an additional selective marker, DHFRdm in the presence or absence of 4OHT and antiCD3/CD28 beads. Expression of EGFRt and Her2t were monitored in the presence or absence of 4OHT and in the presence or absence of antiCD3/CD28 beads. Samples were stained with EGFRt-APC antibody and Herceptin-biotin, followed by SA-PE.
FIG. 8B shows construct A, which comprises the constitutive promoter EF1αp linked to TamR-tf (HEA3) linked to EGFRt, and construct B comprising a synthetic promoter 7×HBD/mE1b linked to a polynucleotide coding for CD19CAR linked to a polynucleotide coding for Her2t linked to a polynucleotide coding for DHFRdm.

CD4 central memory cells were obtained from peripheral blood by selecting cells through flow cytometry for markers CD4, and CD62L and negative for CD45RO. Cells were cultured anti-CD3/anti-CD28 beads for 3 days. After 3 days, CD4 Central memory cells were transduced at a MOI of 5 with a lentivirus which packages constructs A and B. (FIG. 8B). Construct A encodes the chimeric transcription factor HEA3 linked via a ribosomal cleavage sequence, T2A, to the tracking and selection marker EGFRt. (See FIGS. 9A, 9B and 9C; SEQ ID NO: 39; Table 1; SEQ ID NO: 8 and SEQ ID NO: 9). Construct B encodes the synthetic, HEA3-responsive promoter, 7×HBD/mE1b which regulates expression of the transgene CD19CAR-linked via a T2A to Her2t for tracking and selection, and via a second 2a sequence, P2A, to the methotrexate selection gene DHFRdm. (See Table 12; SEQ ID NO: 41; Table 2 SEQ ID NO: 10; FIG. 11; SEQ ID NO: 44; FIG. 12; SEQ ID NO: 46).

On day 21 after transduction, cells were enriched for EGFRt utilizing magnetic bead selection, and subsequently expanded with irradiated feeder cells, IL2, and IL15. Two weeks after expansion, cells were cryopreserved. In the experiment depicted above, CD4+ CEM cells which were mock transduced, or CD4+TamR CD19CAR LV were thawed, placed in culture with CD3/CD28 beads, IL-2, IL-15. CD4+TamRCD19CAR LV were treated or not with 500 nM 4OHT for 24 hours. All samples were harvested washed, then stained with an EGFRt-APC antibody and Her2t-biotin, followed by SA-PE, and analyzed via flow cytometry. The results are shown in FIG. 8.

Results

The results in FIG. 8 show that in the absence of tamoxifen 75.6% of transduced primary CD4 central memory cells express EGFRt, indicating the constitutive expression of construct A. In the presence of tamoxifen and an activating stimulus (e.g. antiCD3/antiCD28 beads), about 14.7% of the primary cells express both EGFRt and Her2t.

Primary CD4 cells transduced with an inducible vector in the presence of the inducer and an activating stimulus express the transgene under control of the inducible promoter as detected by the expression of the marker gene Her2t. However, nonactivated cells expressing the transgene can be readily isolated using immunomagnetic or flow cytometry sorting. Further characterization of these cells will involve detecting of expression of CD19CAR.

The foregoing is illustrative of the present invention, and is not to be construed as limiting thereof. The invention is defined by the following claims, with

TABLE 1

| Sequence of anti-CD19 short spacer chimeric receptor GMCSFRss-CD19scFv-IgG4hinge-CD28tm-41BB-Zeta-T2A-EGFRt |
|---|
| (GMCSFRss) |
| (SEQ ID NO: 2) |
| Atgctgctgctggtgaccagcctgctgctgtgcgagctgccccaccccg |
| cctttctgctgatcccc |
| (CD19scFv) |
| (SEQ ID NO: 3) |
| Gacatccagatgacccagaccacctccagcctgagcgccagcctgggcg |
| accgggtgaccatcagctgccgggccagccaggacatcagcaagtacct |
| gaactggtatcagcagaagcccgacggcaccgtcaagctgctgatctac |
| cacaccagccggctgcacagcggcgtgcccagccggtttagcggcagcg |
| gctccggcaccgactacagcctgaccatctccaacctggaacaggaaga |
| tatcgccacctacttttgccagcagggcaacacactgccctacaccttt |
| ggcggcggaacaaagctggaaatcaccggcagcacctccggcagcggca |
| agcctggcagcggcgagggcagcaccaagggcgaggtgaagctgcagga |
| aagcggccctggcctggtggcccccagccagagcctgagcgtgacctgc |
| accgtgagcggcgtgagcctgcccgactacggcgtgagctggatccggc |
| agcccccccaggaagggcctggaatggctgggcgtgatctggggcagcga |
| gaccacctactacaacagcgccctgaagagccggctgaccatcatcaag |

TABLE 1-continued

| Sequence of anti-CD19 short spacer chimeric receptor GMCSFRss-CD19scFv-IgG4hinge-CD28tm-41BB-Zeta-T2A-EGFRt |
|---|
| gacaacagcaagagccaggtgttcctgaagatgaacagcctgcagaccg |
| acgacaccgccatctactactgcgccaagcactactactacggcggcag |
| ctacgccatggactactggggccagggcaccagcgtgaccgtgagcagc |
| (IgG4hinge) |
| (SEQ ID NO: 4) |
| Gaatctaagtacggaccgccctgccccccttgccct |
| (CD28tm-) |
| (SEQ ID NO: 5) |
| Atgttctgggtgctggtggtggtcggaggcgtgctggcctgctacagcc |
| tgctggtcaccgtggccttcatcatcttttgggtg |
| (41BB) |
| (SEQ ID NO: 6) |
| Aaacggggcagaaagaaactcctgtatatattcaaacaaccatttatga |
| gaccagtacaaactactcaagaggaagatggctgtagctgccgatttcc |
| agaagaagaagaaggaggatgtgaactg |
| (CD3Zeta)- |
| (SEQ ID NO: 7) |
| Cgggtgaagttcagcagaagcgccgacgcccctgcctaccagcagggcc |
| agaatcagctgtacaacgagctgaacctgggcagaagggaagagtacga |
| cgtcctggataagcggagaggccgggaccctgagatgggcggcaagcct |
| cggcggaagaaccccccaggaaggcctgtataacgaactgcagaaagaca |
| agatggccgaggcctacagcgagatcggcatgaagggcgagcggaggcg |
| gggcaagggccacgacggcctgtatcagggcctgtccaccgccaccaag |
| gatacctacgacgccctgcacatgcaggccctgcccccaagg |
| (T2A) |
| (SEQ ID NO: 8) |
| Ctcgagggcggcggagagggcagaggaagtcttctaacatgcggtgacg |
| tggaggagaatcccggccctagg |
| (EGFRt) |
| (SEQ ID NO: 9) |
| Atgcttctcctggtgacaagccactgctctgtgagttaccacacccagc |
| attcctcctgatcccacgcaaagtgtgtaacggaataggtattggtgaa |
| tttaaagactcactctccataaatgctacgaatattaaacacttcaaaa |
| actgcacctccatcagtggcgatctccacatcctgccggtggcatttag |
| gggtgactccttcacacatactcctcctctggatccacaggaactggat |
| attctgaaaaccgtaaaggaaatcacagggtttttgctgattcaggctt |
| ggcctgaaaacaggacggacctccatgcctttgagaacctagaaatcat |
| acgcggcaggaccaagcaacatggtcagttttctcttgcagtcgtcagc |
| ctgaacataacatccttgggattacgctccctcaaggagataagtgatg |
| gagatgtgataatttcaggaaacaaaaatttgtgctatgcaaatacaat |
| aaactggaaaaaactgtttgggacctccggtcagaaaaccaaaattata |
| agcaacagaggtgaaaacagctgcaaggccacaggccaggtctgccatg |
| ccttgtgctcccccgagggctgctggggcccggagcccagggactgcgt |

TABLE 1-continued

| Sequence of anti-CD19 short spacer chimeric receptor GMCSFRss-CD19scFv-IgG4hinge-CD28tm-41BB-Zeta-T2A-EGFRt |
|---|
| ctcttgccggaatgtcagccgaggcagggaatgcgtggacaagtgcaac |
| cttctggagggtgagccaagggagtttgtggagaactctgagtgcatac |
| agtgccacccagagtgcctgcctcaggccatgaacatcacctgcacagg |
| acggggaccagacaactgtatccagtgtgcccactacattgacggcccc |
| cactgcgtcaagacctgcccggcaggagtcatgggagaaaacaacaccc |
| tggtctggaagtacgcagacgccggccatgtgtgccacctgtgccatcc |
| aaactgcacctacggatgcactgggccaggtcttgaaggctgtccaacg |
| aatgggcctaagatcccgtccatcgccactgggatggtgggggccctcc |
| tcttgctgctggtggtggccctggggatcggcctcttcatg*tga* |

TABLE 2

| | |
|---|---|
| | GMCSFRss |
| DNA: | *ATG*CTGCTGCTGGTGACCAGCCTGCTGCTGTGCGAGCTGCCCCACCCCGCC |
| AA: | M L L L V T S L L L C E L P H P A |
| | CD19scFv |
| DNA: | TTTCTGCTGATCCCC:GACATCCAGATGACCCAGACCACCTCCAGCCTGAGC |
| AA: | F L L I P D I Q M T Q T T S S L S |
| DNA: | GCCAGCCTGGGCGACCGGGTGACCATCAGCTGCCGGGCCAGCCAGGACATC |
| AA: | A S L G D R V T I S C R A S Q D I |
| DNA: | AGCAAGTACCTGAACTGGTATCAGCAGAAGCCCGACGGCACCGTCAAGCTG |
| AA: | S K Y L N W Y Q Q K P D G T V K L |
| DNA: | CTGATCTACCACACCAGCCGGCTGCACAGCGGCGTGCCCAGCCGGTTTAGC |
| AA: | L I Y H T S R L H S G V P S R F S |
| DNA: | GGCAGCGGCTCCGGCACCGACTACAGCCTGACCATCTCCAACCTGGAACAG |
| AA: | G S G S G T D Y S L T I S N L E Q |
| DNA: | GAAGATATCGCCACCTACTTTTGCCAGCAGGGCAACACACTGCCCTACACC |
| AA: | E D I A T Y F C Q Q G N T L P Y T |
| DNA: | TTTGGCGGCGGAACAAAGCTGGAAATCACCGGCAGCACCTCCGGCAGCGGC |
| AA: | F G G G T K L E I T G S T S G S G |
| DNA: | AAGCCTGGCAGCGGCGAGGGCAGCACCAAGGGCGAGGTGAAGCTGCAGGAA |
| AA: | K P G S G E G S T K G E V K L Q E |
| DNA: | AGCGGCCCTGGCCTGGTGGCCCCCAGCCAGAGCCTGAGCGTGACCTGCACC |
| AA: | S G P G L V A P S Q S L S V T C T |
| DNA: | GTGAGCGGCGTGAGCCTGCCCGACTACGGCGTGAGCTGGATCCGGCAGCCC |
| AA: | V S G V S L P D Y G V S W I R Q P |
| DNA: | CCCAGGAAGGGCCTGGAATGGCTGGGCGTGATCTGGGGCAGCGAGACCACC |
| AA: | P R K G L E W L G V I W G S E T T |
| DNA: | TACTACAACAGCGCCCTGAAGAGCCGGCTGACCATCATCAAGGACAACAGC |
| AA: | Y Y N S A L K S R L T I I K D N S |
| DNA: | AAGAGCCAGGTGTTCCTGAAGATGAACAGCCTGCAGACCGACGACACCGCC |
| AA: | K S Q V F L K M N S L Q T D D T A |
| DNA: | ATCTACTACTGCGCCAAGCACTACTACTACGGCGGCAGCTACGCCATGGAC |
| AA: | I Y Y C A K H Y Y Y G G S Y A M D |
| | IgG4hinge |
| DNA: | TACTGGGGCCAGGGCACCAGCGTGACCGTGAGCAGC:GAGAGCAAGTACGGA |
| AA: | Y W G Q G T S V T V S S E S K Y G |
| | CD28tm |
| DNA: | CCGCCCTGCCCCCCTTGCCCT:ATGTTCTGGGTGCTGGTGGTGGTCGGAGGC |
| AA: | P P C P P C P M F W V L V V V G G |
| DNA: | GTGCTGGCCTGCTACAGCCTGCTGGTCACCGTGGCCTTCATCATCTTTTGG |
| AA: | V L A C Y S L L V T V A F I I F W |
| | 41B16 |
| DNA: | GTG:AAACGGGGCAGAAAGAAACTCCTGTATATATTCAAACAACCATTTATG |
| AA: | V K R G R K K L L Y I F K Q P F M |

TABLE 2-continued

| | |
|---|---|
| DNA: | AGACCAGTACAAACTACTCAAGAGGAAGATGGCTGTAGCTGCCGATTTCCA |
| AA: | R P V Q T T Q E E D G C S C R F P |
| | CD3Zeta |
| DNA: | GAAGAAGAAGAAGGAGGATGTGAACTGCGGGTGAAG:TTCAGCAGAAGCGCC |
| AA: | E E E E G G C E L R V K F S R S A |
| DNA: | GACGCCCCTGCCTACCAGCAGGGCCAGAATCAGCTGTACAACGAGCTGAAC |
| AA: | D A P A Y Q Q G Q N Q L Y N E L N |
| DNA: | CTGGGCAGAAGGGAAGAGTACGACGTCCTGGATAAGCGGAGAGGCCGGGAC |
| AA: | L G R R E E Y D V L D K R R G R D |
| DNA: | CCTGAGATGGGCGGCAAGCCTCGGCGGAAGAACCCCCAGGAAGGCCTGTAT |
| AA: | P E M G G K P R R K N P Q E G L Y |
| DNA: | AACGAACTGCAGAAAGACAAGATGGCCGAGGCCTACAGCGAGATCGGCATG |
| AA: | N E L Q K D K M A E A Y S E I G M |
| DNA: | AAGGGCGAGCGGAGGCGGGGCAAGGGCCACGACGGCCTGTATCAGGGCCTG |
| AA: | K G E R R R G K G H D G L Y Q G L |
| DNA: | TCCACCGCCACCAAGGATACCTACGACGCCCTGCACATGCAGGCCCTGCCC |
| AA: | S T A T K D T Y D A L H M Q A L P |
| | T2A |
| DNA: | CCAAGG:CTCGAGGGCGGCGGAGAGGGCAGAGGAAGTCTTCTAACATGCGGT |
| AA: | P R L E G G G E G R G S L L T C G |
| | EGFRt |
| DNA: | GACGTGGAGGAGAATCCCGGCCCTAGG:**ATGCTTCTCCTGGTGACAAGCCTT** |
| AA: | D V E E N P G P R M L L L V T S L |
| DNA: | **CTGCTCTGTGAGTTACCACACCCAGCATTCCTCCTGATCCCACGCAAAGTG** |
| AA: | L L C E L P H P A F L L I P R K V |
| DNA: | **TGTAACGGAATAGGTATTGGTGAATTTAAAGACTCACTCTCCATAAATGCT** |
| AA: | C N G I G I G E F K D S L S I N A |
| DNA: | **ACGAATATTAAACACTTCAAAAACTGCACCTCCATCAGTGGCGATCTCCAC** |
| AA: | T N I K H F K N C T S I S G D L H |
| DNA: | **ATCCTGCCGGTGGCATTTAGGGGTGACTCCTTCACACATACTCCTCCTCTG** |
| AA: | I L P V A F R G D S F T H T P P L |
| DNA: | **GATCCACAGGAACTGGATATTCTGAAAACCGTAAAGGAAATCACAGGGTTT** |
| AA: | D P Q E L D I L K T V K E I T G F |
| DNA: | **TTGCTGATTCAGGCTTGGCCTGAAAACAGGACGGACCTCCATGCCTTTGAG** |
| AA: | L L I Q A W P E N R T D L H A F E |
| DNA: | **AACCTAGAAATCATACGCGGCAGGACCAAGCAACATGGTCAGTTTTCTCTT** |
| AA: | N L E I I R G R T K Q H G Q F S L |
| DNA: | **GCAGTCGTCAGCCTGAACATAACATCCTTGGGATTACGCTCCCTCAAGGAG** |
| AA: | A V V S L N I T S L G L R S L K E |
| DNA: | **ATAAGTGATGGAGATGTGATAATTTCAGGAAACAAAAATTTGTGCTATGCA** |
| AA: | I S D G D V I I S G N K N L C Y A |
| DNA: | **AATACAATAAACTGGAAAAAACTGTTTGGGACCTCCGGTCAGAAAACCAAA** |
| AA: | N T I N W K K L F G T S G Q K T K |
| DNA: | **ATTATAAGCAACAGAGGTGAAAACAGCTGCAAGGCCACAGGCCAGGTCTGC** |
| AA: | I I S N R G E N S C K A T G Q V C |
| DNA: | **CATGCCTTGTGCTCCCCCGAGGGCTGCTGGGGCCCGGAGCCCAGGGACTGC** |
| AA: | H A L C S P E G C W G P E P R D C |
| DNA: | **GTCTCTTGCCGGAATGTCAGCCGAGGCAGGGAATGCGTGGACAAGTGCAAC** |
| AA: | V S C R N V S R G R E C V D K C N |
| DNA: | **CTTCTGGAGGGTGAGCCAAGGGAGTTTGTGGAGAACTCTGAGTGCATACAG** |
| AA: | L L E G E P R E F V E N S E C I Q |
| DNA: | **TGCCACCCAGAGTGCCTGCCTCAGGCCATGAACATCACCTGCACAGGACGG** |
| AA: | C H P E C L P Q A M N I T C T G R |

TABLE 2-continued

| | |
|---|---|
| DNA: | **GGACCAGACAACTGTATCCAGTGTGCCCACTACATTGACGGCCCCCACTGC** |
| AA: | G P D N C I Q C A H Y I D G P H C |
| DNA: | **GTCAAGACCTGCCCGGCAGGAGTCATGGGAGAAAACAACACCCTGGTCTGG** |
| AA: | V K T C P A G V M G E N N T L V W |
| DNA: | **AAGTACGCAGACGCCGGCCATGTGTGCCACCTGTGCCATCCAAACTGCACC** |
| AA: | K Y A D A G H V C H L C H P N C T |
| DNA: | **TACGGATGCACTGGGCCAGGTCTTGAAGGCTGTCCAACGAATGGGCCTAAG** |
| AA: | Y G C T G P G L E G C P T N G P K |
| DNA: | **ATCCCGTCCATCGCCACTGGGATGGTGGGGGCCCTCCTCTTGCTGCTGGTG** |
| AA: | I P S I A T G M V G A L L L L L V |
| DNA: | **GTGGCCCTGGGGATCGGCCTCTTCATG*TGA*** (SEQ ID NO: 10) |
| AA: | V A L G I G L F M * (SEQ ID NO: 11) |

TABLE 3

ZXR-014 Nucleotide and amino acid sequences (map of sections)

GMCSFRss: nt2084-2149 (SEQ ID NO: 50)

CD19scFv: nt2150-2884(SEQ ID NO: 51)

Igg4Hinge: nt2885-2920 (SEQ ID NO: 52)

CD28tm: nt2921-3004 (SEQ ID NO: 53)

41BB: nt3005-3130 (SEQ ID NO: 54)

Zeta: nt3131-3466 (SEQ ID NO: 55)

T2A: nt3467-3538 (SEQ ID NO: 56)

EGFRt: nt3539-4612 (SEQ ID NO: 57)

Primers for sequencing:

| Oligo name | Sequence | Region |
|---|---|---|
| oJ02649 | ATCAAAAGAATAG ACCGAGATAGGGT | pre-U5 (SEQ ID NO: 22) |
| oJ02648 | CCGTACCTTTAAG ACCAATGACTTAC | delU3 (SEQ ID NO: 23) |
| oJ02650 | TTGAGAGTTTTCG CCCCG | mid-Ampr (SEQ ID NO: 24) |
| oJ02651 | AATAGACAGATCG CTGAGATAGGT | post-Ampr (SEQ ID NO: 25) |
| oJ02652 | CAGGTATCCGGTA AGCGG | CoE1 ori (SEQ ID NO: 26) |
| oJ02653 | CGACCAGCAACCA TAGTCC | SV40 (SEQ ID NO: 27) |
| oJ02654 | TAGCGGTTTGACT CACGG | CMV (SEQ ID NO: 28) |
| oJ02655 | GCAGGGAGCTAGA ACGATTC | psi (SEQ ID NO: 29) |
| oJ02656 | ATTGTCTGGTATA GTGCAGCAG | RRE (SEQ ID NO: 30) |
| oJ02657 | TCGCAACGGGTTT GCC | EF1p (SEQ ID NO: 31) |
| oJ02658 | AGGAAGATATCGC CACCTACT | CD19Rop (SEQ ID NO: 32) |
| oJ02601 | CGGGTGAAGTTCA GCAGAAG | Zeta (SEQ ID NO: 33) |
| oJ02735 | ACTGTGTTTGCTG ACGCAAC | WPRE (SEQ ID NO: 34) |
| oJ02715 | ATGCTTCTCCTGG TGACAAG | EGFRt (SEQ ID NO: 35) |

TABLE 4

Uniprot P0861 IgG4-Fc (SEQ ID NO: 13)

```
        10         20         30         40
ASTKGPSVFP LAPCSRSTSE STAALGCLVK DYFPEPVTVS

        50         60         70         80
WNSGALTSGV HTFPAVLQSS GLYSLSSVVT VPSSSLGTKT

        90        100        110        120
YTCNVDHKPS NTKVDKRVES KYGPPCPSCP APEFLGGPSV

       130        140        150        160
FLFPPKPKDT LMISRTPEVT CVVVDVSQED PEVQFNWYVD

       170        180        190        200
GVEVHNAKTK PREEQFNSTY RVVSVLTVLH QDWLNGKEYK

       210        220        230        240
CKVSNKGLPS SIEKTISKAK GQPREPQVYT LPPSQEEMTK

       250        260        270        280
NQVSLTCLVK GFYPSDIAVE WESNGQPENN YKTTPPVLDS

       290        300        310        320
DGSFFLYSRL TVDKSRWQEG NVFSCSVMHE ALHNHYTQKS

LSLSLGK
```

1-98 CH1 (SEQ ID NO: 59)

99-110 Hinge (SEQ ID NO: 60)

111-220 CH2 (SEQ ID NO: 61)

221-327 CH3 (SEQ ID NO: 62)

Position 108 S→P (SEQ ID NO: 63)

TABLE 5

| |
|---|
| Uniprot P10747 CD28 (SEQ ID NO: 14) |
| 10 20 30 40 |
| MLRLLLALNL FPSIQVTGNK ILVKQSPMLV AYDNAVNLSC |
| 50 60 70 80 |
| KYSYNLFSRE FRASLHKGLD SAVEVCVVYG NYSQQLQVYS |
| 90 100 110 120 |
| KTGFNCDGKL GNESVTFYLQ NLYVNQTDIY FCKIEVMYPP |
| 130 140 150 160 |
| PYLDNEKSNG TIIHVKGKHL CPSPLFPGPS KPFWVLVVVG |
| 170 180 190 200 |
| GVLACYSLLV TVAFIIFWVR SKRSRLLHSD YMNMTPRRPG |
| 210 220 |
| PTRKHYQPYA PPRDFAAYRS |
| 1-18 signal peptide (SEQ ID NO: 64) |
| 19-152 extracellular domain (SEQ ID NO: 65) |
| 153-179 transmembrane domain (SEQ ID NO: 66) |
| 180-220 intracellular domain (SEQ ID NO: 67) |
| Position 186-187 LL→GG (SEQ ID NO: 68) |

TABLE 6

| |
|---|
| Uniprot Q07011 4-1BB (SEQ ID NO: 15) |
| 10 20 30 40 |
| MGNSCYNIVA TLLLVLNFER TRSLQDPCSN CPAGTFCDNN |
| 50 60 70 80 |
| RNQICSPCPP NSFSSAGGQR TCDICRQCKG VFRTRKECSS |
| 90 100 110 120 |
| TSNAECDCTP GFHCLGAGCS MCEQDCKQGQ ELTKKGCKDC |
| 130 140 150 160 |
| CFGTFNDQKR GICRPWTNCS LDGKSVLVNG TKERDVVCGP |
| 170 180 190 200 |
| SPADLSPGAS SVTPPAPARE PGHSPQIISF FLALTSTALL |
| 210 220 230 240 |
| FLLFFLTLRF SVVKRGRKKL LYIFKQPFMR PVQTTQEEDG |
| 250 |
| CSCRFPEEEE GGCEL |
| 1-23 signal peptide (SEQ ID NO: 69) |
| 24-186 extracellular domain (SEQ ID NO: 70) |
| 187-213 transmembrane domain (SEQ ID NO: 71) |
| 214-255 intracellular domain (SEQ ID NO: 72) |

TABLE 7

| |
|---|
| Uniprot P20963 human CD3ζ Isoform 3 (SEQ ID NO: 16) |
| 10 20 30 40 |
| MKWKALFTAA ILQAQLPITE AQSFGLLDPK LCYLLDGILF |
| 50 60 70 80 |
| IYGVILTALF LRVKFSRSAD APAYQQGQNQ LYNELNLGRR |
| 90 100 110 120 |
| EEYDVLDKRR GRDPEMGGKP QRRKNPQEGL YNELQKDKMA |

TABLE 7-continued

| |
|---|
| 130 140 150 160 |
| EAYSEIGMKG ERRRGKGHDG LYQGLSTATK DTYDALHMQA |
| LPPR |
| 1-21 signal peptide (SEQ ID NO: 73) |
| 22-30 extracellular (SEQ ID NO: 74) |
| 31-51 transmembrane (SEQ ID NO: 75) |
| 52-164 intracellular domain (SEQ ID NO: 76) |
| 61-89 ITAM1 (SEQ ID NO: 77) |
| 100-128 ITAM2 (SEQ ID NO: 78) |
| 131-159 ITAM3 (SEQ ID NO: 79) |

TABLE 8

| Exemplary Hinge region Sequences |
|---|
| Human IgG1 (SEQ ID NO: 17) |
| EPKSCDKTHTCPPCP |
| Human IgG2 (SEQ ID NO: 18) |
| ERKCCVECPPCP |
| Human IgG3 (SEQ ID NO: 19) |
| ELKTPLGDTHTCPRCP (EPKSCDTPPPCPRCP)$_3$ |
| Human IgG4 (SEQ ID NO: 20) |
| ESKYGPPCPSCP |
| Modified Human IgG4 (SEQ ID NO: 21) |
| ESKYGPPCPPCP |
| Modified Human IgG4 (SEQ ID NO: 36) |
| YGPPCPPCP |
| Modified Human IgG4 (SEQ ID NO: 37) |
| KYGPPCPPCP |
| Modified Human IgG4 (SEQ ID NO: 38) |
| EVVKYGPPCPPCP |

TABLE 9

| Her 2 construct-short spacer (SEQ ID NO: 1) GMCSFss-Her2scFv-IgG4hinge-CD28tm-41BB-Zeta-T2A-EGFRt |
|---|
| Leader (SEQ ID NO: 80) |
| Atgcttctcctggtgacaagccactgctctgtgagttaccacaccca |
| gcattcctcctgatccca |
| Her2scFV (SEQ ID NO: 81) |
| Gatatccagatgacccagtccccgagctccctgtccgcctctgtggg |
| cgatagggtcaccatcacctgccgtgccagtcaggatgtgaatactg |
| ctgtagcctggtatcaacagaaaccaggaaaagctccgaaactactg |

TABLE 9-continued

| Her 2 construct-short spacer (SEQ ID NO: 1) GMCSFss-Her2scFv-IgG4hinge-CD28tm-41BB-Zeta-T2A-EGFRt |
|---|
| atttactcggcatccacctctactctggagtcccactcgcttctctg<br>gaccagatctgggacggatttcactctgaccatcagcagtctgcagc<br>cggaagacttcgcaacttattactgtcagcaacattatactactcct<br>cccacgttcggacagggtaccaaggtggagatcaaaggcagtactag<br>cggcggtggctccgggggcggatccggtgggggcggcagcagcgagg<br>ttcagctggtggagtctggcggtggcctggtgcagccagggggctca<br>ctccgtagtcctgtgcagcactggcttcaacattaaagacacctata<br>tacactgggtgcgtcaggccccgggtaagggcctggaatgggagcaa<br>ggatttatcctacgaatggttatactagatatgccgatagcgtcaag<br>ggccctcactataagcgcagacacatccaaaaacacagcctacctgc<br>agatgaacagcctgcgtgctgaggacactgccgtctattattgttct<br>agatggggaggggacggcttctatgctatggactactggggtcaagg<br>aaccctggtcaccgtctcgagt |
| Hinge spacer<br>(SEQ ID NO: 82)<br>Gagagcaagtacggaccgccctgccccccttgccct |
| CD28tm<br>(SEQ ID NO: 83)<br>Atgactgggtgctggtggtggtcggaggcgtgctggcctgctacagc<br>ctgctggtcaccgtggccttcatcatcattgggtg |
| 4-1BB<br>(SEQ ID NO: 84)<br>Aaacggggcagaaagaaactcctgtatatattcaaacaaccatttat<br>gagaccagtacaaactactcaagaggaagatggctgtagctgccgat<br>ttccagaagaagaagaaggaggatgtgaactg |
| CD3 zeta<br>(SEQ ID NO: 85)<br>Cgggtgaagttcagcagaagcgccgacgcccctgcctaccagcaggg<br>ccagaatcagctgtacaacgagctgaacctgggcagaagggaagagt<br>acgacgtcctggataagcggagaggccgggaccctgagatgggcggc<br>aagcctcggcggaagaaccccccaggaaggcctgtataacgaactgca<br>gaaagacaagatggccgaggcctacagcgagatcggcatgaagggcg<br>agcggaggcggggcaagggccacgacggcctgtatcagggcctgtcc<br>accgccaccaaggatacctacgacgccctgcacatgcaggccctgcc<br>cccaagg |

TABLE 9-continued

| Her 2 construct-short spacer (SEQ ID NO: 1) GMCSFss-Her2scFv-IgG4hinge-CD28tm-41BB-Zeta-T2A-EGFRt |
|---|
| T2A<br>(SEQ ID NO: 86)<br>Ctcgagggcggcggagagggcagaggaagtatctaacatgcggtgac<br>gtggaggagaatcccggccctagg |
| tEGFR<br>(SEQ ID NO: 87)<br>atgcttctcctggtgacaagccactgctctgtgagttaccacaccca<br>gcattcctcctgatcccacgcaaagtgtgtaacggaataggtattgg<br>tgaatttaaagactcactctccataaatgctacgaatattaaacact<br>tcaaaaactgcacctccatcagtggcgatctccacatcctgccggtg<br>gcatttaggggtgactccacacacatactcctcctctggatccacag<br>gaactggatattctgaaaaccgtaaaggaaatcacagggtttttgct<br>gattcaggcttggcctgaaaacaggacggacctccatgcctttgaga<br>acctagaaatcatacgcggcaggaccaagcaacatggtcagattctc<br>ttgcagtcgtcagcctgaacataacatccagggattacgctccctca<br>aggagataagtgatggagatgtgataatttcaggaaacaaaaatttg<br>tgctatgcaaatacaataaactggaaaaaactgtttgggacctccgg<br>tcagaaaaccaaaattataagcaacagaggtgaaaacagctgcaagg<br>ccacaggccaggtctgccatgccttgtgctcccccgagggctgctgg<br>ggcccggagcccagggactgcgtctcttgccggaatgtcagccgagg<br>cagggaatgcgtggacaagtgcaaccactggagggtgagccaaggga<br>gtagtggagaactctgagtgcatacagtgccacccagagtgcctgcc<br>tcaggccatgaacatcacctgcacaggacggggaccagacaactgta<br>tccagtgtgcccactacattgacggcccccactgcgtcaagacctgc<br>ccggcaggagtcatgggagaaaacaacaccctggtctggaagtacgc<br>agacgccggccatgtgtgccacctgtgccatccaaactgcacctacg<br>gatgcactgggccaggtcttgaaggctgtccaacgaatgggcctaag<br>atcccgtccatcgccactgggatggtgggggccctcctcttgctgct<br>ggtggtggccctggggatcggcctcttcatgtga |

TABLE 12

| |
|---|
| 7xHBD/mEF1α nucleic acid sequence<br>(SEQ ID NO: 41)<br>Tagttaataatctacaatagttaataatctacaatagttaataatcta<br>caatagttaataatctacaatagttaataatctacaatagttaataat<br>ctacaatagttaataatctacaa |

What is claimed is:

1. A method for inducing expression of a polypeptide in a subject, comprising:

(a) administering a cell to the subject, wherein the cell comprises:

a first nucleic acid comprising an inducible first promoter comprising a nucleotide sequence having at least 95% sequence identity with the nucleotide sequence of SEQ ID NO:41, wherein the first nucleic acid is operably linked to a polynucleotide encoding the polypeptide, and a second nucleic acid comprising a second promoter operably linked to a nucleic acid encoding a transcriptional activator for the first promoter; and (b) administering to the subject an agent selected from the group consisting of tamoxifen, a metabolite of tamoxifen, and an analog of tamoxifen.

2. The method of claim 1, wherein the agent is a metabolite of tamoxifen.

3. The method of claim 2, wherein the agent is selected from 4-hydroxytamoxifen, a desmethyl-metabolite of tamoxifen, or a 4-hydroxy-metabolite of tamoxifen.

4. The method of claim 1, wherein step (a) further comprises culturing the cell in the presence of tamoxifen, a metabolite of tamoxifen, or an analog of tamoxifen, prior to the administration.

5. The method of claim 4, further comprising culturing the cell in the presence of an activating stimulator selected from anti-CD3 and anti-CD28.

6. The method of claim 1, wherein the second promoter is a constitutive promoter.

7. The method of claim 6, wherein the second promoter is an EFla promoter.

8. The method of claim 1, wherein the transcriptional activator comprises an HEA-3 polypeptide.

9. The method of claim 8, wherein the transcriptional activator comprises a polypeptide having at least 95% sequence identity with the amino acid sequence of SEQ ID NO:40.

10. The method of claim 1, wherein the polypeptide is selected from a chimeric antigen receptor (CAR), a cytokine, a chemokine receptor.

11. The method of claim 1, wherein the cell is a T cell, a precursor T cell or a hematopoietic stem cell.

12. The method of claim 11, wherein the cell is a CD4+ T cell, or a CD8+ T cell.

13. The method of claim 12, wherein the cell is a CD8+ cytotoxic T cell selected from the group consisting of a naïve CD8+ T cell, a central memory CD8+ T cell, an effector memory CD8+ T cell, and a bulk CD8+ T cell.

14. The method of claim 12, wherein the cell is a CD4+T helper cell selected from the group consisting of a naïve CD4+ T cell, a central memory CD4+ T cell, an effector memory CD4+ T cell, and a bulk CD4+ T cell.

15. The method of claim 1, wherein the cell is autologous to the subject.

16. The method of claim 1, wherein the cell is allogeneic to the subject.

17. The method of claim 1, wherein the subject is human.

18. A method for inducing expression of a polypeptide in a cell, comprising contacting a cell with an agent selected from the group consisting of tamoxifen, a metabolite of tamoxifen, and an analog of tamoxifen, wherein the cell comprises:

a first nucleic acid comprising an inducible first promoter comprising a nucleotide sequence having at least 95% sequence identity with the nucleotide sequence of SEQ ID NO:41, wherein the first nucleic acid is operably linked to a polynucleotide encoding the polypeptide, and a second nucleic acid comprising a second promoter operably linked to a nucleic acid encoding a transcriptional activator for the first promoter.

19. The method of claim 18, further comprising culturing the cell in the presence of the agent and an activating stimulator selected from anti-CD3 and anti-CD28.

20. The method of claim 18, wherein the transcriptional activator comprises a polypeptide having at least 95% sequence identity with the amino acid sequence of SEQ ID NO:40.

21. A system for inducible expression of a polypeptide comprising:

a first nucleic acid comprising an inducible first promoter comprising a nucleotide sequence having at least 95% sequence identity with the nucleotide sequence of SEQ ID NO:41, wherein the first nucleic acid is operably linked to a polynucleotide encoding the polypeptide; and a second nucleic acid comprising a second promoter operably linked to a nucleic acid encoding a transcriptional activator for the first promoter, wherein the transcriptional activator comprises a polypeptide having at least 95% sequence identity with the amino acid sequence of SEQ ID NO:40.

22. The system of claim 21, further comprising; (i) an activating stimulator selected from anti-CD3 and anti-CD28; or (ii) an agent selected from the group consisting of tamoxifen, a metabolite of tamoxifen, and an analog of tamoxifen.

23. The system of claim 21, further comprising a cell, wherein the cell comprises the first nucleic acid and second nucleic acid.

* * * * *